(12) United States Patent
Colussi et al.

(10) Patent No.: US 11,597,763 B2
(45) Date of Patent: Mar. 7, 2023

(54) ANTI-KV1.3 ANTIBODIES, AND METHODS OF PRODUCTION AND USE THEREOF

(71) Applicant: Tetragenetics, Inc., Arlington, MA (US)

(72) Inventors: Paul A. Colussi, Gloucester, MA (US); Janna Bednenko, Woburn, MA (US); Yelena Bisharyan, Arlington, MA (US); Ashot Papoyan, Arlington, MA (US); Joanna Cardarelli, Charlestown, MA (US); Theodore G. Clark, Ithaca, NY (US); Douglas Kahn, Boston, MA (US); Lore Mariën, Ghent (BE); Bas Van Der Woning, Bachte-Maria-Leerne (NL); Hans De Haard, Oudelande (NL); William D. Harriman, Alameda, CA (US); Ellen J. Collarini, Oakland, CA (US); Alka Agrawal, Cambridge, MA (US)

(73) Assignee: Tetragenetics, Inc., Arlington, MA (US)

( * ) Notice: Subject to any disclaimer, the term of this patent is extended or adjusted under 35 U.S.C. 154(b) by 70 days.

(21) Appl. No.: 16/098,670

(22) PCT Filed: May 2, 2017

(86) PCT No.: PCT/US2017/030612
§ 371 (c)(1),
(2) Date: Nov. 2, 2018

(87) PCT Pub. No.: WO2017/192567
PCT Pub. Date: Nov. 9, 2017

(65) Prior Publication Data
US 2019/0144538 A1  May 16, 2019

Related U.S. Application Data

(60) Provisional application No. 62/330,420, filed on May 2, 2016, provisional application No. 62/416,447, filed on Nov. 2, 2016.

(51) Int. Cl.
*C07K 16/28* (2006.01)
*A61P 37/06* (2006.01)
*C07K 16/44* (2006.01)

(52) U.S. Cl.
CPC ............ *C07K 16/28* (2013.01); *A61P 37/06* (2018.01); *C07K 16/44* (2013.01); *C07K 2317/14* (2013.01); *C07K 2317/23* (2013.01); *C07K 2317/622* (2013.01); *C07K 2317/64* (2013.01); *C07K 2317/76* (2013.01)

(58) Field of Classification Search
None
See application file for complete search history.

(56) References Cited

U.S. PATENT DOCUMENTS

| 2003/0032595 A1 | 2/2003 | Desir et al. |
| 2008/0090999 A1 | 4/2008 | Goldman et al. |
| 2011/0034676 A1 | 2/2011 | Donohoe et al. |
| 2012/0237530 A1 | 9/2012 | Matsuda et al. |
| 2015/0203579 A1 | 7/2015 | Papadopoulos et al. |

FOREIGN PATENT DOCUMENTS

| CN | 102180950 A | 9/2011 |
| CN | 104937105 A | 9/2015 |
| CN | 103713129 B | 2/2016 |
| WO | WO 2007/069247 A2 | 6/2007 |
| WO | WO 2007/139771 A1 | 12/2007 |
| WO | WO 2010/126590 A1 | 11/2010 |
| WO | WO 2014/016737 A1 | 1/2014 |
| WO | WO 2015/193452 A1 | 12/2015 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Commmunications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Entzminger et al. (2017). Sci. Rep. 7(1):1-295 (11 pages).*
Extended European Search Report for Application No. EP 17793147.4 dated Nov. 28, 2019.
International Search Report and Written Opinion for Application No. PCT/US2017/030612 dated Oct. 10, 2017.
International Preliminary Report on Patentability for Application No. PCT/US2017/030612 dated Nov. 15, 2018.

(Continued)

*Primary Examiner* — Christine J Saoud
*Assistant Examiner* — Jon M. Lockard
(74) *Attorney, Agent, or Firm* — Wolf, Greenfield & Sacks, P.C.

(57) ABSTRACT

Anti-Kv1.3 antibodies (mAbs), particularly mAbs that specifically bind to Kv1.3 with high affinity and/or inhibit Kv1.3 function, are disclosed. The amino acid sequences of the CDRs of the light chains and the heavy chains, as well as consensus sequences for these CDRs, of these anti-Kv1.3 mAbs are provided. Additionally, canonical structures for CDRs in the VH and VL regions of anti-Kv1.3 antibodies are provided. The disclosure also provides nucleic acid molecules encoding the anti-Kv1.3 mAbs, expression vectors, host cells, methods for making the anti-Kv1.3 mAbs, and methods for expressing the anti-Kv1.3 mAbs. Finally, methods of using the anti-Kv1.3 mAbs as therapeutics, such as for preventing or treating an autoimmune disorder, are disclosed.

2 Claims, 37 Drawing Sheets

Specification includes a Sequence Listing.

(56) References Cited

OTHER PUBLICATIONS

Liu et al., MAPK phosphatases—regulating the immune response. Nat Rev Immunol. Mar. 2007;7(3):202-12.
Panyi et al., K+ channel blockers: novel tools to inhibit T cell activation leading to specific immunosuppression. Curr Pharm Des. 2006;12(18):2199-220.
Wulff et al., Targeting effector memory T-cells with Kv1.3 blockers. Curr Opin Drug Discov Devel. Jul. 2007;10(4):438-45.
Ding et al., Research Progress of New Target Kv1.3 of Autoimmune Diseases and Its Pharmaceutical Polypeptides. Journal of Hubei Medical University. Oct. 31, 2015;34(5):506-510.
Fan et al., A novel PADRE-Kv1.3 vaccine effectively induces therapeutic antibodies and ameliorates experimental autoimmune encephalomyelitis in rats. Clin Immunol. Aug. 2018;193:98-109. doi: 10.1016/j.clim.2018.02.012. Epub Feb. 27, 2018.
Perez-Verdaguer et al., A. The voltage-gated potassium channel Kv1.3 is a promising multitherapeutic target against human pathologies. Expert Opin Ther Targets. 2016;20(5):577-91. doi: 10.1517/14728222.2016.1112792. Epub Dec. 4, 2015.
Yang et al., The antibody targeting the E314 peptide of human Kv1.3 pore region serves as a novel, potent and specific channel blocker. PLoS One. 2012;7(4):e36379. doi: 10.1371/journal.pone.0036379. Epub Apr. 27, 2012.

\* cited by examiner

Figure 1A

Human Kv1.3 Amino Acid Sequence
(Accession: P22001.3; SEQ ID NO: 1)

```
  1  MDERLSLLRS  PPPPSARHRA  HPPQRPASSG  GAHTLVNHGY  AEPAAGRELP  PDMTVVPGDH
 61  LLEPEVADGG  GAPPQGGCGG  GGCDRYEPLP  PSLPAAGEQD  CCGERVINI   SGLRFETQLK
121  TLCQFPETLL  GDPKRRMRYF  DPLRNEYFFD  RNRPSFDAIL  YYYQSGGRIR  RPVNVPIDIF
181  SEEIRFYQLG  EEAMEKFRED  EGFLREEERP  LPRRDFQRQV  WLLFEYPESS  GPARGIAIVS
241  VLVILISIVI  FCLETLPEFR  DEKDYPASTS  QDSFEAAGNS  TSGSRAGASS  FSDPFFVVET
301  LCIIWFSFEL  LVRFFACPSK  ATFSRNIMNL  IDIVAIIPYF  ITLGTELAER  QGNGQQAMSL
361  AILRVIRLVR  VFRIFKLSRH  SKGLQILGQT  LKASMRELGL  LIFFLFIGVI  LFSSAVYFAE
421  ADDPTSGFSS  IPDAFWWAVV  TMTTVGYGDM  HPVTIGGKIV  GSLCAIAGVL  TIALPVPVIV
481  SNFNYFHRE   TEGEEQSQYM  HVGSCQHLSS  SAEELRKARS  NSTLSKSEYM  VIEEGGMNHS
541  AFPQTPFKTG  NSTATCTTNN  NPNSCVNIKK  IFTDV
```

Figure 1B

Human Kv1.3 Amino Acid Sequence (SEQ ID NO: 2)

```
  1  MDERLSLLRS  PPPPSARHRA  HPPQRPASSG  GAHTLVNHGY  AEPAAGRELP  PDMTVVPGDH
 61  LLEPEVADGG  GAPPQGGCGG  GGCDRYEPLP  PSLPAAGEQD  CCGERVINI   SGLRFETQLK
121  TLCQFPETLL  GDPKRRMRYF  DPLRNEYFFD  RNRPSFDAIL  YYQSGGRIR   RPVNVPIDIF
181  SEEIRFYQLG  EEAMEKFRED  EGFLREEERP  LPRRDFQRQV  WLLFEYPESS  GPARGIAIVS
241  VLVILISIVI  FCLETLPEFR  DEKDYPASTS  QDSFEAAGNS  TSGSRAGASS  FSDPFFVVET
301  LCIIWFSFEL  LVRFFACPSK  ATFSRNIMNL  IDIVAIIPYF  ITLGTELAER  QGNGQQAMSL
361  AILRVIRLVR  VFRIFKLSRH  SKGLQILGQT  LKASMRELGL  LIFFLFIGVI  LFSSAVYFAE
421  ADDPTSGFSS  IPDAFWWAVV  TMTTVGYGDM  HPVTIGGKIV  GSLCAIAGVL  TIALPVPVIV
481  SNFNYFYHRE  TEGEEQSQYM  HVGSCQHLSS  SAEELRKARS  NSTLSKSEYM  VIEEGGMNHS
541  AFPQTPFKTG  NSTATCTTNN  NPNSCVNIKK  IFTDVDYKDD  DDKHHHHHHH  HHH
```

Figures 5A-B

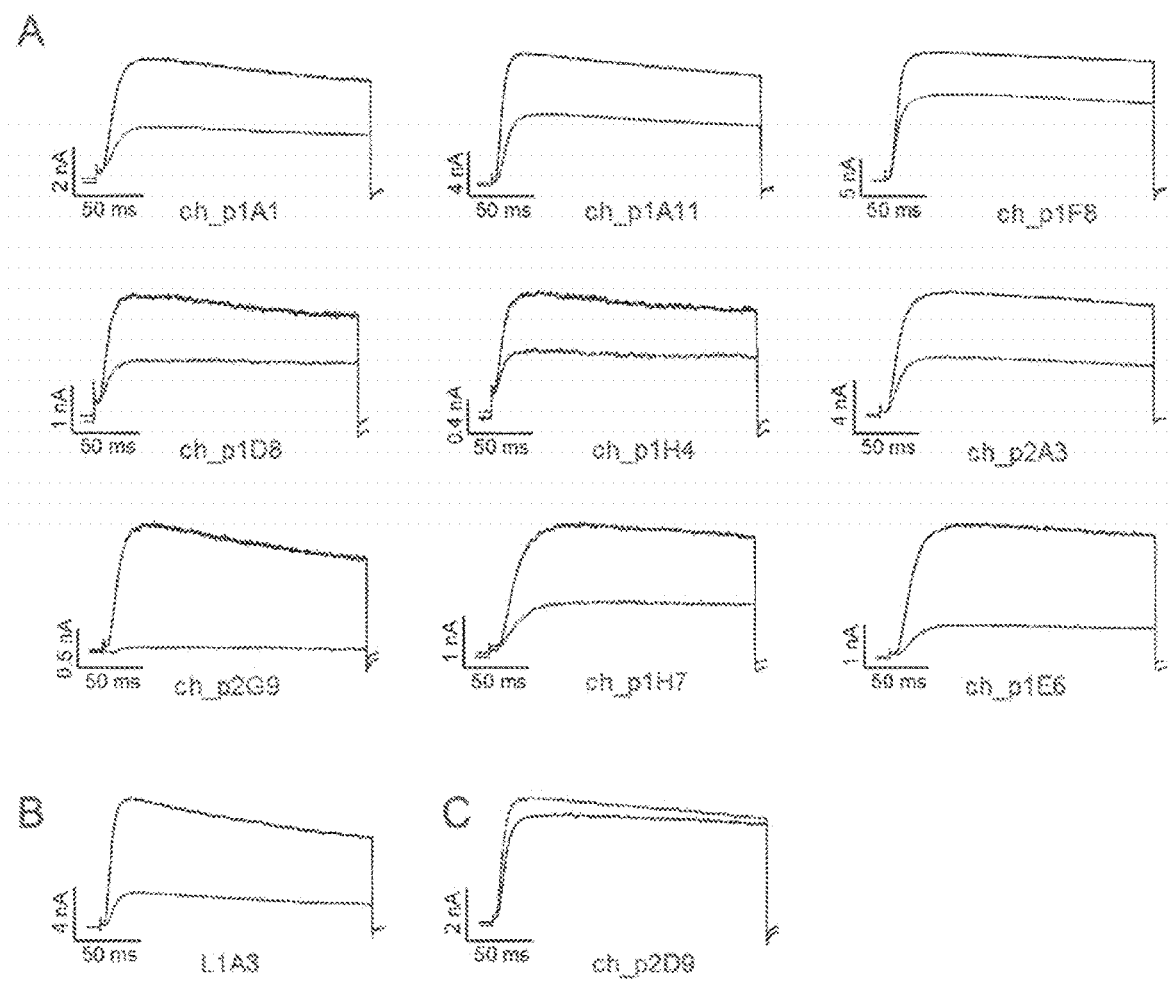
Figures 7A-C

Figure 11A

Light Chain Variable Region Sequence Alignments

| SEQ ID NO. | CLONE NAME | | CDR1 | | CDR2 |
|---|---|---|---|---|---|
| 3 | 19724p1_F8 | -AVTQPASVSANPGETVEITCSGS-----SGSSYYGWYQQKAPGSAPVTVIYDMTNRPSDIP |
| 4 | 19724p1_A9 | ALTQQPASVSANPGETVKITCSGGYNYAGSYYYGWYQQKAPGSAPVTVIYDNTNRPSNIP |
| 5 | 19724p2_A5 | -AVTQPASVSANPGETVKITCSGG-----GSSYYGWYQQKSPGRTPVTVIYDNTNRPSDIP |
| 6 | 19724p2_H10 | -AVTQPASVSANPGETVEITCSGG-----GSSYYGWYQQKSPGRTPVTVIFVTNRPSDIP |
| 7 | 19724p2_A2 | -ALTQPASVSANPGETVEITCSGGRS---DYYYSWHQQEAPGSAPVTLIYNDMTMRPSDIP |
| 8 | 19724p2_F6 | -ALTQPASVSANLGETVRVICSGGYS---RYGYSWHQQKSPGSAPVTLIYNDNKRPSDIP |
| 9 | 19724p1_D2 | -ALTHPASVSANPGETVKVTCSGGYS---NYGYSWHQQKSPGSAPVTVIYNDKRPSDIP |
| 10 | 19724p1_E2 | -ALTQPASVSANPGETVKVTCSGGYS---SYGYSWFQQKSPGSAPVTVIYNDKRPSDIP |
| 11 | 19724p1_H2 | -ALTQPASVSANPGETVKVTCSGGYS---SYGYSWFQQKSPGSALVTVIYSNNQRPSDIP |
| 12 | 19724p2_D2 | -ALTQPASVSANLGGTVEITCSRDDS---GYGYGWYQQKSPGSALVTVIYSNNQRPSDIP |
| 13 | 19724p2_H12 | -ALTQPASVSANLGGTVEITCSRDDS---GYGYGWYQQKSPGSALVTVIYSNNQRPSDIP |
| 14 | 19724p2_H4 | -ALTQPASVSANLGGTVKITCSRDDS---GYGYGWYQQKSPGSAPVTVIYSNNQRPSDIP |
| 15 | 19724p1_C4 | -ALTQPSSVSANPGETVKITCSGGGSYAGSYYYGWHQQKSPGSAPVTVIYNNNKRPSDIP |
| 16 | 19724p2_E6 | -ALTQPSSVSANLGGTVKITCSGG-----SYTYGWFQQKSPGSAPVTVIYNKKRPSDIP |
| 17 | 19724p1_C12 | ALTQQPASVSANPGETVKITCSGG-----SYSYGMFQQKSPGSAPVTVIYSNSQRPSDIP |
| 18 | 19724p1_F7 | ALTQQPASVSANPGETVKITCSGG-----SYSYGMFQQKSSGSALVTVIYSNDNRPSDIP |
| 19 | 19724p1_F9 | -ALTQPASVSANPGETVKITCSGG-----SYSYGWFQQKSPGSALVTVIYTYNDNRPSDIP |
| 20 | 19724p2_B5 | -AVTQPASVSANLGETVKITCSGGS----GSYYYGWFQQKSPGSAPVSVIYEDTKRPSNIP |
| 21 | 19724p2_G9 | -ALTQPASVSANPGETVKITCSGG-----GYFFGWYQQKSPGSAPVTLIYESNKKPSNIP |
| 22 | 19724p1_A11 | -ALTQPASVSTNPGETVKITCSGG-----GYFFGWYQQKSPGSAPVTLIYESMKRPSNIP |
| 23 | 19724p1_H7 | -ALTQPASVSANPGETVKITCSGG-----GYFFGWYQQKSPGSAPVTLIYESNKRPSNIP |

Figure 11A (cont.)

Light Chain Variable Region Sequence Alignments (continued)

| SEQ ID NO. | CLONE NAME | CDR1 | CDR2 |
|---|---|---|---|
| 24 | 19724p2.A3 | -ALTQPASVSANPGETVKITCSGGS------GYFFGWYQQKSPGSAPVTLIYESNKRPSNIP | |
| 25 | 19724p1.H12 | -ALTQPASVSANPGETVKITCSGGGS----SNYYGWYQQKSPGSAPLTVIYWDDERPSNIP | |
| 26 | 19724p1.A5 | -AVTQPASVSANLGGTVEITCSGDGS----SSYYGWFQQKSPGSAPVTLIYYNSKRPSDIP | |
| 27 | 19724p1.E3 | -AVTQPASVSANLGGTVEITCSGDGS----SSYYGWFQQKSPGSAPVTLIYYNSKRPSDIP | |
| 28 | 19724p2.D1 | VLTQQPASVSANPGGTVEITCSGGG------GSYGWYQQKSPGSAPVTLIYRNDKRPSDIP | |
| 29 | 19724p2.H6 | VLTQQPASVSANPGGTVEITCSGGG------GSYGWYQQKSPGSAPVTLIYRNDKRPSDIP | |
| 30 | 19724p1.B11 | -ALTQPASVSANPGETVKITCSGGSY----SNYYGWYQQKSPGSAPVTVIYHNDKRPSDIP | |
| 31 | 19724p1.F3 | -ALTQPASVSANPGETVKITCSGGSY----SNYYGWYQQKSPGSAPVTVIYHNDKRPSDIP | |
| 32 | 19724p2.A7 | -ALSQPASVSANPGETVKITCSGSS------GSYGWYQQKSPGSAPVTVIYWNDKRPSDIP | |
| 33 | 19724p2.C4 | -ALSQPASVSANPGETVKITCSGSS------GSYGWYQQKSPGSAPVTVIYWNDKRPSDIP | |
| 34 | 19724p1.G6 | -ALTQPASVSASLGGTVKITCSGSD----SNNYGWYQQKSPGSAPVTLIYYNNKRPSDIP | |
| 35 | 19724p1.D11 | -ALTQPASVSANPGETVKIPCSGGS------GSSYYGWYQQKSPASAPVTVYENTKRPSDIP | |
| 36 | 19724p2.D9 | -ALTQPASVSANPGGTVEITCSGGG------GSSYYGWFQQKSPASAPVTVYENTKRPSDIP | |
| 37 | 19724p1.A1 | -ALTQPASVSANPGGTVEITCSGGG------SSYYGWFQQKSPASAPVTVYENTKRPSDIP | |
| 38 | 19724p1.H4 | -ALTQPASVSANPGGTVEITCSGGG------SRYYGWFQQKSPGSAPVTVYYNDKRPSDIP | |
| 39 | 19724p1.D8 | -ALTQPASVSANPGGTVEITCSGGSSVSG----YGWYQQKSPGSTPVTVTVIYYNDKRPSDIP | |
| 40 | 19724p2.F7 | -ALTQPASVSANLGGTVKITCSGGNYDGSYYYGWYQQKSPGSAPVTVIYSNNQRPSNIP | |
| 41 | 19724p1.B1 | -ALTQPASVSANPGETVEITCSGG-------GSYGWHQQKSPGSAPVTVIYYNDKRPSDIP | |
| 42 | 19724p1.E6 | -ALTQPASVSANLGETVEITCSGGYSDDGSYYYGWYQQKSPGSAPVTVIYENNKRPSDIP | |

Figure 11B

Light Chain Variable Region Sequence Alignments (continued)

| SEQ ID NO. | CLONE NAME | | CDR3 |
|---|---|---|---|
| 3 | 19724p1_F8 | SRFSGSASGSTATLTITGVQVEDEGVYFCGGYDSNTY-AGIFGAGTTLTVL |
| 4 | 19724p1_A9 | SRFSGSLSGSTATLTITGVQVEDEAVYFCGNEDSST---STFGAGTTLTVL |
| 5 | 19724p2_A5 | SRFSGSKSGSTATLTITGVQAEDEAVYFCGAWEGSS---PAFGAGTTLTVL |
| 6 | 19724p2_H10 | SRFSGSKSGSTATLTITGVQAEDEAVYFCGAWEGSS---PAFGAGTTLTVL |
| 7 | 19724p2_A2 | SRFSGAVSGSTGTLTITGVQAEDEAVYFCGGYDDTIN--PIFGAGTTLTVL |
| 8 | 19724p2_F6 | SRFSGSKSGSTGTLTITGVQAEDEAVYFCGSTDNNGY--PAFGAGTTLTVL |
| 9 | 19724p1_D2 | SRFSGSKSGSTGTLTITGVQAEDEAVYFCGSTDSNGY--PAFGAGTTLTVL |
| 10 | 19724p1_E2 | SRFSGSKSGSTGTLTITGVQAEDEAVYFCGSTDINGY--PAFGAGTTLTVL |
| 11 | 19724p1_H2 | SRFSGSKSGSTGTLTITGVQAEDEAVYFCGSTDINGY--PAFGAGTTLTVL |
| 12 | 19724p2_D2 | SRFSGSKSGSTHALFIAGVRAEDEAVYYCGSFDSSTYVTDIFGAGTTLTVL |
| 13 | 19724p2_H12 | SRFSGSKSGSTHTLTITGVRAEDEAVYYCGSFDSSTYVTDIFGAGTTLTVL |
| 14 | 19724p2_H4 | SRFSGALSGSTNTLTITGVQAEDEAVYFCGSIDSSRT--AAFGAGTTLTVL |
| 15 | 19724p1_C4 | SRFSGSLSGSTNTLTITGVQAEDEAVYFCGSIDSSRT--AAFGAGTTLTVL |
| 16 | 19724p2_E6 | SRFSGSLSGSTNTLTITGVQADDEAVYFCGSTDSSYV--DIFGAGTTLTVL |
| 17 | 19724p1_C12 | SRFSGSLSGSTNTLTITGVRAEDEAVYYCGSTDSSYV--DIFGAGTTLTVL |
| 18 | 19724p1_F7 | SRFSGSASGSTATLTITGVQAEDEAVYFCGSFDSSGD--GIFGAGTTLTVL |
| 19 | 19724p1_F9 | SRFSGSASGSTATLTITGVQAEDEAVYFCGSFDSSGD--GIFGAGTTLTVL |
| 20 | 19724p2_B5 | SRFSGSASGSTATLTITGVRADDEAVYFCGAYDGSTY-IPIFGAGTTLTVL |
| 21 | 19724p2_G9 | SRFSGSTSGSTNTLTITGVQADDEAVYFCGTYDSIEA---IFGAGTTLTVL |
| 22 | 19724p1_A11 | SRFSGSTSGSTNTLTITGVQADDEAVYFCGTYDSIEA---IFGAGTTLTVL |
| 23 | 19724p1_H7 | SRFSGSTSGSTNTLTITGVQADDEAVYFCGTYDSIEA---IFGAGTTLTVL |

Figure 11B (cont.)

Light Chain Variable Region Sequence Alignments (continued)

| SEQ ID NO. | CLONE NAME | | CDR3 | |
|---|---|---|---|---|
| 24 | 19724p2.A3 | SRFSGSTSGSTNTLTITGVQADDEAVYFCGTYDSIEA--- | | IFGAGTTLTVL |
| 25 | 19724p1.H12 | SRFSGSKSGSTVTLTLTGVRAEDEAVYFCGTEDNTG--AAIFGAGTTLTVL | | |
| 26 | 19724p1.A5 | SRFSGSTSGSTTTLTLTGVRAEDEAVYFCCGSIDSS--- | GIFGAGTTLTVL | |
| 27 | 19724p1.E3 | SRFSGSTSGSTTTLTLTGVRAEDEAVYFCCGSIDSS--- | GIFGAGTTLTVL | |
| 28 | 19724p2.D1 | SRFSGSKSGSTATLTLTGVQAEDEAVYYCGNADKTSG--- | TFGAGTTLTVL | |
| 29 | 19724p2.H6 | SRFSGSKSGSTATLTLTGVQAEDEAVYYCGNADKTSG--- | TFGAGTTLTVL | |
| 30 | 19724p1.B11 | SRFSGSTSGSTSTLTITGVQADDEAVYFCGNADSSAGDDAIFGAGTTLTVL | | |
| 31 | 19724p1.F3 | SRFSGSTSGSTSTLTITGVRAEDEAVYFCGNADSSAGDDAIFGAGTTLTVL | | |
| 32 | 19724p2.A7 | SRFSGSKSGSTGTLTITGVQVEDEAVYFCGAREDSSD-TSSFGAGTTLTVL | | |
| 33 | 19724p2.C4 | SRFSGSKSGSTGTLTITGVQVEDEAVYFCGAREDSSD-TSSFGAGTTLTVL | | |
| 34 | 19724p1.G6 | SRFSGSKSGSTGTLTITGVQAEDEAVYYCGAWESSSN-SGVFGAGTTLTVL | | |
| 35 | 19724p1.D11 | SRFSGSKSGSTNTLTITGVQAEDEAVYCCGGYDGSSD-SGIFGAGTTLTVL | | |
| 36 | 19724p2.D9 | SRFSGSKSGSTNTLTITGVRAEDEAVYFCGGYDSSNG--GTFGAGTTLTVL | | |
| 37 | 19724p1.A1 | SRFSGSKSGSTNTLTITGVRAEDEAVYFCGGYDSSNG--GTFGAGTTLTVL | | |
| 38 | 19724p1.H4 | SPFSGSKSGSTNTLTITGVRAEDEAVYFCGGYDSSNG--GTFGAGTTLTVL | | |
| 39 | 19724p1.D8 | SRFSGSRSGSTGTLTLTGVQAEDEAVYFCGSWDSSAG-YSTFGAGTTLTVL | | |
| 40 | 19724p2.F7 | SRFSGSLSGSTNTLTITGVQADDEAIYYCGSADSSSV--LFGAGTTLTVL | | |
| 41 | 19724p1.B1 | SRFSGSLSGSTNTLTITGVRAEDEAVYFCGSWDSSAG--- | IFGAGTTLTVL | |
| 42 | 19724p1.E6 | SRFSGSLSGSTNTLTITGVRAEDEAVYYCGSWDSSAG--- | IFGAGTTLTVL | |

Figure 12

Unique Light Chain CDR Sequence Alignments

| SEQ ID NO. | CDR 1 | SEQ ID NO. | CDR2 | SEQ ID NO. | CDR3 |
|---|---|---|---|---|---|
| 43 | SGS----SGSYYG | 70 | DNTNKRPS | 89 | GGYDSNTY-A |
| 44 | SGGYNYAGSYYYG | 71 | NDNKRPS | 90 | GNEDSST--- |
| 45 | SGG----GSSYYG | 72 | ESNKRPS | 91 | GAWEGSS--- |
| 46 | SGGRS---DYYYS | 73 | YNDKRPS | 92 | GGYDDTIN-- |
| 47 | SGGYS---RYGYS | 74 | SNNQRPS | 93 | GSTDNNGY-- |
| 48 | SGGYS---NYGYS | 75 | NNNKRPS | 94 | GSTDSNGY-- |
| 49 | SGGYS---SYGYS | 76 | YNKKRPS | 95 | GSTDINGY-- |
| 50 | SRDDS---GYGYG | 77 | SNSQRPS | 96 | GSFDSSTYVT |
| 51 | SGGSYAGSYYYG | 78 | YNDNRPS | 97 | GSIDSSRT-- |
| 52 | SGG----SYTYG | 79 | EDTKRPS | 98 | GSTDSSYV-- |
| 53 | SGG----SYSYG | 80 | ESNKKRPS | 99 | GSFDSSGD-- |
| 54 | SGGS----GSYYG | 81 | WDDERPS | 100 | GAYDGSTY-T |
| 55 | SGGS----GYFFG | 82 | YNSKRPS | 101 | GTYDSIEA-- |
| 56 | SGGGS---SNYYG | 83 | RNDKRPS | 102 | GTEDNTG--A |
| 57 | SGDGS---SSYYG | 84 | HNDKRPS | 103 | CGSIDSS--- |
| 58 | SGGG----GSYG | 85 | WNDKRPS | 104 | GNADKTSG-- |
| 59 | SGGSY---SNYYG | 86 | YNNKRPS | 105 | GNADSSAGDD |
| 60 | SGSS----GSYG | 87 | ENTKRPS | 106 | GAREDSSD-T |
| 61 | SGSD----SNNYG | 88 | ENNKRPS | 107 | GAMESSSN-S |
| 62 | SGGS----GSYYG |  |  | 108 | GGYDGSSD-S |
| 63 | SGGG----GSYYG |  |  | 109 | GGYDSSNG-- |
| 64 | SGGG----SSYYG |  |  | 110 | GSWDSSAG-Y |
| 65 | SGGG----SRYYG |  |  | 111 | GSADSSSV-- |
| 66 | SGGSSVSG---YG |  |  | 112 | GSWDSSAG-- |
| 67 | SGGGNYDGSYYYG |  |  |  |  |
| 68 | SGG----GSYYG |  |  |  |  |
| 69 | SGGYSDDGSYYYG |  |  |  |  |

Figure 13A

Heavy Chain Variable Region Sequence Alignments

| SEQ ID NO. | CLONE NAME | | CDR1 | | CDR2 |
|---|---|---|---|---|---|
| 125 | 19724p1_F8 | MAAVTLDESGGGLQTPGGGLSLVCKASGFDFNDYGMGWVRQAPGKGLEFVAGIY-SSGRY |
| 126 | 19724p2_D1 | MAAVTLDESEGGLQTPGGGLSLVCKASGFTFSSYTNMGWVRQAPGKGLEFVAAIS-NDANF |
| 127 | 19724p2_H6 | MAAVTLDESEGGLQTPGGGLSLVCKASGFTFSSYINMGWVRQAPGKGLEFVAAIS-NDANF |
| 128 | 19724p1_C4 | MAAVTLDESGGGLQTPGGTLSLVCKASGFTFSDIYGMGWVRQAPGKGLEYVAEID-SAGSS |
| 129 | 19724p1_E6 | MAAVTLDESGGGLQTPGGTLSLVCKASGFTFSSHGMQWVRQAPGKGLEWVAGIS-RDGSR |
| 130 | 19724p1_A11 | MAAVTLDESGGGLRTPGGALSLVCKGSGFTFSDRGMFWVRQAPGKGLEYVAGIS-SSGRS |
| 131 | 19724p1_H7 | MAAVTLDESGGGLQTPGGALSLVCRGSGPTFSDRGMFWVRQAPGKGLEYVAGIS-SSGRS |
| 132 | 19724p2_A3 | MAAVTLDESGGGLQTPGGALSLVCKASGFTFSSYGMFWVRQAPGKGLEYVAGIS-SSGRS |
| 133 | 19724p2_G9 | MAAVTLDESGGGLQTPGGALSLVCKASGFTFSSYGMFWVRQAPGKGLEYVAGIS-SSGRS |
| 134 | 19724p2_A5 | MAAVTLDESGGGLQTPGGALSLVCKASGFTMSSYAMYWVRQAPGKGLEYVAEIN-AVGST |
| 135 | 19724p2_H10 | MAAVTLDESGGGLQTPGGALSLVCKASGFTMSSYAMYWVRQAPGKGLEYVAEIN-AVGST |
| 136 | 19724p1_A5 | MAAVTLDESGGGLQTPGGALSLVCKASGFTFSSYGMQWVRQAPGKGLEWVAGIS-ATGSE |
| 137 | 19724p1_E3 | MAAVTLDESGGGLQTPGGALSLVCKASGFTFSSYGVQWVRQAPGKGLEWVAGIS-ATGSE |
| 138 | 19724p1_A7 | MAAVTLDESGGGLQTPGGALSLVCKASGFTFSSYQMNWVRQAPGKGLEFVAAIN-SFGNS |
| 139 | 19724p2_C4 | MAAVTLDESGGGLQTPGGALSLVCKASGFTFSSYQMNWVRQAPGKGLEFVAAIN-SFGNS |
| 140 | 19724p1_G6 | MAAVTLDESGGGLQTPGGALSLVCKASGFTFSSYQMNWIRQAPGKGLEWVAAIN-RFGNT |
| 141 | 19724p1_D8 | MAAVTLDESGGGLQTPGGALSLVCKASGFDFSSYQMNWVRQAPGKGLEFVAAIN-RFGNS |
| 142 | 19724p1_E2 | MAAVTLDESGGGLQTPGGALSLVCKASGFTFSSYQMNWTRQAPGKGLEFVAAIN-RFGNS |
| 143 | 19724p1_H2 | MAAVTLDESGGGLQTPGGALSLVCKASGFTFSSYQMNWIRQAPGKGLEFVAAIN-RFGNS |
| 144 | 19724p1_D2 | MAAVTLDESGGGLQTPGGALSLVCKASGFDFSSYQMNWIPQAPGKGLEFVAAIN-RFGNG |
| 145 | 19724p1_F6 | MAAVTLDESGGGLQTPGGALSLVCKASGFTFSTHGMFWVRQAPGKGLEFVAAIN-RFGNS |
| 146 | 19724p1_A9 | MAAVTLDESGGGLQTPGGALSLVCKASGFTFSSYQMNWVRQAPGKGLEYVAKIN-AAGSG |
| 147 | 19724p2_B5 | MAAVTLDESGGGLQTPGGGLSLVCKASGFSFSSYGMFWVRQAPGKGLEFVAEVSSNDGSD |

Figure 13A (cont.)

Heavy Chain Variable Region Sequence Alignments (continued)

| SEQ ID NO. | CLONE NAME | | CDR1 | CDR2 |
|---|---|---|---|---|
| 148 | 19724p2.F7 | MAAVTLDESGGGLQTPGGGLSLVCKASGFDFSSYAMWVRQAPGKGLEWVAGID-DGGSY |
| 149 | 19724p1.B11 | MAAVTLDESGGGLQTPGGGLSLVCKASGFTFSSYAMGWVRQAPGKGLEWVAGID-DDGSD |
| 150 | 19724p1.F3 | MAAVTLDESGGGLQAPGGGLSLVCKASGFTFSSYAMGWVRQAPGKGLEWVAGID-DDGSD |
| 151 | 19724p2.E6 | MAAVTLDESGGGLQTPGGTLSLVCKASGFTFSSFNMPWVRQTPGKGLEWVAGIE-NDGG- |
| 152 | 19724p1.B1 | MAAVTLDESGGGLQTPGGGLSLVCKASGFTFSSYAMFWVRQTPGKGLEYVAEIT-NTGSE |
| 153 | 19724p1.D11 | MAAVTLDESEGGLQTPGGGLSLVCKASGFIFSSFNMPWVRQAPGKGLEVAEIS-DTGTT |
| 154 | 19724p1.C12 | MAAVTLDESGGGLQTPGGGLSLVCKASGFTFSSYSVQWVRQAPGKGLEWVAGIE-NDGGG |
| 155 | 19724p2.A2 | MAAVTLDESGGGLQTPGGALSLVCKASGFSFSSHGMFWVRRTPGKGLEYVAEIT-NTGSE |
| 156 | 19724p1.H12 | MAAVTLDESGGGLQTPGGALSLVCKASGFSTSSYGMMNVRQAPGKGLEWVGVIS-NSGSS |
| 157 | 19724p1.F7 | MAAVTLDESGGGLQTPGGALSLICKASGFTFSSYTMCWVRQAPGKGLEWVGVIS-KDGGS |
| 158 | 19724p1.F9 | MAAVTLDESGGGLQTPGGALSLICKASGFTFSSYTMGWVRQAPGKGLEWVGVIS-KDGGS |
| 159 | 19724p1.A1 | MAAVTLDESGGGLQTPGGTLSLVCKASGFTFSSYAMWVRQAPGKGLEFVASIS-VADSS |
| 160 | 19724p1.H4 | MAAVTLDESGGGLQTPGGTLSLVCKASGFTFSSYAMWVRQAPGKGLEFVASIS-VADSS |
| 161 | 19724p2.D9 | MAAVTLDESGGGLQTPGGALSLVCKASGFTFSSYAMWVRQAPGKGLEFVASIS-VADSS |
| 162 | 19724p2.H12 | MAAVTLEESGGGLQTPGGALSLVCKASGFTFSSFNMNWVRQAPGKGLEWVASIS-NTGSS |
| 163 | 19724p2.D2 | MAAVTLEESGGGLQTPGGALSLVCKASGFTFSSFNMNWVRQAPGKGLEWVASIS-NTGSS |
| 164 | 19724p2.H4 | MAAVTLDESGGGLQTPGGALSLVCKASGFTFSSFNMNWVRQAPGKGLEWVASIS-NTGSS |

Figure 13B

Heavy Chain Variable Region Sequence Alignments (continued)

| SEQ ID NO. | CLONE NAME | CDR2 (continued) | CDR3 |
|---|---|---|---|
| 125 | 19724p1_F8 | TYYGAAVQGRATISRDNGQSTVRLQLNNLRAEDAAIYYCAKNADSGYY------T------ | |
| 126 | 19724p2_D1 | TAYGSAVKGRATISRDNGQSTVRLQLNNLRAEDTATYFCAKSAGTGCN------NGYNCADY | |
| 127 | 19724p2_H6 | TAYGSAVKGRATISRDNGQSTVRLQLNNLRAEDTATYFCAKSAGTGCN------NGYNCADY | |
| 128 | 19724p1_C4 | TYYTPAVRGRATISRDNGQSTVRLQLNNLRAEDTGTYYCTKCSGSG------GC------ | |
| 129 | 19724p1_E6 | TRYGAAVKGRATISRDNGQSTVRLQLNNLRAEDTATYFCAKSAYEC------DGYSCWTF | |
| 130 | 19724p1_A11 | AAYGAAVKGRATISRDNGQSTVRLQLNNLRAEDTATYFCAKSTGTG------YG------ | |
| 131 | 19724p1_H7 | AAYGAAVKGRATISRDNGQSTVRLQLNNLRAEDTATYCCAKSTGTG------YG------ | |
| 132 | 19724p2_A3 | TAYGAAVKGRATISRDNGQSTVRLQLNNLRAEDTATYFCAKSTGTG------YG------ | |
| 133 | 19724p2_G9 | TAYGAAVKGRATISRDMGQSTVRLQLNNLRAEDTATYFCAKSTGTG------YG------ | |
| 134 | 19724p2_A5 | TGYGPAVDGRATISRDNGQSTVRLQLNNLRAEDTATYFCAKSYSN------CGGYSC--A | |
| 135 | 19724p2_H10 | TGYGPAVDGPATISRDNGQSTVRLQLDNLRAEDTATYYCAKSYSN------CGDYSC--A | |
| 136 | 19724p1_A5 | TSYAPAVKGRATISRDNGQSTVRLQLDNLRAEDTATYYCAKAAGSGRC------AGAGGYCN | |
| 137 | 19724p1_E3 | TSYAPAVKGRATISRDNGQSTVRLQLDNLRAEDTATYYCAKAAGSGRC------AGAGGYCN | |
| 138 | 19724p1_A7 | TGHGAAVKGRATISRDGGQSTVRLQLNNLRAEDTGTYYCARGAYD------YCG-GGWCN | |
| 139 | 19724p2_C4 | TGHGAAVKGRATISRDDGQSTVRLQLNNLRAEDTGTYYCAKGAYD------YCGSGGWCN | |
| 140 | 19724p1_G6 | TGPGAAVKGRVTISRDDGQSTVRLQSNLRAEDTGTYYCAKGAYG------YCGSGSWCN | |
| 141 | 19724p1_D8 | TGHGAAVKGRVTISRDDGQSTVRLQLSNLRAEDTATYFCAKGAYG------YCGSGSWCA | |
| 142 | 19724p1_E2 | TGHGAAVKGRVTISRDDGQGTVRLQLSDPRAEDTATYYCAKSAYG------YCGSGSWCS | |
| 143 | 19724p1_H2 | TGHGAAVKGRVTISRDDGQSTVRLQLSDLRAEDTATYYCAKSAYG------YCGSGSWCS | |
| 144 | 19724p1_D2 | TGHGAAVKGRVTISRDNGQSTVRLQLSNLRAEDTATYYCAKGAYG------YCGSGSWCS | |
| 145 | 19724p1_F6 | TGHGAAVKGRVTISRDDGQSTVRLQLSNLRAEDTATYFCAKGAYG------YCGSGSWCS | |
| 146 | 19724p1_A9 | TGYGSAVKGRATISRDNGQSTLRLQLNNLRAEDTGTYYCAKDNYD------CGKSICGAY | |
| 147 | 19724p2_B5 | TSYGSSAVEGRATISRDNGQSTVRLQLNNLRAEDTATYFCAKSSHE------CGKSSCWGY | |

Figure 13B (cont.)

Heavy Chain Variable Region Sequence Alignments (continued)

| SEQ ID NO. | CLONE NAME | CDR2 (continued) | CDR3 |
|---|---|---|---|
| 148 | 19724p2.F7 | TGYGAAVKGRATISRDNGQSTVRLQLNNLRAEDTATYYCARGGL------------- | ------------- |
| 149 | 19724p1.B11 | TLYAPAVKGRATISRDNGQSTVRLQLNNLPAEDTATYYCAKSAGRGYCWNTAGGYRCTPY | |
| 150 | 19724p1.F3 | TLYAPAVKGRATISRDMGQSTVRLQLNNLRAEDTATYYCAKSAGRGYCWNTAGGYRCTPY | |
| 151 | 19724p2.E6 | ADYGAAVKGRGTISRDNGQSTVRLQLNNLRAEDTGTYYCAKTAD------SGSGCIWG | |
| 152 | 19724p1.B1 | TRYGAAVKGRATISRDNGQSTVRLQLNNLRAEDTATYFCARGVYG-Y----CGSGSWCG | |
| 153 | 19724p1.D11 | TYYGSAVKGRATISRDNGQSTVRLQLDMLRAEDTGTYYCAKAAGG-----GCPTC-TY | |
| 154 | 19724p1.C12 | TDYGSAVKGRATISRDNGQSTVRLQLNNLRAEDTATYYCARNAG--------AGCDWG | |
| 155 | 19724p2.A2 | TAYGAAVKGRATISRDNGQSTVRLQLNNLRAEDTGTYFCAKSSYD------CGTGCWGY | |
| 156 | 19724p1.H12 | TNYGAAVKGRATISRDNGQSTVRLQLNNLRAEDTGTYFCAKDFGC------SGSSCVGY | |
| 157 | 19724p1.F7 | TYYGSAVKGRATISRDNGQSTVRLQLNNLRAEDTATYYCARGVS------------- | |
| 158 | 19724p1.F9 | TYYGSAVKGRATISRDNGQSTVRLQLNNLRAEDTATYYCARGVS------------- | |
| 159 | 19724p1.A1 | THYGAAVKGRATISRDNGQSTVRLQLNNLRAEDTGTYYCAKSSYQ-----CADNCWGY | |
| 160 | 19724p1.H4 | THYGAAVKGRATISRDNGQSTVRLQLNNLRAEDTGTYYCAKSSYQ-----CADNCWGY | |
| 161 | 19724p2.D9 | THYGAAVKGRATISRDNGQSTVRLQLNNLRAEDTGTYYCAKSSYQ-----CADNCWGY | |
| 162 | 19724p2.H12 | TAYGAAVKGRATISRDNGQSTVRLQLNNLGAEDTGTYYCTRGS------------- | |
| 163 | 19724p2.D2 | TAYGAAVKGRATISRDNGQSTVRLQLNNLRAEDTGTYYCTRGS------------- | |
| 164 | 19724p2.H4 | TAYGAAVKGRATISRDNGQSTVRLQLNNLRAEDTGTYYCTRGS------------- | |

Figure 13C

Heavy Chain Variable Region Sequence Alignments (continued)

| SEQ ID NO. | CLONE NAME | CDR3 (continued) |
|---|---|---|
| 125 | 19724p1_F8 | GAGYIDAWGHGTEVIVS |
| 126 | 19724p2_D1 | TPGYIDSWGHGTEVIVS |
| 127 | 19724p2_H6 | TPGYIDSWGHGTEVIVS |
| 128 | 19724p1_C4 | AYGEIDTWGHGTEVIVS |
| 129 | 19724p1_E6 | IAGSIDAWGHGTEVIVS |
| 130 | 19724p1_A11 | GVGEIDAWGHGTEVIVS |
| 131 | 19724p1_H7 | GVGEIDAWGHGTEVIVS |
| 132 | 19724p2_A3 | GVGEIDAWGHGTEVIVS |
| 133 | 19724p2_G9 | GVGEIDAWGHGTEVIVS |
| 134 | 19724p2_A5 | -AANIDAWGHGTEVIVS |
| 135 | 19724p2_H10 | -AANIDAWGHGTEVIVS |
| 136 | 19724p1_A5 | -PGSIDTWGHGTEVIVS |
| 137 | 19724p1_E3 | -PGSIDTWGHGTEVIVS |
| 138 | 19724p2_A7 | -TAYIDAWGHGTEVIVS |
| 139 | 19724p2_C4 | -TAYIDAWGHGTEVIVS |
| 140 | 19724p1_G6 | -AAYIDAWGHGTEVIVS |
| 141 | 19724p1_D8 | -AGLIDAWGHGTEVIVS |
| 142 | 19724p1_E2 | -PATIDAWGHGTEVIVS |
| 143 | 19724p1_H2 | -PATIDAWGHGTEVIVS |
| 144 | 19724p1_D2 | -PATIDAWGHGTEVIVS |
| 145 | 19724p1_F6 | -PATIDAWGHGTEVIVS |
| 146 | 19724p1_A9 | -AGSIDAWGHGTEVIVS |
| 147 | 19724p2_B5 | -IGSIDAWGHGTEVIVS |

Figure 13C (cont.)

Heavy Chain Variable Region Sequence Alignments (continued)

| SEQ ID NO. | CLONE NAME | CDR3 (continued) |
|---|---|---|
| 148 | 19724p2.F7 | ----TIDTWGRGTEVIVS |
| 149 | 19724p1.B11 | -LGDMDAWGHGTEVIVS |
| 150 | 19724p1.F3 | -LGDMDAWGHGTEVIVS |
| 151 | 19724p2.E6 | -VGCIDAWGHGTEVIVS |
| 152 | 19724p1.B1 | -THIIDAWGHGTEVIVS |
| 153 | 19724p1.D11 | -TDGIDAWGHGTEVIVS |
| 154 | 19724p1.C12 | -AGCIDAWGHGTEVIVS |
| 155 | 19724p2.A2 | -IGSIDAWGHGTEVIVS |
| 156 | 19724p1.H12 | ---NIDAWGHGTEVIVS |
| 157 | 19724p1.F7 | -SDIDAWGHGTEVIVS |
| 158 | 19724p1.F9 | -SDIDAWGHGTEVIVS |
| 159 | 19724p1.A1 | -PYGIDTWGHGTEVIVS |
| 160 | 19724p1.H4 | -PYGIDTWGHGTEVIVS |
| 161 | 19724p2.D9 | -PYGIDTWGHGTEVIVS |
| 162 | 19724p2.H12 | ---AIDAWGHGTEVIVS |
| 163 | 19724p2.D2 | ---AIDAWGHGTEVIVS |
| 164 | 19724p2.H4 | ---AIDAWGHGTEVIVS |

Figure 14

Unique Heavy Chain CDR Sequence Alignments

| SEQ ID NO. | CDR1 | SEQ ID NO. | CDR2 |
|---|---|---|---|
| 165 | NDYGM | 178 | GIY-SSGRYTYYGAAVQ |
| 166 | SSYNM | 179 | AIS-NDANFTAYGSAVK |
| 167 | SDYGM | 180 | EID-SAGSSTYYTPAVR |
| 168 | SSHGM | 181 | GIS-RDGSRTRYGAAVK |
| 169 | SDRGM | 182 | GIS-SSGRSAAYGAAVK |
| 170 | SSYGM | 183 | GIS-SSGRSTAYGAAVK |
| 171 | SSYAM | 184 | EIN-AVGSTTGYGPAVD |
| 172 | SSYGV | 185 | GIS-ATGSETSYAPAVK |
| 173 | SSYQM | 186 | AIN-SFGNSTGHGAAVK |
| 174 | STHGM | 187 | AIN-RFGNTTGPGAAVK |
| 175 | SSFNM | 188 | AIN-RFGNSTGHGAAVK |
| 176 | SSYSV | 189 | AIN-RFGNGTGHGAAVK |
| 177 | SSYTM | 190 | KIN-AAGSGTGYGSAVK |
|  |  | 191 | EVSSNDGSDTSYGSAVE |
|  |  | 192 | GID-DGGSYTGYGAAVK |
|  |  | 193 | GID-DDGSDTLYAPAVK |
|  |  | 194 | GIE-NDGG-ADYGAAVK |
|  |  | 195 | EIT-NTGSETRYGAAVK |
|  |  | 196 | EIS-DTGTTTYYGSAVK |
|  |  | 197 | GIE-NDGGGTDYGSAVK |
|  |  | 198 | EIT-NTGSETAYGAAVK |
|  |  | 199 | VIS-NSGSSTNYCAAVK |
|  |  | 200 | VIS-KDGGSTYYGSAVK |
|  |  | 201 | SIS-VADSSTHYGAAVK |
|  |  | 202 | SIS-NTGSSTAYGAAVK |

Figure 14 (cont.)

| SEQ ID NO. | CDR 3 |
|---|---|
| 203 | NADSGYY-------T-------GAGYIDAW |
| 204 | SAGTGCN-------NGYNCADYTPGYIDSW |
| 205 | CSGSG---------GC-------AYGEIDTW |
| 206 | SAYEC---------DGYSCWTFIAGSIDAW |
| 207 | STGTG---------YG-------GVGEIDAW |
| 208 | SYSN----------CGGYSC---A-AANIDAW |
| 209 | SYSN----------CGDYSC---A-AANIDAW |
| 210 | AAGSGRC-------AGAGGYCN-PGSIDTW |
| 211 | GAYD----------YCG-GGWCN-TAYIDAW |
| 212 | GAYD----------YCGSGGWCN-TAYIDAW |
| 213 | GAYG----------YCGSGSWCN-AAYIDAW |
| 214 | GAYG----------YCGSGSWCA-AGLIDAW |
| 215 | SAYG----------YCGSGSWCS-PATIDAW |
| 216 | GAYG----------YCGSGSWCS-PATIDAW |
| 217 | DNYD----------CGKSICGAY-AGSIDAW |
| 218 | SSHE----------CGKSSCWGY-IGSIDAW |
| 219 | GGL-----------------------TIDTW |
| 220 | SAGRGYCWMTAGGYRCTPY-LGDMDAW |
| 221 | TAD-----------SGSGCIWG-VGCIDAW |
| 222 | GVYG-Y--------CGSGSWCG-THIIDAW |
| 223 | AAGG----------GCPTC-TY-TDGIDAM |
| 224 | NAG-----------AGCDWG-AGCIDAM |
| 225 | SSYD----------CGTGCWGY-IGSIDAW |
| 226 | DFGC----------SGSSCVGY---NIDAW |
| 227 | GVS---------------------SDIDAM |
| 228 | SSYQ----------CADNCWGY-PYGIDTW |
| 229 | GS------------------------AIDAW |

Figure 15

Light Chain Variable Region Sequence Alignments

| SEQ ID NO. | CLONE NAME | | CDR1 | CDR2 |
|---|---|---|---|---|
| 230 | 3A12_VL | LEIVMTQSPSSVTASAGERVTINCKSSQSVLSGSNQKTYLNWYQQRPGQSPRLLIYYAST |
| 231 | 1A3_VL  | LDIQMTQSPSSVTASVGEKVTINCKSSQSVVSASNQKSYLNWYQQPPGQSPRLLIYYAST |
| 232 | 3B12_VL | LEIVLTQSPSSVTASVGEKVTINCKSSQSVVSGSNQKSYLNWYQQRPGQSPRLLIYYAST |
| 233 | 3B6_VL  | LDLVLTQIPGSLSVVPGESVSISCKSSQSLLH-TDGKTYAYWLQQKPGQRPQLLISQVSI |
| 234 | 3A4_VL  | LATMLTQSPGSLSVVPGESASISCKASQSLMH-TDGKTYFYWLVQKPGQRPQLLIYQVSN |
| 235 | 3B2_VL  | LATMLTQSPGSLSVVPGESASISCKASQSLIH-TDGKTYLYWLROKFGQRPQLLIYQVSN |
| 236 | 3F9_VL  | LDVVLTQTPGSLSVVPGESASISCKTSQSLVR-SDGMTFLYWLLQKPGQSPQRLIYQVSN |
| 237 | 2A10_VL | LATMLTQSPGSLSVVPGESASISCKASESLVF-SDGKTYLYWLLQKPGQSPQRLIYQVSN |
| 238 | 3E12_VL | LATMLTQSPDSLSVVPGESASISCKASQSLIH-TDEKTYLYWLLQKPGQSPQRLIYQVSM |
| 239 | 3F4_VL  | LATMLTQSPGSLSVVPGQSASISCKASQTLVH-SDGKTYFTWLLQKPGQSPQRLIYQVAN |
| 240 | 3E5_VL  | LATMLTQSPGSLSVVPGESASVSCKATQSLVH-SDGKTYLYWLLQKPGQSPQRLIYQVSN |
| 241 | 2A2_VL  | LDLVLTQIPGSLSVVPGESASISCKASQSLVH-SDGKTYLYWLLQKPGQSPQRLIYQVSN |
| 242 | 3F2_VL  | LDLVLTQIPGSLSVVPGESASISCKGSQSLVH-SDGKTYLYWLLHKPGQSPQRLIYQVSN |
| 243 | 3G10_VL | --HSAVT-QPPSVSGTLGKTVTISCAGTSSDVG---YGNYVSWYQQLPGTAPKLLIYRDTT |
| 244 | 3C7_VL  | --HSAVT-QPPSVSGTLGKTLFISCAGTSSDIG---GYNSVSWYQQLPGTAPKLLIYEVNK |
| 245 | 2E2_VL  | --HSAVT-QPPSVSGTLGKTVTISCAGTSSDIG---GYNYVSWYQQLPGTAPKLLIYKVST |
| 246 | 3H5_VL  | --QSALT-QPPSVSGTLGKTVTISCTGTSSDIG---GYNYVSWYQQLPGTAPKLLIYKVST |
| 247 | 1E6_VL  | -QTVVT-QEPSLSVSPGGTVLTCGLSSGSVS---SSNYPNWYQQTPGQAPRLLIYNTNS |
| 248 | 3C9_VL  | -QAVVT-QEPSLSVSPGGTVTLTCGLRSGSVT---SSNYPDWYQQTPGQAPRLLIYNTNS |

Figure 15 (cont.)

Light Chain Variable Region Sequence Alignments (continued)

```
            CDR2 (continued)                                            CDR3
230  3A12_VL  RELGIPDRFSGSGSTTDFTLTISSVQPEDAAVYYCQQA---YSAPYNFGSGTRLEIK-
231  1A3_VL   QELGIPDRFSGSGSTTDFTLTISSVQPEDAAVYYCQQA---YSAPYNFGSGTRLEIK-
232  3B12_VL  QELGIPDRFSGSGSTTDFTLTISSVQPEDAAVYYCQQA---YSAPYSFGSGTRLEIK-
233  3B6_VL   RSSGVSDRFTGSGSGTDFTLKISGVKAEDAGVYYCAQA---THYPWTFGQGTKLEIK-
234  3A4_VL   RDSGVPDTFTGSGSGTDFTLKISGVKATDAGVYYCAQG---THYPISFGSGTRLEIK-
235  3B2_VL   HESGVPDRFTGSGSGTDFTLKISGVKAEDAGVYYCAQA---TYYPYAFGSGTRLEIK-
236  3F9_VL   RGSGVPDRFTGSGSGTDFFTLKINGVKAEDAGVYYCAQA---TYYPLSFGSGTRLEIK-
237  2A10_VL  RGSGVPDRFTGSGSGTDFTLKISGVKAEDAGVYYCAQG---TYFPLTFGSGTRLEIK-
238  3E12_VL  RGSGVPDKFTGSGSGTDFTLKISGVKAEDAGVYYCAQA---TYYPMTFGQGTKLEIK-
239  3F4_VL   RGSGVSDRFTASGSGTDFTLKISGVKAEDAGVYYCAQA---TYYPVTFGQGTKVELK-
240  3E5_VL   RASGVFDRFTGSGSGTDFFTLKISGVKAEDAGVYYCAQA---TYYPVTFGQGTKVELK-
241  2A2_VL   RGSGVPDRFTGSGSGTDFFTLKISGVKAEDAGVYYCAQV---TYYPVTFGQGTKVELK-
242  3F2_VL   RASGVPDRFTGSGSGTDFFTLKISGVKAEDAGVYYCAQG---TYYPLTFGQGTKLEIK-
243  3G10_VL  RASGIPDRFSGSKSGNTASLTISGLQSGDEADYYCASYRTGG--TTIFGGGTHLTVLG
244  3C7_VL   RASGIPDRFSGSKSGNTASLSISGLQSEDEADYYCASYRSRS--NYVFGGGTHLTVLG
245  2E2_VL   RASGIPDRFSGSKSGNTASLTISGLQSEDEADYYCASYRSGG--NLVFGGGTRLTVLG
246  3H5_VL   RASGIPDRFSGSKSGNTASLTISGLQSEDEADYYCASYRSIN--NAVFGGGTHLTVLG
247  1E6_VL   RHSGVPSRYSGSISGNKAALTITGADPEDEADYYCAL--HKGSYTVVFGGGTKLTVLG
248  3C9_VL   RHSGVFSRFSGSTSGNKAALTITGAQPEDEADYYCALYISSGSYNAVFGGGTHLTVLG
```

Figure 16

Unique Light Chain CDR Sequence Alignments

| SEQ ID NO. | CDR 1 | SEQ ID NO. | CDR2 | SEQ ID NO. | CDR3 |
|---|---|---|---|---|---|
| 249 | KSSQVLSGSNQKTYLN | 268 | YASTREL | 281 | QQA---YSAPYN |
| 250 | KSSQSVVSASNQKSYLN | 269 | YASTQEL | 282 | QQA---YSAPYS |
| 251 | KSSQSVVSGSMQKSYLN | 270 | QVSIRSS | 283 | AQA---THYPWT |
| 252 | KSSQSLIH-TDGKTYAY | 271 | QVSNRDS | 284 | AQG---THYPIS |
| 253 | KASQSIMH-TDGKTYFY | 272 | QVSNHES | 285 | AQA---TYYPYA |
| 254 | KASQSLIH-TDGKTYLY | 273 | QVSNRGS | 286 | AQA---TYYPLS |
| 255 | KTSQSLVP-SDGNTFLY | 274 | QVANRGS | 287 | AQG---TYFPLT |
| 256 | KASESLVF-SDGKTYLY | 275 | QVSNRGS | 288 | AQA---TYYPMT |
| 257 | KASQSLIH-TDEKTYLY | 276 | QVSNRAS | 289 | AQA---TYYPVT |
| 258 | KASQTLVH-SDGKTYFT | 277 | RDTTRAS | 290 | AQV---TYYPVT |
| 259 | KATQSLVH-SDGKTYLY | 278 | EVNKRAS | 291 | AQG---TYYPLT |
| 260 | KASQSLVH-SDGKTYLY | 279 | KVSTRAS | 292 | ASYRTGG---TTI |
| 261 | KGSQSLVH-SDGKTYLY | 280 | NTNSRHS | 293 | ASYRSRS---NYV |
| 262 | AGTSSDVG----YGNYVS | | | 294 | ASYRSGG---NLV |
| 263 | AGTSSDIG----GYNSVS | | | 295 | ASYRSIN---NAV |
| 264 | AGTSSDIG----GYNYVS | | | 296 | AL---HKGSYTVV |
| 265 | TGTSSDIG----GYNYVS | | | 297 | ALYISSGSYNAV |
| 266 | GLSSGSVS----SSNYPN | | | | |
| 267 | GLRSGSVT----SSNYPD | | | | |

Figure 17

Heavy Chain Variable Region Sequence Alignments

| SEQ ID NO. | CLONE NAME | | CDR1 | | CDR2 |
|---|---|---|---|---|---|
| 298 | 3C9_VH | QVQVQESGPGLVKPSQTLSLTCTVSGASIATNYYYWTWIRQPPGKGLEWMGAIAYSG-SF |
| 299 | 3C7_VH | QVQLVESGPGLVKPSQTLSLFCAVSGDSITTTYYAWSWIRQAPGKGLEWMGVIPGAG-NT |
| 300 | 1E6_VH | EVQLQESGPGLVKPSQTLSLTCTVSGDSITTTYSAWSMIRQPPGKALEWMGVISNYG-DT |
| 301 | 3G10_VH | QVQVQESGPGLVKPSQTLSLTCTASGGSITTSYSGWGWIRQPPGKGLDWMGVIGYDG-RT |
| 302 | 3F9_VH | QLQLVESGPGLVKPSQTLSLTCIVTGGSITTSGYAWSMIRQPPGKGLEWMGVIGYDG-TN |
| 303 | 3H5_VH | QVQLVESGPGLVKPSQTLSLTCTVFGGSITTNYYAMNWIRQTPGKGLEWMGVIAYDG-AT |
| 304 | 3A4_VH | EVQIVQPGAELRNPGASVKVSCKASGYTF--TKFYIEWNVRQAPGQGLEWMGNILPEDGT |
| 305 | 3R2_VH | ELQLVESGGGLVQPGGSLRLSCAASGFTF---DDYAMTWVRQVPGKGLEWVSTISWKDDTT |
| 306 | 1A3_VH | QVQLVESGGGLVQPGGSLRLSCAASGFTF---SINGMSWVRQAPGKEVEWVSSINSGGEIT |
| 307 | 3A12_VH | ELQLVESGGGLVQPGGSLRLSCAASGFSF---SINGMSWVRQAPGKEVEWVSSINSGGEIT |
| 308 | 3B6_VH | QLQLVESGGGLVQPGGSLPLSCAASGFTF---GAYTMAWLRQAPGKGPEWVSGVNSGGDIT |
| 309 | 2E2_VH | QLQLVESGGGLVQPGGSLRLSCAASGFTF---SSYWMYWVRQAPGKGLEWVSTFGSGS-NT |
| 310 | 3F2_VH | QLQLVESGGGLVQPGGSLRLSCAASGFTF---SSYTMSWVRQAPGKGLEWVSTINSGGV-T |
| 311 | 3B12_VH | QVQVQESGGGLVQPGGSLRLSCAASGFTF---GNYAMSWVRQAPGKGPEWVSGINSGGSSA |
| 312 | 2A10_VH | ------EVQLVESGGGLVQPGGSLRLSCAASGFTF---SSSSMHNVRQAPGKGLEWVSSINSGGDTT |
| 313 | 2A2_VH | QLQLVESGGGLVQPGGSLRLSCAASGFTF---SNYAMTWVRQAPGKGLEWVSAVVNSGGST |
| 314 | 3E5_VH | QVQVQESGGGLVQPGGSLRVSCAASGFTF---SSYYMNWVRQAPGKGLEWVSQINTGGDST |
| 315 | 3F4_VH | QVQLQESGGGLVQPGGSLRLSCAASGFTF---SDYYMNWVRQAPGKGLEWVSQINTGGDRT |
| 316 | 3E12_VH | EVQVQESGGGLVQPGGSLRLSCAASGFTF---GSYAMYWVRQAPGKGPEWVSTINSGGDST |

Figure 17 (cont.)

Heavy Chain Variable Region Sequence Alignments (continued)

```
            CDR2 (continued)                                           CDR3
3C9_VH   298  YYSPSLKSRTSMSWDTSKNHITLRLSSVAPEDTAVYYCARNRGAYYSTGYPGGYEYWGQG
3C7_VH   299  YYSPALKSRATISRDSSKNQFSLHLNSVTPEDTAVYYCAPASTWL-TYGLASGYDYWGQG
1E6_VH   300  YYTPSLKSRTSISRDTSKNQFSLQLNSVTPEDTAVYYCVR-VLYGSKWPIGPNFGSWGQG
3G10_VH  301  YYNPSLKSRTSISRDTSKNQFSLQLSSVTPEDTAVYYCARARPDGSRWYTVGEYDYWGQG
3F9_VH   302  YYSPSLKSRTSISRDFSKNQFSLQLSSVTPEDTAVYYCAR--------------VGWGSWGQG
3H5_VH   303  YFNPSLKSRTSISRDTSKNQFSLQLRSVTPEDTAVYYCALRTRYTGSYQSTPDFGSWGQG
3A4_VH   304  YYAQKFQGRLFTTDTTTSTAYLELTDLRSEDTAVYYCAA----------------TFGSWGQG
3B2_VH   305  DYAESMKGRFTISRDNAKMTLYLQMDSLKPEDTAVYYCAQDP-------------VNFGSWGQG
1A3_VH   306  NYRDSVKGRFTISRDNVKNTLYLQMNSLKPEDTAFYHCVTG-------------IVAYDYWGQG
3A12_VH  307  NYRDSVKGRFTISRDNVKNTLYLQMNSLKPEDTAFYHCVTG-------------IVAYDYWGQG
3B6_VH   308  SYADSVKGRFTISRDNAKNMVYLQMNSLKPEDTAVYYCAADPG-----------MGGQG
2E2_VH   309  WYADSVKGRFTISRDNAKNTLSLQMTSLKSEDTAVYYCAKDPTNGL---GSFTFGSWGQG
3F2_VH   310  NYADSVKGRFTFSRDNAKNTLTLQMNSLKPEDTAVYYCVS--------------SAYSDWGQG
3B12_VH  311  YYEDSVKGRFTISRDNAKDTLYLQMNSLKPEDTAVYYCAISW------------ATYQYWGQG
2A10_VH  312  NYADSVKGRFTISRDNAKNTLYLQMNSLKPEDTAVYYCSA--------------TSYIYWGQG
2A2_VH   313  TYADSVKGRFTISRDNAKNTLYLQMNSLKPEDTAVYYCTY--------------PSLGSWGQG
3F5_VH   314  YYADSVKGRFTISRDNAKNTLYLQMNSLKPDDTALYYCAM--------------GNLGYWGQG
3F4_VH   315  YYTDSVKGRFTISRDNAKNALYLQMNSLKPEDTALYFCVT--------------SSLSSWGQG
3E12_VH  316  NYADSLKGRFTISRDNAKNMLYLQMNSLKPEDTAVYFCVT--------------PGFGSWGQG
```

Figure 17 (cont.)

Heavy Chain Variable Region Sequence Alignments (continued)

| | | |
|---|---|---|
| 298 | 3C9_VH | TQVTVSS |
| 299 | 3C7_VH | TQVTVSS |
| 300 | 1E6_VH | TQVTVSS |
| 301 | 3G10_VH | TQVTVSS |
| 302 | 3F9_VH | TQVTVSS |
| 303 | 3H5_VH | TQVTVSS |
| 304 | 3A4_VH | TQVIVSS |
| 305 | 3B2_VH | TQVTVSS |
| 306 | 1A3_VH | TQVTVSS |
| 307 | 3A12_VH | TQVTVSS |
| 308 | 3B6_VH | TQVTVSS |
| 309 | 2E2_VH | TQVTVSS |
| 310 | 3F2_VH | TQVLVSS |
| 311 | 3B12_VH | TQVTVSS |
| 312 | 2A10_VH | TQVTVSS |
| 313 | 2A2_VH | TQVTVSS |
| 314 | 3E5_VH | TQVSVSS |
| 315 | 3F4_VH | TQVTVSS |
| 316 | 3E12_VH | TQVTVSS |

Figure 18

Unique Heavy Chain CDR Sequence Alignments

| SEQ ID NO. | CDR1 | SEQ ID NO. | CDR2 |
|---|---|---|---|
| 317 | TNYYYWT | 335 | AIAYSG-SFYYSPSLKS |
| 318 | TTYYAWS | 336 | VIPGAG-NTYYSPALKS |
| 319 | TTYSAWS | 337 | VISNYG-DTYTPSLKS |
| 320 | TSYSGWG | 338 | VIGYDG-RTYNPSLKS |
| 321 | TSGYAWS | 339 | VIGYDG-TNYYSPSLKS |
| 322 | TNYYAWN | 340 | VIAYDG-ATYFNPSLKS |
| 323 | KFYIE | 341 | NILPEDGGTYYAQKFQG |
| 324 | DYAMT | 342 | TISWKDDTDIAESMKG |
| 325 | INGMS | 343 | SINSGGEITNYRDSVKG |
| 326 | AYTMA | 344 | GVNSGGDITSYADSVKG |
| 327 | SYWMY | 345 | TFGSGS-NTWYADSVKG |
| 328 | SYTMS | 346 | TINSGGV-TNYADSVKG |
| 329 | NYAMS | 347 | GINSGGSSAYYEDSVKG |
| 330 | SSSMH | 348 | SINSGGDTTNYADSVKG |
| 331 | NYAMT | 349 | VVNSGGGSTTYADSVKG |
| 332 | SYYMN | 350 | QINTGGDSTYYADSVKG |
| 333 | DYIMN | 351 | QINTGGDRTYYTDSVKG |
| 334 | SYAMY | 352 | TINSGGDSTNYADSLKG |

Figure 18 (cont.)

| SEQ ID NO. | CDR3 |
|---|---|
| 353 | NRGAYYSTGYPGGYEY |
| 354 | ASTWL-TYGLASGVDY |
| 355 | -VLYGSKWPIGPNFGS |
| 356 | ARPDGSRWYTVGEVDY |
| 357 | ------------VGMGS |
| 358 | RTRYTGSYQSTPDFGS |
| 359 | -------------TFGS |
| 360 | DP----------VNFGS |
| 361 | G-----------IVAYDY |
| 362 | DPG--------------M |
| 363 | DPTNGL-----GSFTFGS |
| 364 | -----------SAYSD |
| 365 | SW-----------ATYQY |
| 366 | -------------TSYIY |
| 367 | -------------PSLGS |
| 368 | -------------GNLGY |
| 369 | -------------SSLSS |
| 370 | -------------PGFGS |

Figure 19

Light Chain Variable Region Sequence Alignments

| SEQ ID NO. | CLONE NAME | CDR1 | CDR2 |
|---|---|---|---|
| 371 | 19724p3_E12 | AVTQPASVSVSNPGETVEITCSGGG----YYGWYQQKSPGSAPVTVIY | WNDKRPSDIPS |
| 372 | 19724p3_G3  | AVTQPASVSVNPGETVEITCSGGG-----YYGWYQQKSPGSAPVTVIY | WNDKRPSDIPS |
| 373 | 19724p3_D3  | VLTQPASVSANLGGTVEITCSGGS-----NNYGWYQQKSPGSAPVTVIY | SNNQRPSNIPS |
| 374 | 19724p3_G6  | VLTQPASVSANLGGTVEITCSGGS-----MNYGWYQQKSPGSAPVTVIY | SNNQRPSNIPS |
| 375 | 19724p3_F95'| ALTQPSSVSVSANLGGTVKITCSGGYSDAGSYYYGWYQQKSPGSAPVTVIY | SNDKRPSDIPS |
| 376 | 19724p3_F10 | ALTQPASVSANLGGTVEITCSGGYSGY-DYGYGWYQQKSPGSAPVTVIY | SNDKRPSDIPS |
| 377 | 19724p3_G8  | ALTQPASVSANLGGTVEITCSGGYSGY-DYGYGWYQQKSPGSAPVTVIY | SNDKRPSDIPS |
| 378 | 19724p3_A12 | AVTQPASVSANPGETVKITCSGGS-----YEYGWFQQKSPGSALVTVIY | DNTNRPSDIPS |
| 379 | 19724p3_E10 | ALTQPASVSANLGGTVEITCSGGS-----YSYGWFQQKAPGSAPVTVIY | DDTNRPSGIPS |
| 380 | 19724p3_F7  | ALTQPASVSANLGGTVEITCSGGS-----YSYGWFQQKAPGSAPVTVIY | DDTNRPSGIPS |

| SEQ ID NO. | CLONE NAME | CD3 |
|---|---|---|
| 371 | 19724p3_E12 | RFSGSKSGSTATLTITGVRAEDEAVYYCGGYDGSGTDAVFGAGTTLTVL |
| 372 | 19724p3_G3  | RFSGSKSGSTATLTITGVRAEDEAVYYCGDYDGSGTDAVFGAGTTLTVL |
| 373 | 19724p3_D3  | RFSGSKSGSTGLFITGVQAEDDEAVYFCGSYDST-DRDMFGAGTTLTVL |
| 374 | 19724p3_G6  | RFSGSKSGSTGTLFITGVQVEDEAVYFCGSYDST-DRDMFGAGTTLTVL |
| 375 | 19724p3_F95'| RFSGALSGSTATLFITGVQADDEAVYFCGSRDSN-TEAIFGAGTTLTVL |
| 376 | 19724p3_F10 | RFSGSKSGSTGTLFITGVQAEDEAVYFCGSTDSS-YVGIFGAGTTLTVL |
| 377 | 19724p3_G8  | RFSGSKSGSTGTLFITGVQAEDEAVYFCGSTDSS-YVGIFGAGTTLTVL |
| 378 | 19724p3_A12 | RFSGSSSGSANTLTITGVQAEDEAVYYCGSADSS-GWGIFGAGTTLTVL |
| 379 | 19724p3_E10 | RFSGSTSGSTSTLFTTAVQAEDEAVYYCGSWDNSIYAGIFGAGTTLTVL |
| 380 | 19724p3_F7  | RFSGSTSGSTSTLFTTAVQAEDEAVYYCGSWDNSIYAGIFGAGTTLTVL |

Figure 20

Unique Light Chain CDR Sequence Alignments

| SEQ ID NO. | CDR 1 | SEQ ID NO. | CDR2 | SEQ ID NO. | CDR3 |
|---|---|---|---|---|---|
| 381 | SGGG-----YYG | 387 | WNDKRPS | 392 | GGYDGSGTD |
| 382 | SGGS-----NNYG | 388 | SNNQRPS | 393 | GDYDGSGTD |
| 383 | SGGYSDAGSYYYG | 389 | SNDKRPS | 394 | GSYDST-DR |
| 384 | SGGYSGY-DYGYG | 390 | DNTNRPS | 395 | GSRDSN-TE |
| 385 | SGGS-----YEYG | 391 | DDTNRPS | 396 | GSTDSS-YY |
| 386 | SGGS-----YSYG | | | 397 | GSADSS-GN |
| | | | | 398 | GSWDNSTYA |

Figure 21

Heavy Chain Variable Region Sequence Alignments

| SEQ ID NO. | CLONE NAME | CDR1 | CDR2 |
|---|---|---|---|
| 399 | 19724p3_E10_2 | MAAVTLDESGGGLQTPGGGLSLVCKASGFTFSDHGMFWVRQAPGKGLEFVTGISKDGG-A |
| 400 | 19724p3_F7 | MAAVTLDESGGGLQTPGGGLSLVCKASGFTFSDHGMFWVRQAPGKGLEFVTGISKDGG-A |
| 401 | 19724p3_A12 | MAAVTLDESGGGLQTPGGALSLVCKASGFTFSSNMGWVRQAPGKGLEWVAEITSTGR-T |
| 402 | 19724p3_F95' | MAAVTLDESGGGLQTPGGALSLVCKASGFTFSSYDMGWVRQAPGKGLEYVAGITSAGG-G |
| 403 | 19724p3_D3 | MAAVTLDESGGGLQTPGGALSLVCKASGFDFSSYQMNWIRQAPGKGLEFVAAINRFGN-S |
| 404 | 19724p3_G6 | MAAVTLDESGGGLQTPGGALSLVCKASGFDFSSYQMNWIRQAPGKGLEFVAAINRFGN-S |
| 405 | 19724p3_G3 | MAAVTLDESGGGLQTPGGALSLVCKASGFTFSDYAMGWVRQAPGKGLEYVASINRFGN-S |
| 406 | 19724p3_E12 | MAAVTLDESGGGLQTPGGALSLVCKGSGFTFSSFNMIWVRQAPGKGLEYVASIYSGGGGY |
| 407 | 19724p3_F10 | MAAVTLDESGGGLQTPGGALSLVCKASGFDFSSYAMFWVRQAPGKGLEYVASIDDAGG-- |
| 408 | 19724p3_G8 | MAAVTLDESGGGLQTPGGALSLVCKASGFDFSSYAMFWVRQAPGKGLEYVASIDDAGG-- |

CDR2 (continued)

| SEQ ID NO. | CLONE NAME | CDR2 | CDR3 |
|---|---|---|---|
| 399 | 19724p3_E10_2 | TWYATAVDGRATISRDNGQSTLRLQLNNLRAEDTATYFCAKPSNVGACTFSYPSCPY---- |
| 400 | 19724p3_F7 | TWYATAVDGRATISKDNGQSALRLQLNNLRAEDTATYFCAKPSNVGACTFSYPSCPY---- |
| 401 | 19724p3_A12 | TDYGSSAVKGRATISRDNGQSTLRLQLNNLRAEDTGTYYCIRYIDDGS------G------ |
| 402 | 19724p3_F95' | TEYGAAVDGRATISRDNGQSTVRLQLNNLGAEDTGTYYCAKYVGSGGCGRG-S-------- |
| 403 | 19724p3_D3 | TGQGEAVKGRVTISRDDGQSTVRLQLSNLRAEDTATYYCAKGAYGYC-GSG-GWC------ |
| 404 | 19724p3_G6 | TGQGEAVKGRVTISRDDGQSTVRLQLSNLRAEDTATYYCAKGAYGYC-GSG-GWC------ |
| 405 | 19724p3_G3 | TGYAAAVKGRATISRDSGQSTVRLQLNNLRAEDTGIYYCTKSAYSGY-N----------- |
| 406 | 19724p3_E12 | TNYGAAVKGRATISRDNGQSTVRLQLNNLRAEDTATYYCAKDAGSDCWHTD-GWSTYNCG |
| 407 | 19724p3_F10 | TEYGAAVKGRATISRDNGQSTVRLQLNNLRAEDTGTYYCAKDARSRS---R-SWC----- |
| 408 | 19724p3_G8 | TEYGAAVKGRATISRDNGQSTVRLQLNNLRAEDTGTYYCAKDARSRS---R-SWC----- |

Figure 21 (cont.)

Heavy Chain Variable Region Sequence Alignments (continued)

```
                         CDR3 (continued)
399  19724p3_E10_2       TAGSIDAWGHGTEVIVSS
400  19724p3_F7          TAGSIDAWGHGTEVIVSS
401  19724p3_A12         CCGSIDVWGHGTEVIVSS
402  19724p3_F95'        CGDSIDAWGHGTEVIVSS
403  19724p3_D3          GVGNIDAWGHGTEVIVSS
404  19724p3_G6          GVGNIDAWGHGTEVIVSS
405  19724p3_G3          -SGILDAWGHGTEVIVSS
406  19724p3_E12         DSGRIDAWGHGTEVIVSS
407  19724p3_F10         AAGCIDTWGHGTEVIVSS
408  19724p3_G8          AAGCIDTWGHGTEVIVSS
```

Figure 22

Unique Heavy Chain CDR Sequence Alignments

| SEQ ID NO. | CDR1 | SEQ ID NO. | CDR2 |
|---|---|---|---|
| 409 | SDHGM | 416 | GISKLGG-ATWYATAVD |
| 410 | SSSNM | 417 | EITSTGR-TTDYGSAVK |
| 411 | SSYDM | 418 | GITSAGG-GTEYGAAVD |
| 412 | SSYQM | 419 | AINRFGN-STGQGRAVK |
| 413 | SDYAM | 420 | SINRFGN-STGYAAAVK |
| 414 | SSFNM | 421 | SIYSGGGGYTNYGAAVK |
| 415 | SSYAM | 422 | SIDDAGG--TEYGAAVK |

| SEQ ID NO. | CDR3 |
|---|---|
| 423 | FSNVGACTFSYPSCPY---TAGSIDAW |
| 424 | YIDDGS----G-------CCGSIDVW |
| 425 | YVGSGGCGRG-S------CGDSIDAW |
| 426 | GAYGYC-GSG-GWC----GVGNIDAW |
| 427 | SAYSGY-N---------SGILDAW |
| 428 | DAGSDCWHTD-GWSTYNCGDSGRIDAW |
| 429 | DARSRS---R-SWC-----AAGCIDTW |

ANTI-KV1.3 ANTIBODIES, AND METHODS OF PRODUCTION AND USE THEREOF

INCORPORATION BY REFERENCE

This application is a national stage filing under 35 U.S.C. § 371 of international application number PCT/US2017/030612, filed May 2, 2017, and claims the benefit of priority to U.S. Application Ser. No. 62/330,420, filed May 2, 2016 and U.S. Application Ser. No. 62/416,447, filed Nov. 2, 2016, the contents of each of which are hereby incorporated by references in their entireties.

FIELD OF THE INVENTION

The present disclosure relates generally to antibodies, their production and use. Specifically, the present disclosure pertains to antibodies which specifically bind to the human Kv1.3 protein, modulate the activity of the human Kv1.3 protein, methods of producing such antibodies, and diagnostic, therapeutic and clinical methods of using such antibodies.

BACKGROUND

The Kv1.3 protein is a voltage-gated ion channel that conducts the transfer of potassium ions through biological membranes and regulates the membrane potential of both excitable and non-excitable cell types. In particular, Kv1.3 plays a well-characterized role in regulating $Ca^{2+}$ signaling in activated T-effector-memory ($T_{EM}$) and other T-cell subsets (Wulff et al. (2003), Clin. Invest. 111:1703-1713; Beeton et al. (2006), PNAS. 103: 17414-19). Up-regulation of Kv1.3 in $T_{EM}$ cells is associated with sites of inflammation in autoimmune disease (Rus et al. (2005), PNAS102:11094-99); Beeton 2006) and studies have shown that specific Kv1.3 blockers are effective in a number of animal models of inflammation (Beeton et al. (2001), J. Immunol. 166:936-44); Beeton et al. 2006; Koo et al. (1997), J. Immunol. 158, 5210-28; Matheu et al. (2008), Immunity, 29, 602-14; Azam et al. (2007), J. Invest. Deratol. 127, 1419-29; Cheong et al. (2011), Cardiovasc. Res. 89, 282-89; Hyodo et al. (2010), Am. J. Physiol. 299, 1258-69; Gilhar et al. (2011), J. Invest. Dermatol. 131, 118-24). In mice, blocking Kv1.3 activity may alter the phenotype of T-cells in response to antigen and convert them to a suppressive state (Gocke et al (2012), J. Immunol. 188, 5877-5886; Grishkan et al (2015), J. Immunol. 195, 1399-1407; Hu et al (2011), J. Biol. Chem. 287, 1261-1268).

Peptide toxins and their derivatives are being developed as therapeutic agents that inhibit Kv1.3 function for the treatment of autoimmune disease. For example, the peptide toxin ShK derived from the sea anemone *Stichodactyla helianthus* binds to the outer vestibule of the Kv1.3 tetramer with high affinity and occludes ion conductance through the pore (Beeton et al. (2003), J. Biol. Chem., 278, 9928-37)).

Therapeutic antibodies that modulate the function of Kv1.3 represent an alternative class of biologics that could be developed to treat a variety of $T_{EM}$-mediated auto immune disease. A number of anti-Kv1.3 antibodies that recognize both intracellular epitopes and extracellular epitopes are commercially available (e.g., Alomone Labs, Jerusalem, Israel: Anti-Kv1.3 (Extracellular), Cat# APC101; Anti-Kv1.3 (Intracellular), Cat# APC002), but are not functionally active and do not modulate Kv1.3 activity. However, rabbits immunized with a peptide consisting of 14 amino acids located at the external end of the human Kv1.3 pore region produced polyclonal antibodies capable of functionally inhibiting Kv1.3 activity (Yang et al. (2012), PLoS One 7, e36379), indicating that functional anti-Kv1.3 immunoglobulins are viable.

Nevertheless, there remains a need for the identification and development of high-affinity monoclonal antibodies (mAbs) that recognize Kv1.3 and, in particular, the extracellular loop regions that are expected to be critical in exerting a modulating effect on Kv1.3 activity.

SUMMARY

The present invention depends, in part, upon the development of improved immunogenic preparations of human Kv1.3 protein, which have permitted the production of anti-Kv1.3 monoclonal antibodies which are directed to the extracellular domains of the tetrameric Kv1.3 ion channel and which have superior affinity and specificity for Kv1.3. These antibodies have both therapeutic and diagnostic utility.

Thus, in one aspect, the invention provides anti-Kv1.3 monoclonal antibodies (mAbs), particularly mAbs that modulate Kv1.3 functional activity. In particular, the invention provides the amino acid sequences of the CDRs of the light chains and the heavy chains, as well as consensus sequences for these CDRs, and enables the production of a variety of antibodies and other immunoglobulin-based molecules comprising these CDRs. Additionally, the invention provides predicted canonical structures for the CDRs in the light and heavy chain variable domains, and thereby enables the production of additional antibodies and other immunoglobulin-based molecules which specifically bind to Kv1.3

In another aspect, the invention provides nucleic acid molecules encoding the anti-Kv1.3 mAbs and other immunoglobulin-based molecules, expression vectors comprising such nucleic acids, host cells comprising such nucleic acids or vectors, methods for making the anti-Kv1.3 mAbs and other immunoglobulin-based molecules, and methods for expressing the anti-Kv1.3 mAbs and other immunoglobulin-based molecules. Finally, methods of using the anti-Kv1.3 mAbs and other immunoglobulin-based molecules as therapeutic drugs or diagnostic reagents are provided.

In another aspect, the invention provides an antibody that specifically binds to a human Kv1.3 protein comprising: an immunoglobulin heavy chain and an immunoglobulin light chain, wherein the variable region of said light chain comprises: (i) a CDR1 region comprising an amino acid sequence selected from the group consisting of SEQ ID NOs: 43-69; 249-267; 381-386; (ii) a CDR2 region comprising an amino acid sequence selected from the group consisting of SEQ ID NOs: 70-88; 268-280; 387-391; and/or (iii) a CDR3 region comprising an amino acid sequence selected from the group consisting of SEQ ID NOs: 89-112; 281-297; 392-398.

In another aspect, the invention provides an antibody that specifically binds to a human Kv1.3 protein comprising: an immunoglobulin heavy chain and an immunoglobulin light chain, wherein the variable region of said heavy chain comprises: (i) a CDR1 region comprising an amino acid sequence selected from the group consisting of SEQ ID NOs: 165-177; 317-334; 409-415; (ii) a CDR2 region comprising an amino acid sequence selected from the group consisting of SEQ ID NOs: 178-202; 335-352; 416-422; and/or (iii) a CDR3 region comprising an amino acid sequence selected from the group consisting of SEQ ID NOs: 203-229; 353-370; 423-429.

In another aspect, the invention provides an antibody that specifically binds to a human Kv1.3 protein comprising: an immunoglobulin heavy chain and an immunoglobulin light chain, wherein the variable region of said light chain comprises: (i) a CDR1 region comprising an amino acid sequence selected from the group consisting of VL CDR1 Motifs 1-6; (ii) a CDR2 region comprising an amino acid sequence selected from the group consisting of VL CDR2 Motifs 1-6; and/or (iii) a CDR3 region comprising an amino acid sequence selected from the group consisting of VL CDR3 Motifs 1-6.

In another aspect, the invention provides an antibody that specifically binds to a human Kv1.3 protein comprising: an immunoglobulin heavy chain and an immunoglobulin light chain, wherein the variable region of said heavy chain comprises: (i) a CDR1 region comprising an amino acid sequence selected from the group consisting of VH CDR1 Motifs 1-6; (ii) a CDR2 region comprising an amino acid sequence selected from the group consisting of VH CDR2 Motifs 1-6; and/or (iii) a CDR3 region comprising an amino acid sequence selected from the group consisting of VH CDR3 Motif 1-6.

In some embodiments, the invention provides an antibody preparation comprising an antibody as described herein. In some embodiments, the invention provides an antibody preparation wherein said preparation is a monoclonal antibody preparation. In some embodiments, the invention provides an antibody preparation wherein said preparation is a mixture of at least two monoclonal antibody preparations.

In another aspect, the invention provides an isolated nucleic acid molecule encoding a heavy chain or light chain of any one of the antibodies as described herein. In some embodiments, the invention provides an isolated nucleic acid molecule wherein said nucleic acid molecule is selected from the group consisting of a cloning vector, an expression vector, a heterologous recombination vector and a viral integration vector. In some embodiments, the invention provides a cell transformed with the nucleic acid. In some embodiments, said cell is a mammalian cell. In some embodiments, said cell is a rodent cell. In some embodiments, said cell is a Chinese Hamster Ovary (CHO) cell. In some embodiments, said cell is a human cell.

In another aspect, the invention provides a method of isolating a cell expressing a Kv1.3 protein comprising: (a) obtaining a population of cells; (b) contacting the population of cells with a multiplicity of antibodies as described herein; and (c) separating cells in the population that specifically bind the antibodies from cells in the population that do not specifically bind the antibodies. In some embodiments, the cells are separated by fluorescence activated cell sorting. In some embodiments, the cells are separated using an immobilized secondary antibody by fluorescence activated cell sorting.

In another aspect, the invention provides a method for preventing or treating an autoimmune disorder in humans a subject comprising administering to the subject a therapeutically effective amount of the antibody preparation described herein. In some embodiments, the antibody preparation inhibits Kv1.3 potassium channels, thereby preventing or treating the autoimmune disorder. In some embodiments, autoreactive effector memory T cells of the subject are depleted, thereby preventing or treating the autoimmune disorder. In some embodiments, the autoimmune disorder is selected from the group of: Multiple sclerosis; Myasthenia gravis; Autoimmune neuropathies; Guillain-Barre Syndrome; Autoimmune uveitis; Crohn's Disease; Ulcerative colitis; Primary biliary cirrhosis; Autoimmune hepatitis; Autoimmune thrombocytopenia; Type-1 diabetes mellitus; Addison's Disease; Grave's Disease; Hashimoto's thyroiditis; Autoimmune orchitis; Behcet's Disease; Rheumatoid arthritis; Bone resorption associated with periodontal disease; Systemic lupus erythematosus; Scleroderma Polymyositis, dermatomyositisis; Pemphigus vulgaris; Spondyloarthropathies; Ankylosing spondylitis; and Sjogren's syndrome.

In another aspect, the invention provides a method for preventing or treating graft versus vs host disease in a subject said method comprising administering to the subject a therapeutically effective amount of an antibody preparation described herein. In some embodiments, the antibody preparation inhibits Kv1.3 potassium channels, thereby preventing or treating graft versus host disease. In some embodiments, autoreactive effector memory T cells of the subject are depleted, thereby preventing or treating graft versus host disease.

These and other aspects and embodiments of the invention are illustrated and described below. Other compositions, methods and features will become apparent to one with skill in the art upon examination of the following drawings and detailed description. It is intended that all such additional compositions and methods and features are within the scope of the present invention.

BRIEF DESCRIPTION OF THE FIGURES

The following drawings are illustrative of embodiments of the invention and are not meant to limit the scope of the invention as encompassed by the claims.

FIG. 1A provides the amino acid sequence of the human Kv1.3 protein (ACCESSION NO: P22001.3) (SEQ ID NO: 1). FIG. 1B shows the Kv1.3 amino acid sequence modified with C-terminal FLAG (bold italics) and 10×His (underlined) tags (SEQ ID NO: 2).

FIG. 5A illustrates a Kv1.3 proteoliposome (the blocks represent Kv1.3 protein in a phospholipid bilayer). FIG. 5B shows Kv1.3 magnetic beads labeled with a commercial anti-Kv1.3 antibody.

FIG. 7A shows functional inhibition of Kv1.3 activity by antibodies (p1A1, p1A11, p1F8, p1D8, p1H4, p2A3, p2G9, p1H7 and p1E6) derived from chicken (ch_) FIG. 7B shows functional inhibition of Kv1.3 activity by an antibody (1A3) derived from Llama (L) FIG. 7C shows an example of a specific anti-Kv1.3 antibody derived from chicken (p2D9), which does not functionally inhibit Kv1.3 activity. Activity of Kv1.3 was determined by whole-cell patch clamp electrophysiology in L929 human fibroblast cells transiently expressing human Kv1.3. The top lines show control electrophysiology recordings of cells in the absence of antibody. The bottom lines show electrophysiology recordings of cells incubated with 400 nM antibody.

FIGS. 11A-11B show an alignment of light chain variable regions of anti-Kv1.3 antibodies produced in chickens according to the invention (SEQ ID NOs: 3-42). Approximate locations of CDR1, 2 and 3 are highlighted by bold, underlined text.

FIG. 12 shows alignments of unique light chain CDR sequences produced in chickens according to the invention (SEQ ID NOs: 43-112).

FIGS. 13A-13C show an alignment of heavy chain variable regions of anti-Kv1.3 antibodies produced in chickens according to the invention (SEQ ID NOs: 125-164). Approximate locations of CDR1, 2 and 3 are highlighted by bold, underlined text.

FIG. 14 shows alignments of unique heavy chain CDR sequences produced in chickens according to the invention (SEQ ID NOs: 165-229).

FIG. 15 shows an alignment of light chain variable regions of anti-Kv1.3 antibodies produced in llamas according to the invention (SEQ ID NOs: 230-248). Approximate locations of CDR1, 2 and 3 are highlighted by bold, underlined text.

FIG. 16 shows an alignment of unique llama light chain CDR sequences produced in llamas according to the invention (SEQ ID NOs: 249-297).

FIG. 17 shows an alignment of heavy chain variable regions of anti-Kv1.3 antibodies produced in llamas according to the invention (SEQ ID NOs: 298-316). Approximate locations of CDR1, 2 and 3 are highlighted by bold, underlined text.

FIG. 18 shows alignments of unique llama heavy chain CDR sequences produced in llamas according to the invention (SEQ ID NOs: 317-370).

FIG. 19 shows an alignment of light chain variable regions of anti-Kv1.3 antibodies produced in chickens according to the invention (SEQ ID NOs: 371-380) and distinct from those shown in FIGS. 11A-11B. Approximate locations of CDR1, 2 and 3 are highlighted by bold, underlined text.

FIG. 20 shows an alignment of unique light chain CDR sequences as shown in FIG. 19 and as produced according to the invention (SEQ ID NOs: 381-398).

FIG. 21 shows an alignment of heavy chain variable regions of anti-Kv1.3 antibodies produced in chickens according to the invention (SEQ ID NOs: 399-408) and distinct from those shown in FIGS. 13A-13C. Approximate locations of CDR1, 2 and 3 are highlighted by bold, underlined text.

FIG. 22 shows an alignment of unique heavy chain CDR sequences as shown in FIG. 21 and as produced according to the invention (SEQ ID NOs: 409-429).

DETAILED DESCRIPTION

Figure 2:
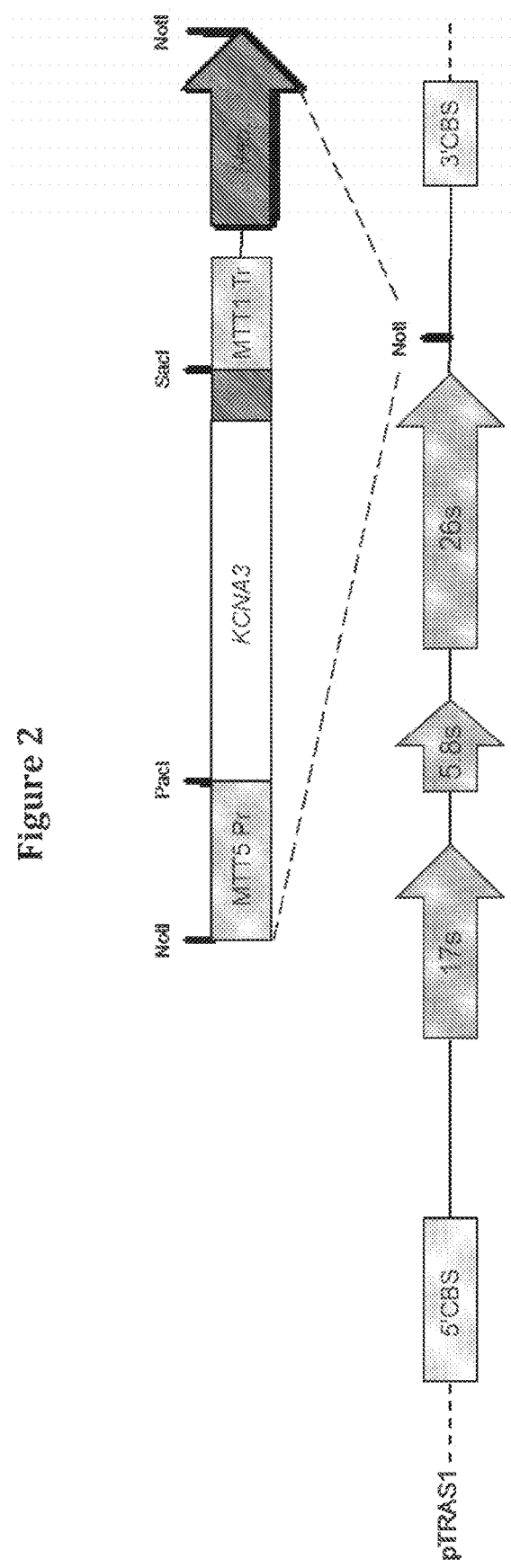
FIG. 2 shows an expression construct design placing a human Kv1.3 encoding gene (KCNA3) under control of the *Tetrahymena* MTT5 promoter and placement of the entire expression construct in the NotI restriction site of the *Tetrahymena* ribosomal DNA vector, pTRAS1.

The present disclosure relates to isolated antibodies (Abs), particularly Abs that bind specifically to human Kv1.3 with high affinity and Abs that modulate Kv1.3 functional activity. In certain embodiments, the anti-Kv1.3 Abs are derived from particular heavy and light chain sequences and/or comprise particular structural features, such as CDR regions, comprising particular amino acid sequences. This disclosure provides isolated anti-Kv1.3 Abs, methods of making such anti-Kv1.3 Abs, immunoconjugates and bispecific molecules comprising such anti-Kv1.3 Abs, and methods of expressing such anti-Kv1.3 Abs. This disclosure also relates to methods of using the anti-Kv1.3 Abs as therapeutic treatment for auto-immune diseases or as diagnostic reagents.

Definitions

All scientific and technical terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

The term "antibody" or abbreviation "Ab," as used herein, includes whole antibodies and any antigen binding fragment (i.e., "antigen-binding portion") or single chains thereof, with or without native glycosylation. A complete "antibody" refers to a glycoprotein comprising at least two heavy (H) chains and two light (L) chains inter-connected by disulfide bonds or an antigen binding portion thereof. Each heavy chain includes a heavy chain variable region ($V_H$) and a heavy chain constant region. The heavy chain constant region is comprised of three domains, $C_{H1}$, $C_{H2}$, and $C_{H3}$. Each light chain includes a light chain variable region ($V_L$) and a light chain constant region with one domain, $C_L$. The $V_H$ and $V_L$ regions can be further subdivided into complementarity determining regions (CDR) and framework regions (FR). The $V_H$ and $V_L$ regions each include three CDRs, designated CDR1, CDR2 and CDR3, that interact with an antigen (e.g., Kv1.3).

The term "antigen-binding portion" of an antibody, as used herein, refers to one or more fragments of an antibody that retain the ability to specifically bind to an antigen (e.g., Kv1.3). Examples of binding fragments encompassed within the term "antigen-binding portion" of an antibody include a Fab fragment, F(ab')$_2$ fragment, Fab' fragment, Fd fragment, Fv fragment, scFv fragment, dAb fragment, and an isolated CDR.

The term "monoclonal antibody" or "monoclonal antibody preparation," as used herein, refers to a preparation of antibody molecules consisting essentially of antibodies having a single heavy chain amino acid sequence and a single light chain amino acid sequence (but which may have heterogeneous glycosylation).

The term "humanized antibody," as used herein, includes antibodies having constant region and variable region framework regions (FRs) but not CDRs derived from human germline immunoglobulin sequences.

The term "recombinant antibody," as used herein, includes all antibodies prepared, expressed, created, or isolated by recombinant means. In certain embodiments, recombinant antibodies are isolated from a host cell transformed to express the antibody (e.g., from a transfectoma). In other embodiments, recombinant antibodies are isolated from a recombinant, combinatorial antibody library, such as a phage display library. Recombinant antibodies may also be prepared, expressed, created, or isolated by any other means that involve splicing of human immunoglobulin gene sequences to other DNA sequences.

The term "isotype," as used herein, refers to the heavy chain class (e.g., IgA, IgD, IgE, IgG, and IgM for human antibodies) or light chain class (e.g., kappa or lambda in humans) encoded by the constant region genes. The term "subtype" refers to subclasses within the subtype (e.g., IgA$_1$, IgA$_2$, IgG$_1$, IgG$_2$, IgG$_3$, IgG$_4$ in humans).

The phrase "an antibody specific for" a specified antigen is used interchangeably herein with the phrase "an antibody which specifically binds to" a specified antigen. As used herein, the term "$K_a$" refers to the association rate and the term "$K_d$" to the dissociation rate of a particular antibody-antigen complex. The term "$K_D$" refers to the dissociation constant, which is obtained from the ratio of $K_d$ to $K_a$ and expressed as a molar concentration (M). According to some embodiments, an antibody that "specifically binds to human Kv1.3" is intended to refer to an antibody that binds to human Kv1.3 with a $K_D$ of $5 \times 10^{-8}$ M or less, more preferably $1 \times 10^{-8}$ M or less.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The patent, scientific and technical literature referred to herein establish knowledge that was available to those skilled in the art at the time of filing. The entire disclosures of the issued U.S. patents, published and pending patent applications, and other publications that are cited herein are hereby incorporated by reference to the same extent as if each was specifically and individually indicated to be incorporated by reference. In the case of any inconsistencies, the present disclosure will prevail.

Anti-Kv1.3 Antibodies

The invention provides a variety of new antibodies with high affinity against the human Kv1.3 protein, particularly epitopes on the extracellular loops and which modulate the activity of Kv1.3 function. The antibodies may comprise the complete VH and VL regions disclosed herein, or may comprise only the CDR sequences disclosed herein in combination with known human or other mammalian (e.g., human) or avian (e.g., chicken) framework regions. In addition, based upon specific CDR sequences disclosed herein, sequence motifs for consensus CDR sequences are provided, and antibodies that comprise CDR sequences defined by these motifs, in combination with known human or other mammalian or avian framework regions, are also provided. Furthermore, possible canonical structures for each CDR of the VL and VH regions are assigned, and antibodies that comprise CDRs belonging to the disclosed structural motifs, in combination with known human or other mammalian or avian framework regions, are also provided.

The CDR sequences of the invention (including both the CDRs disclosed in FIGS. 11-22 and the CDRs defined by the sequence motifs disclosed herein) can be combined with other immunoglobulin sequences according to methods well known in the art to produce immunoglobulin molecules with antigen-binding specificity determined by the CDRs of the invention.

In some embodiments, the CDRs of the invention are combined with framework region (FR) and constant domain (CH or CL) sequences from other antibodies. For example, although some of the CDRs disclosed herein are derived from chicken B cells and have chicken FR and constant domain sequences, they can be recombined with human or other mammalian or avian FR and constant domain sequences to produce humanized or other recombinant antibodies. Similarly, CDRs disclosed herein that are derived from llamas can be recombined with human or other mammalian constant domain sequences to produce humanized or other recombinant antibodies. The production of such recombinant antibodies is well known to those of skill in the art and requires only routine experimentation.

The type of constant regions included in such recombinant antibodies can be chosen according to their intended use. For example, if the antibodies are intended for therapeutic use to target Kv1.3-expressing cells for destruction, heavy chain constant domains (i.e., Fc regions) of IgG subtypes can be used. If the antibodies are intended only as reagents for labeling cells (e.g., for fluorescence-activated cell sorting (FACS)), a complete antibody, antigen binding fragment (Fab), single-chain variable fragment (scFV), single domain antibody (sdAb) or even non-antibody immunoglobulin molecule (e.g., an MHC receptor extracellular domain) can be used with the CDRs of the invention.

The CDRs of the invention can be selected independently such that the CDR1, CDR2 and CDR3 sequences of a given variable light (VL) chain or variable heavy (VH) chain can be chosen from different original VL and VH chains, from different VL and VH CDR motifs, or from a combination of the disclosed CDRs and motifs. However, sequences for light chain CDRs should be selected from the disclosed VL CDRs or VL CDR motifs, and sequences for heavy chain CDRs should be selected from the disclosed VH CDRs or VH CDR motifs. Similarly, the sequences for CDR1 regions should be selected from the disclosed CDR1 or CDR1 motif sequences, the sequences for CDR2 regions should be selected from the disclosed CDR2 or CDR2 motif sequences, and the sequences for CDR3 regions should be selected from the disclosed CDR3 or CDR3 motif sequences, for VL or VH chains as appropriate.

In certain aspects, the invention provides a Kv1.3 binding antibody or antigen binding portion thereof with the binding specificity of any one of the antibodies described in FIGS. 11-22.

In certain aspects, the invention provides a Kv1.3 binding antibody or antigen binding portion thereof, wherein the antibody or antigen binding portion thereof comprises a VH chain that is 90%, 91%, 92%, 93%, 94%, 95%, 96%, 97%, 98%, 99% or 100% identical to the VH chain of an antibody from FIG. 13, 17, or 21 and a VL chain that is 90%, 91%, 92%, 93%, 94%, 95%, 96%, 97%, 98%, 99% or 100% identical to the VL chain of an antibody from FIG. 11, 15, or 19.

In certain aspects, the invention provides a Kv1.3 binding antibody or antigen binding portion thereof wherein the antibody or antigen binding portion thereof comprises the VH chain of an antibody from FIG. 13, 17, or 21 and the VL chain of an antibody from FIG. 11, 15, or 19.

In certain embodiments, the antibody or antigen binding portion thereof is fully humanized and recombinantly produced. In certain embodiments, the antibody or antigen binding portion thereof is not naturally occurring. In certain embodiments, the antibody comprises the pairing of VH and VL chains as isolated from an animal immunized with Kv1.3. In certain embodiments, the antibody comprises the pairing of VH and VL chains as isolated from an animal immunized with Kv1.3, wherein the Fc portion of the antibody is not the isotype or portion of the pair of VH and VL chains as isolated from the immunized animal. In certain embodiments, the antibody comprises a pairing of VH and VL chains, wherein the VH or VL individually could be isolated from the immunized animal. In some embodiments, the antibody comprises VH chain or CDRs of a VH chain of one clonal cell line, and VL or CDRs of another clonal cell line. In certain embodiments, the antibody comprises the pairing of VH and VL chains as isolated from an animal immunized with Kv1.3 modified by substituting one or more amino acids.

In certain embodiments, the antibody or antigen binding portion thereof comprises a VH which comprises the CDR1, CDR2, and CDR3 of an antibody from FIG. 13, 17, or 21. In certain embodiments, the antibody or antigen binding portion thereof comprises a VL which comprises the CDR1, CDR2, and CDR3 of an antibody from FIG. 11, 15, or 19.

In certain embodiments, the antibody or antigen binding portion thereof comprises a VH which comprises the CDR1, CDR2, and CDR3 of an antibody from FIG. 13, 17, or 21 and further comprises the complementary VL which comprises the CDR1, CDR2, CDR3 of an antibody from FIG. 11, 15, or 19.

In certain aspects, the invention provides a pharmaceutical composition comprising any one of the antibodies of the invention or antigen binding portion thereof or any combination thereof. In certain aspects, the invention provides pharmaceutical compositions including any one of the antibodies of the invention or antigen binding portion thereof and a pharmaceutically acceptable carrier.

Comparing the sequences of the antibodies and their affinity and inhibition of Kv1.3, a skilled artisan can readily determine sequence identity, compare sequence length and determine the percent sequence identity and/or changes, including percent sequence identity and/or changes in the VH and VL sequences, including percent sequence identity and/or changes in the CDRs, as well as the specific positions and types of substitutions which can be tolerated while affinity and inhibition of Kv1.3 is maintained.

In certain embodiments, the invention provides antibodies that are 99%, 98%, 97%, 96%, 95%, 94%, 93%, 92%, 91%, 90%, 89%, 88%, 87%, 86%, 85%, 84%, 83%, 82%, 81%, 80% identical to the VH and VL amino acid sequences of the antibodies described herein wherein the antibody binds and inhibits Kv1.3. In certain embodiments, the invention provides antibodies which are 99%, 98%, 97%, 96%, 95%, 94%, 93%, 92%, 91%, 90%, 89%, 88%, 87%, 86%, 85%, 84%, 83%, 82%, 81%, 80% identical to the CDR1, 2, and/or 3 of VH and CDR1, 2, and/or 3 VL amino acid sequences of the antibodies described herein wherein the antibody binds and inhibits Kv1.3.

Methods of Using Anti-Kv1.3 Antibodies

The anti-Kv1.3 antibodies of the invention can be used in standard methods of immunoaffinity purification, immunohistochemistry and immunotherapy, but with specific application to cells and tissue expressing the Kv1.3 protein.

For example, the anti-Kv1.3 antibodies of the invention can be used to isolate cells expressing Kv1.3 from a mixed population of cells including only a fraction of cells that express Kv1.3. For example, individual cells can be subjected to techniques such as FACs using fluorescently-labeled anti-Kv1.3 antibodies or immunoaffinity purification using immobilized anti-Kv1.3 antibodies.

Similarly, immobilized anti-Kv1.3 antibodies can be used for purification of Kv1.3 protein from lysates derived from Kv1.3 expressing cells. Kv1.3 protein can be purified while remaining associated with cell membrane fragments or following dissociation from biological membranes after, for example, treatment with a variety of detergents. Additionally, Kv1.3 can be purified in such a manner while in association with small molecules or biologics (e.g., peptides, mAbs, etc.) that specifically bind Kv1.3. Such purified Kv1.3 preparations will have utility in techniques used for determining structural information regarding Kv1.3 both with and without bound molecules (e.g., crystallography, cryoEM). Furthermore, such preparations will have utility in screening a variety of libraries (e.g., small molecule, mAb) for molecules that specifically interact with Kv1.3.

Alternatively, immunohistochemistry may be performed using the anti-Kv1.3 antibodies of the invention to identify cells or tissues expressing Kv1.3 and/or to quantify Kv1.3 expression in such cells.

In addition, the anti-Kv1.3 antibodies of the invention can be used therapeutically to target Kv1.3-expressing cells, particularly $T_{EM}$ cells, and/or to inhibit the function of Kv1.3 in such cells. Additionally, the anti-Kv1.3 antibodies of the invention that bind to Kv1.3 and that may or may not inhibit Kv1.3 activity may deplete target Kv1.3 expressing cells, particularly $T_{EM}$ cells, via cytotoxic Fc mediated effector functions such as antibody-dependent cell-mediated cytotoxicity (ADCC) and complement dependent cytotoxicity (CDC). Furthermore, anti-Kv1.3 antibodies of the invention conjugated to moieties that inhibit Kv1.3 function can also be used therapeutically. Antibody-drug conjugates of the anti-Kv1.3 antibodies of the invention can also be used to deliver therapeutic drugs to Kv1.3-expressing cells.

In autoimmune diseases, specific autoreactive T cells can undergo differentiation into chronically activated memory T cells that contribute to pathogenesis by migrating to inflamed tissues and secreting cytokines. Although not bound by any mechanism of action, in some embodiments, blocking Kv1.3 activity may alter the phenotype of T cells in response to an antigen and convert T cells to a suppressive state that is beneficial in treating autoimmune disease. In chronic autoimmune diseases, there is clonal expansion of T effector memory (TEM) cells. It has been shown that in cells with a Kv1.3 loss of function mutation, T central memory (TCM) cells fail to differentiate into T effector memory (TEM) cells, and TEM cells even revert back into TCM cells. (Hu et al. (2012), J. of Biological Chemistry, 287(2), 1261-68). Thus, in some embodiments, the antibody or antigen binding portion thereof inhibits Kv1.3 function to treat autoimmune immune disorders. Accordingly, the Kv1.3 binding antibodies or antigen binding portion thereof of the invention can be used in methods for preventing or treating an autoimmune disorder in a subject. The method comprises administering to the subject a therapeutically effective amount of an antibody or antigen binding portion thereof as described herein. In some embodiments, the antibody or antigen binding portion thereof inhibits Kv1.3 potassium channels. In some embodiments, the autoreactive effector memory T cells of the subject are depleted or reduced. In some embodiments, the subject is suspected of or evaluated for having an autoimmune disease. In some embodiments, the subject is a human.

In some embodiments, the autoimmune disorder is multiple sclerosis, myasthenia gravis, autoimmune neuropathies, Guillain-Barre syndrome, autoimmune uveitis, Crohn's disease, ulcerative colitis, primary biliary cirrhosis, autoimmune hepatitis, autoimmune thrombocytopenia, Type-1 diabetes mellitus, Addison's disease, Grave's disease, Hashimoto's thyroiditis, autoimmune orchitis, Behcet's disease, rheumatoid arthritis, bone resorption associated with periodontal disease, systemic lupus erythematosus, scleroderma polymyositis, dermatomyositisis, pemphigus vulgaris, spondyloarthropathies, ankylosing spondylitis, or Sjogren's syndrome.

Graft versus host disease (GvHD) can occur following the transplantation of tissue from a donor to a recipient. GvHD is caused by recipient reactive T-cells from the donor organ, which recognize and destroy MHC-mismatched host tissues. Accordingly, the Kv1.3 binding antibodies or antigen binding portion thereof of the invention can be used in methods for preventing or treating GvHD in a subject. The method comprises administering to the subject a therapeutically effective amount of an antibody or antigen binding portion thereof as described herein. In some embodiments, the antibody or antigen binding portion thereof inhibits Kv1.3 potassium channels. In some embodiments, the autoreactive effector memory T cells of the subject are depleted or reduced. In some embodiments, the subject has received an organ transplant from a non-genetically identical donor. In some embodiments, the subject is a human.

In some embodiments, the Kv1.3 binding antibodies or antigen binding portion thereof of the invention can be used in methods for inhibiting Kv1.3 potassium channels in a subject. The method comprises administering to the subject the antibody described herein in an amount that is effective in inhibiting Kv1.3 potassium channels. In some embodiments, the subject is a human.

Nucleic Acid Molecules Encoding Anti-Kv1.3 Antibodies

The invention also provides nucleic acid molecules encoding the anti-Kv1.3 antibodies of the invention. Such nucleic acids can be designed using standard tables for the universal genetic code to choose codons that will encode the desired amino acid sequence, or specialized codon tables can be used that reflect codon biases characteristic of different organisms. Thus, for example, to optimize expression of the anti-Kv1.3 antibodies of the invention in CHO cells, a nucleic acid encoding the desired antibody can be designed using a codon table optimized for CHO cells.

The nucleic acids encoding the anti-Kv1.3 antibodies of the invention can be included in a wide variety of vectors known in the art, including cloning vectors (e.g., bacterial or mammalian cloning vectors), transformation vectors (e.g., homologous recombination, viral integration or autonomously replicating vectors) and expression vectors (e.g., high copy number, inducible or constitutive mammalian expression vectors).

Cells Expressing Anti-Kv1.3 Antibodies

Also provided are host cells expressing heterologous sequences encoding the anti-Kv1.3 antibodies of the invention. Such host cells can be useful for commercial production of the anti-Kv1.3 antibodies of the invention, and can be produced by transforming appropriate host cells with expression vectors described above.

In some embodiments the invention provides mammalian cells, including CHO cells, expressing the anti-Kv1.3 antibodies of the invention. However, those of skill in the art can express the antibodies in a variety of host cells, including bacterial, yeast, insect and mammalian systems. See, e.g., Verma et al. (1998), J. Immunol. Methods 216(1-2):165-81, incorporated by reference in its entirety herein.

Pharmaceutical Compositions

In certain aspects, the invention provides a pharmaceutical composition comprising an antibody described herein wherein the composition is used for therapeutic purposes such as but not limited to treatments and/or prevention of autoimmune diseases or GvHD. In certain aspects, the invention provides a pharmaceutical composition comprising an antibody described herein in combination with any other suitable antibody or composition for treating and/or preventing autoimmune diseases or GvHD. In certain embodiments, the pharmaceutical compositions comprise one or more nucleic acids that encode the antibodies described herein. In certain embodiments, these nucleic acids can be expressed by any suitable vector for expression of antibodies.

Various methods to make pharmaceutical compositions are known in the art and are contemplated by the invention. In some embodiments, the compositions include excipient suitable for a biologic molecule such as the antibodies described herein. In some embodiments, the antibodies could be produced in specific cell lines and conditions so as to control glycosylation of the antibody.

In certain aspects, the invention provides that the antibodies or antigen binding portion thereof described herein can be formulated as a composition (e.g., a pharmaceutical composition). Suitable compositions can comprise the antibody or antigen binding portion thereof dissolved or dispersed in a pharmaceutically acceptable carrier (e.g., an aqueous medium). The compositions can be sterile and can be administered by intravenous, e.g., as a bolus or by continuous infusion. The administration can be by intramuscular, intraperitoneal, intracerobrospinal, subcutaneous, intra-articular, intrasynovial, intrathecal, oral tropical, or by inhalation. The antibody or antigen binding portion thereof can also be formulated as a composition appropriate for topical administration to the skin or mucosa. Such compositions can take the form of liquids, ointments, creams, gels and pastes. Standard formulation techniques can be used in preparing suitable compositions.

The antibodies or antigen binding portion thereof described herein can be administered to subjects with autoimmune disease and/or with graft versus host disease and used to kill T cells by virtue of the antibodies or antigen binding portion thereof binding to the surface of T cells expressing Kv1.3 cells.

Suitable dose ranges can depend on the antibody or antigen binding portion thereof and on the nature of the formulation and route of administration. Optimum doses can be determined by one skilled in the art without undue experimentation.

EXAMPLES

Preparation of Kv1.3 Immunogen and B-Cell and Phage Screening Reagents

The gene encoding human Kv1.3 protein (FIG. 1A; SEQ ID NO:1) was optimized for expression in *Tetrahymena thermophila*. The optimized Kv1.3 gene was further modified by the incorporation of nucleotides encoding dual affinity FLAG (DYKDDDDK) and 10× His tags at the Kv1.3 C-terminus (FIG. 1B: SEQ ID NO:2). The optimized Kv1.3 gene was synthesized and cloned into an expression cassette placing control of Kv1.3 gene expression under an inducible *Tetrahymena thermophila* metallothionein promoter (FIG. 2). The entire expression cassette containing the Kv1.3 gene was subsequently cloned into a *Tetrahymena thermophila* high copy number ribosomal DNA expression vector, pTRAS1 (FIG. 2; U.S. Pat. No. 8,664,374). Mating *Tetrahymena* cells were transformed with Kv1.3 containing pTRAS1 and viable transformants were selected in media containing a selective agent for transformants. Cells expressing Kv1.3 following induction of gene expression were selected for preparation of Kv1.3 immunogen. Cultures (>1 L) of transformant *Tetrahymena* cells were grown and induced to express Kv1.3, harvested, and lysed by microfluidization. Membrane fractions were collected by centrifugation and then frozen for subsequent purification.

Figure 3:
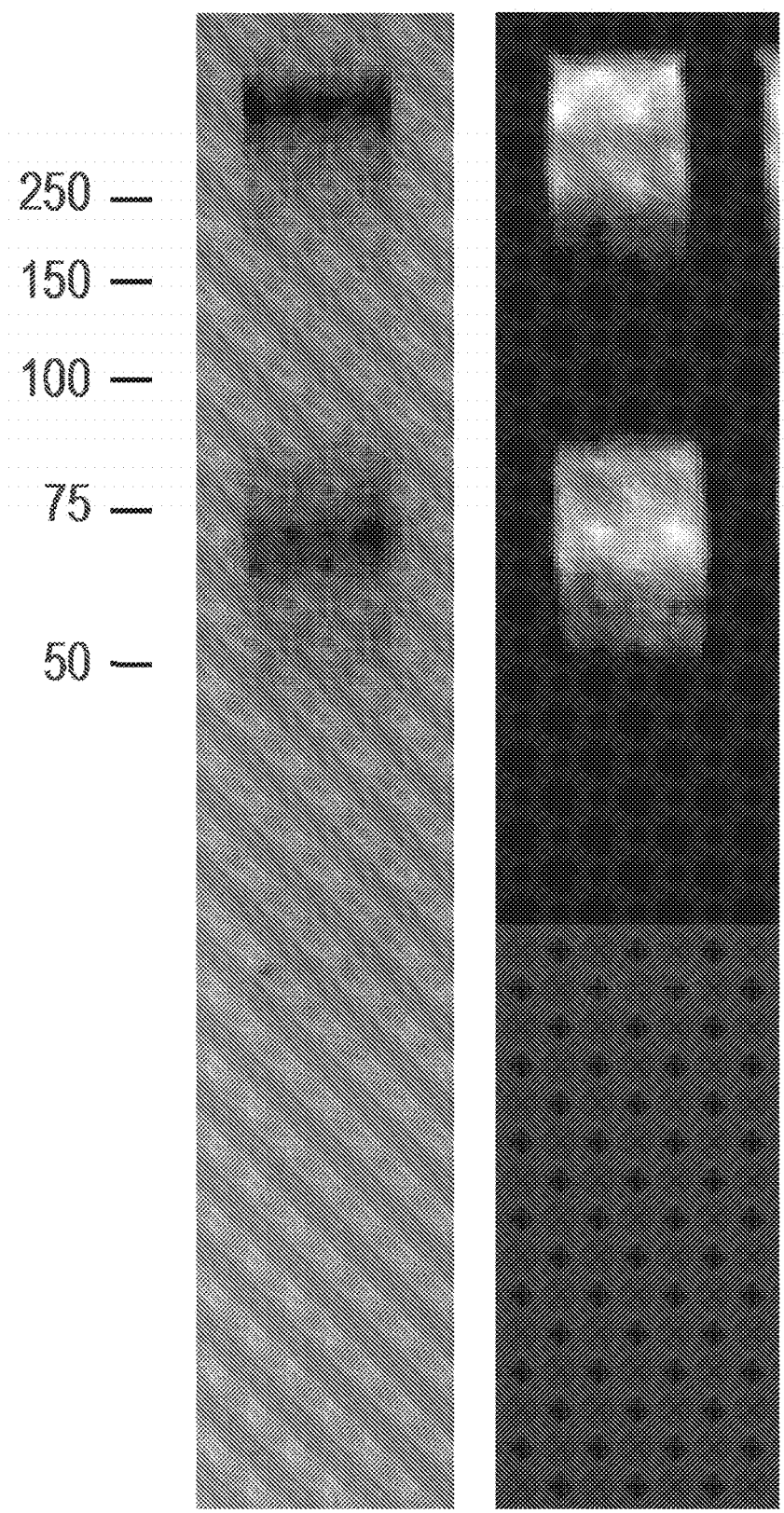
FIG. 3 shows SDS-PAGE and Western analysis of Kv1.3 proteoliposome immunogen preparations. The left panel shows Kv1.3 resolved on SDS-PAGE and detected by Coomassie stain. The right panel shows anti-Kv1.3 Western analysis using an anti-Kv1.3 extracellular loop antibody. Note that Kv1.3 resolves as two distinct species: a monomer corresponding to the predicted molecular weight (~66 kDa) and a higher molecular weight (>250 kDa) species.

Kv1.3 was extracted from *Tetrahymena* membranes in buffer containing Fos-Choline detergent and subsequently purified by NiNTA chromatography. Purified Kv1.3 was reconstituted into liposomes consisting of 10 mg/ml phosphatidylcholine to produce Kv1.3 proteoliposomes. FIG. 3 shows SDS-PAGE and Western analysis of Kv1.3 proteoliposome immunogen samples.

Antibody Generation

Figure 4:
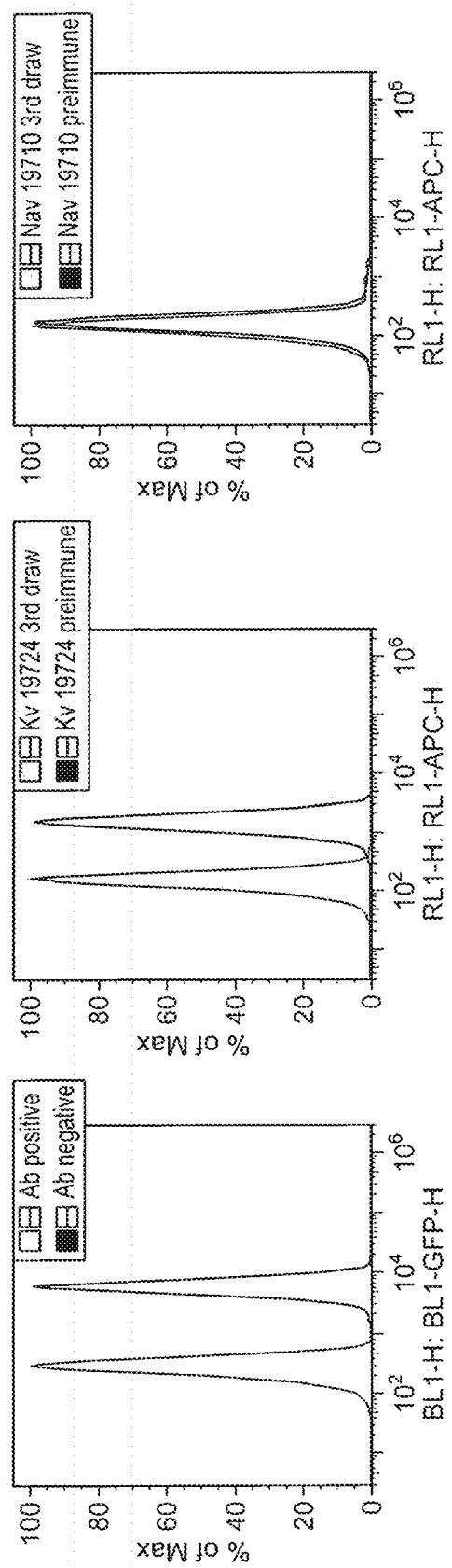
FIG. 4 shows FACS analysis of anti-Kv1.3 antibody titers in sera of immunized chickens. FACS analysis was carried out with Kv1.3 magnetic beads. The left panel is a control analysis showing the distribution of beads incubated with or without commercial anti-Kv1.3 antibody. The middle panel shows distribution of Kv1.3 beads incubated with either preimmune sera or sera from Kv1.3 immunized chickens ($3^{rd}$ draw). The right panel shows the distribution of Kv1.3 beads incubated with either preimmune sera or sera from chickens immunized with a non-related ion channel ($3^{rd}$ draw).
Figure 5:
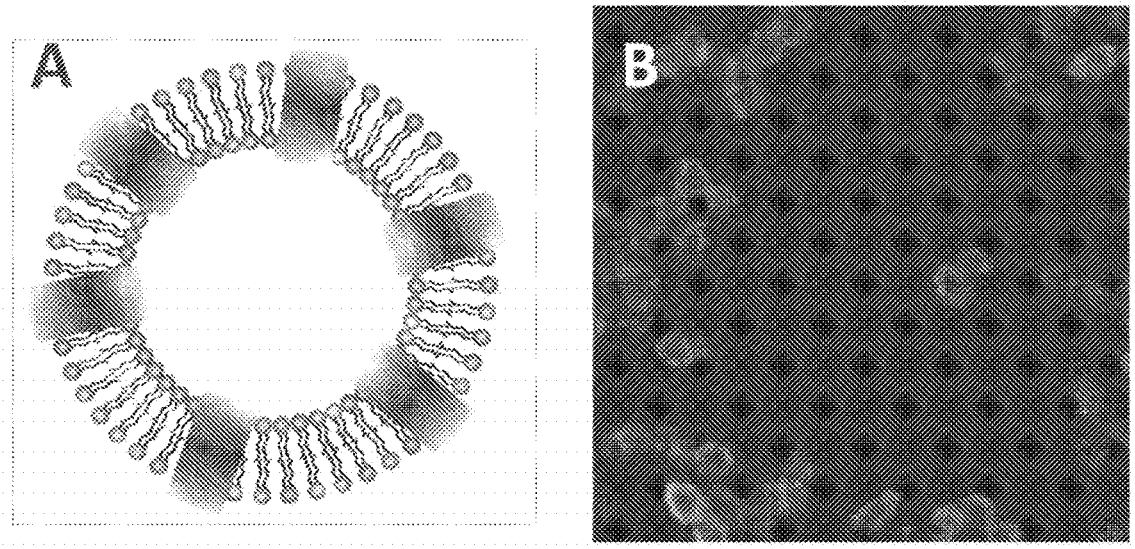
FIGS. 5A-5B show Kv1.3 formulations used in Glucan Enzymatic Method (GEM) assays to isolate anti-Kv1.3 antibodies.

Chicken Derived Antibodies:

Kv1.3 proteoliposomes were used to immunize chickens, and to increase the immune response through boosting. Following a period of increased specific anti-Kv1.3 antibody titer in the sera, animals were sacrificed and splenocytes harvested. Table 1 shows anti-Kv1.3 antibody titer results. Specificity was determined by comparing ELISA signals in wells coated with either Kv1.3 or a non-related ion channel, Nav1.8. Additionally, FIG. 4 shows specific anti-Kv1.3 antibody titer in sera by FACS analysis using Kv1.3 coated magnetic beads. No specific signal was observed by FACS using Kv1.3 magnetic beads from sera derived from animals immunized with a non-related ion channel, i.e., Nav1.8. Splenic B cells producing anti-Kv1.3 antibody were identified by fluorescence using a GEM assay (U.S. Pat. Nos. 8,030,095 and 8,415,173) incorporating either Kv1.3 proteoliposomes or Kv1.3 attached to magnetic beads (FIGS. 5A and B).

TABLE 1

Anti-Kv1.3 antibody titers in immunized chickens.

| | Kv1.3 | | Nav1.8 | |
|---|---|---|---|---|
| Dilution | Pre-Immune | Final Draw | Pre-Immune | Final Draw |
| 50 | 0.242 | 3.354 | 0.066 | 0.444 |
| 250 | 0.063 | 2.433 | 0.051 | 0.141 |
| 1250 | 0.051 | 1.587 | 0.057 | 0.081 |
| 6250 | 0.046 | 0.621 | 0.048 | 0.058 |
| 31250 | 0.038 | 0.155 | 0.05 | 0.05 |
| 156250 | 0.045 | 0.074 | 0.049 | 0.06 |
| 781250 | 0.035 | 0.051 | 0.054 | 0.049 |

Figure 6:
FIG. 6 illustrates bivalent scFv-Fc antibody design expressed in HEK293 cells. The construct includes a leader sequence (Le), a variable light chain (VL), a linker region (Li), a variable heavy chain (VH) and an Fc domain of human IgG1 (hIgG1-Fc).

Variable light and heavy chain genes from individual B cells identified by GEM assay were amplified by PCR and cloned into a mammalian expression vector as fusions to human IgG1 Fc to generate genes encoding bivalent scFv-Fc antibodies (FIG. 6). Antibodies were expressed in HEK293 cells and supernatants assayed by ELISA to confirm specific binding to Kv1.3 compared to a non-related ion channel (Nav1.8). Table 2 below shows ELISA results of cloned scFv-Fc antibodies identified in GEM assays using Kv1.3 proteoliposome. Table 3 below shows ELISA results of cloned scFv-Fc antibodies identified in GEM assays using Kv1.3 magnetic beads.

TABLE 2

ELISA analysis of anti-Kv1.3 antibodies derived from chickens.

| | 19724p1.A1 | | 19724p1.A11 | | 19724p1.A5 | | 19724p1.A9 | | 19724p1.B1 | | 19724p1.B11 | |
|---|---|---|---|---|---|---|---|---|---|---|---|---|
| | Kv1.3 | Nav1.8 | Kv1.3 | Nav1.8 | Kv1.3 | Nav1.8 | Kv1.3 | Nav1.8 | Kv1.3 | Nav1.8 | Kv1.3 | Nav1.8 |
| 50 | 1.231 | 0.072 | 1.209 | 0.07 | 1.08 | 0.054 | 1.24 | 0.074 | 1.119 | 0.068 | 1.134 | 0.074 |
| 250 | 1.496 | 0.052 | 1.482 | 0.05 | 1.169 | 0.056 | 1.486 | 0.053 | 1.375 | 0.064 | 1.235 | 0.057 |
| 1250 | 1.216 | 0.075 | 1.277 | 0.059 | 1.195 | 0.066 | 1.404 | 0.067 | 1.382 | 0.065 | 0.109 | 0.067 |
| 6250 | 1.101 | 0.055 | 1.156 | 0.067 | 1.224 | 0.061 | 0.94 | 0.064 | 1.308 | 0.057 | 0.95 | 0.05 |

| | 19724p1.C12 | | 19724p1.C4 | | 19724p1.D11 | | 19724p1.D2 | | 19724p1.D8 | | 19724p1.E2 | |
|---|---|---|---|---|---|---|---|---|---|---|---|---|
| | Kv1.3 | Nav1.8 | Kv1.3 | Nav1.8 | Kv1.3 | Nav1.8 | Kv1.3 | Nav1.8 | Kv1.3 | Nav1.8 | Kv1.3 | Nav1.8 |
| 50 | 1.337 | 0.06 | 1.096 | 0.06 | 1.181 | 0.059 | 0.86 | 0.062 | 1.053 | 0.065 | 1.278 | 0.061 |
| 250 | 0.103 | 0.053 | 1.029 | 0.07 | 1.116 | 0.063 | 1.004 | 0.047 | 1.207 | 0.048 | 1.43 | 0.047 |
| 1250 | 1.526 | 0.083 | 1.203 | 0.056 | 1.078 | 0.072 | 0.904 | 0.06 | 1.066 | 0.062 | 1.533 | 0.053 |
| 6250 | 1.075 | 0.051 | 1.105 | 0.051 | 0.869 | 0.057 | 0.638 | 0.074 | 0.693 | 0.058 | 1.283 | 0.062 |

TABLE 2-continued

ELISA analysis of anti-Kv1.3 antibodies derived from chickens.

| | 19724p1.E3 | | 19724p1.F3 | | 19724p1.F6 | | 19724p1.F7 | | 19724p1.F8 | | 19724p1.F9 | |
|---|---|---|---|---|---|---|---|---|---|---|---|---|
| | Kv1.3 | Nav1.8 | Kv1.3 | Nav1.8 | Kv1.3 | Nav1.8 | Kv1.3 | Nav1.8 | Kv1.3 | Nav1.8 | Kv1.3 | Nav1.8 |
| 50 | 1.029 | 0.061 | 1.199 | 0.077 | 1.385 | 0.072 | 1.357 | 0.08 | 1.802 | 1.435 | 1.399 | 0.065 |
| 250 | 1.349 | 0.053 | 1.268 | 0.054 | 1.321 | 0.066 | 1.372 | 0.064 | 1.487 | 1.007 | 1.359 | 0.05 |
| 1250 | 1.22 | 0.051 | 1.194 | 0.053 | 1.512 | 0.067 | 1.358 | 0.061 | 1.113 | 0.436 | 1.392 | 0.062 |
| 6250 | 0.83 | 0.068 | 0.945 | 0.075 | 1.239 | 0.068 | 1.353 | 0.068 | 0.523 | 0.183 | 1.317 | 0.072 |

| | 19724p1.G6 | | 19724p1.H12 | | 19724p1.H2 | | 19724p1.H4 | | 19724p1.H7 | | 19724p1.B5 (neg) | |
|---|---|---|---|---|---|---|---|---|---|---|---|---|
| | Kv1.3 | Nav1.8 | Kv1.3 | Nav1.8 | Kv1.3 | Nav1.8 | Kv1.3 | Nav1.8 | Kv1.3 | Nav1.8 | Kv1.3 | Nav1.8 |
| 50 | 1.64 | 0.059 | 1.291 | 0.077 | 1.328 | 0.064 | 1.344 | 0.062 | 1.358 | 0.071 | 0.078 | 0.053 |
| 250 | 1.54 | 0.056 | 1.424 | 0.09 | 1.466 | 0.085 | 1.253 | 0.066 | 1.267 | 0.065 | 0.082 | 0.067 |
| 1250 | 1.307 | 0.051 | 1.167 | 0.081 | 1.397 | 0.083 | 1.122 | 0.077 | 1.149 | 0.08 | 0.073 | 0.08 |
| 6250 | 1.155 | 0.062 | 1.213 | 0.083 | 1.202 | 0.086 | 0.811 | 0.094 | 1.009 | 0.083 | 0.088 | 0.084 |

| | 19724p1.E6 (neg) | | Mock | |
|---|---|---|---|---|
| | Kv1.3 | Nav1.8 | Kv1.3 | Nav1.8 |
| 50 | 0.077 | 0.06 | 0.071 | 0.04 |
| 250 | 0.074 | 0.074 | 0.071 | 0.053 |
| 1250 | 0.077 | 0.077 | 0.066 | 0.067 |
| 6250 | 0.084 | 0.084 | 0.09 | 0.081 |

TABLE 3

ELISA analysis of anti-Kv1.3 antibodies derived from chickens.

| | 19724p2.A2 | | 19724p2.A3 | | 19724p2.A5 | | 19724p2.A7 | | 19724p2.B5 | | 19724p2.C4 | |
|---|---|---|---|---|---|---|---|---|---|---|---|---|
| | Kv1.3 | Nav1.8 | Kv1.3 | Nav1.8 | Kv1.3 | Nav1.8 | Kv1.3 | Nav1.8 | Kv1.3 | Nav1.8 | Kv1.3 | Nav1.8 |
| 50 | 0.621 | 0.039 | 0.972 | 0.058 | 0.693 | 0.062 | 0.795 | 0.042 | 0.577 | 0.07 | 0.876 | 0.052 |
| 250 | 0.459 | 0.051 | 0.945 | 0.053 | 0.747 | 0.059 | 0.781 | 0.051 | 0.361 | 0.052 | 0.829 | 0.051 |
| 1250 | 0.219 | 0.055 | 0.931 | 0.051 | 0.584 | 0.055 | 0.568 | 0.047 | 0.149 | 0.051 | 0.828 | 0.044 |
| 6250 | 0.083 | 0.054 | 0.671 | 0.053 | 0.29 | 0.055 | 0.278 | 0.056 | 0.061 | 0.053 | 0.412 | 0.065 |

| | 19724p2.D1 | | 19724p2.D2 | | 19724p2.D9 | | 19724p2.E6 | | 19724p2.F7 | | 19724p2.G9 | |
|---|---|---|---|---|---|---|---|---|---|---|---|---|
| | Kv1.3 | Nav1.8 | Kv1.3 | Nav1.8 | Kv1.3 | Nav1.8 | Kv1.3 | Nav1.8 | Kv1.3 | Nav1.8 | Kv1.3 | Nav1.8 |
| 50 | 0.951 | 0.055 | 0.77 | 0.056 | 0.813 | 0.056 | 0.878 | 0.071 | 0.701 | 0.061 | 0.955 | 0.059 |
| 250 | 0.853 | 0.053 | 0.501 | 0.054 | 0.974 | 0.063 | 0.921 | 0.063 | 0.63 | 0.061 | 0.994 | 0.073 |
| 1250 | 0.914 | 0.046 | 0.254 | 0.051 | 0.753 | 0.065 | 0.934 | 0.063 | 0.501 | 0.054 | 0.919 | 0.074 |
| 6250 | 0.671 | 0.053 | 0.132 | 0.056 | 0.557 | 0.06 | 0.59 | 0.063 | 0.303 | 0.066 | 0.638 | 0.07 |

| | 19724p2.H10 | | 19724p2.H12 | | 19724p2.H4 | | 19724p2.H6 | |
|---|---|---|---|---|---|---|---|---|
| | Kv1.3 | Nav1.8 | Kv1.3 | Nav1.8 | Kv1.3 | Nav1.8 | Kv1.3 | Nav1.8 |
| 50 | 0.853 | 0.049 | 0.542 | 0.046 | 0.598 | 0.057 | 0.912 | 0.065 |
| 250 | 0.882 | 0.061 | 0.477 | 0.049 | 0.506 | 0.063 | 0.966 | 0.059 |
| 1250 | 0.893 | 0.064 | 0.363 | 0.062 | 0.285 | 0.05 | 0.99 | 0.054 |
| 6250 | 0.173 | 0.051 | 0.146 | 0.052 | 0.136 | 0.064 | 0.77 | 0.052 |

Llama Derived Antibodies:

Llamas were immunized with DNA encoding human Kv1.3 and boosted with Kv1.3 proteoliposomes. Once specific anti-Kv1.3 antibody titers were detected phage libraries were constructed and phage panned using Kv1.3 magnetic beads. Positive clones were sequenced and purified scFv-Fc antibodies were confirmed to specifically bind to Kv1.3 by ELISA.

Analysis of Anti-Kv1.3 Antibodies

Anti-Kv1.3 antibody clones were tested (i) for their ability to bind native Kv1.3 on a human T-cell line, and/or (ii) their ability to modulate the functionality of Kv1.3 activity (Tables 4 and 7).

The human leukemic T cell line Jurkat expresses Kv1.3 on the cell surface (Gasiorowska et al. (2012), *Cell Mol Biol Lett.* 17:559-570). The ability of each of the GEM discovered antibodies to bind Jurkat cells was analyzed by FACS. Table 4 shows that six clones (19724p1.A11, 19724p1.D8, 19724p1.H7, 19724p1.E6, 19724p2.A3, 19724p2.G9) bound Jurkat cells with signals significantly higher (average signal approximately 3,370) than background levels associated with other antibodies (average signal approximately 193). Additionally three clones (19724p2.D2, 19724p2.D9 and 19724p2.E6) show signals that are slightly higher than background levels (average signal approximately 314). Of the antibodies that are FACS positive for Jurkat binding, one clone (19724p1.E6) does not show binding to Kv1.3 by ELISA. This result may indicate that this antibody recognizes a conformational dependent Kv1.3 epitope that is maintained in the Kv1.3 proteoliposomes used for the initial GEM selection and in native Kv1.3 channels present on the Jurkat cell surface, but that is lost during the ELISA procedure, presumably when Kv1.3 is bound to the wells of the ELISA plate.

surface area, and access resistance were continuously monitored during recordings to ensure minimal current rundown. FIG. 7 shows that ten antibody clones (chicken antibodies p1A11, p1D8, p1H7, P1E6, p2A3, p2G9, p1A1, p1F8, p1H4 and llama antibody L1A3) functionally inhibit Kv1.3 activity. Dose-response analysis shows that the most potent antibodies have $IC_{50}$ values of 6 nM (p1E6), 46 nM (p2G9)

TABLE 4

Antibody ELISA and functional analysis of anti-Kv1.3 antibodies derived from chickens.

| anti-Kv1.3 Antibody Clone | Kv1.3 ELISA | Nav1.8 ELISA (neg) | Jurkat Binding (MFI) | % Kv1.3 inhibition (400 nM) Average | SEM (+/−) | n |
|---|---|---|---|---|---|---|
| 19724p1.A1 | positive | negative | 198 | 50.28 | 13.02 | 8 |
| 19724p1.A11 | positive | negative | 9401 | 56.51 | 10.1 | 6 |
| 19724p1.A5 | positive | negative | 181 | 0 | 0 | 3 |
| 19724p1.A9 | positive | negative | 208 | 0 | 0 | 2 |
| 19724p1.B1 | positive | negative | 180 | 0 | 0 | 3 |
| 19724p1.B11 | positive | negative | 185 | 0 | 0 | 2 |
| 19724p1.C12 | positive | negative | 191 | 0 | 0 | 4 |
| 19724p1.C4 | positive | negative | 187 | 0 | 0 | 2 |
| 19724p1.D11 | positive | negative | 180 | 0 | 0 | 2 |
| 19724p1.D2 | positive | negative | 177 | 0 | 0 | 2 |
| 19724p1.D8 | positive | negative | 1757 | 54.47 | 1.52 | 3 |
| 19724p1.E2 | positive | negative | 202 | 0 | 0 | 2 |
| 19724p1.E3 | positive | negative | 205 | 0 | 0 | 2 |
| 19724p1.F3 | positive | negative | 180 | 0 | 0 | 2 |
| 19724p1.F6 | positive | negative | 181 | 0 | 0 | 2 |
| 19724p1.F7 | positive | negative | 185 | 0 | 0 | 2 |
| 19724p1.F8 | positive | positive | 174 | 44.34 | 12.12 | 3 |
| 19724p1.F9 | positive | negative | 206 | 0 | 0 | 2 |
| 19724p1.G6 | positive | negative | 193 | 0 | 0 | 2 |
| 19724p1.H12 | positive | negative | 198 | 0 | 0 | 2 |
| 19724p1.H2 | positive | negative | 209 | 0 | 0 | 2 |
| 19724p1.H4 | positive | negative | 222 | 45.99 | 12.38 | 6 |
| 19724p1.H7 | positive | negative | 1168 | 47.32 | 12.42 | 2 |
| 19724p1.E6 | negative | negative | 4776 | 82.28 | 10.45 | 12 |
| 19724p2.A2 | positive | negative | 205 | 0 | 0 | 2 |
| 19724p2.A3 | positive | negative | 1960 | 45.02 | 3.5 | 2 |
| 19724p2.A5 | positive | negative | 171 | 0 | 0 | 2 |
| 19724p2.A7 | positive | negative | 170 | 0 | 0 | 2 |
| 19724p2.B5 | positive | negative | 183 | 0 | 0 | 2 |
| 19724p2.C4 | positive | negative | 190 | 0 | 0 | 2 |
| 19724p2.D1 | positive | negative | 188 | 0 | 0 | 2 |
| 19724p2.D2 | positive | negative | 264 | 0 | 0 | 2 |
| 19724p2.D9 | positive | negative | 298 | 0 | 0 | 2 |
| 19724p2.E6 | positive | negative | 380 | 0 | 0 | 2 |
| 19724p2.F7 | positive | negative | 180 | 0 | 0 | 2 |
| 19724p2.G9 | positive | negative | 1157 | 75.35 | 11.65 | 11 |
| 19724p2.H10 | positive | negative | 172 | 0 | 0 | 2 |
| 19724p2.H12 | positive | negative | 174 | 0 | 0 | 2 |
| 19724p2.H4 | positive | negative | 172 | 0 | 0 | 2 |
| 19724p2.H6 | positive | negative | 177 | 0 | 0 | 2 |

Figure 9:
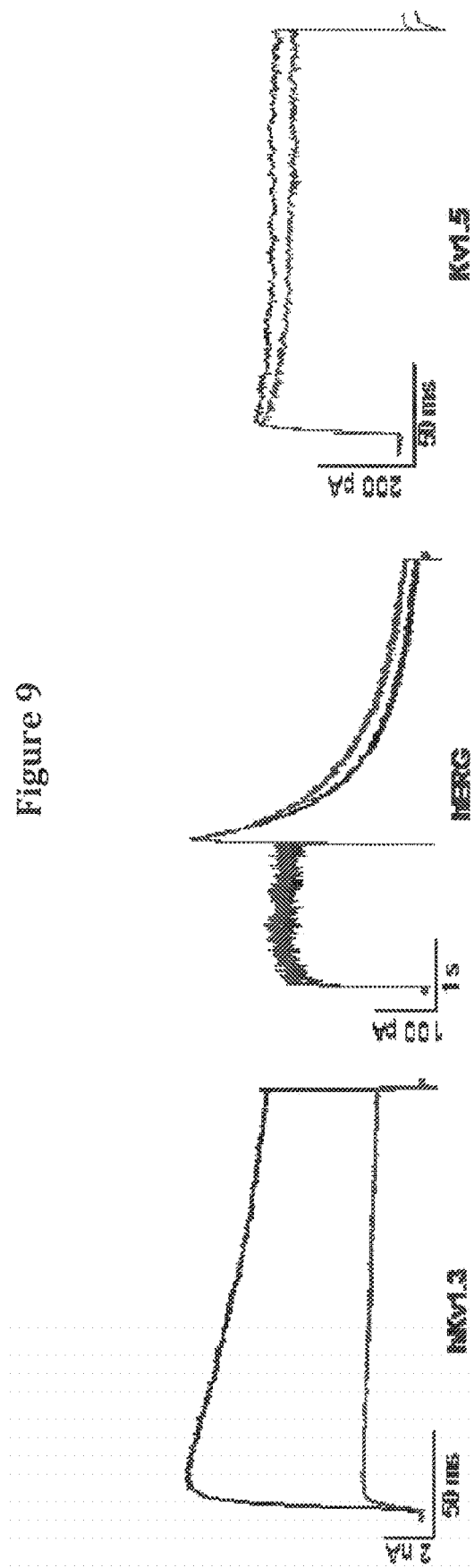
FIG. 9 shows selectivity of antibody p1A1 for blocking Kv1.3 activity compared to other Kv family members, Kv1.5 and Kv11.1 (hERG).
Figure 10:
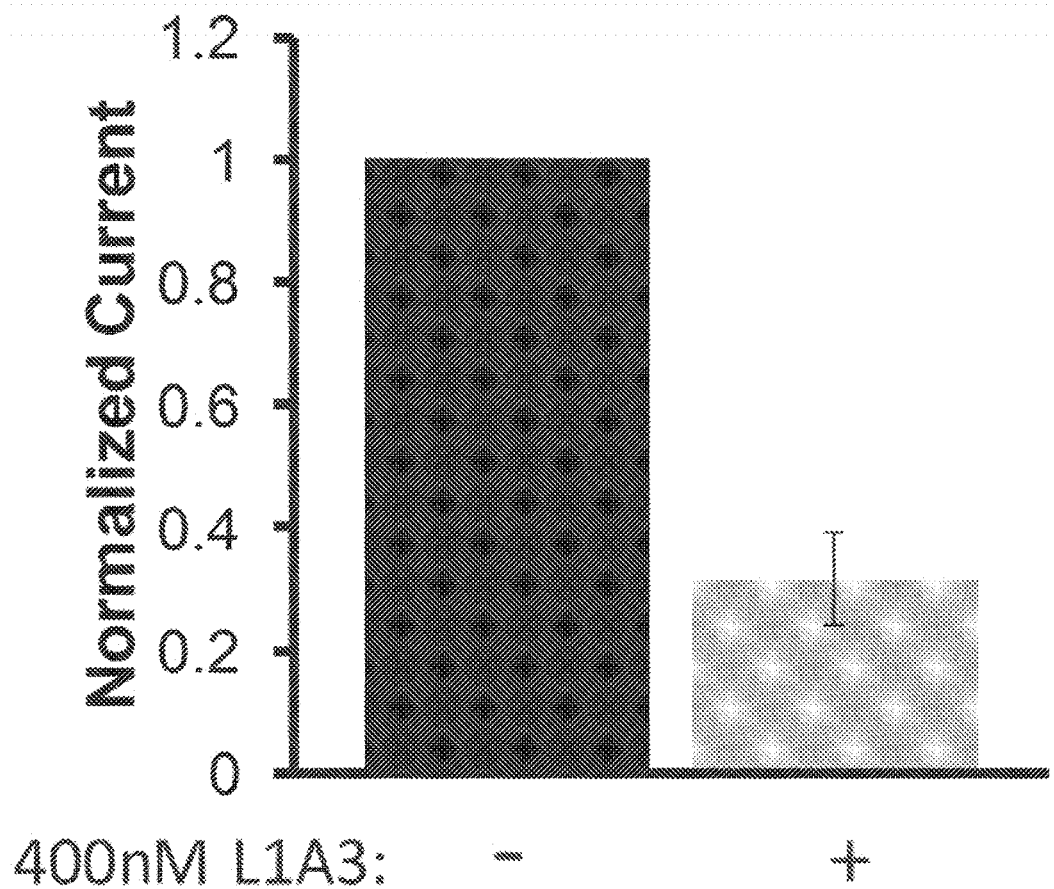
FIG. 10 shows that antibody L1A3 inhibited the function of native Kv1.3 in CD3/CD28 activated monkey T cells.

Anti-Kv1.3 antibodies were tested for inhibition of human Kv1.3 channels transiently expressed in L929 human fibroblast cells. Cells were plated on cover-slips coated with poly-L-lysine 24 hours post-transfection for whole-cell patch clamp using an EPC-10 HEKA amplifier. Control currents were recorded in normal Ringers solution containing: 160 mM NaCl, 4.5 mM KCl, 2 mM $CaCl_2$, 1 mM $MgCl_2$, 10 mM HEPES (adjusted to pH 7.4 and 290-310 mOsm). Patch pipettes were pulled from soda lime glass (micro-hematocrit tubes, Kimble Chase, Rochester, N.Y.) to a resistance of 2-3 MΩ and filled with an internal pipette solution containing: 45 mM KF, 2 mM $MgCl_2$, 10 mM HEPES, 10 mM EGTA (pH 7.2, 290-310 mOsm). Currents were recorded using depolarizing pulses to 40 mV applied every 30 seconds for 200 milliseconds. Antibodies were freshly diluted in normal Ringers solution immediately prior to bath perfusion. Cell capacitance, a direct measure of cell and 109 nM (L1A3) (FIG. 8). Additionally, antibodies have shown selective inhibition of Kv1.3 over other Kv family members (FIG. 9) and inhibition of Kv1.3 in activated rhesus monkey T cells indicating that they will demonstrate similar activity against Kv1.3 in human T cells (FIG. 10).

Antibody Sequence Analyses

Antibodies Derived from Chickens:

B-cell clones producing potentially useful anti-Kv1.3 antibodies were subjected to DNA sequencing and the corresponding amino acid sequences of light and heavy chain variable domains were deduced. Sequences are disclosed for forty antibodies derived from the GEM screen described above.

Variable Light Chain Sequences

VL Sequence Alignments.

Alignments of all of the VL sequences described above are shown in FIGS. 11A-11B. The figure indicates the approximate locations of the three CDR regions (bold, underscore) and the SEQ ID NO corresponding to each sequence.

Unique VL CDR Sequences.

Alignments of the unique CDR sequences of the VLs of FIGS. 11A-11B are shown in FIG. 12. Of the 40 VL sequences, there are 27 unique CDR1 sequences, 19 unique CDR2 sequences and 24 unique CDR3 sequences, as shown in FIG. 12.

VL CDR Consensus Sequences.

Based on the sequences disclosed in FIG. 12, as well as structure/function characteristics of the naturally occurring amino acids, consensus sequences for the VL CDRs can be determined.

One consensus sequence is VL CDR1 Motif 1:

(SEQ ID NO: 113)
$X_1 X_2 X_3 X_4 X_5 X_6 X_7 X_8 X_9 X_{10} X_{11} X_{12} X_{13}$ where $X_1$ is S, T or C; $X_2$ is G, A, V, L, I, M, R, K or H; $X_3$ G, A, V, L, I, M, D, E, S, T or C; $X_4$ is Y, F, W, R, K, H, D, E, G, A, S, T, C or absent; $X_5$ is N, Q, S, T, C, Y, F, W or absent; $X_6$ is Y, F, W, V, L, I, M, A, G, D, E or absent; $X_7$ is A, G, V, L, I, M, S, T, C, D, E or absent; $X_8$ is S, T, C, G, A, V, L, I, M or absent; $X_9$ is G, A, V, L, I, M, S, T, C, D, E, R, K, H, W, F, Y or absent; $X_{10}$ is S, T, C, Y, F, W, N, Q, G, A, V, L, I, M, R, K, H or absent; $X_{11}$ is Y, F, W, G, A, V, L, I, M, T, S, C, N, Q or absent; $X_{12}$ is Y, F or W and $X_{13}$ is G, A, V, L, I, M, S, T or C. In some embodiments, $X_1$ is limited to S; and/or $X_2$ is limited to G or R; and/or $X_3$ is limited to G, D or S; and/or $X_4$ is limited to Y, R, D, G, S or absent; and/or $X_5$ is limited to N, S, Y or absent; and/or $X_6$ is limited to Y, V, D or absent; and/or $X_7$ is limited to A, S, D or absent; and/or $X_8$ is limited to S, G or absent; and/or $X_9$ is limited to G, S, D, R, W or absent; and/or $X_{10}$ is limited to S, Y, N, G, R or absent; and/or $X_{11}$ is limited to Y, G, T, S, F, N or absent; and/or $X_{12}$ is limited to Y or F; and/or $X_{13}$ is limited to G or S. In some embodiments, the subsequence $X_1 X_2 X_3$ is limited to S G G; in some embodiments, the subsequence $X_1 X_2 X_3$ is limited to S G S; in some embodiments, the subsequence $X_1 X_2 X_3$ is limited to S R D; and in some embodiments, the subsequence $X_1 X_2 X_3$ is limited to S G D.

Noting in particular that the VL CDR1 sequences of SEQ ID NOs: 3, 21, 22, 23, 24, 37, 38, 39 and 42 are derived from antibodies that inhibit Kv1.3 function distinct from the others in FIGS. 11A-11B, an alternative consensus sequence is VL CDR1 Motif 2:

(SEQ ID NO: 114)
$X_1 X_2 X_3 X_4 X_5 X_6 X_7 X_8 X_9 X_{10} X_{11} X_{12} X_{13}$ where $X_1$ is S, T or C; $X_2$ is G, A, V, L, I or M; $X_3$ is G, A, V, L, I, M, S, T or C; $X_4$ is Y, F, W or absent; $X_5$ is S, T, C or absent; $X_6$ is D, E or absent; $X_7$ is D, E, S, T, C or absent; $X_8$ is G, V, L, I, M, A, S, T or C; $X_9$ is G, V, L, I, M, A, S, T or C; $X_{10}$ is Y, F, W, S, T, C, K, R or H; $X_{11}$ is Y, F, W, G, V, L, I, M or A; $X_{12}$ is Y, F or W and $X_{13}$ is G, V, L, I, M or A. In some embodiments, $X_1$ is limited to S; and/or $X_2$ is limited to G; and/or $X_3$ is limited to G or S; and/or $X_4$ is limited to Y or absent; and/or $X_5$ is limited to S or absent; and/or $X_6$ is limited to D or absent; and/or $X_7$ is limited to D, S or absent; and/or $X_8$ is limited to G, S or absent; and/or $X_9$ is limited to S, G or V; and/or $X_{10}$ is limited to Y, S or R; and/or $X_{11}$ is limited to Y, F or G; and/or $X_{12}$ is limited to Y or F; and/or $X_{13}$ is limited to G. In some embodiments, the subsequence $X_1 X_2 X_3$ is limited to S G G; and in some embodiments, the subsequence $X_1 X_2 X_3$ is limited to S G S.

Noting in particular that the VL CDR1 sequences of SEQ ID NO: 21, 22, 23, 24, 39 and 42 are derived from antibodies that are FACS positive for Jurkat cell binding distinct from the others in FIGS. 11A-11B, an alternative consensus sequence is VL CDR1 Motif 3:

(SEQ ID NO: 115)
$X_1 X_2 X_3 X_4 X_5 X_6 X_7 X_8 X_9 X_{10} X_{11} X_{12} X_{13}$

Where $X_1$ is S, T or C; $X_2$ is G, A, V, I, L or M; $X_3$ is G, A, V, I, L or M; $X_4$ is S, T, C, Y, F or W; $X_5$ is S, T, C, G, A, V, I, L or M; $X_6$ is V, A, I, L, M, G, D, E or absent; $X_7$ is S, T, C, D, E or absent; $X_8$ is G, A, V, I, L, M or absent; $X_9$ is S, T, C or absent; $X_{10}$ is Y, F, W or absent; $X_{11}$ is F, Y, W or absent; $X_{12}$ is F, Y or W and $X_{13}$ is G, V, L, I, M or A. In some embodiments $X_1$ is limited to S; and/or $X_2$ is limited to G; and/or $X_3$ is limited to G; and/or $X_4$ is limited to S or Y; and/or $X_5$ is limited to S or G; and/or $X_6$ is limited to D, V or absent; and/or $X_7$ is limited to S, D or absent; and/or $X_8$ is limited to G or absent; and/or $X_9$ is limited to S or absent; and/or $X_{10}$ is limited to Y or absent; and/or $X_{11}$ is limited to F, Y or absent; and/or $X_{12}$ is limited to F or Y; and/or $X_{13}$ is limited to G. In some embodiments the subsequence $X_1 X_2 X_3$ is limited to S G G.

Noting in particular that the VL CDR1 sequence of SEQ ID NO: 42 is derived from an antibody that may recognize a conformational Kv1.3 epitope distinct from the others in FIG. 11A-11B, an alternative consensus sequence is VL CDR1 Motif 4:

(SEQ ID NO: 116)
$X_1 X_2 X_3 X_4 X_5 X_6 X_7 X_8 X_9 X_{10} X_{11} X_{12} X_{13}$ where $X_1$ is S, T or C; $X_2$ is G, A, V, I, L or M; $X_3$ is G, A, V, I, L or M; $X_4$ is Y, F or W; $X_5$ is S, T or C; $X_6$ is D or E; $X_7$ is D or E; $X_8$ is G, A, V, I, L or M; $X_9$ is S, T or C; $X_{10}$ is Y, F or W; $X_{11}$ is Y, F or W; $X_{12}$ is Y, F or W; and $X_{13}$ is G, A, V, I, L or M. In some embodiments $X_1$ is limited to S; and/or $X_2$ is limited to G; and/or $X_3$ is limited to G; and/or $X_4$ is limited to Y; and/or $X_5$ is limited to S; and/or $X_6$ is limited to D; and/or $X_7$ is limited to D; and/or $X_8$ is limited to G; and/or $X_9$ is limited to S; and/or $X_{10}$ is limited to Y; and/or $X_{11}$ is limited to Y; and/or $X_{12}$ is limited to Y; and/or $X_{13}$ is limited to G.

For the VL CDR2, one consensus sequence is VL CDR2 Motif 1:

(SEQ ID NO: 117)
$Y_1 Y_2 Y_3 Y_4 Y_5 Y_6 Y_7$ where $Y_1$ is D, E, N, Q, Y, F, W, S, T, C, R, K or H; $Y_2$ is N, Q, D, E, S, T or C; and $Y_3$ is T, S, C, N, Q, D, E, K, R or H; $Y_4$ is N, Q, K, R, H, E or D; $Y_5$ is R, K or H; $Y_6$ is P and $Y_7$ is S, T or C. In some embodiments, $Y_1$ is limited to D, N, E, Y, S, W, R or H; and/or $Y_2$ is limited to N, D or S; and/or $Y_3$ is limited to T, N, D, K or S; and/or $Y_4$ is limited to N, K, Q or E; and/or $Y_5$ is limited to R or K; and/or $Y_6$ is limited to P; and/or $Y_7$ is limited to S.

Noting in particular that the VL CDR2 sequences of SEQ ID NOs: 3, 21, 22, 23, 24, 37, 38, 39 and 42 are derived from antibodies that inhibit Kv1.3 function distinct from the others in FIGS. 11A-11B, an alternative consensus sequence is VL CDR2 Motif 2:

$$Y_1 \ Y_2 \ Y_3 \ Y_4 \ Y_5 \ Y_6 \ Y_7 \quad \text{(SEQ ID NO: 118)}$$

where $Y_1$ is D, E, Y, F or W; $Y_2$ is N, Q, S, T or C; $Y_3$ is T, S, C, D, E, N or Q; $Y_4$ is K, R, H, N or Q; $Y_5$ is R, K or H; $Y_6$ is P and $Y_7$ is S, T or C. In some embodiments, $Y_1$ is limited to D, E or Y; and/or $Y_2$ is limited to N or S; and/or $Y_3$ is limited to T, D or N; and/or $Y_4$ is limited K or N; and/or $Y_5$ is limited to R or K; and/or $Y_6$ is limited to P; and/or $Y_7$ is limited to S.

Noting in particular that the VL CDR2 sequences of SEQ ID NO: 21, 22, 23, 24, 39 and 42 are derived from antibodies that are FACS positive for Jurkat cell binding distinct from the others in FIGS. 11A-11B, an alternative consensus sequence is VL CDR2 Motif 3:

$$Y_1 \ Y_2 \ Y_3 \ Y_4 \ Y_5 \ Y_6 \ Y_7 \quad \text{(SEQ ID NO: 119)}$$

where $Y_1$ is Y, F, W, D or E; $Y_2$ is N, Q, S, T or C; $Y_3$ is D, E, N or Q; $Y_4$ is K, R or H; $Y_5$ is R, K or H; $Y_6$ is P; $Y_7$ is S, T or C. In some embodiments, $Y_1$ is limited to Y or E; and/or $Y_2$ is limited to N or S; and/or $Y_3$ is limited to D or N; and/or $Y_4$ is limited to K; and/or $Y_5$ is limited to R or K; and/or $Y_6$ is limited to P; and/or $Y_7$ is limited to S.

Noting in particular that the VL CDR2 sequence of SEQ ID NO: 42 is derived from an antibody that may recognize a conformational Kv1.3 epitope distinct from the others in FIGS. 11A-11B, an alternative consensus sequence is VL CDR2 Motif 4:

$$Y_1 \ Y_2 \ Y_3 \ Y_4 \ Y_5 \ Y_6 \ Y_7 \quad \text{(SEQ ID NO: 120)}$$

where $Y_1$ is E or D; $Y_2$ is N or Q; $Y_3$ is N or Q; $Y_4$ is K, R or H; $Y_5$ is R, K or H; $Y_6$ is P; and $Y_7$ is S, T or C. In some embodiments, $Y_1$ is limited to E; and/or $Y_2$ is limited to N; and/or $Y_3$ is limited to N; and/or $Y_4$ is limited to K; and/or $Y_5$ is limited to R; and/or $Y_6$ is limited to P; and/or $Y_7$ is limited to S.

For the VL CDR3, one consensus sequence is VL CDR3 Motif 1:

$$Z_1 \ Z_2 \ Z_3 \ Z_4 \ Z_5 \ Z_6 \ Z_7 \ Z_8 \ Z_9 \ Z_{10} \quad \text{(SEQ ID NO: 121)}$$

where $Z_1$ is G, A, V, L, I, M, C, S or T; $Z_2$ is G, A, N, Q, V, L, I, M, S, T or C; $Z_3$ is Y, F, W, E, D, T, S, C, I, V, L, M, A, G, R, K or H; $Z_4$ is D, E, I, V, L, M, G or A; $Z_5$ is S, T, C, G, A, D, E, N, Q, I, V, L, M, K, R or H; $Z_6$ is N, Q, S, T, C, I, V, L, M, G or A; $Z_7$ is T, S, C, I, V, L, M, A, G, R, K, H, Y, F, W, D, E, N or Q; $Z_8$ is Y, F, W, N, Q, T, S, C, V, L, I, M, A, D, E, G or absent; $Z_9$ is V, L, I, M, A, G, D, E or absent; and $Z_{10}$ is A, G, V, L, I, M, T, S, C, D, E, Y, F, W or absent. In some embodiments, $Z_1$ is limited to G or C; and/or $Z_2$ is limited to G, N, A, S or T; and/or $Z_3$ is limited to Y, E, W, T, F, I, S, A or R; and/or $Z_4$ is limited to D, E or I; and/or $Z_5$ is limited to S, G, D, N, I or K; and/or $Z_6$ is limited to N, S, T or I; and/or $Z_7$ is limited to T, I, G, R, Y, E, S, A or N; and/or $Z_8$ is limited to Y, N, T, V, D, G or absent; and/or $Z_9$ is limited to V, D or absent; and/or $Z_{10}$ is limited to A, T, D, S, Y or absent.

Figure 8B:
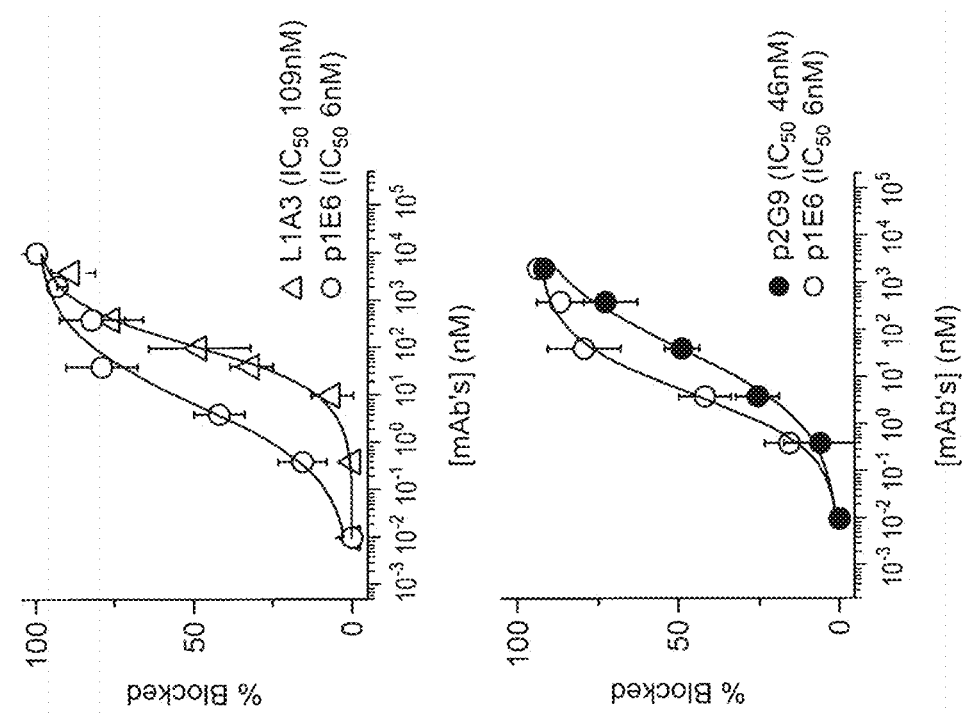
FIG. 8B shows dose-response curves comparing antibody p1E6 with antibody L1A3 (top panel) and p2G9 (bottom panel). $IC_{50}$ values for each antibody were calculated as 6 nM (p1E6), 46 nM (p2G9) and 10 9 nM (L1A3).
Figure 8A:
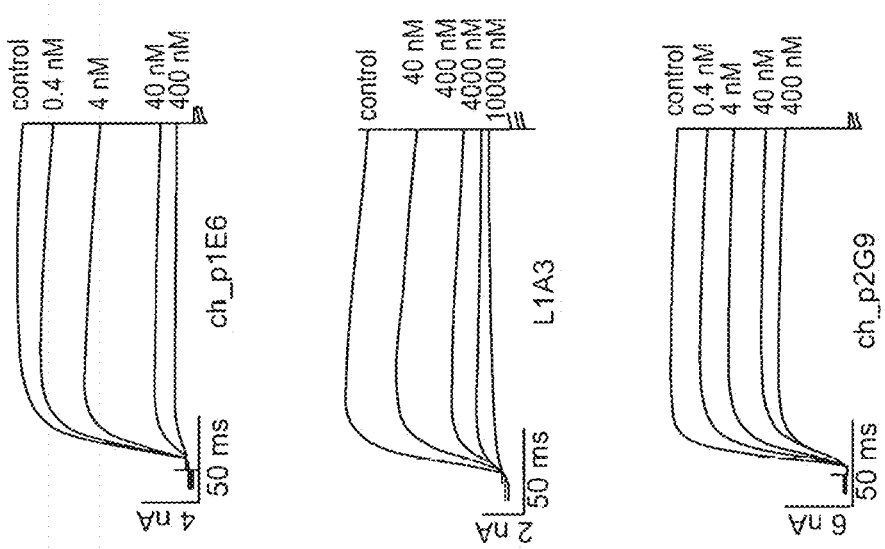
FIG. 8A shows dose response analysis of three antibodies (p1E6, L1A3 and p2G9) derived from chicken (ch_) that block Kv1.3 activity. Current recordings of cells incubated with ten-fold dilutions of antibody are shown.

Noting in particular that the VL CDR3 sequences of SEQ ID NOs: 3, 21, 22, 23, 24, 37, 38, 39 and 42 are derived from antibodies that inhibit Kv1.3 function distinct from the others in FIGS. 8A-8B, an alternative consensus sequence is VL CDR3 Motif 2:

$$Z_1 \ Z_2 \ Z_3 \ Z_4 \ Z_5 \ Z_6 \ Z_7 \ Z_8 \ Z_9 \quad \text{(SEQ ID NO: 122)}$$

where $Z_1$ is G, A, V, L, I or M; $Z_2$ is G, A, V, L, I, M, S, T or C; $Z_3$ is Y, F or W; $Z_4$ is D or E; $Z_5$ is S, T or C; $Z_6$ is S, T, C, N, Q, I, V, L, M, A or G; $Z_7$ is N, Q, T, S, C, D, E, I, V, L, M, A or G; $Z_8$ is G, A, V, L, I, M, Y, F or W; and $Z_9$ is F, Y, W, A, V, L, I, M, G or absent. In some embodiments, $Z_1$ is limited to G; and/or $Z_2$ is limited to G, T or S; and/or $Z_3$ is limited to Y or W; and/or $Z_4$ is limited to D; and/or $Z_5$ is limited to S; and/or $Z_6$ is limited to S, N or I; and/or $Z_7$ is limited to N, T, E or A; and/or $Z_8$ is G, Y or A; and/or $Z_9$ is limited to Y, A or absent.

Noting in particular that the VL CDR3 sequences of SEQ ID NO: 21, 22, 23, 24, 39 and 42 are derived from antibodies that are FACS positive for Jurkat cell binding distinct from the others in FIGS. 11A-11B, an alternative consensus sequence is VL CDR3 Motif 3:

$$Z_1 \ Z_2 \ Z_3 \ Z_4 \ Z_5 \ Z_6 \ Z_7 \ Z_8 \ Z_9 \quad \text{(SEQ ID NO: 123)}$$

where $Z_1$ is G, A, V, L, I or M; $Z_2$ is T, S or C; $Z_3$ is Y, F or W; $Z_4$ is D or E; $Z_5$ is S, T or C; $Z_6$ is I, V, L, M, A, G, S, T or C; $Z_7$ is E, D, A, G, V, L, I or M; $Z_8$ is A, G, V, L, I or M; and $Z_9$ is Y, F, W or absent. In some embodiments $Z_1$ is limited to G; and/or $Z_2$ is limited T or S; and/or $Z_3$ is limited to Y or W; and/or $Z_4$ is limited to D; and/or $Z_5$ is limited to S; and/or $Z_6$ is limited to I or S; and/or $Z_7$ is limited E or A; and/or $Z_8$ is limited to A or G; and/or $Z_9$ is limited to Y or absent.

Noting in particular that the VL CDR3 sequence of SEQ ID NO: 42 is derived from an antibody that may recognize a conformational Kv1.3 epitope distinct from the others in FIGS. 11A-11B, an alternative consensus sequence is VL CDR3 Motif 4:

$$Z_1 \ Z_2 \ Z_3 \ Z_4 \ Z_5 \ Z_6 \ Z_7 \ Z_8 \quad \text{(SEQ ID NO: 124)}$$

where $Z_1$ is G, A, V, L, I or M; $Z_2$ is S, T or C; $Z_3$ is W, F or Y; $Z_4$ is D or E; $Z_5$ is S, T or C; $Z_6$ is S, T or C; $Z_7$ is A, G, V, L, I or M; and $Z_8$ is G, A, V, L, I or M. In some embodiments $Z_1$ is limited to G; and/or $Z_2$ is limited S; and/or $Z_3$ is limited W; and/or $Z_4$ is limited to D; and/or $Z_5$ is limited to S; and/or $Z_6$ is limited to S; and/or $Z_7$ is limited to A; and/or $Z_8$ is limited to G.

Variable Heavy Chain Sequences

VH Sequence Alignments.

Alignments of all of the VH sequences described above are shown in FIGS. 13A-13C. The figures indicate the approximate locations of the three CDR regions (bold, underscore) and the SEQ ID NO corresponding to each sequence.

Unique VH CDR Sequences.

Alignments of the unique CDR sequences of the VHs of FIGS. 13A-13C are shown in FIG. 14. Of the 40 VH sequences, there are 13 unique CDR1 sequences, 25 unique CDR2 sequences and 27 unique CDR3 sequences, as shown in FIG. 14.

VH CDR Consensus Sequences.

Based on the sequences disclosed in FIG. 14, as well as structure/function characteristics of the naturally occurring amino acids, consensus sequences for the VH CDRs can be determined.

For the VH CDR1, one consensus sequence is VH CDR1 Motif 1:

$$X_1 \ X_2 \ X_3 \ X_4 \ X_5 \quad \text{(SEQ ID NO: 442)}$$

where $X_1$ is N, Q, S, T or C; $X_2$ is D, E, S, T or C; $X_3$ is Y, F, W, H, K or R; $X_4$ is G, A, N, Q, V, L, M, I, S, T or C; and $X_5$ is M, V, L, I, G or A. In some embodiments, $X_1$ is limited to N or S; and/or $X_2$ is limited to D, S or T; and/or $X_3$ is limited to Y, H, R or F; and/or $X_4$ is limited to G, N, A, Q, S or T; and/or $X_5$ is limited to M or V.

Noting in particular that the VH CDR1 sequence of SEQ ID NOs: 125, 129, 130, 131, 132, 133, 141, 159 and 160 are derived from antibodies that inhibit Kv1.3 function distinct from the others in FIGS. 13A-13C, an alternative consensus sequence is VH CDR1 Motif 2:

$$X_1 \ X_2 \ X_3 \ X_4 \ X_5 \quad \text{(SEQ ID NO: 443)}$$

where $X_1$ is S, T, C, N or Q; $X_2$ is S, T, C, D or E; $X_3$ is Y, F, W, K, R or H; $X_4$ is G, A, V, L, I or M; $X_5$ is M, A, V, L, G or I. In some embodiments, $X_1$ is limited to S or N; and/or $X_2$ is limited to S or D; and/or $X_3$ is limited to Y, R or H; and/or $X_4$ is limited to A or G; and/or $X_5$ is limited to M.

Noting in particular that the VH CDR1 sequences of SEQ ID NOs: 129, 130, 131, 132, 133 and 141 are derived from antibodies that are FACS positive for Jurkat cell binding distinct from the others in FIGS. 13A-13C, an alternative consensus sequence is VH CDR1 Motif 3:

$$X_1 \ X_2 \ X_3 \ X_4 \ X_5 \quad \text{(SEQ ID NO: 444)}$$

where $X_1$ is S, T or C; $X_2$ is D, E, S, T or C; $X_3$ is R, K, H, Y, F or W; $X_4$ is G, A, V, L, I, M, N or Q; and $X_5$ is M, A, G, V, L, or I. In some embodiments, $X_1$ is limited to S; and/or $X_2$ is limited to D or S; and/or $X_3$ is limited to R, Y or H; and/or $X_4$ is limited to G or Q; and/or $X_5$ is limited to M.

Noting in particular that the VH CDR1 sequence of SEQ ID NO: 129 is derived from an antibody that may recognize a conformational Kv1.3 epitope distinct from the others in FIGS. 10-10C, an alternative consensus sequence is VH CDR1 Motif 4:

$$X_1 \ X_2 \ X_3 \ X_4 \ X_5 \quad \text{(SEQ ID NO: 445)}$$

where $X_1$ is S, T or C; $X_2$ is S, T or C; $X_3$ is H, R or K; $X_4$ is G, A, V, I, L or M; and $X_5$ is M, A, G, I, L, or V. In some embodiments, $X_1$ is limited to S; and/or $X_2$ is limited to S; and/or $X_3$ is limited to H; and/or $X_4$ is limited to G; and/or $X_5$ is limited to M.

For the VH CDR2, one consensus sequence is VH CDR2 Motif 1:

$$Y_1Y_2Y_3Y_4Y_5Y_6Y_7Y_8Y_9Y_{10}Y_{11}Y_{12}Y_{13}Y_{14}Y_{15}Y_{16}Y_{17} \quad \text{(SEQ ID NO: 446)}$$

where $Y_1$ is G, A, V, L, I, M, E, D, K, R, H, S, T or C; $Y_2$ is I, V, L, M or A; $Y_3$ is Y, F, W, S, T, C, D, E, N or Q; $Y_4$ is S, T, C or absent; $Y_5$ is S, T, C, N, Q, R, K, H, A, G, V, L, I, M, D or E; $Y_6$ is S, T, C, D, E, A, G, V, L, I, M, F, Y or W; $Y_7$ is G, A, V, L, I, M, D or E; $Y_8$ is R, K, H, N, Q, S, T, C, G, A, V, L, I or M; $Y_9$ is Y, F, W, S, T, C, R, K, H, E, D, G, A, V, L, I, M or absent; $Y_{10}$ is T, S, C, A, G, V, L, I or M; $Y_{11}$ is Y, F, W, A, G, V, L, I, M, R, K, H, S, T, C, D, E, N or Q; $Y_{12}$ is Y, F, W, H, K, R or P; $Y_{13}$ G, A, V, L, I, M, T, S or C; $Y_{14}$ is A, G, V, L, I, M, S, T, C or P; $Y_{15}$ is A, G, V, L, I or M; $Y_{16}$ is V, L, I, M, A or G; and $Y_{17}$ is Q, N, K, R, H, D or E. In some embodiments, $Y_1$ is limited to G, A, E, K, V or S; and/or $Y_2$ is limited to I or V; and/or $Y_3$ is limited to Y, S, D, N, E or T; and/or $Y_4$ is limited to S or absent; and/or $Y_5$ is limited to absents, N, R, A, D, K or V; and/or $Y_6$ is limited to S, D, A, V, T, F or G; and/or $Y_7$ is limited to G, A or D; and/or $Y_8$ is limited to R, N, S, G or T; and/or $Y_9$ is limited to Y, F, S, R, T, E, G, D or absent; and/or $Y_{10}$ is limited to T or A; and/or Y11 is limited to Y, A R, G, S, L, D, N or H; and/or Y12 is limited to Y, H or P; and/or Y13 is limited to G, T or A; and/or Y14 is limited to A, S or P; and/or Y15 is limited to A; and/or Y16 is limited to V; and/or Y17 is limited to Q, K, R, D or E.

Noting in particular that the VH CDR2 sequence of SEQ ID NOs: 125, 129, 130, 131, 132, 133, 141, 159 and 160 are derived from antibodies that inhibit Kv1.3 function distinct from the others in FIGS. 13A-13C, an alternative consensus sequence is VH CDR2 Motif 2:

$$Y_1 \ Y_2 \ Y_3 \ Y_4 \ Y_5 \ Y_6 \ Y_7 \ Y_8 \ Y_9 \ Y_{10} \ Y_{11} \ Y_{12} \ Y_{13} \ Y_{14} \ Y_{15} \ Y_{16}Y_{17} \quad \text{(SEQ ID NO: 447)}$$

where $Y_1$ is S, T, C, G, A, V, L, I, M or absent; $Y_2$ is I, V, L, M, A or G; $Y_3$ is I, V, L, M, A, G, S, T, C, Y, F or W; $Y_4$ is N, Q, S, T, C or absent; $Y_5$ is A, V, L, I, M, G, S, T, C, R, K or H; $Y_6$ is D, E, G, A, V, L, I, M, F, W, S, T or C; $Y_7$ is D, E, G, A, V, L, I, A or M; $Y_8$ is S, T, C, N, Q, R, K or H; $Y_9$ is T, S, C, Y, F, W, R, K or H; $Y_{10}$ is S, T, C, A, V, L, I, M or G; $Y_{11}$ is Y, F, W K, R, H, G, V, L, I, M or A; $Y_{12}$ is Y, F, W, K, R or H; $Y_{13}$ is A, G, V, L, I or M; $Y_{14}$ is A, G, V, L, I or M; $Y_{15}$ is V, L, I, M, A or G; $Y_{16}$ is V, L, I, M, A or G and $Y_{17}$ is K, R, H, Q or N. In some embodiments, $Y_1$ is limited to S, G or absent; and/or $Y_2$ is limited to I, A or G; and/or $Y_3$ is limited to S, Y or I; and/or $Y_4$ is limited to N, S or absent; and/or $Y_5$ is limited to V, S or R; and/or $Y_6$ is limited to D, A, F or S; and/or $Y_7$ is limited to D or G; and/or $Y_8$ is limited to S, N or R; and/or $Y_9$ is limited to S, Y or R; and/or $Y_{10}$ is limited to T or A; and/or $Y_{11}$ is limited to Y, H, G, R or A; and/or $Y_{12}$ is limited to Y or H; and/or $Y_{13}$ is limited to G; and/or $Y_{14}$ is limited to A; and/or $Y_{15}$ is limited to A; and/or $Y_{16}$ is limited to V; and/or $Y_{17}$ is K or Q Noting in particular that the VH CDR2 sequences of SEQ ID NOs: 129, 130, 131, 132, 133 and 141 are derived from antibodies that are FACS positive for Jurkat cell binding distinct from the others in FIGS. 13A-13C, an alternative consensus sequence is VH CDR2 Motif 3:

$$Y_1 \ Y_2 \ Y_3 \ Y_4 \ Y_5 \ Y_6 \ Y_7 \ Y_8 \ Y_9 \ Y_{10} \ Y_{11} \ Y_{12} \ Y_{13} \ Y_{14} \ Y_{15} \quad \text{(SEQ ID NO: 448)}$$

$$Y_{16}$$

where $Y_1$ is G, A, V, L, I or M; $Y_2$ is I, V, L, A, G or M; $Y_3$ is S, T, C, N or Q; $Y_4$ is S, T, C, R, K or H; $Y_5$ is S, T, C, F, Y, W, D or E; $Y_6$ is G, A, V, L, I or M; $Y_7$ is R, K, H, N, Q, S, T or C; $Y_8$ is S, T, C, R, K or H; $Y_9$ is S, T, C, A, G, V, L, I or M; $Y_{10}$ is A, G, V, L, I, M, R, K or H; $Y_{11}$ is Y, F, W, H, R or K; $Y_{12}$ is G, A, V, I, L or M; $Y_{13}$ is A, G, V, I, L or M; $Y_{14}$ is A, G, V, I, L or M; $Y_{15}$ is V, A, G, I, L or M; and $Y_{16}$ is K, R or H. In some embodiments, $Y_1$ is limited to G or A; and/or $Y_2$ is limited to I; and/or $Y_3$ is limited to S or N; and/or $Y_4$ is limited to S or R; and/or $Y_5$ is limited to S, F or D; and/or $Y_6$ is limited to G; and/or $Y_7$ is limited to R, N or S; and/or $Y_8$ is limited to S or R; and/or $Y_9$ is limited to A or T; and/or $Y_{10}$ is limited to A, G or R; and/or $Y_{11}$ is limited to Y or H; and/or $Y_{12}$ is limited to G; and/or $Y_{13}$ is limited to A; and/or $Y_{14}$ is limited to A; and/or $Y_{15}$ is limited to V; and/or $Y_{16}$ is limited to K.

Noting in particular that the VH CDR2 sequence of SEQ ID NO: 129 is derived from an antibody that may recognize a conformational Kv1.3 epitope distinct from the others in FIGS. 13A-13C, an alternative consensus sequence is VH CDR2 Motif 4:

$$Y_1 \ Y_2 \ Y_3 \ Y_4 \ Y_5 \ Y_6 \ Y_7 \ Y_8 \ Y_9 \ Y_{10} \ Y_{11} \ Y_{12} \ Y_{13} \ Y_{14} \ Y_{15} \quad \text{(SEQ ID NO: 449)}$$

$$Y_{16}$$

where $Y_1$ is G, A, V, I, L or M; $Y_2$ is I, V, L, M, G or A; $Y_3$ is S, T or C; $Y_4$ is R, K or H; $Y_5$ is D or E; $Y_6$ is G, A, V, I, L or M; $Y_7$ is S, T or C; $Y_8$ is R, K or H; $Y_9$ is T, S or C; $Y_{10}$ is R, K or H; $Y_{11}$ is Y, F or W; $Y_{12}$ is G, A, V, I, L or M; $Y_{13}$ is A, G, V, I, L or M; $Y_{14}$ is A, G, V, I, L or M; $Y_{15}$ is V, G, A, I, L or M; and $Y_{16}$ is K, R or H. In some embodiments, $Y_1$ is limited to G; and/or $Y_2$ is limited to I; and/or $Y_3$ is limited to S; and/or $Y_4$ is limited to R; and/or $Y_5$ is limited to D; and/or $Y_6$ is limited to G; and/or $Y_7$ is limited to S; and/or $Y_8$ is limited to R; and/or $Y_9$ is limited to T; and/or $Y_{10}$ is limited to R; and/or $Y_{11}$ is limited to Y; and/or $Y_{12}$ is limited to G; and/or $Y_{13}$ is limited to A; and/or $Y_{14}$ is limited to A; and/or $Y_{15}$ is limited to V; and/or $Y_{16}$ is limited to K.

For the VH CDR3, one consensus sequence is VH CDR3 Motif 1:

$$Z_1 \ Z_2 \ Z_3 \ Z_4 \ Z_5 \ Z_6 \ Z_7 \ Z_8 \ Z_9 \ Z_{10} \ Z_{11} \ Z_{12} \ Z_{13} \ Z_{14} \ Z_{15} \quad \text{(SEQ ID NO: 450)}$$

$$Z_{16} \ Z_{17} \ Z_{18} \ Z_{19} \ Z_{20} \ Z_{21} \ Z_{22} \ Z_{23} \ Z_{24} \ Z_{25} \ Z_{26} \ Z_{27}$$

where $Z_1$ is N, Q, S, T, C, A, G, V, L, I, M, D or E; $Z_2$ is A, G, V, L, I, M, S, T, C, Y, F, W, N or Q; $Z_3$ is D, E, G, A, V, L, I, M, Y, F, W, S, T, C, H, R, K or absent; $Z_4$ is S, T, C, E, D, N, Q, G, A, V, I, L, M, R, K, H or absent; $Z_5$ is G, A, V, L, I, M, C, S, T or absent; $Z_6$ is Y, F, W, C, S, T, R, K, H or absent; $Z_7$ is Y, F, W, N, Q, C, S, T or absent; $Z_8$ is W, F, Y or absent; $Z_9$ is N, Q or absent; $Z_{10}$ is T, S, C or absent; $Z_{11}$ is C, S, T, Y, F, W, A, G, V, L, I, M or absent; $Z_{12}$ is T, S, C, N, Q, G, A, V, L, I, M, D, E, Y, F, W or absent; $Z_{13}$ is G, A, V, L, I, M, C, S, T, D, E, K, R, H or absent; $Z_{14}$ is Y, F, W, A, G, V, L, I, M, S, T, C, P, D, E or absent; $Z_{15}$ is N, Q, S, T, C, G, A, V, L, I, M, R, K, H or absent; $Z_{16}$ is S, T, G, A, V, L, I, M or absent; $Z_{17}$ is A, G, V, L, I M, W, F, Y, T, S, C, D, E or absent; $Z_{18}$ is D, E, T, S, C, A, G, V, L, I, M, P, W, F, Y or absent; $Z_{19}$ is Y, F, W, A, G, V, L, I, M, N, Q, S, T, C or absent; $Z_{20}$ is G, A, V, L, I, M, T, S, C or absent; $Z_{21}$ is A, G, V, L, I, M, P, Y, F, W, S, T, C or absent; $Z_{22}$ is G, A, V, L, I, M, H, K, R, D, E, S, T, C, Y, F, W or absent; $Z_{23}$ is Y, F, W, E, D, S, T, C, N, Q, L, A, G, V, I or M; $Z_{24}$ is I, V, L, A, G or M; $Z_{25}$ is D or E, $Z_{26}$ is A, G, V, L, I, M, S, T or C; and $Z_{27}$ is W, F or Y. In some embodiments, $Z_1$ is limited to N, S, C, A, G, D or T; and/or $Z_2$ is limited to A, S, T, Y, N, G, V or F; and/or $Z_3$ is limited to D, G, Y, S, H, L or absent; and/or $Z_4$ is limited to S, T, E, N, D, G, R, C, Q or absent; and/or $Z_5$ is limited to G, C or absent; and/or $Z_6$ is limited to Y, C, R or absent; and/or $Z_7$ is limited to Y, N, C or absent; and/or $Z_8$ is limited to W or absent; and/or $Z_9$ is limited to N or absent; and/or $Z_{10}$ is limited to T or absent; and/or $Z_{11}$ is limited to C, Y, A or absent; and/or $Z_{12}$ is limited to T, N, G, D, Y, A, C, S or absent; and/or $Z_{13}$ is limited to G, C, D, K, A or absent; and/or $Z_{14}$ is limited to Y, A, S, P, T, D or absent; and/or $Z_{15}$ is limited to N, S, G, I, R, T or absent; and/or $Z_{16}$ is limited to C, G, S or absent; and/or $Z_{17}$ is limited to A, W, Y, G, T, I, D, V or absent; and/or $Z_{18}$ is limited to D, T, C, A, G, P, W or absent; and/or $Z_{19}$ is limited to Y, F, A, N, S, G or absent; and/or $Z_{20}$ is limited to G, T, A, I or absent; and/or $Z_{21}$ is limited to A, P, Y, V, T, I, L or absent; and/or $Z_{22}$ is limited to G, A, H, D, S, Y or absent; and/or $Z_{23}$ is limited to Y, E, S, N, L, T, D, C, I, G or A; and/or $Z_{24}$ is limited to I or M; and/or $Z_{26}$ is limited to A, S or T; and/or $Z_{27}$ is limited to W.

Noting in particular that the VH CDR3 sequence of SEQ ID NOs: 125, 129, 130, 131, 132, 133, 141, 159 and 160 are derived from antibodies that inhibit Kv1.3 function distinct from the others in FIGS. 13A-13C, an alternative consensus sequence is VH CDR3 Motif 2:

$$Z_1 \ Z_2 \ Z_3 \ Z_4 \ Z_5 \ Z_6 \ Z_7 \ Z_8 \ Z_9 \ Z_{10} \ Z_{11} \ Z_{12} \ Z_{13} \ Z_{14} \ Z_{15} \quad \text{(SEQ ID NO: 451)}$$

$$Z_{16} \ Z_{17} \ Z_{18} \ Z_{19} \ Z_{20} \ Z_{21}$$

Where $Z_1$ is S, T, C, V, L, I, M, A or G or absent; $Z_2$ is S, T, C, V, L, I, M, A or G or absent; $Z_3$ is Y, F, W or absent; $Z_4$ is Q, N, D, E, V, L, I, M, A, G or absent; $Z_5$ is C, S, T, N, Q, Y, F, W or absent; $Z_6$ is A, G, V, L, I, M, S, T, C, D or E; $Z_7$ is G, V, L, I, M, A, D, E, S, T, C or absent; $Z_8$ is D, E, Y, F, W, G, V, L, I, M, A, S, T or C; $Z_9$ is C, S, T, N, Q, G, V, L, I, M or A; $Z_{10}$ is C, S, T, F, Y, W, G, V, L, I, M or A; $Z_{11}$ is F, Y or W; $Z_{12}$ is T, S, C or absent; $Z_{13}$ is G, V, L, I, M, A, F, Y, W, S, T or C; $Z_{14}$ is Y, F, W, G, V, L, I, M or A; $Z_{15}$ is P, G, A, V, I, L or M; $Z_{16}$ is F, Y, W, G, V, L, I, M or A; $Z_{17}$ is G, A, V, I, L, M, S, T, C, D, E, F, Y or W; $Z_{18}$ is V, L, I, M, A or G; $Z_{19}$ is D or E; $Z_{20}$ is S, T, C, V, L, I, M, A or G; $Z_{21}$ is W, F or Y. In some embodiments, Z1 is limited to S, G or absent; and/or Z2 is limited to S, A or absent; and/or Z3 is limited to Y or absent; and/or Z4 is limited to Q, E, G or absent; and/or Z5 is limited to C, Y, N or absent; and/or Z6 is limited to A, D, S, C or A; and/or Z7 is limited to G, T, D or absent; and/or Z8 is limited to D, Y, G or S; and/or Z9 is limited to N, S, T or G; and/or Z10 is limited to C, G, S or Y; and/or Z11 is limited to W or Y; and/or Z12 is limited T or absent; and/or Z13 is limited to G, F, C or T; and/or Z14 is limited to Y, I G or A; and/or Z15 is limited to P, A or V; and/or Z16 is limited to Y or G; and/or Z17 is limited to G, S, E, L or Y; and/or Z18 is limited to I; and/or Z19 is limited to D; and/or Z20 is limited to T or A; and/or Z21 is limited to W.

Noting in particular that the VH CDR3 sequences of SEQ ID NOs: 129, 130, 131, 132, 133 and 141 are derived from antibodies that are FACS positive for Jurkat cell binding distinct from the others in FIGS. 13A-13C, an alternative consensus sequence is VH CDR3 Motif 3:

(SEQ ID NO: 452)
$Z_1Z_2Z_3Z_4Z_5Z_6Z_7Z_8Z_9Z_{10}Z_{11}Z_{12}Z_{13}Z_{14}Z_{15}Z_{16}Z_{17}Z_{18}Z_{19}$ $Z_{20}Z_{21}$ where $Z_1$ is G, A, V, I, L, M, S, T, C or absent; $Z_2$ is A, G, V, I, L, M or absent; $Z_3$ is Y, F, W or absent; $Z_4$ is D, E, G, A, V, I, L, M or absent; $Z_5$ is S, T, C, Y, F, W or absent; $Z_6$ is D, E, S, T or C; $Z_7$ is T, S, C, G, A, V, I, L or M; $Z_8$ is Y, F, W, S, T, C, G, A, V, I, L or M; $Z_9$ is T, S, C, G, A, V, I, L or M; $Z_{10}$ is S, T or C; $Z_{11}$ is G, V, L, I, M, A, Y, F or W; $Z_{12}$ is S, T, C, Y, F or W; $Z_{13}$ is F, Y, W, G, A, V, I, L, M or absent; $Z_{14}$ is G, A, V, I, L or M; $Z_{15}$ is G, A, V, I, L or M; $Z_{16}$ is G, A, V, L, I or M; $Z_{17}$ is E, D, S, T, C, G, A, V, I, L or M; $Z_{18}$ is V, L, I, M, A or G; $Z_{19}$ is D or E; $Z_{20}$ is V, L, I, M, A or G; and $Z_{21}$ is W, F or Y. In some embodiments, $Z_1$ is limited to G, S or absent; and/or $Z_2$ is limited to A or absent; and/or $Z_3$ is limited to Y or absent; and/or $Z_4$ is limited to G, E or absent; and/or $Z_5$ is limited to Y, C or absent; and/or $Z_6$ is limited to D, C or absent; and/or $Z_7$ is limited to S or G; and/or $Z_8$ is limited to T, S or Y; and/or $Z_9$ is limited to S or G; and/or $Z_{10}$ is limited to T, C or S; and/or $Z_{11}$ is limited to G or W; and/or $Z_{12}$ is limited to Y, C or T; and/or $Z_{13}$ is limited to G, F or absent; and/or $Z_{14}$ is limited to G, A or I; and/or $Z_{15}$ is limited to V or A; and/or $Z_{16}$ is G; and/or $Z_{17}$ is limited to E, L or S; and/or $Z_{18}$ is limited to I; and/or $Z_{19}$ is limited to D; and/or $Z_{20}$ is limited to A; and/or $Z_{21}$ is limited to W.

Noting in particular that the VH CDR3 sequence of SEQ ID NO: 129 is derived from an antibody that may recognize a conformational Kv1.3 epitope distinct from the others in FIGS. 10A-10C, an alternative consensus sequence is VH CDR3 Motif 4:

(SEQ ID NO: 453)
$Z_1Z_2Z_3Z_4Z_5Z_6Z_7Z_8Z_9Z_{10}Z_{11}Z_{12}Z_{13}Z_{14}Z_{15}Z_{16}Z_{17}Z_{18}Z_{19}$ $Z_{20}Z_{21}$ where $Z_1$ is S, T or C; $Z_2$ is A, G, V, I, L or M; $Z_3$ is Y, F or W; $Z_4$ is E or D; $Z_5$ is C, S or T; $Z_6$ is D or E; $Z_7$ is G, A, V, I, L or M; $Z_8$ is Y, F or W; $Z_9$ is S, T or C; $Z_{10}$ is S, T or C; $Z_{11}$ is W, F or Y; $Z_{12}$ is T, S or C; $Z_{13}$ is E or D; $Z_{14}$ is I, A, G, V, L or M; $Z_{15}$ is A, G, V, I, L or M; $Z_{16}$ is G, A, V, I, L or M; $Z_{17}$ is S, T or C; $Z_{18}$ is I, G, A, V, L or M; $Z_{19}$ is D or E; $Z_{20}$ is A, G, V, I, L or M; and $Z_{21}$ is W, F or Y. In other embodiments, $Z_1$ is limited to S; and/or $Z_2$ is limited to A; and/or $Z_3$ is limited to Y; and/or $Z_4$ is limited to E; and/or $Z_5$ is limited to C; and/or $Z_6$ is limited to D; and/or $Z_7$ is limited to G; and/or $Z_8$ is limited to Y; and/or $Z_9$ is limited to S; and/or $Z_{10}$ is limited to C; and/or $Z_{11}$ is limited to W; and/or $Z_{12}$ is limited to T; and/or $Z_{13}$ is limited to E; and/or $Z_{14}$ is limited to I; and/or $Z_{15}$ is limited to A; and/or $Z_{16}$ is limited to G; and/or $Z_{17}$ is limited to S; and/or $Z_{18}$ is limited to I; and/or $Z_{19}$ is limited to D; and/or $Z_{20}$ is limited to A; and/or $Z_{21}$ is limited to W.

CDR Canonical Structures

Prediction of CDR structures in light and heavy chain variable regions is based on the work of Chothia and colleagues (e.g., Chothia et al. (1987), *J. Mol. Biol.* 196: 901-17; Al-Lazikani et al. (1997), *J. Mol. Biol.* 273:927-48), and focuses on conserved canonical CDR structures displayed by immunoglobulin hypervariable regions (North et al. (2011), *J. Mol. Biol.* 406(2):228-56). To determine potential canonical structures associated with the disclosed anti-Kv1.3 antibodies derived from chickens (Table 4), light and heavy chain variable regions from each anti-Kv1.3 clone were submitted for sequence analysis in the "SAbDAb" structural antibody database (Dunbar et al. (2014), *Nucleic Acids Res.* 42:D1140-D1146). The RSCB Protein Data Bank (PDB) structures with the highest percentage identity were further analyzed in the PyIgClassify database to identify the associated CDR loop conformations. In some instances more than one PDB structure with the same percent identity was identified by SAbDAb analysis. In those cases, the canonical structures for each PDB hit was determined with the PyIgClassify database (Table 5).

TABLE 5

PDB structure and CDR canonical structure assignments of anti-Kv1.3 antibodies derived from chickens.

| SAbDAb Sequence Analysis | | | | | | | |
|---|---|---|---|---|---|---|---|
| mAb Clone | PDB Structure | Percent Identity (full variable region) | PyIgClassify CDR Canonical Structure Assignments | | | | |
| | | | H1 | H2 | H3 | L1 | L2 | L3 |
| 19724p2.A2 | 5d72 | 60.28 | H1-13-1 | H2-12-1 | H3-8-2 | L1-11-3 | L2-6-* | L3-9-* |
| | 5d70 | 60.28 | H1-13-1 | H2-10-2 | H3-8-2 | L1-11-3 | | L3-9-* |
| 19724p2.A3 | 5d70 | 65.09 | H1-13-1 | H2-10-2 | H3-8-2 | L1-11-3 | | L3-9-* |
| 19724p2.A5 | 4qci | 63.01 | H1-13-1 | H2-10-2 | H3-13-* | L1-11-3 | L2-8-1 | L3-9-* |
| 19724p2.A7 | 5d7s | 63.33 | H1-13-1 | H2-12-1 | H3-8-2 | L1-11-3 | L2-6-* | L3-9-* |
| | 5c7x | 63.33 | H1-13-1 | H2-12-1 | H3-8-2 | L1-11-3 | L2-6-* | L3-9-* |
| 19724p2.B5 | 5d71 | 60.56 | H1-13-1 | H2-12-1 | H3-8-2 | L1-11-3 | | L3-9-* |
| | 5d70 | 60.56 | H1-13-1 | H2-10-2 | H3-8-2 | L1-11-3 | | L3-9-* |
| 19724p2.C4 | 5d7s | 63.5 | H1-13-1 | H2-12-1 | H3-8-2 | L1-11-3 | L2-6-* | L3-9-* |
| | 5c7x | 63.5 | H1-13-1 | H2-12-1 | H3-8-2 | L1-11-3 | L2-6-* | L3-9-* |
| 19724p2.D1 | 5d72 | 63.67 | H1-13-1 | H2-12-1 | H3-8-2 | L1-11-3 | L2-6-* | L3-9-* |
| | 5d70 | 63.67 | H1-13-1 | H2-10-2 | H3-8-2 | L1-11-3 | | L3-9-* |

TABLE 5-continued

PDB structure and CDR canonical structure assignments of anti-Kv1.3 antibodies derived from chickens.

SAbDAb Sequence Analysis

| mAb Clone | PDB Structure | Percent Identity (full variable region) | H1 | H2 | H3 | L1 | L2 | L3 |
|---|---|---|---|---|---|---|---|---|
| 19724p2.D2 | 5d72 | 64.31 | H1-13-1 | H2-12-1 | H3-8-2 | L1-11-3 | L2-6-* | L3-9-* |
|  | 5d70 | 64.31 | H1-13-1 | H2-10-2 | H3-8-2 | L1-11-3 |  | L3-9-* |
| 19724p2.D9 | 4qhu | 62.79 | H1-13-1 | H2-10-* | H3-8-2 | L1-11-3 | L2-8-1 | L3-11-1 |
| 19724p2.E6 | 5d72 | 64.28 | H1-13-1 | H2-12-1 | H3-8-2 | L1-11-3 | L2-6-* | L3-9-* |
| 19724p2.F7 | 5d72 | 65.72 | H1-13-1 | H2-12-1 | H3-8-2 | L1-11-3 | L2-6-* | L3-9-* |
|  | 5d70 | 65.72 | H1-13-1 | H2-10-2 | H3-8-2 | L1-11-3 |  | L3-9-* |
| 19724p2.G9 | 5d70 | 65.09 | H1-13-1 | H2-10-2 | H3-8-2 | L1-11-3 |  | L3-9-* |
| 19724p2.H10 | 5d71 | 62.73 | H1-13-1 | H2-10-2 | H3-8-2 | L1-11-3 |  | L3-9-* |
| 19724p2.H12 | 5d72 | 64.31 | H1-13-1 | H2-12-1 | H3-8-2 | L1-11-3 | L2-6-* | L3-9-* |
|  | 5d70 | 64.31 | H1-13-1 | H2-10-2 | H3-8-2 | L1-11-3 |  | L3-9-* |
| 19724p2.H4 | 5d72 | 64.78 | H1-13-1 | H2-12-1 | H3-8-2 | L1-11-3 | L2-6-* | L3-9-* |
|  | 5d70 | 64.78 | H1-13-1 | H2-10-2 | H3-8-2 | L1-11-3 |  | L3-9-* |
| 19724p2.H6 | 5d72 | 63.67 | H1-13-1 | H2-12-1 | H3-8-2 | L1-11-3 | L2-6-* | L3-9-* |
|  | 5d70 | 63.67 | H1-13-1 | H2-10-2 | H3-8-2 | L1-11-3 |  | L3-9-* |
| 19724p1_A1 | 4qhu | 62.79 | H1-13-1 | H2-10-* | H3-8-2 | L1-11-3 | L2-8-1 | L3-11-1 |
| 19724p1_A5 | 5d71 | 64.31 | H1-13-1 | H2-10-2 | H3-8-2 | L1-11-3 |  | L3-9-* |
| 19724p1_A9 | 5d72 | 62.61 | H1-13-1 | H2-12-1 | H3-8-2 | L1-11-3 | L2-6-* | L3-9-* |
|  | 5d70 | 62.61 | H1-13-1 | H2-10-2 | H3-8-2 | L1-11-3 |  | L3-9-* |
| 19724p1_A11 | 5d70 | 63.03 | H1-13-1 | H2-10-2 | H3-8-2 | L1-11-3 |  | L3-9-* |
| 19724p1_B1 | 5d72 | 64.92 | H1-13-1 | H2-12-1 | H3-8-2 | L1-11-3 | L2-6-* | L3-9-* |
|  | 5d70 | 64.92 | H1-13-1 | H2-10-2 | H3-8-2 | L1-11-3 |  | L3-9-* |
| 19724p1_B11 | 5d70 | 66.19 | H1-13-1 | H2-10-2 | H3-8-2 | L1-11-3 |  | L3-9-* |
| 19724p1_C4 | 5d72 | 62.61 | H1-13-1 | H2-12-1 | H3-8-2 | L1-11-3 | L2-6-* | L3-9-* |
|  | 5d70 | 62.61 | H1-13-1 | H2-10-2 | H3-8-2 | L1-11-3 |  | L3-9-* |
| 19724p1_C12 | 5d72 | 66.82 | H1-13-1 | H2-12-1 | H3-8-2 | L1-11-3 | L2-6-* | L3-9-* |
| 19724p1_D2 | 5d72 | 62.73 | H1-13-1 | H2-12-1 | H3-8-2 | L1-11-3 | L2-6-* | L3-9-* |
| 19724p1_D8 | 5d72 | 63.38 | H1-13-1 | H2-12-1 | H3-8-2 | L1-11-3 | L2-6-* | L3-9-* |
| 19724p1_D11 | 5d70 | 62.91 | H1-13-1 | H2-10-2 | H3-8-2 | L1-11-3 |  | L3-9-* |
| 19724p1_E2 | 5d72 | 61.5 | H1-13-1 | H2-12-1 | H3-8-2 | L1-11-3 | L2-6-* | L3-9-* |
| 19724p1_E3 | 5d71 | 63.38 | H1-13-1 | H2-10-2 | H3-8-2 | L1-11-3 |  | L3-9-* |
| 19724p1_E6 | 5d70 | 64.95 | H1-13-1 | H2-10-2 | H3-8-2 | L1-11-3 |  | L3-9-* |
| 19724p1_F3 | 5d70 | 66.19 | H1-13-1 | H2-10-2 | H3-8-2 | L1-11-3 |  | L3-9-* |
| 19724p1_F6 | 5d72 | 60.37 | H1-13-1 | H2-12-1 | H3-8-2 | L1-11-3 | L2-6-* | L3-9-* |
| 19724p1_F7 | 5d72 | 66.35 | H1-13-1 | H2-12-1 | H3-8-2 | L1-11-3 | L2-6-* | L3-9-* |
|  | 5d70 | 66.35 | H1-13-1 | H2-10-2 | H3-8-2 | L1-11-3 |  | L3-9-* |
| 19724p1_F8 | 5d72 | 62.08 | H1-13-1 | H2-12-1 | H3-8-2 | L1-11-3 | L2-6-* | L3-9-* |
|  | 5d70 | 62.08 | H1-13-1 | H2-10-2 | H3-8-2 | L1-11-3 |  | L3-9-* |
| 19724p1_F9 | 5d72 | 66.82 | H1-13-1 | H2-12-1 | H3-8-2 | L1-11-3 | L2-6-* | L3-9-* |
|  | 5d70 | 66.82 | H1-13-1 | H2-10-2 | H3-8-2 | L1-11-3 |  | L3-9-* |
| 19724p1_G6 | 5d72 | 63.67 | H1-13-1 | H2-12-1 | H3-8-2 | L1-11-3 | L2-6-* | L3-9-* |
|  | 5d7s | 63.67 | H1-13-1 | H2-12-1 | H3-8-2 | L1-11-3 | L2-6-* | L3-9-* |
|  | 5c7x | 63.67 | H1-13-1 | H2-12-1 | H3-8-2 | L1-11-3 | L2-6-* | L3-9-* |
| 19724p1_H2 | 5d72 | 61.97 | H1-13-1 | H2-12-1 | H3-8-2 | L1-11-3 | L2-6-* | L3-9-* |
| 19724p1_H4 | 4qhu | 62.79 | H1-13-1 | H2-10-* | H3-8-2 | L1-11-3 | L2-8-1 | L3-11-1 |
| 19724p1_H7 | 5d70 | 62.85 | H1-13-1 | H2-10-2 | H3-8-2 | L1-11-3 |  | L3-9-* |
| 19724p1_H12 | 5d70 | 63.84 | H1-13-1 | H2-10-2 | H3-8-2 | L1-11-3 |  | L3-9-* |

*SAbDAb: Sequence searches based on full variable domain

Based on this analysis, anti-Kv1.3 antibodies may be comprised of the following PDB structures: 5d72, 5d70, 4qci, 5d7s, 5c7x, 5d71 and 4qhu.

Based on the PDB structures, anti-Kv1.3 antibodies may have the following canonical CDR structures: H1CDR is H1-13-1; H2 CDR is H2-12-1, H2-10-2 or H2-10-*; H3 CDR is H3-8-2 or H3-13-*; L1 CDR is L1-11-3; L2 CDR is L2-6-* or L2-8-1; and L3 CDR is L3-9-* or L3-11-1.

Noting in particular that anti-Kv1.3 antibody clones 19724p1_F8, 19724p1_A1, 19724p2_A3, 19724p2_G9, 19724p1_A11, 19724p1_D8, 19724p1_E6, 19724p1_H4 and 19724p1_H7 inhibit Kv1.3 activity, distinct from other discovered antibodies, the associated PDB structures of anti-Kv1.3 antibodies may comprise 5d72, 5d70 and 4qhu (Table 6). Based on these PDB structure assignments, functionally inhibiting Kv1.3 antibodies may comprise the following canonical CDR sequences: H1 CDR is H1-13-1; H2 CDR is H2-12-1, H2-10-2 or H2-10-*; H3 CDR is H3-8-2; L1 CDR is L1-11-3; L2 CDR is L2-6-* or L2-8-1 and L3 CDR is L3-9-* or L3-11-1.

Noting in particular that anti-Kv1.3 antibody clones 19724p1_A11, 19724p1_H7, 19724p2.G9, 19724p2.A3, 19724p1.E6 and 19724_D8 are FACS positive for Jurkat binding, distinct from other discovered antibodies, the associated PDB structures of anti-Kv1.3 antibodies may comprise 5d70 and 5d72 (Table 6). Based on these PDB structure assignments, FACS positive Jurkat binding Kv1.3 antibodies may comprise the following canonical CDR sequences: H1 CDR is H1-13-1; H2 CDR is H2-10-2 or H2-12-1; H3 CDR is H3-8-2; L1 CDR is L1-11-3; L2 CDR is L2-6-* and L3 CDR is L3-9-*.

Noting in particular that anti-Kv1.3 antibody clone 19724p1_E6 may recognize a conformational Kv1.3 epitope, distinct from other discovered antibodies, the associated PDB structures of anti-Kv1.3 antibodies may be comprised of 5d70 (Table 6). Based on this PDB structure assignment, conformational Kv1.3 antibodies may comprise the following canonical CDR sequences: H1 CDR is H1-13-1; H2 CDR is H2-10-2; H3 CDR is H3-8-2; L1 CDR is L1-11-3; and L3 CDR is L3-9-*.

TABLE 6

PDB structure and CDR canonical structure assignments of select anti-Kv1.3 antibodies derived from chickens.

| mAb Characteristic | Clones | PDB Structure | PyIgClassify CDR Canonical Structure Assignments | | | | | |
|---|---|---|---|---|---|---|---|---|
| | | | H1 | H2 | H3 | L1 | L2 | L3 |
| Inhibit Kv1.3 Activity | 19724p1_F8 | 5d72 | H1-13-1 | H2-12-1 | H3-8-2 | L1-11-3 | L2-6-* | L3-9-* |
| | | 5d70 | H1-13-1 | H2-10-2 | H3-8-2 | L1-11-3 | | L3-9-* |
| | 19724p1_A1 | 4qhu | H1-13-1 | H2-10-* | H3-8-2 | L1-11-3 | L2-8-1 | L3-11-1 |
| | 19724p2_A3 | 5d70 | H1-13-1 | H2-10-2 | H3-8-2 | L1-11-3 | | L3-9-* |
| | 19724p2_G9 | 5d70 | H1-13-1 | H2-10-2 | H3-8-2 | L1-11-3 | | L3-9-* |
| | 19724p1_A11 | 5d70 | H1-13-1 | H2-10-2 | H3-8-2 | L1-11-3 | | L3-9-* |
| | 19724p1_D8 | 5d72 | H1-13-1 | H2-12-1 | H3-8-2 | L1-11-3 | L2-6-* | L3-9-* |
| | 19724p1_E6 | 5d70 | H1-13-1 | H2-10-2 | H3-8-2 | L1-11-3 | | L3-9-* |
| | 19724p1_H4 | 4qhu | H1-13-1 | H2-10-* | H3-8-2 | L1-11-3 | L2-8-1 | L3-11-1 |
| | 19724p1_H7 | 5d70 | H1-13-1 | H2-10-2 | H3-8-2 | L1-11-3 | | L3-9-* |
| FACS Positive Jurkat Binding | 19724p1_A11 | 5d70 | H1-13-1 | H2-10-2 | H3-8-2 | L1-11-3 | | L3-9-* |
| | 19724p1_H7 | 5d70 | H1-13-1 | H2-10-2 | H3-8-2 | L1-11-3 | | L3-9-* |
| | 19724p2.G9 | 5d70 | H1-13-1 | H2-10-2 | H3-8-2 | L1-11-3 | | L3-9-* |
| | 19724p2.A3 | 5d70 | H1-13-1 | H2-10-2 | H3-8-2 | L1-11-3 | | L3-9-* |
| | 19724p1_D8 | 5d72 | H1-13-1 | H2-12-1 | H3-8-2 | L1-11-3 | L2-6-* | L3-9-* |
| | 19724p1_E6 | 5d70 | H1-13-1 | H2-10-2 | H3-8-2 | L1-11-3 | | L3-9-* |
| Recognizes Conformational epitope | 19724p1E6 | 5d70 | H1-13-1 | H2-10-2 | H3-8-2 | L1-11-3 | | L3-9-* |

Additional clones producing potentially useful anti-Kv1.3 antibodies were DNA sequenced and the corresponding amino acid sequences of light and heavy chain variable domains were deduced. Sequences are disclosed for ten antibodies derived from the GEM screen described above.

Variable Light Chain Sequences

VL Sequence Alignments.

Alignments of all of the VL sequences described above are shown in FIG. 19. The figure indicates the approximate locations of the three CDR regions (bold, underscore) and the SEQ ID NO corresponding to each sequence.

Unique VL CDR Sequences.

Alignments of the unique CDR sequences of the VLs of FIG. 19 are shown in FIG. 20. Of the 10 VL sequences, there are 6 unique CDR1 sequences, 5 unique CDR2 sequences and 7 unique CDR3 sequences, as shown in FIG. 20.

Variable Heavy Chain Sequences

VH Sequence Alignments.

Alignments of all of the VH sequences described above are shown in FIG. 21. The figure indicates the approximate locations of the three CDR regions (bold, underscore) and the SEQ ID NO corresponding to each sequence.

Unique VH CDR Sequences.

Alignments of the unique CDR sequences of the VHs of FIG. 21 are shown in FIG. 22. Of the 10 VH sequences, there are 7 unique CDR1 sequences, 7 unique CDR2 sequences and 7 unique CDR3 sequences, as shown in FIG. 22.

Antibodies Derived from Llamas:

Clones producing potentially useful anti-Kv1.3 antibodies were DNA sequenced and the corresponding amino acid sequences of light and heavy chain variable domains were deduced. Sequences are disclosed for nineteen antibodies derived from Kv1.3 immunized llamas as described above.

Variable Light Chain Sequences

VL Sequence Alignments.

Alignments of all of the VL sequences described above are shown in FIG. 15. The figure indicates the approximate locations of the three CDR regions (bold, underscore) and the SEQ ID NO corresponding to each sequence.

Unique VL CDR Sequences.

Alignments of the unique CDR sequences of the VLs of FIG. 15 are shown in FIG. 16. Of the 19 VL sequences, there are 19 unique CDR1 sequences, 13 unique CDR2 sequences and 17 unique CDR3 sequences, as shown in FIG. 16.

VL CDR Consensus Sequences.

Based on the sequences disclosed in FIG. 16, as well as structure/function characteristics of the naturally occurring amino acids, consensus sequences for the VL CDRs can be determined.

One consensus sequence is VL CDR1 Motif 5:

(SEQ ID NO: 430)
$X_1X_2X_3X_4X_5X_6X_7X_8X_9X_{10}X_{11}X_{12}X_{13}X_{14}X_{15}X_{16}X_{17}$ where $X_1$ is K, R, H, V, L, I, M, A, G, S, T or C; $X_2$ is S, T, C, G, V, L, I, M or A; $X_3$ is S, T, C, K, R or H; $X_4$ is Q, N, E, D, S, T or C; $X_5$ is S, T, C, G, V, L, I, M or A; $X_6$ is V, L, I, M, A, G, D, E, S, T or C; $X_7$ is A, G, V, L, I, or M; $X_8$ is S, T, C, H, K, R, F, W, Y, G, V, L, I, M or A; $X_9$ is G, A, V, L, I, M or absent; $X_{10}$ is S, T, C or absent; $X_{11}$ is N, Q, D, E or absent; $X_{12}$ is Q, N, G, V, L, I, M, A, E, D, Y, F, W, S, T or C; $X_{13}$ is K, R, H, N, Q, G, V, L, I, M, A, F, Y, W, S, T or C; $X_{14}$ is T, S, C, N or Q; $X_{15}$ is F, Y, W, S, T or C; X16 is G, V, L, I, M, A, F, Y, W or P and $X_{17}$ is N, Q, Y, F, W, T, S, C, D or E. In some embodiments, $X_1$ is limited to K, A, T or G; and/or $X_2$ is limited to S, A, T, G or L; and/or $X_3$ is limited to S, T or R; and/or $X_4$ is limited to Q, E or S; and/or $X_5$ is limited to S, T or G; and/or $X_6$ is limited to V, L, D or S; and/or $X_7$ is limited to L, V, M or I; and/or $X_8$ is limited to S, H, R, F, G or T; and/or $X_9$ is limited to G, A or absent; and/or $X_{10}$ is limited to S, T or absent; and/or $X_{11}$ is limited to N, D or absent; and/or $X_{12}$ is limited to Q, G, E, Y or S; and/or $X_{13}$ is limited to K, N, G, Y or S; and/or $X_{14}$ is limited to T, S or N; and/or $X_{15}$ is limited to Y or S; and/or $X_{16}$ is limited to L, A, F, V or P; and/or $X_{17}$ is limited to N, Y, T, S or D.

Noting in particular that the VL CDR1 sequence of SEQ ID NO: 231 is derived from an antibody that inhibits Kv1.3 function distinct from the others in FIG. 15, an alternative consensus sequence is VL CDR1 Motif 6:

$$X_1X_2X_3X_4X_5X_6X_7X_8X_9X_{10}X_{11}X_{12}X_{13}X_{14}X_{15}X_{16}X_{17}$$ (SEQ ID NO: 431)

where $X_1$ is K, R or H; $X_2$ is S, T or C; $X_3$ is S, T or C; $X_4$ is Q or N; $X_5$ is S, T, or C; $X_6$ is V, L, I, M, A or G; $X_7$ is V, L, I, M, A or G; $X_8$ is S, T or C; $X_9$ is V, L, I, M, A or G; $X_{10}$ is S, T or C; $X_{11}$ is N or Q; $X_{12}$ is N or Q; $X_{13}$ is K, R or H; $X_{14}$ is S, T or C; $X_{15}$ is Y, F or W; $X_{16}$ is V, L, I, M, A or G; and $X_{17}$ is N or Q. In some embodiments, $X_1$ is limited to K; and/or $X_2$ is limited to S; and/or $X_3$ is limited to S; and/or $X_4$ is limited to Q; and/or $X_5$ is limited to S; and/or $X_6$ is limited to V; and/or $X_7$ is limited to V; and/or $X_8$ is limited to S; and/or $X_9$ is limited to A; and/or $X_{10}$ is limited to S; and/or $X_{11}$ is limited to N; and/or $X_{12}$ is limited to Q; and/or $X_{13}$ is limited to K; and/or $X_{14}$ is limited to S; and/or $X_{15}$ is limited to Y; and/or $X_{16}$ is limited to L; and/or $X_{17}$ is limited to N.

For the VL CDR2, one consensus sequence is VL CDR2 Motif 5:

$$Y_1Y_2Y_3Y_4Y_5Y_6Y_7$$ (SEQ ID NO: 432)

where $Y_1$ is Y, F, W, Q, N, R, K, H, E or D; $Y_2$ is V, L, I, M, A, G, D, E, S, T or C; and $Y_3$ is S, T, C, V, L, I, M, A, G, N or Q; $Y_4$ is S, T, C, N, Q, K, R, H, V, L, I, M, A or G; $Y_5$ is R, K, H, Q or N; $Y_6$ is E, D, S, T, C, G, V, L, I, M, A, K, R or H and $Y_7$ is V, L, I, M, A, G, S, T or C. In some embodiments, $Y_1$ is limited to Y, Q, R, E, K or N; and/or $Y_2$ is limited to A, V, D or T; and/or $Y_3$ is limited to S, A, T or N; and/or $Y_4$ is limited to T, N, K, S or I; and/or $Y_5$ is limited to R, Q or H; and/or $Y_6$ is limited to E, S, D, G, A or H; and/or $Y_7$ is limited to L or S.

Noting in particular that the VL CDR2 sequences of SEQ ID NO: 231 is derived from an antibody that inhibits Kv1.3 function distinct from the others in FIG. 15, an alternative consensus sequence is VL CDR2 Motif 6:

$$Y_1Y_2Y_3Y_4Y_5Y_6Y_7$$ (SEQ ID NO: 433)

where $Y_1$ is Y, F or W; $Y_2$ is V, L, I, M, A or G; $Y_3$ is S, T or C; $Y_4$ is S, T or C; $Y_5$ is Q or N; $Y_6$ is E or D; and $Y_7$ is V, L, I, M, A or G. In some embodiments, $Y_1$ is limited to Y; and/or $Y_2$ is limited to A; and/or $Y_3$ is limited to S; and/or $Y_4$ is limited T; and/or $Y_5$ is limited to Q; and/or $Y_6$ is limited to E; and/or $Y_7$ is limited to L.

For the VL CDR3, one consensus sequence is VL CDR3 Motif 5:

$$Z_1Z_2Z_3Z_4Z_5Z_6Z_7Z_8Z_9Z_{10}Z_{11}Z_{12}$$ (SEQ ID NO: 434)

where $Z_1$ is Q, N, V, L, I, M, A or G; $Z_2$ is Q, N, S, T, C, V, L, I, M, A or G; $Z_3$ is V, L, I, M, A, G, F, Y, W or absent; $Z_4$ is K, R, H, V, L, I, M, A, G or absent; $Z_5$ is S, T, C, R, K, H or absent; $Z_6$ is V, L, I, M, A, G, R, K, H, S, T, C or absent; $Z_7$ is Y, F, W, S, T, C, G, V, L, I, M, A, N or Q; $Z_8$ is S, T, C, R, K, H, Y, F, W or absent; $Z_9$ is V, L, I, M, A, G, Y, F, W or absent; $Z_{10}$ is P, S, T, C, N or Q; $Z_{11}$ is F, Y, W, V, L, I, M, A, G, S, T or C; and $Z_{12}$ is N, Q, S, T, C, G, V, L, I, M, A or G. In some embodiments, $Z_1$ is limited to Q or A; and/or $Z_2$ is limited to Q, S or L; and/or $Z_3$ is limited to A, G, V, Y or absent; and/or $Z_4$ is limited to R, I or absent; and/or $Z_5$ is limited to T, S, H or absent; and/or $Z_6$ is limited to G, R, I, K, S or absent; and/or $Z_7$ is limited to Y, T, G, S or N; and/or $Z_8$ is limited to S, H, Y or absent; and/or $Z_9$ is limited to A, Y, F or absent; and/or $Z_{10}$ is limited to P, T or N; and/or $Z_{11}$ is limited to Y, W, I, L, M, V, T or A; and/or $Z_{12}$ is limited to N, S, T, A, I or V.

Noting in particular that the VL CDR3 sequences of SEQ ID NO 231 is derived from an antibody that inhibits Kv1.3 function distinct from the others in FIG. 15, an alternative consensus sequence is VL CDR3 Motif 6:

$$Z_1Z_2Z_3Z_4Z_5Z_6Z_7Z_8Z_9$$ (SEQ ID NO: 435)

where $Z_1$ is Q or N; $Z_2$ is Q or N; $Z_3$ is V, L, I, M, A or G; $Z_4$ is Y, F or W; $Z_5$ is S, T or C; $Z_6$ is V, L, I, M, A or G; $Z_7$ is P; $Z_8$ is Y, F or W; and $Z_9$ is N or Q. In some embodiments, $Z_1$ is limited to Q; and/or $Z_2$ is limited to Q; and/or $Z_3$ is limited to A; and/or $Z_4$ is limited to Y; and/or $Z_5$ is limited to S; and/or $Z_6$ is limited to A; and/or $Z_7$ is limited to P; and/or $Z_8$ is Y; and/or $Z_9$ is limited to N.

Variable Heavy Chain Sequences

VH Sequence Alignments.

Alignments of all of the VH sequences described above are shown in FIG. 17. The figure indicates the approximate locations of the three CDR regions (bold, underscore) and the SEQ ID NO corresponding to each sequence.

Unique VH CDR Sequences.

Alignments of the unique CDR sequences of the VHs of FIG. 17 are shown in FIG. 18. Of the 19 VH sequences, there are 18 unique CDR1 sequences, 18 unique CDR2 sequences and 18 unique CDR3 sequences, as shown in FIG. 18.

VH CDR Consensus Sequences.

Based on the sequences disclosed in FIG. 18, as well as structure/function characteristics of the naturally occurring amino acids, consensus sequences for the VH CDRs can be determined.

For the VH CDR1, one consensus sequence is VH CDR1 Motif 5:

$$X_1X_2X_3X_4X_5X_6X_7$$ (SEQ ID NO: 436)

where $X_1$ is S, T, C or absent; $X_2$ S, T, C, N, Q or absent; $X_3$ is Y, F, W, G, V, L, I, M, A, K, R, H, D, E, S, T, C, N or Q; $X_4$ is Y, F, W, S, T, C, N or Q; and $X_5$ is Y, F, W, V, L, I, M, A, G, S, T or C; $X_6$ is F, Y, W, V, L, I, M, A or G; and $X_7$ is S, T, C, V, L, I, M, A, G, N, Q, D, E, F, Y, W, K, R, or H. In some embodiments, $X_1$ is limited to T or absent; and/or $X_2$ is limited to T, S, N or absent; and/or $X_3$ is limited to Y, G, K, D, I, A, S or N; and/or $X_4$ is limited to Y, S, F, N or S; and/or $X_5$ is limited to Y, A, G, T, W or S; and/or $X_6$ is limited to W, I or M; and/or X7 is limited to T, S, G, N, E, A, Y or H.

Noting in particular that the VH CDR1 sequence of SEQ ID NO: 306 is derived from an antibody that inhibit Kv1.3 function distinct from the others in FIG. 17, an alternative consensus sequence is VH CDR1 Motif 6:

$X_1X_2X_3X_4X_5$ (SEQ ID NO: 437)

where $X_1$ is V, L, I, M, A or G; $X_2$ is N or Q; $X_3$ is V, L, I, M, A or G; $X_4$ is V, L, I, M, A or G; and $X_5$ is S, T or C. In some embodiments, $X_1$ is limited to I; and/or $X_2$ is limited to N; and/or $X_3$ is limited to G; and/or $X_4$ is limited to M; and/or $X_5$ is limited to S.

For the VH CDR2, one consensus sequence is VH CDR2 Motif 5:

$Y_1Y_2Y_3Y_4Y_5Y_6Y_7Y_8Y_9Y_{10}Y_{11}Y_{12}Y_{13}Y_{14}Y_{15}Y_{16}Y_{17}$ (SEQ ID NO: 438)

where $Y_1$ is V, L, I, M, A, G, N, Q, S, T or C; $Y_2$ is V, L, I, M, A, G, F, W or Y; $Y_3$ is V, L, I, M, A, G, P, S, T, C, N or Q; $Y_4$ is F, Y, W, V, L, I, M, A, G, N, Q, P, S, T or C; $Y_5$ is S, T, C, V, L, I, M, A, G, Y, F, W, D, E, K, R or H; $Y_6$ is V, L, I, M, A, G, D, E, S, T or C; $Y_7$ is V, L, I, M, A, G, D, E, S, T, C or absent; $Y_8$ is S, T, C, N, Q, D, E, R, K, H, V, L, I, M, A, G, N, Q or absent; $Y_9$ is F, Y, W, S, T, C, N, Q, V, L, I, M, A or G; $Y_{10}$ is Y, F, W, D, E, N, Q, S, T or C; $Y_{11}$ is Y, F or W; $Y_{12}$ is S, T, C, N, Q, V, L, I, M, A, G, R, K, H, D or E; $Y_{13}$ is P, N, Q, E or D; $Y_{14}$ is S, T, C, V, L, I, M, A, G, K, R or H; $Y_{15}$ is V, L, I, M, A, G, F, Y or W; $Y_{16}$ is K, R, H, N or Q; and $Y_{17}$ is S, T, C, V, L, I, M, A or G. In some embodiments, $Y_1$ is limited to A, V, N, T, S, G or Q; and/or $Y_2$ is limited to I, V or F; and/or $Y_3$ is limited to A, P, S, G, L or N; and/or $Y_4$ is limited to Y, G, N, P, W, S or T; and/or $Y_5$ is limited to S, A, Y, D, E, K or G; and/or $Y_6$ is limited to G, D or S; and/or $Y_7$ is limited to G, D, E, V, S or absent; and/or $Y_8$ is limited to S, N, D, R, T, A, G, I, N or absent; and/or $Y_9$ is limited to F, T, N or A; and/or $Y_{10}$ is limited to Y, D, N, S, W or T; and/or Y11 is limited to Y or F; and/or Y12 is limited to S, T, N, A, R or E; and/or Y13 is limited to P, Q, E or D; and/or Y14 is limited to S, A or K; and/or Y15 is limited to L, F, M or V; and/or Y16 is limited to K or Q; and/or Y17 is limited to S or G.

Noting in particular that the VH CDR2 sequence of SEQ ID NO: 306 is derived from an antibody that inhibits Kv1.3 function distinct from the others in FIG. 17, an alternative consensus sequence is VH CDR2 Motif 6:

$Y_1Y_2Y_3Y_4Y_5Y_6Y_7Y_8Y_9Y_{10}Y_{11}Y_{12}Y_{13}Y_{14}Y_{15}Y_{16}Y_{17}$ (SEQ ID NO: 439)

where $Y_1$ is S, T or C; $Y_2$ is V, L, I, M, A or G; $Y_3$ is N or Q; $Y_4$ is S, T or C; $Y_5$ is V, L, I, M, A or G; $Y_6$ is V, L, I, M, A or G; $Y_7$ is E or D; $Y_8$ is V, L, I, M, A or G; $Y_9$ is S, T or C; $Y_{10}$ is N or Q; $Y_{11}$ is Y, F or W; $Y_{12}$ is R, K or H; $Y_{13}$ is D or E; $Y_{14}$ is S, T or C; $Y_{15}$ is V, L, I, M A or G; $Y_{16}$ is K, R or H; and $Y_{17}$ is V, L, I, M, A or G. In some embodiments, $Y_1$ is limited to S; and/or $Y_2$ is limited to I; and/or $Y_3$ is limited to N; and/or $Y_4$ is limited to S; and/or $Y_5$ is limited to G; and/or $Y_6$ is limited to G; and/or $Y_7$ is limited to E; and/or $Y_8$ is limited to I; and/or $Y_9$ is limited to T; and/or $Y_{10}$ is limited to N; and/or $Y_{11}$ is limited to Y; and/or $Y_{12}$ is limited to R; and/or $Y_{13}$ is limited to D; and/or $Y_{14}$ is limited to S; and/or $Y_{15}$ is limited to V; and/or $Y_{16}$ is limited to K; and/or $Y_{17}$ is limited to G.

For the VH CDR3, one consensus sequence is VH CDR3 Motif 5:

$Z_1Z_2Z_3Z_4Z_5Z_6Z_7Z_8Z_9Z_{10}Z_{11}Z_{12}Z_{13}Z_{14}Z_{15}Z_{16}$ (SEQ ID NO: 440)

where $Z_1$ is N, Q, V, L, I, M, A, G, R, K, H, D, E, S, T, C or absent; $Z_2$ is R, K, H, S, T, C, V, L, I, M, A, G, P, F, Y, W or absent; $Z_3$ is V, L, I, M, A, G, S, T, C, P, R, K, H or absent; $Z_4$ is V, L, I, M, A, G, F, Y, W, D, E, N, Q or absent; $Z_5$ is F, Y, W, V, L, I, M, A, G, S, T, C or absent; $Z_6$ is F, Y, W, S, T, C, V, L, I, M, A, G or absent; $Z_7$ is S, T, C, K, R, H or absent; $Z_8$ is S, T, C, F, Y, W or absent; $Z_9$ is V, L, I, M, A, G, P, F, Y, W, Q, N or absent; $Z_{10}$ is F, Y, W, V, L, I, M, A, G, S, T, C or absent; $Z_{11}$ is P, V, L, I, M, A, G, S, T, C or absent; $Z_{12}$ is V, L, I, M, A, G, S, T, C, P, F, Y, W or absent; $Z_{13}$ is V, L, I, M, A, G, N, Q, E, D, S, T, C or absent; $Z_{14}$ is Y, F, W, V, L, I, M, A, G or absent; $Z_{15}$ is E, D, V, L, I, M, A, G, S, T, C, Q, N or absent; and $Z_{16}$ is F, Y, W, S, T, C, V, L, I, M, A, G, D or E. In some embodiments, $Z_1$ is limited to N, A, R, D, G, S or absent; and/or $Z_2$ is limited to R, S, V, T, P, W or absent; and/or $Z_3$ is limited to G, T, L, P, R or absent; and/or $Z_4$ is limited to A, W, Y, D, N or absent; and/or $Z_5$ is limited to Y, L, G, T or absent; and/or $Z_6$ is limited to Y, S, G, L or absent; and/or $Z_7$ is limited to S, T, K, R or absent; and/or $Z_8$ is limited to T, Y, W or absent; and/or $Z_9$ is limited to G, P, Y, Q or absent; and/or $Z_{10}$ is limited to Y, L, I, T, S, G or absent; and/or $Z_{11}$ is limited to P, A, G, V, T, I, S or absent; and/or $Z_{12}$ is limited to G, S, P, V, F, A, T or absent; and/or $Z_{13}$ is limited to G, N, E, D, T, A, S or absent; and/or $Z_{14}$ is limited to Y, F, W, L or absent; and/or $Z_{15}$ is limited to E, D, G, S, Q, I or absent; and/or $Z_{16}$ is limited to Y, S, M or D.

Noting in particular that the VH CDR3 sequence of SEQ ID NO: 306 is derived from an antibody that inhibits Kv1.3 function distinct from the others in FIG. 17, an alternative consensus sequence is VH CDR3 Motif 6:

$Z_1Z_2Z_3Z_4Z_5Z_6Z_7$ (SEQ ID NO: 441)

Where $Z_1$ is V, L, I, M, A or G; $Z_2$ is V, L, I, M, A or G; $Z_3$ is V, L, I, M, A or G; $Z_4$ is V, L, I, M, A or G; $Z_5$ is Y, F or W; $Z_6$ is D or E; and $Z_7$ is Y, F or W. In some embodiments, $Z_1$ is limited to G; and/or Z2 is limited to I; and/or Z3 is limited to V; and/or Z4 is limited to A; and/or Z5 is limited to Y; and/or Z6 is limited to D; and/or Z7 is limited to Y.

CDR Canonical Structures

To determine potential canonical structures associated with the disclosed anti-Kv1.3 antibodies derived from llamas (Table 7), light and heavy chain variable regions from each anti-Kv1.3 clone were submitted for sequence analysis in the "SAbDAb" structural antibody database (Dunbar et al. (2014), *Nucleic Acids Res.* 42:D1140-D1146). The RSCB Protein Data Bank (PDB) structures with the highest percentage identity were further analyzed in the PyIgClassify database to identify the associated CDR loop conformations. In some instances more than one PDB structure with the same percent identity was identified by SAbDAb analysis. In those cases, the canonical structures for each PDB hit was determined with the PyIgClassify database (Table 8).

TABLE 7

Antibody ELISA and functional analysis of anti-Kv1.3 antibodies derived from llama's.

| anti-Kv1.3 Antibody Clone | Kv1.3 ELISA | Nav1.8 ELISA (neg) | % Kv1.3 inhibition (400 nM) Average | SEM (+/−) | n |
|---|---|---|---|---|---|
| 3A12 | positive | negative | 0 | 0 | 2 |
| 1A3 | positive | negative | 73.53 | 8.71 | 3 |
| 3B12 | positive | negative | 0 | 0 | 1 |
| 3B6 | positive | negative | 0 | 0 | 2 |
| 3A4 | positive | negative | 0 | 0 | 2 |
| 3B2 | positive | negative | 0 | 0 | 2 |
| 3F9 | positive | negative | 0 | 0 | 1 |
| 2A10 | positive | negative | 0 | 0 | 5 |
| 3E12 | positive | negative | 0 | 0 | 2 |
| 3F4 | positive | negative | 0 | 0 | 1 |
| 3E5 | positive | negative | 0 | 0 | 2 |
| 2A2 | positive | negative | 0 | 0 | 2 |
| 3F2 | positive | negative | 0 | 0 | 1 |
| 3G10 | positive | negative | 0 | 0 | 1 |
| 3C7 | positive | negative | 0 | 0 | 2 |
| 2E2 | positive | negative | 0 | 0 | 1 |
| 3H5 | positive | negative | 0 | 0 | 1 |
| 1E6 | positive | negative | 0 | 0 | 4 |
| 3C9 | positive | negative | 0 | 0 | 1 |

Based on this analysis, anti-Kv1.3 antibodies may be comprised of the following PDB structures: 5i1d, 3qos, 5kna, 5kmv, 5tzt, 4lkx, 4ojf, 4hix, 4zs7, 5f6i, 4rav and 4o9h.

Based on the PDB structures, anti-Kv1.3 antibodies may have the following canonical CDR structures: H1CDR is H1-13-1, H1-14-1 or H1-15-cis11-*; H2 CDR is H2-10-12, H2-9-1, H2-10-2 or H2-10-6; H3 CDR is H3-12-*, H3-10-*, H3-11-*, H3-14-* or H3-8-2; L1 CDR is L1-17-1, L1-16-1, L1-14-2 or L1-14-1; L2 CDR is L2-8-1 or L2-8-2; and L3 CDR is L3-9-cis7-1, L3-10-cis6-*, L3-9-* or L3-10-*.

Noting in particular that anti-Kv1.3 antibody clones 1A3 inhibits Kv1.3 activity, distinct from other discovered antibodies, the associated PDB structures of anti-Kv1.3 antibodies may comprise 5i1d or 3qos (Table 8). Based on these PDB structure assignments, functionally inhibiting Kv1.3 antibodies may comprise the following canonical CDR sequences: H1 CDR is H1-13-1; H2 CDR is H2-10-12; H3 CDR is H3-12-*; L1 CDR is L1-17-1; L2 CDR is L2-8-1 and L3 CDR is L3-9-cis7-1.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

TABLE 8

| PDB structure and CDR canonical structure assignments of anti-Kv1.3 antibodies derived from llama's. | | | | | | | | |
|---|---|---|---|---|---|---|---|---|
| SAbDAb SequenceAnalysis | | | | | | | | |
| mAb | PDB | Percent Identity (full variable | PyIgClassify CDR Canonical Structure Assignments | | | | | |
| Clone | Structure | region) | H1 | H2 | H3 | L1 | L2 | L3 |
| 3A12 | 5i1d | 74.77 | H1-13-1 | H2-10-12 | H3-12-* | L1-17-1 | L2-8-1 | L3-9-cis7-1 |
| | 3qos | 74.77 | | | | | | |
| 1A3 | 5i1d | 73.79 | H1-13-1 | H2-10-12 | H3-12-* | L1-17-1 | L2-8-1 | L3-9-cis7-1 |
| | 3qos | 73.79 | | | | | | |
| 3B12 | 5i1d | 74.23 | H1-13-1 | H2-10-12 | H3-12-* | L1-17-1 | L2-8-1 | L3-9-cis7-1 |
| | 3qos | 74.23 | | | | | | |
| 3B6 | 5kna | 73.21 | | | | | | |
| | 5kmv | 73.21 | | | | | | |
| 3A4 | 5tzt | 70.22 | | | | | | |
| 3B2 | 5kna | 70.98 | | | | | | |
| | 5kmv | 70.98 | | | | | | |
| 3F9 | 4lkx | 73.66 | H1-14-1 | H2-9-1 | H3-10-* | L1-16-1 | L2-8-2 | L3-9-cis7-1 |
| 2A10 | 4ojf | 77.31 | H1-13-1 | H2-10-6 | H3-12-* | L1-16-1 | L2-8-1 | L3-9-cis7-1 |
| | 4hix | 77.31 | H1-13-1 | H2-10-6 | H3-12-* | L1-16-1 | L2-8-1 | L3-9-cis7-1 |
| 3.00E+12 | 5kna | 75 | | | | | | |
| | 5kmv | 75 | | | | | | |
| | 4ojf | 75 | H1-13-1 | H2-10-6 | H3-12-* | L1-16-1 | L2-8-1 | L3-9-cis7-1 |
| | 4hix | 75 | H1-13-1 | H2-10-6 | H3-12-* | L1-16-1 | L2-8-1 | L3-9-cis7-1 |
| 3F4 | 4ojf | 75.89 | H1-13-1 | H2-10-6 | H3-12-* | L1-16-1 | L2-8-1 | L3-9-cis7-1 |
| | 4hix | 75.89 | H1-13-1 | H2-10-6 | H3-12-* | L1-16-1 | L2-8-1 | L3-9-cis7-1 |
| 3E5 | 5kna | 77.23 | | | | | | |
| | 5kmv | 77.23 | | | | | | |
| 2A2 | 5kna | 79.01 | | | | | | |
| | 5kmv | 79.01 | | | | | | |
| 3F2 | 5kna | 77.57 | | | | | | |
| | 5kmv | 77.57 | | | | | | |
| 3G10 | 4zs7 | 79.74 | H1-15-cis11-* | H2-9-1 | H3-14-* | L1-14-2 | L2-8-1 | L3-10-cis6-* |
| 3C7 | 4zs7 | 78.44 | H1-15-cis11-* | H2-9-1 | H3-14-* | L1-14-2 | L2-8-1 | L3-10-cis6-* |
| 2E2 | 5f6i | 76.88 | H1-13-1 | H2-10-2 | H3-10-* | L1-14-2 | L2-8-1 | L3-10-* |
| | 4rav | 76.88 | H1-13-1 | H2-10-2 | H3-8-2 | L1-14-2 | L2-8-2 | L3-9-* |
| 3H5 | 4zs7 | 82.17 | H1-15-cis11-* | H2-9-1 | H3-14-* | L1-14-2 | L2-8-1 | L3-10-cis6-* |
| 1E6 | 4o9h | 69.91 | H1-13-1 | H2-10-2 | H3-11-* | L1-14-1 | L2-8-1 | L3-9-* |
| 3C9 | 409h | 70.35 | H1-13-1 | H2-10-2 | H3-11-* | L1-14-1 | L2-8-1 | L3-9-* |

We claim:

1. An antibody that specifically binds to a human Kv1.3 protein, the antibody comprising an immunoglobulin heavy chain and an immunoglobulin light chain, wherein:
   the variable region of said light chain comprises a light chain variable region comprising a CDR1 region of SEQ ID NO: 55, a CDR2 region of SEQ ID NO: 72, and a CDR3 region of SEQ ID NO: 101; and the variable region of said heavy chain comprises a CDR1 region of SEQ ID NO: 169, a CDR2 region of SEQ ID NO: 182, and a CDR3 region of SEQ ID NO: 207.

2. The antibody of claim 1, wherein the variable region of said light chain comprises a light chain variable region comprising an amino acid sequence of SEQ ID NO: 22, and wherein the variable region of said heavy chain comprises an amino acid sequence of SEQ ID NO: 130.

* * * * *

SEQUENCE LISTING

<160> NUMBER OF SEQ ID NOS: 455

<210> SEQ ID NO 1
<211> LENGTH: 575
<212> TYPE: PRT
<213> ORGANISM: Homo sapiens

<400> SEQUENCE: 1

```
Met Asp Glu Arg Leu Ser Leu Leu Arg Ser Pro Pro Pro Ser Ala
1               5                   10                  15

Arg His Arg Ala His Pro Pro Gln Arg Pro Ala Ser Ser Gly Gly Ala
            20                  25                  30

His Thr Leu Val Asn His Gly Tyr Ala Glu Pro Ala Ala Gly Arg Glu
                35                  40                  45

Leu Pro Pro Asp Met Thr Val Val Pro Gly Asp His Leu Leu Glu Pro
        50                  55                  60

Glu Val Ala Asp Gly Gly Ala Pro Gln Gly Gly Cys Gly Gly
65                  70                  75                  80

Gly Gly Cys Asp Arg Tyr Glu Pro Leu Pro Ser Leu Pro Ala Ala
                85                  90                  95

Gly Glu Gln Asp Cys Cys Gly Glu Arg Val Val Ile Asn Ile Ser Gly
            100                 105                 110

Leu Arg Phe Glu Thr Gln Leu Lys Thr Leu Cys Gln Phe Pro Glu Thr
        115                 120                 125

Leu Leu Gly Asp Pro Lys Arg Arg Met Arg Tyr Phe Asp Pro Leu Arg
    130                 135                 140

Asn Glu Tyr Phe Phe Asp Arg Asn Arg Pro Ser Phe Asp Ala Ile Leu
145                 150                 155                 160

Tyr Tyr Tyr Gln Ser Gly Gly Arg Ile Arg Arg Pro Val Asn Val Pro
                165                 170                 175

Ile Asp Ile Phe Ser Glu Ile Arg Phe Tyr Gln Leu Gly Glu Glu
        180                 185                 190

Ala Met Glu Lys Phe Arg Glu Asp Glu Gly Phe Leu Arg Glu Glu Glu
    195                 200                 205

Arg Pro Leu Pro Arg Arg Asp Phe Gln Arg Gln Val Trp Leu Leu Phe
210                 215                 220

Glu Tyr Pro Glu Ser Ser Gly Pro Ala Arg Gly Ile Ala Ile Val Ser
225                 230                 235                 240

Val Leu Val Ile Leu Ile Ser Ile Val Ile Phe Cys Leu Glu Thr Leu
                245                 250                 255

Pro Glu Phe Arg Asp Glu Lys Asp Tyr Pro Ala Ser Thr Ser Gln Asp
            260                 265                 270

Ser Phe Glu Ala Ala Gly Asn Ser Thr Ser Gly Ser Arg Ala Gly Ala
        275                 280                 285

Ser Ser Phe Ser Asp Pro Phe Phe Val Val Glu Thr Leu Cys Ile Ile
    290                 295                 300

Trp Phe Ser Phe Glu Leu Leu Val Arg Phe Phe Ala Cys Pro Ser Lys
305                 310                 315                 320

Ala Thr Phe Ser Arg Asn Ile Met Asn Leu Ile Asp Ile Val Ala Ile
                325                 330                 335

Ile Pro Tyr Phe Ile Thr Leu Gly Thr Glu Leu Ala Glu Arg Gln Gly
            340                 345                 350

Asn Gly Gln Gln Ala Met Ser Leu Ala Ile Leu Arg Val Ile Arg Leu
        355                 360                 365
```

```
Val Arg Val Phe Arg Ile Phe Lys Leu Ser Arg His Ser Lys Gly Leu
    370                 375                 380

Gln Ile Leu Gly Gln Thr Leu Lys Ala Ser Met Arg Glu Leu Gly Leu
385                 390                 395                 400

Leu Ile Phe Phe Leu Phe Ile Gly Val Ile Leu Phe Ser Ser Ala Val
                405                 410                 415

Tyr Phe Ala Glu Ala Asp Asp Pro Thr Ser Gly Phe Ser Ser Ile Pro
            420                 425                 430

Asp Ala Phe Trp Trp Ala Val Val Thr Met Thr Val Gly Tyr Gly
            435                 440                 445

Asp Met His Pro Val Thr Ile Gly Gly Lys Ile Val Gly Ser Leu Cys
    450                 455                 460

Ala Ile Ala Gly Val Leu Thr Ile Ala Leu Pro Val Pro Val Ile Val
465                 470                 475                 480

Ser Asn Phe Asn Tyr Phe Tyr His Arg Glu Thr Glu Gly Glu Glu Gln
                485                 490                 495

Ser Gln Tyr Met His Val Gly Ser Cys Gln His Leu Ser Ser Ser Ala
            500                 505                 510

Glu Glu Leu Arg Lys Ala Arg Ser Asn Ser Thr Leu Ser Lys Ser Glu
        515                 520                 525

Tyr Met Val Ile Glu Glu Gly Gly Met Asn His Ser Ala Phe Pro Gln
    530                 535                 540

Thr Pro Phe Lys Thr Gly Asn Ser Thr Ala Thr Cys Thr Thr Asn Asn
545                 550                 555                 560

Asn Pro Asn Ser Cys Val Asn Ile Lys Lys Ile Phe Thr Asp Val
                565                 570                 575

<210> SEQ ID NO 2
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Glu Arg Leu Ser Leu Leu Arg Ser Pro Pro Pro Ser Ala
1               5                   10                  15

Arg His Arg Ala His Pro Pro Gln Arg Pro Ala Ser Ser Gly Gly Ala
            20                  25                  30

His Thr Leu Val Asn His Gly Tyr Ala Glu Pro Ala Ala Gly Arg Glu
        35                  40                  45

Leu Pro Pro Asp Met Thr Val Val Pro Gly Asp His Leu Leu Glu Pro
    50                  55                  60

Glu Val Ala Asp Gly Gly Ala Pro Pro Gln Gly Gly Cys Gly Gly
65                  70                  75                  80

Gly Gly Cys Asp Arg Tyr Glu Pro Leu Pro Pro Ser Leu Pro Ala Ala
                85                  90                  95

Gly Glu Gln Asp Cys Cys Gly Glu Arg Val Val Ile Asn Ile Ser Gly
            100                 105                 110

Leu Arg Phe Glu Thr Gln Leu Lys Thr Leu Cys Gln Phe Pro Glu Thr
        115                 120                 125

Leu Leu Gly Asp Pro Lys Arg Arg Met Arg Tyr Phe Asp Pro Leu Arg
    130                 135                 140

Asn Glu Tyr Phe Phe Asp Arg Asn Arg Pro Ser Phe Asp Ala Ile Leu
145                 150                 155                 160
```

```
Tyr Tyr Tyr Gln Ser Gly Gly Arg Ile Arg Arg Pro Val Asn Val Pro
                165                 170                 175

Ile Asp Ile Phe Ser Glu Glu Ile Arg Phe Tyr Gln Leu Gly Glu Glu
            180                 185                 190

Ala Met Glu Lys Phe Arg Glu Asp Gly Phe Leu Arg Glu Glu Glu
            195                 200                 205

Arg Pro Leu Pro Arg Arg Asp Phe Gln Arg Gln Val Trp Leu Leu Phe
    210                 215                 220

Glu Tyr Pro Glu Ser Ser Gly Pro Ala Arg Gly Ile Ala Ile Val Ser
225                 230                 235                 240

Val Leu Val Ile Leu Ile Ser Ile Val Ile Phe Cys Leu Glu Thr Leu
                245                 250                 255

Pro Glu Phe Arg Asp Glu Lys Asp Tyr Pro Ala Ser Thr Ser Gln Asp
            260                 265                 270

Ser Phe Glu Ala Ala Gly Asn Ser Thr Ser Gly Ser Arg Ala Gly Ala
    275                 280                 285

Ser Ser Phe Ser Asp Pro Phe Phe Val Val Glu Thr Leu Cys Ile Ile
    290                 295                 300

Trp Phe Ser Phe Glu Leu Leu Val Arg Phe Phe Ala Cys Pro Ser Lys
305                 310                 315                 320

Ala Thr Phe Ser Arg Asn Ile Met Asn Leu Ile Asp Ile Val Ala Ile
            325                 330                 335

Ile Pro Tyr Phe Ile Thr Leu Gly Thr Glu Leu Ala Glu Arg Gln Gly
            340                 345                 350

Asn Gly Gln Gln Ala Met Ser Leu Ala Ile Leu Arg Val Ile Arg Leu
        355                 360                 365

Val Arg Val Phe Arg Ile Phe Lys Leu Ser Arg His Ser Lys Gly Leu
    370                 375                 380

Gln Ile Leu Gly Gln Thr Leu Lys Ala Ser Met Arg Glu Leu Gly Leu
385                 390                 395                 400

Leu Ile Phe Phe Leu Phe Ile Gly Val Ile Leu Phe Ser Ser Ala Val
            405                 410                 415

Tyr Phe Ala Glu Ala Asp Asp Pro Thr Ser Gly Phe Ser Ser Ile Pro
        420                 425                 430

Asp Ala Phe Trp Trp Ala Val Val Thr Met Thr Thr Val Gly Tyr Gly
        435                 440                 445

Asp Met His Pro Val Thr Ile Gly Gly Lys Ile Val Gly Ser Leu Cys
450                 455                 460

Ala Ile Ala Gly Val Leu Thr Ile Ala Leu Pro Val Pro Val Ile Val
465                 470                 475                 480

Ser Asn Phe Asn Tyr Phe Tyr His Arg Glu Thr Glu Gly Glu Glu Gln
                485                 490                 495

Ser Gln Tyr Met His Val Gly Ser Cys Gln His Leu Ser Ser Ser Ala
        500                 505                 510

Glu Glu Leu Arg Lys Ala Arg Ser Asn Ser Thr Leu Ser Lys Ser Glu
            515                 520                 525

Tyr Met Val Ile Glu Glu Gly Gly Met Asn His Ser Ala Phe Pro Gln
        530                 535                 540

Thr Pro Phe Lys Thr Gly Asn Ser Thr Ala Thr Cys Thr Thr Asn Asn
545                 550                 555                 560

Asn Pro Asn Ser Cys Val Asn Ile Lys Lys Ile Phe Thr Asp Val Asp
                565                 570                 575
```

Tyr Lys Asp Asp Asp Lys His His His His His His His His
                580                 585                 590

His

<210> SEQ ID NO 3
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Val Thr Gln Pro Ala Ser Val Ser Ala Asn Pro Gly Glu Thr Val
1               5                   10                  15

Glu Ile Thr Cys Ser Gly Ser Ser Gly Ser Tyr Tyr Gly Trp Tyr Gln
            20                  25                  30

Gln Lys Ala Pro Gly Ser Ala Pro Val Thr Val Ile Tyr Asp Asn Thr
        35                  40                  45

Asn Arg Pro Ser Asp Ile Pro Ser Arg Phe Ser Gly Ser Ala Ser Gly
    50                  55                  60

Ser Thr Ala Thr Leu Thr Ile Thr Gly Val Gln Val Glu Asp Glu Gly
65                  70                  75                  80

Val Tyr Phe Cys Gly Gly Tyr Asp Ser Asn Thr Tyr Ala Gly Ile Phe
                85                  90                  95

Gly Ala Gly Thr Thr Leu Thr Val Leu
            100                 105

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Leu Thr Gln Gln Pro Ala Ser Val Ser Ala Asn Pro Gly Glu Thr
1               5                   10                  15

Val Lys Ile Thr Cys Ser Gly Gly Tyr Asn Tyr Ala Gly Ser Tyr Tyr
            20                  25                  30

Tyr Gly Trp Tyr Gln Gln Lys Ala Pro Gly Ser Ala Pro Val Thr Val
        35                  40                  45

Ile Tyr Asp Asn Thr Asn Arg Pro Ser Asn Ile Pro Ser Arg Phe Ser
    50                  55                  60

Gly Ser Leu Ser Gly Ser Thr Ala Thr Leu Thr Ile Thr Gly Val Gln
65                  70                  75                  80

Val Glu Asp Glu Ala Val Tyr Phe Cys Gly Asn Glu Asp Ser Ser Thr
                85                  90                  95

Ser Thr Phe Gly Ala Gly Thr Thr Leu Thr Val Leu
            100                 105

<210> SEQ ID NO 5
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Ala Val Thr Gln Pro Ala Ser Val Ser Ala Asn Pro Gly Glu Thr Val
1               5                   10                  15

Lys Ile Thr Cys Ser Gly Gly Ser Ser Tyr Tyr Gly Trp Tyr Gln
            20                  25                  30

Gln Lys Ser Pro Gly Arg Thr Pro Val Thr Val Ile Tyr Asp Asn Thr
        35                  40                  45

Asn Arg Pro Ser Asp Ile Pro Ser Arg Phe Ser Gly Ser Lys Ser Gly
    50                  55                  60

Ser Thr Ala Thr Leu Thr Ile Thr Gly Val Gln Ala Glu Asp Glu Ala
65                  70                  75                  80

Val Tyr Phe Cys Gly Ala Trp Glu Gly Ser Ser Pro Ala Phe Gly Ala
                85                  90                  95

Gly Thr Thr Leu Thr Val Leu
                100

<210> SEQ ID NO 6
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Val Thr Gln Pro Ala Ser Val Ser Ala Asn Pro Gly Glu Thr Val
1               5                   10                  15

Lys Ile Thr Cys Ser Gly Gly Ser Ser Tyr Tyr Gly Trp Tyr Gln
            20                  25                  30

Gln Lys Ser Pro Gly Arg Thr Pro Val Thr Val Ile Tyr Asp Asn Thr
        35                  40                  45

Asn Arg Pro Ser Asp Ile Pro Ser Arg Phe Ser Gly Ser Lys Ser Gly
    50                  55                  60

Ser Thr Ala Thr Leu Thr Ile Thr Gly Val Gln Ala Glu Asp Glu Ala
65                  70                  75                  80

Val Tyr Phe Cys Gly Ala Trp Glu Gly Ser Ser Pro Ala Phe Gly Ala
                85                  90                  95

Gly Thr Thr Leu Thr Val Leu
                100

<210> SEQ ID NO 7
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Leu Thr Gln Pro Ala Ser Val Ser Ala Asn Pro Gly Glu Thr Val
1               5                   10                  15

Glu Ile Thr Cys Ser Gly Gly Arg Ser Asp Tyr Tyr Tyr Ser Trp His
            20                  25                  30

Gln Gln Glu Ala Pro Gly Ser Ala Pro Val Thr Leu Ile Tyr Asn Asp
        35                  40                  45

Asn Lys Arg Pro Ser Asp Ile Pro Ser Arg Phe Ser Gly Ala Val Ser
    50                  55                  60

Gly Ser Thr Gly Thr Leu Thr Ile Thr Gly Val Gln Ala Glu Asp Glu
65                  70                  75                  80
```

-continued

Ala Val Tyr Phe Cys Gly Gly Tyr Asp Asp Thr Ile Asn Pro Ile Phe
                85                  90                  95

Gly Ala Gly Thr Thr Leu Thr Val Leu
            100                 105

<210> SEQ ID NO 8
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Leu Thr Gln Pro Ala Ser Val Ser Ala Asn Leu Gly Glu Thr Val
1               5                   10                  15

Lys Val Ile Cys Ser Gly Gly Tyr Ser Arg Tyr Gly Tyr Ser Trp His
                20                  25                  30

Gln Gln Lys Ser Pro Gly Ser Ala Pro Val Thr Leu Ile Tyr Glu Ser
            35                  40                  45

Asn Lys Arg Pro Ser Asp Ile Pro Ser Arg Phe Ser Gly Ser Lys Ser
        50                  55                  60

Gly Ser Thr Gly Thr Leu Thr Ile Thr Gly Val Gln Ala Glu Asp Glu
65                  70                  75                  80

Ala Val Tyr Phe Cys Gly Ser Thr Asp Asn Asn Gly Tyr Pro Ala Phe
                85                  90                  95

Gly Ala Gly Thr Thr Leu Thr Val Leu
            100                 105

<210> SEQ ID NO 9
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Leu Thr His Pro Ala Ser Val Ser Ala Asn Pro Gly Glu Thr Val
1               5                   10                  15

Lys Val Thr Cys Ser Gly Gly Tyr Ser Asn Tyr Gly Tyr Ser Trp His
                20                  25                  30

Gln Gln Lys Ser Pro Gly Ser Ala Pro Val Thr Val Ile Tyr Tyr Asn
            35                  40                  45

Asp Lys Arg Pro Ser Asp Ile Pro Ser Arg Phe Ser Gly Ser Lys Ser
        50                  55                  60

Gly Ser Thr Ala Thr Leu Thr Ile Thr Gly Val Gln Ala Glu Asp Glu
65                  70                  75                  80

Ala Val Tyr Phe Cys Gly Ser Thr Asp Ser Asn Gly Tyr Pro Ala Phe
                85                  90                  95

Gly Ala Gly Thr Thr Leu Thr Val Leu
            100                 105

<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Leu Thr Gln Pro Ala Ser Val Ser Ala Asn Pro Gly Glu Thr Val
1               5                   10                  15

Lys Val Thr Cys Ser Gly Gly Tyr Ser Ser Tyr Gly Tyr Ser Trp Phe
            20                  25                  30

Gln Gln Lys Ser Pro Gly Ser Ala Pro Val Thr Val Ile Tyr Tyr Asn
        35                  40                  45

Asp Lys Arg Pro Ser Asp Ile Pro Ser Arg Phe Ser Gly Ser Lys Ser
    50                  55                  60

Gly Ser Thr Gly Thr Leu Thr Ile Thr Gly Val Gln Ala Glu Asp Glu
65                  70                  75                  80

Ala Val Tyr Phe Cys Gly Ser Thr Asp Ile Asn Gly Tyr Pro Ala Phe
                85                  90                  95

Gly Ala Gly Thr Thr Leu Thr Val Leu
            100                 105

<210> SEQ ID NO 11
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Leu Thr Gln Pro Ala Ser Val Ser Ala Asn Pro Gly Glu Thr Val
1               5                   10                  15

Lys Val Thr Cys Ser Gly Gly Tyr Ser Ser Tyr Gly Tyr Ser Trp Phe
            20                  25                  30

Gln Gln Lys Ser Pro Gly Ser Ala Pro Val Thr Val Ile Tyr Tyr Asn
        35                  40                  45

Asp Lys Arg Pro Ser Asp Ile Pro Ser Arg Phe Ser Gly Ser Lys Ser
    50                  55                  60

Gly Ser Thr Gly Thr Leu Thr Ile Thr Gly Val Gln Ala Glu Asp Glu
65                  70                  75                  80

Ala Val Tyr Phe Cys Gly Ser Thr Asp Ile Asn Gly Tyr Pro Ala Phe
                85                  90                  95

Gly Ala Gly Thr Thr Leu Thr Val Leu
            100                 105

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Leu Thr Gln Pro Ala Ser Val Ser Ala Asn Leu Gly Gly Thr Val
1               5                   10                  15

Glu Ile Thr Cys Ser Arg Asp Asp Ser Gly Tyr Gly Tyr Gly Trp Tyr
            20                  25                  30

Gln Gln Lys Ser Pro Gly Ser Ala Leu Val Thr Val Ile Tyr Ser Asn
        35                  40                  45

Asn Gln Arg Pro Ser Asp Ile Pro Ser Arg Phe Ser Gly Ser Lys Ser
    50                  55                  60

Gly Ser Thr His Ala Leu Thr Ile Ala Gly Val Arg Ala Glu Asp Glu
65                  70                  75                  80

Ala Val Tyr Tyr Cys Gly Ser Phe Asp Ser Thr Tyr Val Thr Asp
                85                  90                  95

Ile Phe Gly Ala Gly Thr Thr Leu Thr Val Leu
            100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Leu Thr Gln Pro Ala Ser Val Ser Ala Asn Leu Gly Gly Thr Val
1               5                   10                  15

Glu Ile Thr Cys Ser Arg Asp Asp Ser Gly Tyr Gly Tyr Gly Trp Tyr
                20                  25                  30

Gln Gln Lys Ser Pro Gly Ser Ala Leu Val Thr Val Ile Tyr Ser Asn
            35                  40                  45

Asn Gln Arg Pro Ser Asp Ile Pro Ser Arg Phe Ser Gly Ser Lys Ser
50                  55                  60

Gly Ser Thr His Thr Leu Thr Ile Thr Gly Val Arg Ala Glu Asp Glu
65                  70                  75                  80

Ala Val Tyr Tyr Cys Gly Ser Phe Asp Ser Ser Thr Tyr Val Thr Asp
                85                  90                  95

Ile Phe Gly Ala Gly Thr Thr Leu Thr Val Leu
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Leu Thr Gln Pro Ala Ser Val Ser Ala Asn Leu Gly Gly Thr Val
1               5                   10                  15

Glu Ile Thr Cys Ser Arg Asp Asp Ser Gly Tyr Gly Tyr Gly Trp Tyr
                20                  25                  30

Gln Gln Lys Ser Pro Gly Ser Ala Leu Val Thr Val Ile Tyr Ser Asn
            35                  40                  45

Asn Gln Arg Pro Ser Asp Ile Pro Ser Arg Phe Ser Gly Ser Lys Ser
50                  55                  60

Gly Ser Thr His Thr Leu Thr Ile Thr Gly Val Arg Ala Glu Asp Glu
65                  70                  75                  80

Ala Val Tyr Tyr Cys Gly Ser Phe Asp Ser Ser Thr Tyr Val Thr Asp
                85                  90                  95

Ile Phe Gly Ala Gly Thr Thr Leu Thr Val Leu
            100                 105

<210> SEQ ID NO 15
<211> LENGTH: 108
<212> TYPE: PRT
<213> ORGANISM: Artificial Sequence
<220> FEATURE:

-continued

<223> OTHER INFORMATION: Description of Artificial Sequence: Synthetic
    polypeptide

<400> SEQUENCE: 15

Ala Leu Thr Gln Pro Ser Ser Val Ser Ala Asn Pro Gly Glu Thr Val
1               5                   10                  15

Lys Ile Thr Cys Ser Gly Gly Ser Tyr Ala Gly Ser Tyr Tyr Tyr
            20                  25                  30

Gly Trp His Gln Gln Lys Ser Pro Gly Ser Ala Pro Val Thr Val Ile
        35                  40                  45

Tyr Asn Asn Asn Lys Arg Pro Ser Asp Ile Pro Ser Arg Phe Ser Gly
50                  55                  60

Ala Leu Ser Gly Ser Thr Asn Thr Leu Thr Ile Thr Gly Val Gln Ala
65                  70                  75                  80

Glu Asp Glu Ala Val Tyr Phe Cys Gly Ser Ile Asp Ser Ser Arg Thr
                85                  90                  95

Ala Ala Phe Gly Ala Gly Thr Thr Leu Thr Val Leu
            100                 105

<210> SEQ ID NO 16
<211> LENGTH: 103
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 16

Ala Leu Thr Gln Pro Ser Ser Val Ser Ala Asn Leu Gly Gly Thr Val
1               5                   10                  15

Lys Ile Thr Cys Ser Gly Gly Ser Tyr Thr Tyr Gly Trp Phe Gln Gln
            20                  25                  30

Lys Ser Pro Gly Ser Ala Pro Val Thr Val Ile Tyr Tyr Asn Lys Lys
        35                  40                  45

Arg Pro Ser Asp Ile Pro Ser Arg Phe Ser Gly Ser Leu Ser Gly Ser
    50                  55                  60

Thr Asn Thr Leu Thr Ile Thr Gly Val Gln Ala Asp Asp Glu Ala Val
65                  70                  75                  80

Tyr Tyr Cys Gly Ser Thr Asp Ser Ser Tyr Val Asp Ile Phe Gly Ala
                85                  90                  95

Gly Thr Thr Leu Thr Val Leu
            100

<210> SEQ ID NO 17
<211> LENGTH: 104
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 17

Ala Leu Thr Gln Gln Pro Ala Ser Val Ser Ala Asn Pro Gly Glu Thr
1               5                   10                  15

Val Lys Ile Thr Cys Ser Gly Gly Ser Tyr Ser Tyr Gly Trp Phe Gln
            20                  25                  30

Gln Lys Ser Pro Gly Ser Ala Pro Val Thr Val Ile Tyr Ser Asn Ser
        35                  40                  45

Gln Arg Pro Ser Asn Ile Pro Ser Arg Phe Ser Gly Ser Leu Ser Gly

```
                     50                  55                  60
Ser Thr Asn Thr Leu Thr Ile Thr Gly Val Arg Ala Glu Asp Glu Ala
 65                  70                  75                  80

Val Tyr Tyr Cys Gly Ser Thr Asp Ser Ser Tyr Val Asp Ile Phe Gly
                 85                  90                  95

Ala Gly Thr Thr Leu Thr Val Leu
            100

<210> SEQ ID NO 18
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Leu Thr Gln Gln Pro Ala Ser Val Ser Ala Asn Pro Gly Glu Thr
 1               5                  10                  15

Val Lys Ile Thr Cys Ser Gly Gly Ser Tyr Ser Tyr Gly Trp Phe Gln
                20                  25                  30

Gln Lys Ser Ser Gly Ser Ala Leu Val Thr Val Ile Tyr Tyr Asn Asp
             35                  40                  45

Asn Arg Pro Ser Asp Ile Pro Ser Arg Phe Ser Gly Ser Ala Ser Gly
         50                  55                  60

Ser Thr Ala Thr Leu Thr Ile Thr Gly Val Gln Ala Glu Asp Glu Ala
 65                  70                  75                  80

Val Tyr Phe Cys Gly Ser Phe Asp Ser Ser Gly Asp Gly Ile Phe Gly
                 85                  90                  95

Ala Gly Thr Thr Leu Thr Val Leu
            100

<210> SEQ ID NO 19
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Leu Thr Gln Gln Pro Ala Ser Val Ser Ala Asn Pro Gly Glu Thr
 1               5                  10                  15

Val Lys Ile Thr Cys Ser Gly Gly Ser Tyr Ser Tyr Gly Trp Phe Gln
                20                  25                  30

Gln Lys Ser Pro Gly Ser Ala Leu Val Thr Val Ile Tyr Tyr Asn Asp
             35                  40                  45

Asn Arg Pro Ser Asp Ile Pro Ser Arg Phe Ser Gly Ser Ala Ser Gly
         50                  55                  60

Ser Thr Ala Thr Leu Thr Ile Thr Gly Val Gln Ala Glu Asp Glu Ala
 65                  70                  75                  80

Val Tyr Phe Cys Gly Ser Phe Asp Ser Ser Gly Asp Gly Ile Phe Gly
                 85                  90                  95

Ala Gly Thr Thr Leu Thr Val Leu
            100

<210> SEQ ID NO 20
<211> LENGTH: 106
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 20

Ala Val Thr Gln Pro Ala Ser Val Ser Ala Asn Leu Gly Glu Thr Val
1               5                   10                  15

Lys Ile Thr Cys Ser Gly Gly Ser Gly Ser Tyr Tyr Tyr Gly Trp Phe
            20                  25                  30

Gln Gln Lys Ser Pro Gly Ser Ala Pro Val Ser Val Ile Tyr Glu Asp
        35                  40                  45

Thr Lys Arg Pro Ser Asn Ile Pro Ser Arg Phe Ser Gly Ser Ala Ser
    50                  55                  60

Gly Ser Thr Ala Thr Leu Ile Ile Thr Gly Val Arg Ala Asp Asp Glu
65                  70                  75                  80

Ala Val Tyr Phe Cys Gly Ala Tyr Asp Gly Ser Thr Tyr Thr Pro Ile
                85                  90                  95

Phe Gly Ala Gly Thr Thr Leu Thr Val Leu
                100                 105

<210> SEQ ID NO 21
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Leu Thr Gln Pro Ala Ser Val Ser Ala Asn Pro Gly Glu Thr Val
1               5                   10                  15

Lys Ile Thr Cys Ser Gly Gly Ser Gly Tyr Phe Phe Gly Trp Tyr Gln
            20                  25                  30

Gln Lys Ser Pro Gly Ser Ala Pro Val Thr Leu Ile Tyr Glu Ser Asn
        35                  40                  45

Lys Lys Pro Ser Asn Ile Pro Ser Arg Phe Ser Gly Ser Thr Ser Gly
    50                  55                  60

Ser Thr Asn Thr Leu Thr Ile Thr Gly Val Gln Ala Asp Asp Glu Ala
65                  70                  75                  80

Val Tyr Phe Cys Gly Thr Tyr Asp Ser Ile Glu Ala Ile Phe Gly Ala
                85                  90                  95

Gly Thr Thr Leu Thr Val Leu
            100

<210> SEQ ID NO 22
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Leu Thr Gln Pro Ala Ser Val Ser Thr Asn Pro Gly Glu Thr Val
1               5                   10                  15

Lys Ile Thr Cys Ser Gly Gly Ser Gly Tyr Phe Phe Gly Trp Tyr Gln
            20                  25                  30

Gln Lys Ser Pro Gly Ser Ala Pro Val Thr Leu Ile Tyr Glu Ser Asn
        35                  40                  45

```
Lys Arg Pro Ser Asn Ile Pro Ser Arg Phe Ser Gly Ser Thr Ser Gly
        50                  55                  60

Ser Thr Asn Thr Leu Thr Ile Thr Gly Val Gln Ala Asp Asp Glu Ala
 65                  70                  75                  80

Val Tyr Phe Cys Gly Thr Tyr Asp Ser Ile Glu Ala Ile Phe Gly Ala
                    85                  90                  95

Gly Thr Thr Leu Thr Val Leu
                100

<210> SEQ ID NO 23
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Leu Thr Gln Pro Ala Ser Val Ser Ala Asn Pro Gly Glu Thr Val
 1               5                  10                  15

Lys Ile Thr Cys Ser Gly Gly Ser Gly Tyr Phe Phe Gly Trp Tyr Gln
                20                  25                  30

Gln Lys Ser Pro Gly Ser Ala Pro Val Thr Leu Ile Tyr Glu Ser Asn
            35                  40                  45

Lys Arg Pro Ser Asn Ile Pro Ser Arg Phe Ser Gly Ser Thr Ser Gly
        50                  55                  60

Ser Thr Asn Thr Leu Thr Ile Thr Gly Val Gln Ala Asp Asp Glu Ala
 65                  70                  75                  80

Val Tyr Phe Cys Gly Thr Tyr Asp Ser Ile Glu Ala Ile Phe Gly Ala
                    85                  90                  95

Gly Thr Thr Leu Thr Val Leu
                100

<210> SEQ ID NO 24
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Leu Thr Gln Pro Ala Ser Val Ser Ala Asn Pro Gly Glu Thr Val
 1               5                  10                  15

Lys Ile Thr Cys Ser Gly Gly Ser Gly Tyr Phe Phe Gly Trp Tyr Gln
                20                  25                  30

Gln Lys Ser Pro Gly Ser Ala Pro Val Thr Leu Ile Tyr Glu Ser Asn
            35                  40                  45

Lys Arg Pro Ser Asn Ile Pro Ser Arg Phe Ser Gly Ser Thr Ser Gly
        50                  55                  60

Ser Thr Asn Thr Leu Thr Ile Thr Gly Val Gln Ala Asp Asp Glu Ala
 65                  70                  75                  80

Val Tyr Phe Cys Gly Thr Tyr Asp Ser Ile Glu Ala Ile Phe Gly Ala
                    85                  90                  95

Gly Thr Thr Leu Thr Val Leu
                100

<210> SEQ ID NO 25
```

<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Leu Thr Gln Pro Ala Ser Val Ser Ala Asn Pro Gly Glu Thr Val
1               5                   10                  15

Lys Ile Thr Cys Ser Gly Gly Ser Ser Asn Tyr Tyr Gly Trp Tyr
            20                  25                  30

Gln Gln Lys Ser Pro Gly Ser Ala Pro Leu Thr Val Ile Tyr Trp Asp
        35                  40                  45

Asp Glu Arg Pro Ser Asn Ile Pro Ser Arg Phe Ser Gly Ser Lys Ser
    50                  55                  60

Gly Ser Thr Val Thr Leu Thr Leu Thr Gly Val Arg Ala Glu Asp Glu
65                  70                  75                  80

Ala Val Tyr Phe Cys Gly Thr Glu Asp Asn Thr Gly Ala Ala Ile Phe
                85                  90                  95

Gly Ala Gly Thr Thr Leu Thr Val Leu
            100                 105

<210> SEQ ID NO 26
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Val Thr Gln Pro Ala Ser Val Ser Ala Asn Leu Gly Gly Thr Val
1               5                   10                  15

Glu Ile Thr Cys Ser Gly Asp Gly Ser Ser Tyr Tyr Gly Trp Phe
            20                  25                  30

Gln Gln Lys Ser Pro Gly Ser Ala Pro Val Thr Leu Ile Tyr Tyr Asn
        35                  40                  45

Ser Lys Arg Pro Ser Asp Ile Pro Ser Arg Phe Ser Gly Ser Thr Ser
    50                  55                  60

Gly Ser Thr Thr Thr Leu Thr Ile Thr Gly Val Arg Ala Glu Asp Glu
65                  70                  75                  80

Ala Val Tyr Phe Cys Cys Gly Ser Ile Asp Ser Ser Gly Ile Phe Gly
                85                  90                  95

Ala Gly Thr Thr Leu Thr Val Leu
            100

<210> SEQ ID NO 27
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Val Thr Gln Pro Ala Ser Val Ser Ala Asn Leu Gly Gly Thr Val
1               5                   10                  15

Glu Ile Thr Cys Ser Gly Asp Gly Ser Ser Tyr Tyr Gly Trp Phe
            20                  25                  30

```
Gln Gln Lys Ser Pro Gly Ser Ala Pro Val Thr Leu Ile Tyr Tyr Asn
            35                  40                  45

Ser Lys Arg Pro Ser Asp Ile Pro Ser Arg Phe Ser Gly Ser Thr Ser
 50                  55                  60

Gly Ser Thr Thr Thr Leu Thr Ile Thr Gly Val Arg Ala Glu Asp Glu
 65                  70                  75                  80

Ala Val Tyr Phe Cys Cys Gly Ser Ile Asp Ser Ser Gly Ile Phe Gly
                 85                  90                  95

Ala Gly Thr Thr Leu Thr Val Leu
                100
```

<210> SEQ ID NO 28
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Val Leu Thr Gln Gln Pro Ala Ser Val Ser Ala Asn Pro Gly Gly Thr
 1               5                  10                  15

Val Glu Ile Thr Cys Ser Gly Gly Gly Ser Tyr Gly Trp Tyr Gln
                20                  25                  30

Gln Lys Ser Pro Gly Ser Ala Pro Val Thr Leu Ile Tyr Arg Asn Asp
            35                  40                  45

Lys Arg Pro Ser Asp Ile Pro Ser Arg Phe Ser Gly Ser Lys Ser Gly
 50                  55                  60

Ser Thr Ala Thr Leu Thr Ile Thr Gly Val Gln Ala Glu Asp Glu Ala
 65                  70                  75                  80

Val Tyr Tyr Cys Gly Asn Ala Asp Lys Thr Ser Gly Thr Phe Gly Ala
                 85                  90                  95

Gly Thr Thr Leu Thr Val Leu
                100
```

<210> SEQ ID NO 29
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Val Leu Thr Gln Gln Pro Ala Ser Val Ser Ala Asn Pro Gly Gly Thr
 1               5                  10                  15

Val Glu Ile Thr Cys Ser Gly Gly Gly Ser Tyr Gly Trp Tyr Gln
                20                  25                  30

Gln Lys Ser Pro Gly Ser Ala Pro Val Thr Leu Ile Tyr Arg Asn Asp
            35                  40                  45

Lys Arg Pro Ser Asp Ile Pro Ser Arg Phe Ser Gly Ser Lys Ser Gly
 50                  55                  60

Ser Thr Ala Thr Leu Thr Ile Thr Gly Val Gln Ala Glu Asp Glu Ala
 65                  70                  75                  80

Val Tyr Tyr Cys Gly Asn Ala Asp Lys Thr Ser Gly Thr Phe Gly Ala
                 85                  90                  95

Gly Thr Thr Leu Thr Val Leu
                100
```

```
<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Leu Thr Gln Pro Ala Ser Val Ser Ala Asn Pro Gly Glu Thr Val
1               5                   10                  15

Lys Ile Thr Cys Ser Gly Gly Ser Tyr Ser Asn Tyr Tyr Gly Trp Tyr
                20                  25                  30

Gln Gln Lys Ser Pro Gly Ser Ala Pro Val Thr Val Ile Tyr His Asn
        35                  40                  45

Asp Lys Arg Pro Ser Asp Ile Pro Ser Arg Phe Ser Gly Ser Thr Ser
    50                  55                  60

Gly Ser Thr Ser Thr Leu Thr Ile Thr Gly Val Gln Ala Asp Asp Glu
65                  70                  75                  80

Ala Val Tyr Phe Cys Gly Asn Ala Asp Ser Ser Ala Gly Asp Asp Ala
                85                  90                  95

Ile Phe Gly Ala Gly Thr Thr Leu Thr Val Leu
                100                 105

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Leu Thr Gln Pro Ala Ser Val Ser Ala Asn Pro Gly Glu Thr Val
1               5                   10                  15

Lys Ile Thr Cys Ser Gly Gly Ser Tyr Ser Asn Tyr Tyr Gly Trp Tyr
                20                  25                  30

Gln Gln Lys Ser Pro Gly Ser Ala Pro Val Thr Val Ile Tyr His Asn
        35                  40                  45

Asp Lys Arg Pro Ser Asp Ile Pro Ser Arg Phe Ser Gly Ser Thr Ser
    50                  55                  60

Gly Ser Thr Ser Thr Leu Thr Ile Thr Gly Val Gln Ala Asp Asp Glu
65                  70                  75                  80

Ala Val Tyr Phe Cys Gly Asn Ala Asp Ser Ser Ala Gly Asp Asp Ala
                85                  90                  95

Ile Phe Gly Ala Gly Thr Thr Leu Thr Val Leu
                100                 105

<210> SEQ ID NO 32
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Leu Ser Gln Pro Ala Ser Val Ser Ala Asn Pro Gly Glu Thr Val
1               5                   10                  15

Lys Ile Thr Cys Ser Gly Ser Ser Gly Ser Tyr Gly Trp Tyr Gln Gln
```

```
            20                  25                  30
Lys Ser Pro Gly Ser Ala Pro Val Thr Val Ile Tyr Trp Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Val Glu Asp Glu Ala Val
65                  70                  75                  80

Tyr Phe Cys Gly Ala Arg Glu Asp Ser Ser Asp Thr Ser Ser Phe Gly
                85                  90                  95

Ala Gly Thr Thr Leu Thr Val Leu
            100

<210> SEQ ID NO 33
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Leu Ser Gln Pro Ala Ser Val Ser Ala Asn Pro Gly Glu Thr Val
1               5                   10                  15

Lys Ile Thr Cys Ser Gly Ser Gly Ser Tyr Gly Trp Tyr Gln Gln
            20                  25                  30

Lys Ser Pro Gly Ser Ala Pro Val Thr Val Ile Tyr Trp Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Val Glu Asp Glu Ala Val
65                  70                  75                  80

Tyr Phe Cys Gly Ala Arg Glu Asp Ser Ser Asp Thr Ser Ser Phe Gly
                85                  90                  95

Ala Gly Thr Thr Leu Thr Val Leu
            100

<210> SEQ ID NO 34
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Leu Thr Gln Pro Ala Ser Val Ser Ala Ser Leu Gly Gly Thr Val
1               5                   10                  15

Lys Ile Thr Cys Ser Gly Ser Asp Ser Asn Asn Tyr Gly Trp Tyr Gln
            20                  25                  30

Gln Lys Ser Pro Gly Ser Ala Pro Val Thr Val Ile Tyr Tyr Asn Asp
            35                  40                  45

Lys Arg Pro Ser Asp Ile Pro Ser Arg Phe Ser Gly Ser Lys Ser Gly
        50                  55                  60

Ser Thr Gly Thr Leu Thr Ile Thr Gly Val Gln Ala Glu Asp Glu Ala
65                  70                  75                  80

Val Tyr Tyr Cys Gly Ala Trp Glu Ser Ser Asn Ser Gly Val Phe
                85                  90                  95

Gly Ala Gly Thr Thr Leu Thr Val Leu
```

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Leu Thr Gln Pro Ala Ser Val Ser Ala Asn Pro Gly Glu Thr Val
1               5                   10                  15

Lys Ile Pro Cys Ser Gly Gly Ser Gly Ser Tyr Tyr Gly Trp Tyr
            20                  25                  30

Gln Gln Lys Ser Pro Gly Ser Ala Pro Val Thr Leu Ile Tyr Tyr Asn
        35                  40                  45

Asn Lys Arg Pro Ser Asp Ile Pro Ser Arg Phe Ser Gly Ser Lys Ser
    50                  55                  60

Gly Ser Thr Gly Thr Leu Thr Ile Thr Gly Val Gln Ala Glu Asp Glu
65                  70                  75                  80

Ala Val Tyr Tyr Cys Gly Gly Tyr Asp Gly Ser Ser Asp Ser Gly Ile
                85                  90                  95

Phe Gly Ala Gly Thr Thr Leu Thr Val Leu
            100                 105

<210> SEQ ID NO 36
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Leu Thr Gln Pro Ala Ser Val Ser Ala Asn Pro Gly Gly Thr Val
1               5                   10                  15

Glu Ile Thr Cys Ser Gly Gly Gly Ser Tyr Tyr Gly Trp Phe Gln
            20                  25                  30

Gln Lys Ser Pro Ala Ser Ala Pro Val Thr Val Ile Tyr Glu Asn Thr
        35                  40                  45

Lys Arg Pro Ser Asp Ile Pro Ser Arg Phe Ser Gly Ser Lys Ser Gly
    50                  55                  60

Ser Thr Asn Thr Leu Thr Ile Thr Gly Val Arg Ala Glu Asp Glu Ala
65                  70                  75                  80

Val Tyr Phe Cys Gly Gly Tyr Asp Ser Ser Asn Gly Gly Thr Phe Gly
                85                  90                  95

Ala Gly Thr Thr Leu Thr Val Leu
            100

<210> SEQ ID NO 37
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Leu Thr Gln Pro Ala Ser Val Ser Ala Asn Pro Gly Gly Thr Val
1               5                   10                  15

Glu Ile Thr Cys Ser Gly Gly Ser Ser Tyr Tyr Gly Trp Phe Gln
            20                  25                  30

Gln Lys Ser Pro Ala Ser Ala Pro Val Thr Val Ile Tyr Glu Asn Thr
        35                  40                  45

Lys Arg Pro Ser Asp Ile Pro Ser Arg Phe Ser Gly Ser Lys Ser Gly
50                  55                  60

Ser Thr Asn Thr Leu Thr Ile Thr Gly Val Arg Ala Glu Asp Glu Ala
65                  70                  75                  80

Val Tyr Phe Cys Gly Gly Tyr Asp Ser Ser Asn Gly Thr Phe Gly
                85                  90                  95

Ala Gly Thr Thr Leu Thr Val Leu
            100

<210> SEQ ID NO 38
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Leu Thr Gln Pro Ala Ser Val Ser Ala Asn Pro Gly Gly Thr Val
1               5                   10                  15

Glu Ile Thr Cys Ser Gly Gly Ser Arg Tyr Tyr Gly Trp Phe Gln
            20                  25                  30

Gln Lys Ser Pro Ala Ser Ala Pro Val Thr Val Ile Tyr Glu Asn Thr
        35                  40                  45

Lys Arg Pro Ser Asp Ile Pro Ser Arg Phe Ser Gly Ser Lys Ser Gly
50                  55                  60

Ser Thr Asn Thr Leu Thr Ile Thr Gly Val Arg Ala Glu Asp Glu Ala
65                  70                  75                  80

Val Tyr Phe Cys Gly Gly Tyr Asp Ser Ser Asn Gly Thr Phe Gly
                85                  90                  95

Ala Gly Thr Thr Leu Thr Val Leu
            100

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Leu Thr Gln Pro Ala Ser Val Ser Ala Asn Pro Gly Gly Thr Val
1               5                   10                  15

Glu Ile Thr Cys Ser Gly Gly Ser Ser Val Ser Gly Tyr Gly Trp Tyr
            20                  25                  30

Gln Gln Lys Ser Pro Gly Ser Thr Pro Val Thr Val Ile Tyr Tyr Asn
        35                  40                  45

Asp Lys Arg Pro Ser Asp Ile Pro Ser Arg Phe Ser Gly Ser Lys Ser
50                  55                  60

Gly Ser Thr Gly Thr Leu Thr Ile Thr Gly Val Gln Ala Glu Asp Glu
65                  70                  75                  80

Ala Val Tyr Phe Cys Gly Ser Trp Asp Ser Ser Ala Gly Tyr Ser Thr
                85                  90                  95

```
Phe Gly Ala Gly Thr Thr Leu Thr Val Leu
            100                 105
```

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ala Leu Thr Gln Pro Ala Ser Val Ser Ala Asn Leu Gly Gly Thr Val
1               5                   10                  15

Lys Ile Thr Cys Ser Gly Gly Gly Asn Tyr Asp Gly Ser Tyr Tyr Tyr
                20                  25                  30

Gly Trp Tyr Gln Gln Lys Ser Pro Gly Ser Ala Pro Val Thr Val Ile
            35                  40                  45

Tyr Ser Asn Asn Gln Arg Pro Ser Asn Ile Pro Ser Arg Phe Ser Gly
50                  55                  60

Ser Leu Ser Gly Ser Thr Asn Thr Leu Thr Ile Thr Gly Val Gln Ala
65                  70                  75                  80

Asp Asp Glu Ala Ile Tyr Tyr Cys Gly Ser Ala Asp Ser Ser Ser Val
                85                  90                  95

Leu Phe Gly Ala Gly Thr Thr Leu Thr Val Leu
            100                 105
```

<210> SEQ ID NO 41
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Ala Leu Thr Gln Pro Ala Ser Val Ser Ala Asn Pro Gly Glu Thr Val
1               5                   10                  15

Glu Ile Thr Cys Ser Gly Gly Gly Ser Tyr Tyr Gly Trp His Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Leu Ser Gly Ser
            50                  55                  60

Thr Asn Thr Leu Thr Ile Thr Gly Val Arg Ala Glu Asp Glu Ala Val
65                  70                  75                  80

Tyr Tyr Cys Gly Ser Trp Asp Ser Ser Ala Gly Ile Phe Gly Ala Gly
                85                  90                  95

Thr Thr Leu Thr Val Leu
            100
```

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Ala Leu Thr Gln Pro Ala Ser Val Ser Ala Asn Leu Gly Glu Thr Val
1               5                   10                  15

Glu Ile Thr Cys Ser Gly Gly Tyr Ser Asp Asp Gly Ser Tyr Tyr Tyr
            20                  25                  30

Gly Trp Tyr Gln Gln Lys Ser Pro Gly Ser Ala Pro Val Thr Val Ile
        35                  40                  45

Tyr Glu Asn Asn Lys Arg Pro Ser Asp Ile Pro Ser Arg Phe Ser Gly
    50                  55                  60

Ser Leu Ser Gly Ser Thr Asn Thr Leu Thr Ile Thr Gly Val Arg Ala
65                  70                  75                  80

Glu Asp Glu Ala Val Tyr Tyr Cys Gly Ser Trp Asp Ser Ser Ala Gly
                85                  90                  95

Ile Phe Gly Ala Gly Thr Thr Leu Thr Val Leu
            100                 105

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Gly Ser Ser Gly Ser Tyr Tyr Gly
1               5

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly Gly Tyr Asn Tyr Ala Gly Ser Tyr Tyr Tyr Gly
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gly Gly Gly Ser Ser Tyr Tyr Gly
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Gly Gly Arg Ser Asp Tyr Tyr Tyr Ser
1               5                   10

<210> SEQ ID NO 47
```

```
<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gly Gly Tyr Ser Arg Tyr Gly Tyr Ser
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly Gly Tyr Ser Asn Tyr Gly Tyr Ser
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Gly Gly Tyr Ser Ser Tyr Gly Tyr Ser
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Arg Asp Asp Ser Gly Tyr Gly Tyr Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Gly Gly Gly Ser Tyr Ala Gly Ser Tyr Tyr Tyr Gly
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Ser Gly Gly Ser Tyr Thr Tyr Gly
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gly Gly Ser Tyr Ser Tyr Gly
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gly Gly Ser Gly Ser Tyr Tyr Tyr Gly
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Gly Gly Ser Gly Tyr Phe Phe Gly
1               5

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Gly Gly Ser Ser Asn Tyr Tyr Gly
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Gly Asp Gly Ser Ser Ser Tyr Tyr Gly
1               5                   10

<210> SEQ ID NO 58
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 58

Ser Gly Gly Gly Gly Ser Tyr Gly
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Gly Gly Ser Tyr Ser Asn Tyr Tyr Gly
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Gly Ser Ser Gly Ser Tyr Gly
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Gly Ser Asp Ser Asn Asn Tyr Gly
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Gly Gly Ser Gly Ser Ser Tyr Tyr Gly
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Gly Gly Gly Gly Ser Tyr Tyr Gly
1               5
```

```
<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gly Gly Gly Ser Ser Tyr Tyr Gly
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gly Gly Gly Ser Arg Tyr Tyr Gly
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Gly Gly Ser Ser Val Ser Gly Tyr Gly
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gly Gly Gly Asn Tyr Asp Gly Ser Tyr Tyr Tyr Gly
1               5                   10

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Gly Gly Gly Ser Tyr Tyr Gly
1               5

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

```
Ser Gly Gly Tyr Ser Asp Asp Gly Ser Tyr Tyr Tyr Gly
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Asn Thr Asn Arg Pro Ser
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asn Asp Asn Lys Arg Pro Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Ser Asn Lys Arg Pro Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Asn Asp Lys Arg Pro Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Asn Asn Gln Arg Pro Ser
1               5

<210> SEQ ID NO 75
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 75

Asn Asn Asn Lys Arg Pro Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Asn Lys Lys Arg Pro Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Asn Ser Gln Arg Pro Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Asn Asp Asn Arg Pro Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Asp Thr Lys Arg Pro Ser
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Ser Asn Lys Lys Pro Ser
1               5
```

```
<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Asp Asp Glu Arg Pro Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Tyr Asn Ser Lys Arg Pro Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Asn Asp Lys Arg Pro Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Asn Asp Lys Arg Pro Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Trp Asn Asp Lys Arg Pro Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 86

Tyr Asn Asn Lys Arg Pro Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Asn Thr Lys Arg Pro Ser
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Asn Asn Lys Arg Pro Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Tyr Asp Ser Asn Thr Tyr Ala
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Asn Glu Asp Ser Ser Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ala Trp Glu Gly Ser Ser
1               5

<210> SEQ ID NO 92
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 92

Gly Gly Tyr Asp Asp Thr Ile Asn
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Thr Asp Asn Asn Gly Tyr
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Thr Asp Ser Asn Gly Tyr
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Thr Asp Ile Asn Gly Tyr
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ser Phe Asp Ser Ser Thr Tyr Val Thr
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ser Ile Asp Ser Ser Arg Thr
1               5
```

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Thr Asp Ser Ser Tyr Val
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Ser Phe Asp Ser Ser Gly Asp
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ala Tyr Asp Gly Ser Thr Tyr Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Thr Tyr Asp Ser Ile Glu Ala
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Thr Glu Asp Asn Thr Gly Ala
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 103

Cys Gly Ser Ile Asp Ser Ser
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Asn Ala Asp Lys Thr Ser Gly
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Asn Ala Asp Ser Ser Ala Gly Asp Asp
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ala Arg Glu Asp Ser Ser Asp Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Ala Trp Glu Ser Ser Ser Asn Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Tyr Asp Gly Ser Ser Asp Ser
1               5

<210> SEQ ID NO 109
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Tyr Asp Ser Ser Asn Gly
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Ser Trp Asp Ser Ser Ala Gly Tyr
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ser Ala Asp Ser Ser Ser Val
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Ser Trp Asp Ser Ser Ala Gly
1               5

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: G, A, V, L, I, M, R, K or H
<220> FEATURE:
<221> NAME/KEY: MOD_RES
<222> LOCATION: (3)..(3)
<223> OTHER INFORMATION: G, A, V, L, I, M, D, E, S, T or C
<220> FEATURE:
<221> NAME/KEY: MOD_RES
<222> LOCATION: (4)..(4)
<223> OTHER INFORMATION: Y, F, W, R, K, H, D, E, G, A, S, T, C or absent
<220> FEATURE:
<221> NAME/KEY: MOD_RES
```

```
<222> LOCATION: (5)..(5)
<223> OTHER INFORMATION: N, Q, S, T, C, Y, F, W or absent
<220> FEATURE:
<221> NAME/KEY: MOD_RES
<222> LOCATION: (6)..(6)
<223> OTHER INFORMATION: Y, F, W, V, L, I, M, A, G, D, E or absent
<220> FEATURE:
<221> NAME/KEY: MOD_RES
<222> LOCATION: (7)..(7)
<223> OTHER INFORMATION: A, G, V, L, I, M, S, T, C, D, E or absent
<220> FEATURE:
<221> NAME/KEY: MOD_RES
<222> LOCATION: (8)..(8)
<223> OTHER INFORMATION: S, T, C, G, A, V, L, I, M or absent
<220> FEATURE:
<221> NAME/KEY: MOD_RES
<222> LOCATION: (9)..(9)
<223> OTHER INFORMATION: G, A, V, L, I, M, S, T, C, D, E, R, K, H, W, F,
      Y or absent
<220> FEATURE:
<221> NAME/KEY: MOD_RES
<222> LOCATION: (10)..(10)
<223> OTHER INFORMATION: S, T, C, Y, F, W, N, Q, G, A, V, L, I, M, R, K,
      H or absent
<220> FEATURE:
<221> NAME/KEY: MOD_RES
<222> LOCATION: (11)..(11)
<223> OTHER INFORMATION: Y, F, W, G, A, V, L, I, M, T, S, C, N, Q or
      absent
<220> FEATURE:
<221> NAME/KEY: MOD_RES
<222> LOCATION: (12)..(12)
<223> OTHER INFORMATION: Y, F or W
<220> FEATURE:
<221> NAME/KEY: MOD_RES
<222> LOCATION: (13)..(13)
<223> OTHER INFORMATION: G, A, V, L, I, M, S, T or C

<400> SEQUENCE: 113

Xaa Xaa Xaa Xaa Xaa Xaa Xaa Xaa Xaa Xaa Xaa Xaa Xaa
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: G, A, V, L, I or M
<220> FEATURE:
<221> NAME/KEY: MOD_RES
<222> LOCATION: (3)..(3)
<223> OTHER INFORMATION: G, A, V, L, I, M, S, T or C
<220> FEATURE:
<221> NAME/KEY: MOD_RES
<222> LOCATION: (4)..(4)
<223> OTHER INFORMATION: Y, F, W or absent
<220> FEATURE:
<221> NAME/KEY: MOD_RES
<222> LOCATION: (5)..(5)
<223> OTHER INFORMATION: S, T, C or absent
<220> FEATURE:
<221> NAME/KEY: MOD_RES
<222> LOCATION: (6)..(6)
<223> OTHER INFORMATION: D, E or absent
<220> FEATURE:
<221> NAME/KEY: MOD_RES
<222> LOCATION: (7)..(7)
<223> OTHER INFORMATION: D, E, S, T, C or absent
```

```
<220> FEATURE:
<221> NAME/KEY: MOD_RES
<222> LOCATION: (8)..(8)
<223> OTHER INFORMATION: G, V, L, I, M, A, S, T or C
<220> FEATURE:
<221> NAME/KEY: MOD_RES
<222> LOCATION: (9)..(9)
<223> OTHER INFORMATION: G, V, L, I, M, A, S, T or C
<220> FEATURE:
<221> NAME/KEY: MOD_RES
<222> LOCATION: (10)..(10)
<223> OTHER INFORMATION: Y, F, W, S, T, C, K, R or H
<220> FEATURE:
<221> NAME/KEY: MOD_RES
<222> LOCATION: (11)..(11)
<223> OTHER INFORMATION: Y, F, W, G, V, L, I, M or A
<220> FEATURE:
<221> NAME/KEY: MOD_RES
<222> LOCATION: (12)..(12)
<223> OTHER INFORMATION: Y, F or W
<220> FEATURE:
<221> NAME/KEY: MOD_RES
<222> LOCATION: (13)..(13)
<223> OTHER INFORMATION: G, V, L, I, M or A

<400> SEQUENCE: 114

Xaa Xaa Xaa Xaa Xaa Xaa Xaa Xaa Xaa Xaa Xaa Xaa Xaa
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: G, A, V, I, L or M
<220> FEATURE:
<221> NAME/KEY: MOD_RES
<222> LOCATION: (3)..(3)
<223> OTHER INFORMATION: G, A, V, I, L or M
<220> FEATURE:
<221> NAME/KEY: MOD_RES
<222> LOCATION: (4)..(4)
<223> OTHER INFORMATION: S, T, C, Y, F or W
<220> FEATURE:
<221> NAME/KEY: MOD_RES
<222> LOCATION: (5)..(5)
<223> OTHER INFORMATION: S, T, C, G, A, V, I, L or M
<220> FEATURE:
<221> NAME/KEY: MOD_RES
<222> LOCATION: (6)..(6)
<223> OTHER INFORMATION: V, A, I, L, M, G, D, E or absent
<220> FEATURE:
<221> NAME/KEY: MOD_RES
<222> LOCATION: (7)..(7)
<223> OTHER INFORMATION: S, T, C, D, E or absent
<220> FEATURE:
<221> NAME/KEY: MOD_RES
<222> LOCATION: (8)..(8)
<223> OTHER INFORMATION: G, A, V, I, L, M or absent
<220> FEATURE:
<221> NAME/KEY: MOD_RES
<222> LOCATION: (9)..(9)
<223> OTHER INFORMATION: S, T, C or absent
<220> FEATURE:
<221> NAME/KEY: MOD_RES
<222> LOCATION: (10)..(10)
<223> OTHER INFORMATION: Y, F, W or absent
<220> FEATURE:
```

```
<221> NAME/KEY: MOD_RES
<222> LOCATION: (11)..(11)
<223> OTHER INFORMATION: F, Y, W or absent
<220> FEATURE:
<221> NAME/KEY: MOD_RES
<222> LOCATION: (12)..(12)
<223> OTHER INFORMATION: F, Y or W
<220> FEATURE:
<221> NAME/KEY: MOD_RES
<222> LOCATION: (13)..(13)
<223> OTHER INFORMATION: G, V, L, I, M or A

<400> SEQUENCE: 115

Xaa Xaa Xaa Xaa Xaa Xaa Xaa Xaa Xaa Xaa Xaa Xaa Xaa
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: G, A, V, I, L or M
<220> FEATURE:
<221> NAME/KEY: MOD_RES
<222> LOCATION: (3)..(3)
<223> OTHER INFORMATION: G, A, V, I, L or M
<220> FEATURE:
<221> NAME/KEY: MOD_RES
<222> LOCATION: (4)..(4)
<223> OTHER INFORMATION: Y, F or W
<220> FEATURE:
<221> NAME/KEY: MOD_RES
<222> LOCATION: (5)..(5)
<223> OTHER INFORMATION: S, T or C
<220> FEATURE:
<221> NAME/KEY: MOD_RES
<222> LOCATION: (6)..(6)
<223> OTHER INFORMATION: D or E
<220> FEATURE:
<221> NAME/KEY: MOD_RES
<222> LOCATION: (7)..(7)
<223> OTHER INFORMATION: D or E
<220> FEATURE:
<221> NAME/KEY: MOD_RES
<222> LOCATION: (8)..(8)
<223> OTHER INFORMATION: G, A, V, I, L or M
<220> FEATURE:
<221> NAME/KEY: MOD_RES
<222> LOCATION: (9)..(9)
<223> OTHER INFORMATION: S, T or C
<220> FEATURE:
<221> NAME/KEY: MOD_RES
<222> LOCATION: (10)..(10)
<223> OTHER INFORMATION: Y, F or W
<220> FEATURE:
<221> NAME/KEY: MOD_RES
<222> LOCATION: (11)..(11)
<223> OTHER INFORMATION: Y, F or W
<220> FEATURE:
<221> NAME/KEY: MOD_RES
<222> LOCATION: (12)..(12)
<223> OTHER INFORMATION: Y, F or W
<220> FEATURE:
<221> NAME/KEY: MOD_RES
<222> LOCATION: (13)..(13)
<223> OTHER INFORMATION: G, A, V, I, L or M

<400> SEQUENCE: 116
```

```
Xaa Xaa Xaa Xaa Xaa Xaa Xaa Xaa Xaa Xaa Xaa Xaa Xaa
1               5                   10
```

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, N, Q, Y, F, W, S, T, C, R, K or H
<220> FEATURE:
<221> NAME/KEY: MOD_RES
<222> LOCATION: (2)..(2)
<223> OTHER INFORMATION: N, Q, D, E, S, T or C
<220> FEATURE:
<221> NAME/KEY: MOD_RES
<222> LOCATION: (3)..(3)
<223> OTHER INFORMATION: T, S, C, N, Q, D, E, K, R or H
<220> FEATURE:
<221> NAME/KEY: MOD_RES
<222> LOCATION: (4)..(4)
<223> OTHER INFORMATION: N, Q, K, R, H, E or D
<220> FEATURE:
<221> NAME/KEY: MOD_RES
<222> LOCATION: (5)..(5)
<223> OTHER INFORMATION: R, K or H
<220> FEATURE:
<221> NAME/KEY: MOD_RES
<222> LOCATION: (7)..(7)
<223> OTHER INFORMATION: S, T or C

<400> SEQUENCE: 117

```
Xaa Xaa Xaa Xaa Xaa Pro Xaa
1               5
```

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, Y, F or W
<220> FEATURE:
<221> NAME/KEY: MOD_RES
<222> LOCATION: (2)..(2)
<223> OTHER INFORMATION: N, Q, S, T or C
<220> FEATURE:
<221> NAME/KEY: MOD_RES
<222> LOCATION: (3)..(3)
<223> OTHER INFORMATION: T, S, C, D, E, N or Q
<220> FEATURE:
<221> NAME/KEY: MOD_RES
<222> LOCATION: (4)..(4)
<223> OTHER INFORMATION: K, R, H, N or Q
<220> FEATURE:
<221> NAME/KEY: MOD_RES
<222> LOCATION: (5)..(5)
<223> OTHER INFORMATION: R, K or H
<220> FEATURE:
<221> NAME/KEY: MOD_RES
<222> LOCATION: (7)..(7)
<223> OTHER INFORMATION: S, T or C

<400> SEQUENCE: 118

```
Xaa Xaa Xaa Xaa Xaa Pro Xaa
1               5
```

```
<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F, W, D or E
<220> FEATURE:
<221> NAME/KEY: MOD_RES
<222> LOCATION: (2)..(2)
<223> OTHER INFORMATION: N, Q, S, T or C
<220> FEATURE:
<221> NAME/KEY: MOD_RES
<222> LOCATION: (3)..(3)
<223> OTHER INFORMATION: D, E, N or Q
<220> FEATURE:
<221> NAME/KEY: MOD_RES
<222> LOCATION: (4)..(4)
<223> OTHER INFORMATION: K, R or H
<220> FEATURE:
<221> NAME/KEY: MOD_RES
<222> LOCATION: (5)..(5)
<223> OTHER INFORMATION: R, K or H
<220> FEATURE:
<221> NAME/KEY: MOD_RES
<222> LOCATION: (7)..(7)
<223> OTHER INFORMATION: S, T or C

<400> SEQUENCE: 119

Xaa Xaa Xaa Xaa Xaa Pro Xaa
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E or D
<220> FEATURE:
<221> NAME/KEY: MOD_RES
<222> LOCATION: (2)..(2)
<223> OTHER INFORMATION: N or Q
<220> FEATURE:
<221> NAME/KEY: MOD_RES
<222> LOCATION: (3)..(3)
<223> OTHER INFORMATION: N or Q
<220> FEATURE:
<221> NAME/KEY: MOD_RES
<222> LOCATION: (4)..(4)
<223> OTHER INFORMATION: K, R or H
<220> FEATURE:
<221> NAME/KEY: MOD_RES
<222> LOCATION: (5)..(5)
<223> OTHER INFORMATION: R, K or H
<220> FEATURE:
<221> NAME/KEY: MOD_RES
<222> LOCATION: (7)..(7)
<223> OTHER INFORMATION: S, T or C

<400> SEQUENCE: 120

Xaa Xaa Xaa Xaa Xaa Pro Xaa
1               5

<210> SEQ ID NO 121
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, V, L, I, M, C, S or T
<220> FEATURE:
<221> NAME/KEY: MOD_RES
<222> LOCATION: (2)..(2)
<223> OTHER INFORMATION: G, A, N, Q, V, L, I, M, S, T or C
<220> FEATURE:
<221> NAME/KEY: MOD_RES
<222> LOCATION: (3)..(3)
<223> OTHER INFORMATION: Y, F, W, E, D, T, S, C, I, V, L, M, A, G, R, K
      or H
<220> FEATURE:
<221> NAME/KEY: MOD_RES
<222> LOCATION: (4)..(4)
<223> OTHER INFORMATION: D, E, I, V, L, M, G or A
<220> FEATURE:
<221> NAME/KEY: MOD_RES
<222> LOCATION: (5)..(5)
<223> OTHER INFORMATION: S, T, C, G, A, D, E, N, Q, I, V, L, M, K, R or
      H
<220> FEATURE:
<221> NAME/KEY: MOD_RES
<222> LOCATION: (6)..(6)
<223> OTHER INFORMATION: N, Q, S, T, C, I, V, L, M, G or A
<220> FEATURE:
<221> NAME/KEY: MOD_RES
<222> LOCATION: (7)..(7)
<223> OTHER INFORMATION: T, S, C, I, V, L, M, A, G, R, K, H, Y, F, W, D,
      E, N or Q
<220> FEATURE:
<221> NAME/KEY: MOD_RES
<222> LOCATION: (8)..(8)
<223> OTHER INFORMATION: Y, F, W, N, Q, T, S, C, V, L, I, M, A, D, E, G
      or absent
<220> FEATURE:
<221> NAME/KEY: MOD_RES
<222> LOCATION: (9)..(9)
<223> OTHER INFORMATION: V, L, I, M, A, G, D, E or absent
<220> FEATURE:
<221> NAME/KEY: MOD_RES
<222> LOCATION: (10)..(10)
<223> OTHER INFORMATION: A, G, V, L, I, M, T, S, C, D, E, Y, F, W or
      absent

<400> SEQUENCE: 121

Xaa Xaa Xaa Xaa Xaa Xaa Xaa Xaa Xaa Xaa
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, V, L, I or M
<220> FEATURE:
<221> NAME/KEY: MOD_RES
<222> LOCATION: (2)..(2)
<223> OTHER INFORMATION: G, A, V, L, I, M, S, T or C
<220> FEATURE:
<221> NAME/KEY: MOD_RES
<222> LOCATION: (3)..(3)
<223> OTHER INFORMATION: Y, F or W
<220> FEATURE:
<221> NAME/KEY: MOD_RES
```

```
<222> LOCATION: (4)..(4)
<223> OTHER INFORMATION: D or E
<220> FEATURE:
<221> NAME/KEY: MOD_RES
<222> LOCATION: (5)..(5)
<223> OTHER INFORMATION: S, T or C
<220> FEATURE:
<221> NAME/KEY: MOD_RES
<222> LOCATION: (6)..(6)
<223> OTHER INFORMATION: S, T, C, N, Q, I, V, L, M, A or G
<220> FEATURE:
<221> NAME/KEY: MOD_RES
<222> LOCATION: (7)..(7)
<223> OTHER INFORMATION: N, Q, T, S, C, D, E, I, V, L, M, A or G
<220> FEATURE:
<221> NAME/KEY: MOD_RES
<222> LOCATION: (8)..(8)
<223> OTHER INFORMATION: G, A, V, L, I, M, Y, F or W
<220> FEATURE:
<221> NAME/KEY: MOD_RES
<222> LOCATION: (9)..(9)
<223> OTHER INFORMATION: F, Y, W, A, V, L, I, M, G or absent

<400> SEQUENCE: 122

Xaa Xaa Xaa Xaa Xaa Xaa Xaa Xaa Xaa
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, V, L, I or M
<220> FEATURE:
<221> NAME/KEY: MOD_RES
<222> LOCATION: (2)..(2)
<223> OTHER INFORMATION: T, S or C
<220> FEATURE:
<221> NAME/KEY: MOD_RES
<222> LOCATION: (3)..(3)
<223> OTHER INFORMATION: Y, F or W
<220> FEATURE:
<221> NAME/KEY: MOD_RES
<222> LOCATION: (4)..(4)
<223> OTHER INFORMATION: D or E
<220> FEATURE:
<221> NAME/KEY: MOD_RES
<222> LOCATION: (5)..(5)
<223> OTHER INFORMATION: S, T or C
<220> FEATURE:
<221> NAME/KEY: MOD_RES
<222> LOCATION: (6)..(6)
<223> OTHER INFORMATION: I, V, L, M, A, G, S, T or C
<220> FEATURE:
<221> NAME/KEY: MOD_RES
<222> LOCATION: (7)..(7)
<223> OTHER INFORMATION: E, D, A, G, V, L, I or M
<220> FEATURE:
<221> NAME/KEY: MOD_RES
<222> LOCATION: (8)..(8)
<223> OTHER INFORMATION: A, G, V, L, I or M
<220> FEATURE:
<221> NAME/KEY: MOD_RES
<222> LOCATION: (9)..(9)
<223> OTHER INFORMATION: Y, F, W or absent

<400> SEQUENCE: 123

Xaa Xaa Xaa Xaa Xaa Xaa Xaa Xaa Xaa
1               5
```

```
<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, V, L, I or M
<220> FEATURE:
<221> NAME/KEY: MOD_RES
<222> LOCATION: (2)..(2)
<223> OTHER INFORMATION: S, T or C
<220> FEATURE:
<221> NAME/KEY: MOD_RES
<222> LOCATION: (3)..(3)
<223> OTHER INFORMATION: W, F or Y
<220> FEATURE:
<221> NAME/KEY: MOD_RES
<222> LOCATION: (4)..(4)
<223> OTHER INFORMATION: D or E
<220> FEATURE:
<221> NAME/KEY: MOD_RES
<222> LOCATION: (5)..(5)
<223> OTHER INFORMATION: S, T or C
<220> FEATURE:
<221> NAME/KEY: MOD_RES
<222> LOCATION: (6)..(6)
<223> OTHER INFORMATION: S, T or C
<220> FEATURE:
<221> NAME/KEY: MOD_RES
<222> LOCATION: (7)..(7)
<223> OTHER INFORMATION: A, G, V, L, I or M
<220> FEATURE:
<221> NAME/KEY: MOD_RES
<222> LOCATION: (8)..(8)
<223> OTHER INFORMATION: G, A, V, L, I or M

<400> SEQUENCE: 124

Xaa Xaa Xaa Xaa Xaa Xaa Xaa Xaa
1               5

<210> SEQ ID NO 125
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Ala Ala Val Thr Leu Asp Glu Ser Gly Gly Gly Leu Gln Thr Pro
1               5                   10                  15

Gly Gly Gly Leu Ser Leu Val Cys Lys Ala Ser Gly Phe Asp Phe Asn
            20                  25                  30

Asp Tyr Gly Met Gly Trp Val Arg Gln Ala Pro Gly Lys Gly Leu Glu
        35                  40                  45

Phe Val Ala Gly Ile Tyr Ser Ser Gly Arg Tyr Thr Tyr Tyr Gly Ala
    50                  55                  60

Ala Val Gln Gly Arg Ala Thr Ile Ser Arg Asp Asn Gly Gln Ser Thr
65                  70                  75                  80

Val Arg Leu Gln Leu Asn Asn Leu Arg Ala Glu Asp Ala Ala Ile Tyr
                85                  90                  95

Tyr Cys Ala Lys Asn Ala Asp Ser Gly Tyr Tyr Thr Gly Ala Gly Tyr
            100                 105                 110

Ile Asp Ala Trp Gly His Gly Thr Glu Val Ile Val Ser
        115                 120                 125
```

<210> SEQ ID NO 126
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Ala Ala Val Thr Leu Asp Glu Ser Glu Gly Gly Leu Gln Thr Pro
1               5                   10                  15

Gly Gly Gly Leu Ser Leu Val Cys Lys Ala Ser Gly Phe Thr Phe Ser
            20                  25                  30

Ser Tyr Asn Met Gly Trp Val Arg Gln Ala Pro Gly Lys Gly Leu Glu
        35                  40                  45

Phe Val Ala Ala Ile Ser Asn Asp Ala Asn Phe Thr Ala Tyr Gly Ser
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Phe Cys Ala Lys Ser Ala Gly Thr Gly Cys Asn Asn Gly Tyr Asn Cys
            100                 105                 110

Ala Asp Tyr Thr Pro Gly Tyr Ile Asp Ser Trp Gly His Gly Thr Glu
        115                 120                 125

Val Ile Val Ser
    130

<210> SEQ ID NO 127
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Ala Ala Val Thr Leu Asp Glu Ser Glu Gly Gly Leu Gln Thr Pro
1               5                   10                  15

Gly Gly Gly Leu Ser Leu Val Cys Arg Ala Ser Gly Phe Thr Phe Ser
            20                  25                  30

Ser Tyr Asn Met Gly Trp Val Arg Gln Ala Pro Gly Lys Gly Leu Glu
        35                  40                  45

Phe Val Ala Ala Ile Ser Asn Asp Ala Asn Phe Thr Ala Tyr Gly Ser
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Phe Cys Ala Lys Ser Ala Gly Thr Gly Cys Asn Asn Gly Tyr Asn Cys
            100                 105                 110

Ala Asp Tyr Thr Pro Gly Tyr Ile Asp Ser Trp Gly His Gly Thr Glu
        115                 120                 125

Val Ile Val Ser
    130

<210> SEQ ID NO 128

<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Ala Ala Val Thr Leu Asp Glu Ser Gly Gly Gly Leu Gln Thr Pro
1               5                   10                  15

Gly Gly Thr Leu Ser Leu Val Cys Lys Ala Ser Gly Phe Thr Phe Ser
            20                  25                  30

Asp Tyr Gly Met Gly Trp Val Arg Gln Ala Pro Gly Lys Gly Leu Glu
        35                  40                  45

Tyr Val Ala Glu Ile Asp Ser Ala Gly Ser Ser Thr Tyr Tyr Thr Pro
50                  55                  60

Ala Val Arg Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Thr Lys Cys Ser Gly Ser Gly Cys Ala Tyr Gly Glu Ile
            100                 105                 110

Asp Thr Trp Gly His Gly Thr Glu Val Ile Val Ser
        115                 120

<210> SEQ ID NO 129
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Ala Ala Val Thr Leu Asp Glu Ser Gly Gly Gly Leu Gln Thr Pro
1               5                   10                  15

Gly Gly Thr Leu Ser Leu Val Cys Lys Ala Ser Gly Phe Thr Phe Ser
            20                  25                  30

Ser His Gly Met Gln Trp Val Arg Gln Ala Pro Gly Lys Gly Leu Glu
        35                  40                  45

Trp Val Ala Gly Ile Ser Arg Asp Gly Ser Arg Thr Arg Tyr Gly Ala
50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Ile Tyr
                85                  90                  95

Phe Cys Ala Lys Ser Ala Tyr Glu Cys Asp Gly Tyr Ser Cys Trp Thr
            100                 105                 110

Phe Ile Ala Gly Ser Ile Asp Ala Trp Gly His Gly Thr Glu Val Ile
        115                 120                 125

Val Ser
130

<210> SEQ ID NO 130
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Ala Ala Val Thr Leu Asp Glu Ser Gly Gly Gly Leu Arg Thr Pro
1               5                   10                  15

Gly Gly Ala Leu Ser Leu Val Cys Lys Gly Ser Gly Phe Thr Phe Ser
            20                  25                  30

Asp Arg Gly Met Phe Trp Val Arg Gln Ala Pro Gly Lys Gly Leu Glu
        35                  40                  45

Tyr Val Ala Gly Ile Ser Ser Ser Gly Arg Ser Ala Ala Tyr Gly Ala
50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Phe Cys Ala Lys Ser Thr Gly Thr Gly Tyr Gly Gly Val Gly Glu Ile
            100                 105                 110

Asp Ala Trp Gly His Gly Thr Glu Val Ile Val Ser
        115                 120

<210> SEQ ID NO 131
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Ala Ala Val Thr Leu Asp Glu Ser Gly Gly Gly Leu Gln Thr Pro
1               5                   10                  15

Gly Gly Ala Leu Ser Leu Val Cys Lys Gly Ser Gly Phe Thr Phe Ser
            20                  25                  30

Asp Arg Gly Met Phe Trp Val Arg Gln Ala Pro Gly Lys Gly Leu Glu
        35                  40                  45

Tyr Val Ala Gly Ile Ser Ser Ser Gly Arg Ser Ala Ala Tyr Gly Ala
50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Cys Cys Ala Lys Ser Thr Gly Thr Gly Tyr Gly Gly Val Gly Glu Ile
            100                 105                 110

Asp Ala Trp Gly His Gly Thr Glu Val Ile Val Ser
        115                 120

<210> SEQ ID NO 132
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gly Met Phe Trp Val Arg Gln Ala Pro Gly Lys Gly Leu Glu
            35                  40                  45

Tyr Val Ala Gly Ile Ser Ser Gly Arg Ser Thr Ala Tyr Gly Ala
 50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95

Phe Cys Ala Lys Ser Thr Gly Thr Gly Tyr Gly Val Gly Glu Ile
            100                 105                 110

Asp Ala Trp Gly His Gly Thr Glu Val Ile Val Ser
            115                 120

<210> SEQ ID NO 133
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Ala Ala Val Thr Leu Asp Glu Ser Gly Gly Gly Leu Gln Thr Pro
 1               5                  10                  15

Gly Gly Ala Leu Ser Leu Val Cys Lys Ala Ser Gly Phe Thr Phe Ser
                 20                  25                  30

Ser Tyr Gly Met Phe Trp Val Arg Gln Ala Pro Gly Lys Gly Leu Glu
            35                  40                  45

Tyr Val Ala Gly Ile Ser Ser Gly Arg Ser Thr Ala Tyr Gly Ala
 50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95

Phe Cys Ala Lys Ser Thr Gly Thr Gly Tyr Gly Val Gly Glu Ile
            100                 105                 110

Asp Ala Trp Gly His Gly Thr Glu Val Ile Val Ser
            115                 120

<210> SEQ ID NO 134
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Ala Ala Val Thr Leu Asp Glu Ser Gly Gly Gly Leu Gln Thr Pro
 1               5                  10                  15

Gly Gly Ala Leu Ser Leu Val Cys Lys Ala Ser Gly Phe Thr Met Ser
                 20                  25                  30

Ser Tyr Ala Met Tyr Trp Val Arg Gln Ala Pro Gly Lys Gly Leu Glu
            35                  40                  45

Tyr Val Ala Glu Ile Asn Ala Val Gly Ser Thr Thr Gly Tyr Gly Pro
 50                  55                  60

Ala Val Asp Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
            85                  90                  95

Tyr Cys Ala Lys Ser Tyr Ser Asn Cys Gly Gly Tyr Ser Cys Ala Ala
            100                 105                 110

Ala Asn Ile Asp Ala Trp Gly His Gly Thr Glu Val Ile Val Ser
        115                 120                 125

<210> SEQ ID NO 135
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Met Ser
            20                  25                  30

Ser Tyr Ala Met Tyr Trp Val Arg Gln Ala Pro Gly Lys Gly Leu Glu
        35                  40                  45

Tyr Val Ala Glu Ile Asn Ala Val Gly Ser Thr Thr Gly Tyr Gly Pro
    50                  55                  60

Ala Val Asp Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
            85                  90                  95

Tyr Cys Ala Lys Ser Tyr Ser Asn Cys Gly Asp Tyr Ser Cys Ala Ala
            100                 105                 110

Ala Asn Ile Asp Ala Trp Gly His Gly Thr Glu Val Ile Val Ser
        115                 120                 125

<210> SEQ ID NO 136
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gly Met Gln Trp Val Arg Gln Ala Pro Gly Lys Gly Leu Glu
        35                  40                  45

Trp Val Ala Gly Ile Ser Ala Thr Gly Ser Glu Thr Ser Tyr Ala Pro
    50                  55                  60

Ala Val Lys Gly Arg Ala Thr Ile Ser Arg Asp Asn Gly Gln Ser Thr
65                  70                  75                  80

Val Arg Leu Gln Leu Asp Asn Leu Arg Ala Glu Asp Thr Ala Thr Tyr
            85                  90                  95

Tyr Cys Ala Lys Ala Ala Gly Ser Gly Arg Cys Ala Gly Ala Gly Gly
            100                 105                 110

Tyr Cys Asn Pro Gly Ser Ile Asp Thr Trp Gly His Gly Thr Glu Val
        115                 120                 125

Ile Val Ser
    130

<210> SEQ ID NO 137
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Ala Ala Val Thr Leu Asp Glu Ser Glu Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gly Val Gln Trp Val Arg Gln Ala Pro Gly Lys Gly Leu Glu
        35                  40                  45

Trp Val Ala Gly Ile Ser Ala Thr Gly Ser Glu Thr Ser Tyr Ala Pro
50                  55                  60

Ala Val Lys Gly Arg Ala Thr Ile Ser Arg Asp Asn Gly Gln Ser Thr
65                  70                  75                  80

Val Arg Leu Gln Leu Asp Asn Leu Arg Ala Glu Asp Thr Ala Thr Tyr
                85                  90                  95

Tyr Cys Ala Lys Ala Ala Gly Ser Gly Arg Cys Ala Gly Ala Gly Gly
            100                 105                 110

Tyr Cys Asn Pro Gly Ser Ile Asp Thr Trp Gly His Gly Thr Glu Val
        115                 120                 125

Ile Val Ser
    130

<210> SEQ ID NO 138
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gln Met Asn Trp Val Arg Gln Ala Pro Gly Lys Gly Leu Glu
        35                  40                  45

Phe Val Ala Ala Ile Asn Ser Phe Gly Asn Ser Thr Gly His Gly Ala
50                  55                  60

Ala Val Lys Gly Arg Ala Thr Ile Ser Arg Asp Asp Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Ala Lys Gly Ala Tyr Asp Tyr Cys Gly Gly Gly Trp Cys Asn
            100                 105                 110

Thr Ala Tyr Ile Asp Ala Trp Gly His Gly Thr Glu Val Ile Val Ser
        115                 120                 125

<210> SEQ ID NO 139
<211> LENGTH: 129

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gln Met Asn Trp Val Arg Gln Ala Pro Gly Lys Gly Leu Glu
        35                  40                  45

Phe Val Ala Ala Ile Asn Ser Phe Gly Asn Ser Thr Gly His Gly Ala
    50                  55                  60

Ala Val Lys Gly Arg Ala Thr Ile Ser Arg Asp Asp Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Ala Lys Gly Ala Tyr Asp Tyr Cys Gly Ser Gly Gly Trp Cys
                100                 105                 110

Asn Thr Ala Tyr Ile Asp Ala Trp Gly His Gly Thr Glu Val Ile Val
            115                 120                 125

Ser

<210> SEQ ID NO 140
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gln Met Asn Trp Ile Arg Gln Ala Pro Gly Lys Gly Leu Glu
        35                  40                  45

Trp Val Ala Ala Ile Asn Arg Phe Gly Asn Thr Thr Gly Pro Gly Ala
    50                  55                  60

Ala Val Lys Gly Arg Val Thr Ile Ser Arg Asp Asp Gly Gln Ser Thr
65                  70                  75                  80

Val Arg Leu Gln Leu Ser Asn Leu Arg Ala Glu Asp Thr Gly Thr Tyr
                85                  90                  95

Tyr Cys Ala Lys Gly Ala Tyr Gly Tyr Cys Gly Ser Gly Ser Trp Cys
                100                 105                 110

Asn Ala Ala Tyr Ile Asp Ala Trp Gly His Gly Thr Glu Val Ile Val
            115                 120                 125

Ser

<210> SEQ ID NO 141
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Ala Ala Val Thr Leu Asp Glu Ser Gly Gly Gly Leu Gln Thr Pro
1               5                   10                  15

Gly Gly Gly Leu Ser Leu Val Cys Lys Ala Ser Gly Phe Asp Phe Ser
            20                  25                  30

Ser Tyr Gln Met Asn Trp Val Arg Gln Ala Pro Gly Lys Gly Leu Glu
        35                  40                  45

Phe Val Ala Ala Ile Asn Arg Phe Gly Asn Ser Thr Gly His Gly Ala
    50                  55                  60

Ala Val Lys Gly Arg Val Thr Ile Ser Arg Asp Asp Gly Gln Ser Thr
65                  70                  75                  80

Val Arg Leu Gln Leu Ser Asn Leu Arg Ala Glu Asp Thr Ala Thr Tyr
                85                  90                  95

Phe Cys Ala Lys Gly Ala Tyr Gly Tyr Cys Gly Ser Gly Ser Trp Cys
            100                 105                 110

Ala Ala Gly Leu Ile Asp Ala Trp Gly His Gly Thr Glu Val Ile Val
        115                 120                 125

Ser

<210> SEQ ID NO 142
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Gln Met Asn Trp Ile Arg Gln Ala Pro Gly Lys Gly Leu Glu
        35                  40                  45

Phe Val Ala Ala Ile Asn Arg Phe Gly Asn Ser Thr Gly His Gly Ala
    50                  55                  60

Ala Val Lys Gly Arg Val Thr Ile Ser Arg Asp Asp Gly Gln Gly Thr
65                  70                  75                  80

Val Arg Leu Gln Leu Ser Asp Pro Arg Ala Glu Asp Thr Ala Thr Tyr
                85                  90                  95

Tyr Cys Ala Lys Ser Ala Tyr Gly Tyr Cys Gly Ser Gly Ser Trp Cys
            100                 105                 110

Ser Pro Ala Thr Ile Asp Ala Trp Gly His Gly Thr Glu Val Ile Val
        115                 120                 125

Ser

<210> SEQ ID NO 143
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Ala Ala Val Thr Leu Asp Glu Ser Gly Gly Gly Leu Gln Thr Pro
1               5                   10                  15

```
Gly Gly Ala Leu Ser Leu Val Cys Lys Ala Ser Gly Phe Thr Phe Ser
            20                  25                  30

Ser Tyr Gln Met Asn Trp Ile Arg Gln Ala Pro Gly Lys Gly Leu Glu
        35                  40                  45

Phe Val Ala Ala Ile Asn Arg Phe Gly Asn Ser Thr Gly His Gly Ala
    50                  55                  60

Ala Val Lys Gly Arg Val Thr Ile Ser Arg Asp Asp Gly Gln Ser Thr
65                  70                  75                  80

Val Arg Leu Gln Leu Ser Asp Leu Arg Ala Glu Asp Thr Ala Thr Tyr
                85                  90                  95

Tyr Cys Ala Lys Ser Ala Tyr Gly Tyr Cys Gly Ser Gly Ser Trp Cys
            100                 105                 110

Ser Pro Ala Thr Ile Asp Ala Trp Gly His Gly Thr Glu Val Ile Val
            115                 120                 125

Ser

<210> SEQ ID NO 144
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Ala Ala Val Thr Leu Asp Glu Ser Gly Gly Gly Leu Gln Thr Pro
1               5                   10                  15

Gly Gly Gly Leu Ser Leu Val Cys Lys Ala Ser Gly Phe Asp Phe Ser
            20                  25                  30

Ser Tyr Gln Met Asn Trp Ile Arg Gln Ala Pro Gly Lys Gly Leu Glu
        35                  40                  45

Phe Val Ala Ala Ile Asn Arg Phe Gly Asn Gly Thr Gly His Gly Ala
    50                  55                  60

Ala Val Lys Gly Arg Val Thr Ile Ser Arg Asp Asp Gly Gln Ser Thr
65                  70                  75                  80

Val Arg Leu Gln Leu Asn Asn Leu Arg Ala Glu Asp Thr Ala Thr Tyr
                85                  90                  95

Tyr Cys Ala Lys Gly Ala Tyr Gly Tyr Cys Gly Ser Gly Ser Trp Cys
            100                 105                 110

Ser Pro Ala Thr Ile Asp Ala Trp Gly His Gly Thr Glu Val Ile Val
            115                 120                 125

Ser

<210> SEQ ID NO 145
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Asp Phe Ser
            20                  25                  30

Ser Tyr Gln Met Asn Trp Ile Arg Gln Ala Pro Gly Lys Gly Leu Glu
```

```
                35                  40                  45
Phe Val Ala Ala Ile Asn Arg Phe Gly Asn Ser Thr Gly His Gly Ala
         50                  55                  60
Ala Val Lys Gly Arg Val Thr Ile Ser Arg Asp Asp Gly Gln Ser Thr
 65                  70                  75                  80
Val Arg Leu Gln Leu Ser Asn Leu Arg Ala Glu Asp Thr Ala Thr Tyr
                 85                  90                  95
Phe Cys Ala Lys Gly Ala Tyr Tyr Cys Gly Ser Gly Ser Trp Cys
            100                 105                 110
Ser Pro Ala Thr Ile Asp Ala Trp Gly His Gly Thr Glu Val Ile Val
            115                 120                 125
Ser

<210> SEQ ID NO 146
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Met Ala Ala Val Thr Leu Asp Glu Ser Gly Gly Gly Leu Gln Thr Pro
 1               5                   10                  15
Gly Gly Ala Leu Ser Leu Val Cys Lys Ala Ser Gly Phe Thr Phe Ser
                 20                  25                  30
Thr His Gly Met Phe Trp Val Arg Gln Ala Pro Gly Lys Gly Leu Glu
            35                  40                  45
Tyr Val Ala Lys Ile Asn Ala Ala Gly Ser Gly Thr Gly Tyr Gly Ser
         50                  55                  60
Ala Val Lys Gly Arg Ala Thr Ile Ser Arg Asp Asn Gly Gln Ser Thr
 65                  70                  75                  80
Leu Arg Leu Gln Leu Asn Asn Leu Arg Ala Glu Asp Thr Gly Thr Tyr
                 85                  90                  95
Tyr Cys Ala Lys Asp Asn Tyr Asp Cys Gly Lys Ser Ile Cys Gly Ala
            100                 105                 110
Tyr Ala Gly Ser Ile Asp Ala Trp Gly His Gly Thr Glu Val Ile Val
            115                 120                 125
Ser

<210> SEQ ID NO 147
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Ala Ala Val Thr Leu Asp Glu Ser Gly Gly Gly Leu Gln Thr Pro
 1               5                   10                  15
Gly Gly Gly Leu Ser Leu Val Cys Lys Ala Ser Gly Phe Ser Phe Ser
                 20                  25                  30
Ser Tyr Gly Met Phe Trp Val Arg Gln Ala Pro Gly Lys Gly Leu Glu
            35                  40                  45
Tyr Val Ala Glu Val Ser Ser Asn Asp Gly Ser Asp Thr Ser Tyr Gly
         50                  55                  60
```

```
Ser Ala Val Glu Gly Arg Ala Thr Ile Ser Arg Asp Asn Gly Gln Ser
 65                  70                  75                  80

Thr Val Arg Leu Gln Leu Asn Asn Leu Arg Ala Glu Asp Thr Ala Thr
                 85                  90                  95

Tyr Phe Cys Ala Lys Ser Ser His Glu Cys Gly Lys Ser Ser Cys Trp
            100                 105                 110

Gly Tyr Ile Gly Ser Ile Asp Ala Trp Gly His Gly Thr Glu Val Ile
            115                 120                 125

Val Ser
    130

<210> SEQ ID NO 148
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ala Ala Val Thr Leu Asp Glu Ser Gly Gly Gly Leu Gln Thr Pro
 1               5                  10                  15

Gly Gly Gly Leu Ser Leu Val Cys Lys Ala Ser Gly Phe Asp Phe Ser
            20                  25                  30

Ser Tyr Ala Met Met Trp Val Arg Gln Ala Pro Gly Lys Gly Leu Glu
         35                  40                  45

Trp Val Ala Gly Ile Asp Asp Gly Ser Tyr Thr Gly Tyr Gly Ala
 50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95

Tyr Cys Ala Arg Gly Gly Leu Thr Ile Asp Thr Trp Gly Arg Gly Thr
            100                 105                 110

Glu Val Ile Val Ser
        115

<210> SEQ ID NO 149
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Ala Ala Val Thr Leu Asp Glu Ser Gly Gly Gly Leu Gln Thr Pro
 1               5                  10                  15

Gly Gly Gly Leu Ser Leu Val Cys Lys Ala Ser Gly Phe Thr Phe Ser
            20                  25                  30

Ser Tyr Ala Met Gly Trp Val Arg Gln Ala Pro Gly Lys Gly Leu Glu
         35                  40                  45

Trp Val Ala Gly Ile Asp Asp Asp Gly Ser Asp Thr Leu Tyr Ala Pro
 50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95
```

Tyr Cys Ala Lys Ser Ala Gly Arg Gly Tyr Cys Trp Asn Thr Ala Gly
            100                 105                 110

Gly Tyr Arg Cys Thr Pro Tyr Leu Gly Asp Met Asp Ala Trp Gly His
        115                 120                 125

Gly Thr Glu Val Ile Val Ser
    130                 135

<210> SEQ ID NO 150
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Ala Ala Val Thr Leu Asp Glu Ser Gly Gly Gly Leu Gln Ala Pro
1               5                   10                  15

Gly Gly Gly Leu Ser Leu Val Cys Lys Ala Ser Gly Phe Thr Phe Ser
            20                  25                  30

Ser Tyr Ala Met Gly Trp Val Arg Gln Ala Pro Gly Lys Gly Leu Glu
        35                  40                  45

Trp Val Ala Gly Ile Asp Asp Asp Gly Ser Asp Thr Leu Tyr Ala Pro
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Tyr Cys Ala Lys Ser Ala Gly Arg Gly Tyr Cys Trp Asn Thr Ala Gly
            100                 105                 110

Gly Tyr Arg Cys Thr Pro Tyr Leu Gly Asp Met Asp Ala Trp Gly His
        115                 120                 125

Gly Thr Glu Val Ile Val Ser
    130                 135

<210> SEQ ID NO 151
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Phe Asn Met Phe Trp Val Arg Gln Thr Pro Gly Lys Gly Leu Glu
        35                  40                  45

Trp Val Ala Gly Ile Glu Asn Asp Gly Gly Ala Asp Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Thr Ala Asp Ser Gly Ser Gly Cys Ile Trp Gly Val Gly
            100                 105                 110

Cys Ile Asp Ala Trp Gly His Gly Thr Glu Val Ile Val Ser
            115                 120                 125

<210> SEQ ID NO 152
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Ala Ala Val Thr Leu Asp Glu Ser Gly Gly Leu Gln Thr Pro
1               5                   10                  15

Gly Gly Thr Leu Ser Leu Val Cys Lys Ala Ser Gly Phe Thr Phe Ser
            20                  25                  30

Ser Tyr Ala Met Phe Trp Val Arg Gln Thr Pro Gly Lys Gly Leu Glu
            35                  40                  45

Tyr Val Ala Glu Ile Thr Asn Thr Gly Ser Glu Thr Arg Tyr Gly Ala
        50                  55                  60

Ala Val Lys Gly Arg Gly Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Phe Cys Ala Lys Gly Val Tyr Tyr Cys Gly Ser Gly Ser Trp Cys
            100                 105                 110

Gly Thr His Ile Ile Asp Ala Trp Gly His Gly Thr Glu Val Ile Val
            115                 120                 125

Ser

<210> SEQ ID NO 153
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Ala Ala Val Thr Leu Asp Glu Ser Glu Gly Gly Leu Gln Thr Pro
1               5                   10                  15

Gly Gly Gly Leu Ser Leu Val Cys Lys Ala Ser Gly Phe Ile Phe Ser
            20                  25                  30

Ser Phe Asn Met Phe Trp Val Arg Gln Ala Pro Gly Lys Gly Leu Glu
            35                  40                  45

Leu Val Ala Glu Ile Ser Asp Thr Gly Thr Thr Thr Tyr Tyr Gly Ser
        50                  55                  60

Ala Val Lys Gly Arg Ala Thr Ile Ser Arg Asp Asn Gly Gln Ser Thr
65                  70                  75                  80

Val Arg Leu Gln Leu Asp Asn Leu Arg Ala Glu Asp Thr Gly Thr Tyr
                85                  90                  95

Tyr Cys Ala Lys Ala Ala Gly Gly Cys Pro Thr Cys Thr Tyr Thr
            100                 105                 110

Asp Gly Ile Asp Ala Trp Gly His Gly Thr Glu Val Ile Val Ser
            115                 120                 125

<210> SEQ ID NO 154
<211> LENGTH: 125
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 154

Met Ala Ala Val Thr Leu Asp Glu Ser Gly Gly Gly Leu Gln Thr Pro
1               5                   10                  15

Gly Gly Gly Leu Ser Leu Val Cys Lys Ala Ser Gly Phe Thr Phe Ser
            20                  25                  30

Ser Tyr Ser Val Gln Trp Val Arg Gln Ala Pro Gly Lys Gly Leu Glu
        35                  40                  45

Trp Val Ala Gly Ile Glu Asn Asp Gly Gly Thr Asp Tyr Gly Ser
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Ala Thr Tyr
                85                  90                  95

Tyr Cys Ala Arg Asn Ala Gly Ala Gly Cys Asp Trp Gly Ala Gly Cys
                100                 105                 110

Ile Asp Ala Trp Gly His Gly Thr Glu Val Ile Val Ser
            115                 120                 125

<210> SEQ ID NO 155
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Ser Phe Ser
            20                  25                  30

Ser His Gly Met Phe Trp Val Arg Arg Thr Pro Gly Lys Gly Leu Glu
        35                  40                  45

Tyr Val Ala Glu Ile Thr Asn Thr Gly Ser Glu Thr Ala Tyr Gly Ala
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Thr Tyr
                85                  90                  95

Phe Cys Ala Lys Ser Ser Tyr Asp Cys Gly Thr Gly Cys Trp Gly Tyr
                100                 105                 110

Ile Gly Ser Ile Asp Ala Trp Gly His Gly Thr Glu Val Ile Val Ser
            115                 120                 125

<210> SEQ ID NO 156
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Ala Ala Val Thr Leu Asp Glu Ser Gly Gly Gly Leu Gln Thr Pro
1               5                   10                  15

-continued

Gly Gly Ala Leu Ser Leu Val Cys Lys Ala Ser Gly Phe Ser Ile Ser
                20                  25                  30

Ser Tyr Gly Met Met Trp Val Arg Gln Ala Pro Gly Lys Gly Leu Glu
            35                  40                  45

Trp Val Gly Val Ile Ser Asn Ser Gly Ser Ser Thr Asn Tyr Gly Ala
 50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Gly Ile Tyr
                85                  90                  95

Phe Cys Ala Lys Asp Phe Gly Cys Ser Gly Ser Ser Cys Val Gly Tyr
            100                 105                 110

Asn Ile Asp Ala Trp Gly His Gly Thr Glu Val Ile Val Ser
        115                 120                 125

<210> SEQ ID NO 157
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Ala Ala Val Thr Leu Asp Glu Ser Gly Gly Gly Leu Gln Thr Pro
 1               5                  10                  15

Gly Gly Ala Leu Ser Leu Ile Cys Lys Ala Ser Gly Phe Thr Phe Ser
                20                  25                  30

Ser Tyr Thr Met Gly Trp Val Arg Gln Ala Pro Gly Lys Gly Leu Glu
            35                  40                  45

Trp Val Gly Val Ile Ser Lys Asp Gly Gly Ser Thr Tyr Tyr Gly Ser
 50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                85                  90                  95

Tyr Cys Ala Arg Gly Val Ser Ser Asp Ile Asp Ala Trp Gly His Gly
            100                 105                 110

Thr Glu Val Ile Val Ser
        115

<210> SEQ ID NO 158
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Ala Ala Val Thr Leu Asp Glu Ser Gly Gly Gly Leu Gln Thr Pro
 1               5                  10                  15

Gly Gly Ala Leu Ser Leu Ile Cys Lys Ala Ser Gly Phe Thr Phe Ser
                20                  25                  30

Ser Tyr Thr Met Gly Trp Val Arg Gln Ala Pro Gly Lys Gly Leu Glu
            35                  40                  45

Trp Val Gly Val Ile Ser Lys Asp Gly Gly Ser Thr Tyr Tyr Gly Ser
 50                  55                  60

```
Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Ala Thr Tyr
                 85                  90                  95

Tyr Cys Ala Arg Gly Val Ser Ser Asp Ile Asp Ala Trp Gly His Gly
            100                 105                 110

Thr Glu Val Ile Val Ser
        115

<210> SEQ ID NO 159
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ala Ala Val Thr Leu Asp Glu Ser Gly Gly Gly Leu Gln Thr Pro
  1               5                  10                  15

Gly Gly Thr Leu Ser Leu Val Cys Lys Ala Ser Gly Phe Thr Phe Ser
                 20                  25                  30

Ser Tyr Ala Met Met Trp Val Arg Gln Ala Pro Gly Lys Gly Leu Glu
             35                  40                  45

Phe Val Ala Ser Ile Ser Val Ala Asp Ser Ser Thr His Tyr Gly Ala
         50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Gly Thr Tyr
                 85                  90                  95

Tyr Cys Ala Lys Ser Ser Tyr Gln Cys Ala Asp Asn Cys Trp Gly Tyr
            100                 105                 110

Pro Tyr Gly Ile Asp Thr Trp Gly His Gly Thr Glu Val Ile Val Ser
            115                 120                 125

<210> SEQ ID NO 160
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Ala Ala Val Thr Leu Asp Glu Ser Gly Gly Gly Leu Gln Thr Pro
  1               5                  10                  15

Gly Gly Thr Leu Ser Leu Val Cys Lys Ala Ser Gly Phe Thr Phe Ser
                 20                  25                  30

Ser Tyr Ala Met Met Trp Val Arg Gln Ala Pro Gly Lys Gly Leu Glu
             35                  40                  45

Phe Val Ala Ser Ile Ser Val Ala Asp Ser Ser Thr His Tyr Gly Ala
         50                  55                  60

Ala Val Lys Gly Arg Ala Thr Ile Ser Arg Asp Asn Gly Gln Ser Thr
 65                  70                  75                  80

Val Arg Leu Gln Leu Asn Asn Leu Arg Ala Glu Asp Thr Gly Thr Tyr
                 85                  90                  95

Tyr Cys Ala Lys Ser Ser Tyr Gln Cys Ala Asp Asn Cys Trp Gly Tyr
            100                 105                 110
```

-continued

Pro Tyr Gly Ile Asp Thr Trp Gly His Gly Thr Glu Val Ile Val Ser
            115                 120                 125

<210> SEQ ID NO 161
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Ala Ala Val Thr Leu Asp Glu Ser Gly Gly Gly Leu Gln Thr Pro
1               5                   10                  15

Gly Gly Thr Leu Ser Leu Val Cys Lys Ala Ser Gly Phe Thr Phe Ser
            20                  25                  30

Ser Tyr Ala Met Met Trp Val Arg Gln Ala Pro Gly Lys Gly Leu Glu
        35                  40                  45

Phe Val Ala Ser Ile Ser Val Ala Asp Ser Ser Thr His Tyr Gly Ala
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Ala Lys Ser Ser Tyr Gln Cys Ala Asp Asn Cys Trp Gly Tyr
            100                 105                 110

Pro Tyr Gly Ile Asp Thr Trp Gly His Gly Thr Glu Val Ile Val Ser
            115                 120                 125

<210> SEQ ID NO 162
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Phe Asn Met Asn Trp Val Arg Gln Ala Pro Gly Lys Gly Leu Glu
        35                  40                  45

Trp Val Ala Ser Ile Ser Asn Thr Gly Ser Ser Thr Ala Tyr Gly Ala
    50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Gly Ala Glu Asp Thr Gly Thr Tyr
                85                  90                  95

Tyr Cys Thr Arg Gly Ser Ala Ile Asp Ala Trp Gly His Gly Thr Glu
            100                 105                 110

Val Ile Val Ser
        115

<210> SEQ ID NO 163
<211> LENGTH: 116
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 163

Met Ala Ala Val Thr Leu Glu Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Phe Asn Met Asn Trp Val Arg Gln Ala Pro Gly Lys Gly Leu Glu
        35                  40                  45

Trp Val Ala Ser Ile Ser Asn Thr Gly Ser Ser Thr Ala Tyr Gly Ala
50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Thr Arg Gly Ser Ala Ile Asp Ala Trp Gly His Gly Thr Glu
            100                 105                 110

Val Ile Val Ser
        115

<210> SEQ ID NO 164
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Phe Asn Met Asn Trp Val Arg Gln Ala Pro Gly Lys Gly Leu Glu
        35                  40                  45

Trp Val Ala Ser Ile Ser Asn Thr Gly Ser Ser Thr Ala Tyr Gly Ala
50                  55                  60

Ala Val Lys Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Thr Tyr
                85                  90                  95

Tyr Cys Thr Arg Gly Ser Ala Ile Asp Ala Trp Gly His Gly Thr Glu
            100                 105                 110

Val Ile Val Ser
        115

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asn Asp Tyr Gly Met
1               5
```

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Ser Tyr Asn Met
1               5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Asp Tyr Gly Met
1               5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Ser His Gly Met
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ser Asp Arg Gly Met
1               5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Ser Tyr Gly Met
1               5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 171

Ser Ser Tyr Ala Met
1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Ser Tyr Gly Val
1               5

<210> SEQ ID NO 173
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Ser Tyr Gln Met
1               5

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Thr His Gly Met
1               5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ser Phe Asn Met
1               5

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Ser Tyr Ser Val
1               5

<210> SEQ ID NO 177
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 177

Ser Ser Tyr Thr Met
1               5

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Ile Tyr Ser Ser Gly Arg Tyr Thr Tyr Tyr Gly Ala Ala Val Gln
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Ile Ser Asn Asp Ala Asn Phe Thr Ala Tyr Gly Ser Ala Val Lys
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Glu Ile Asp Ser Ala Gly Ser Ser Thr Tyr Tyr Thr Pro Ala Val Arg
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Ile Ser Arg Asp Gly Ser Arg Thr Arg Tyr Gly Ala Ala Val Lys
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ile Ser Ser Ser Gly Arg Ser Ala Ala Tyr Gly Ala Ala Val Lys
1               5                   10                  15
```

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Ile Ser Ser Ser Gly Arg Ser Thr Ala Tyr Gly Ala Ala Val Lys
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Ile Asn Ala Val Gly Ser Thr Thr Gly Tyr Gly Pro Ala Val Asp
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Ile Ser Ala Thr Gly Ser Glu Thr Ser Tyr Ala Pro Ala Val Lys
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ile Asn Ser Phe Gly Asn Ser Thr Gly His Gly Ala Ala Val Lys
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Ile Asn Arg Phe Gly Asn Thr Thr Gly Pro Gly Ala Ala Val Lys
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ile Asn Arg Phe Gly Asn Ser Thr Gly His Gly Ala Ala Val Lys
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Ile Asn Arg Phe Gly Asn Gly Thr Gly His Gly Ala Ala Val Lys
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Lys Ile Asn Ala Ala Gly Ser Gly Thr Gly Tyr Gly Ser Ala Val Lys
1               5                   10                  15

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Val Ser Ser Asn Asp Gly Ser Asp Thr Ser Tyr Gly Ser Ala Val
1               5                   10                  15

Glu

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Ile Asp Asp Gly Gly Ser Tyr Thr Gly Tyr Gly Ala Ala Val Lys
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Ile Asp Asp Asp Gly Ser Asp Thr Leu Tyr Ala Pro Ala Val Lys
1               5                   10                  15

```
<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Ile Glu Asn Asp Gly Gly Ala Asp Tyr Gly Ala Ala Val Lys
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Glu Ile Thr Asn Thr Gly Ser Glu Thr Arg Tyr Gly Ala Ala Val Lys
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Glu Ile Ser Asp Thr Gly Thr Thr Thr Tyr Tyr Gly Ser Ala Val Lys
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Ile Glu Asn Asp Gly Gly Gly Thr Asp Tyr Gly Ser Ala Val Lys
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Glu Ile Thr Asn Thr Gly Ser Glu Thr Ala Tyr Gly Ala Ala Val Lys
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199
```

```
Val Ile Ser Asn Ser Gly Ser Ser Thr Asn Tyr Gly Ala Ala Val Lys
1               5                   10                  15
```

```
<210> SEQ ID NO 200
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Val Ile Ser Lys Asp Gly Gly Ser Thr Tyr Tyr Gly Ser Ala Val Lys
1               5                   10                  15
```

```
<210> SEQ ID NO 201
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Ile Ser Val Ala Asp Ser Ser Thr His Tyr Gly Ala Ala Val Lys
1               5                   10                  15
```

```
<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Ile Ser Asn Thr Gly Ser Ser Thr Ala Tyr Gly Ala Ala Val Lys
1               5                   10                  15
```

```
<210> SEQ ID NO 203
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Ala Asp Ser Gly Tyr Tyr Thr Gly Ala Gly Tyr Ile Asp Ala Trp
1               5                   10                  15
```

```
<210> SEQ ID NO 204
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Ala Gly Thr Gly Cys Asn Asn Gly Tyr Asn Cys Ala Asp Tyr Thr
1               5                   10                  15

Pro Gly Tyr Ile Asp Ser Trp
            20
```

```
<210> SEQ ID NO 205
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Ser Gly Ser Gly Gly Cys Ala Tyr Gly Glu Ile Asp Thr Trp
1               5                   10                  15

<210> SEQ ID NO 206
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Ala Tyr Glu Cys Asp Gly Tyr Ser Cys Trp Thr Phe Ile Ala Gly
1               5                   10                  15

Ser Ile Asp Ala Trp
            20

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Thr Gly Thr Gly Tyr Gly Gly Val Gly Glu Ile Asp Ala Trp
1               5                   10                  15

<210> SEQ ID NO 208
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Tyr Ser Asn Cys Gly Gly Tyr Ser Cys Ala Ala Ala Asn Ile Asp
1               5                   10                  15

Ala Trp

<210> SEQ ID NO 209
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Tyr Ser Asn Cys Gly Asp Tyr Ser Cys Ala Ala Ala Asn Ile Asp
1               5                   10                  15

Ala Trp

<210> SEQ ID NO 210
<211> LENGTH: 22
<212> TYPE: PRT
```

<213> ORGANISM: Artificial Sequence
<220> FEATURE:
<223> OTHER INFORMATION: Description of Artificial Sequence: Synthetic
     peptide

<400> SEQUENCE: 210

Ala Ala Gly Ser Gly Arg Cys Ala Gly Ala Gly Gly Tyr Cys Asn Pro
1               5                   10                  15

Gly Ser Ile Asp Thr Trp
            20

<210> SEQ ID NO 211
<211> LENGTH: 19
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 211

Gly Ala Tyr Asp Tyr Cys Gly Gly Gly Trp Cys Asn Thr Ala Tyr Ile
1               5                   10                  15

Asp Ala Trp

<210> SEQ ID NO 212
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 212

Gly Ala Tyr Asp Tyr Cys Gly Ser Gly Gly Trp Cys Asn Thr Ala Tyr
1               5                   10                  15

Ile Asp Ala Trp
            20

<210> SEQ ID NO 213
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 213

Gly Ala Tyr Gly Tyr Cys Gly Ser Gly Ser Trp Cys Asn Ala Ala Tyr
1               5                   10                  15

Ile Asp Ala Trp
            20

<210> SEQ ID NO 214
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 214

Gly Ala Tyr Gly Tyr Cys Gly Ser Gly Ser Trp Cys Ala Ala Gly Leu
1               5                   10                  15

Ile Asp Ala Trp
            20

<210> SEQ ID NO 215
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Ala Tyr Gly Tyr Cys Gly Ser Gly Ser Trp Cys Ser Pro Ala Thr
1               5                   10                  15

Ile Asp Ala Trp
            20

<210> SEQ ID NO 216
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Ala Tyr Gly Tyr Cys Gly Ser Gly Ser Trp Cys Ser Pro Ala Thr
1               5                   10                  15

Ile Asp Ala Trp
            20

<210> SEQ ID NO 217
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asp Asn Tyr Asp Cys Gly Lys Ser Ile Cys Gly Ala Tyr Ala Gly Ser
1               5                   10                  15

Ile Asp Ala Trp
            20

<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Ser His Glu Cys Gly Lys Ser Ser Cys Trp Gly Tyr Ile Gly Ser
1               5                   10                  15

Ile Asp Ala Trp
            20

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Gly Leu Thr Ile Asp Thr Trp
1               5

<210> SEQ ID NO 220
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Ala Gly Arg Gly Tyr Cys Trp Asn Thr Ala Gly Gly Tyr Arg Cys
1               5                   10                  15

Thr Pro Tyr Leu Gly Asp Met Asp Ala Trp
            20                  25

<210> SEQ ID NO 221
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Ala Asp Ser Gly Ser Gly Cys Ile Trp Gly Val Gly Cys Ile Asp
1               5                   10                  15

Ala Trp

<210> SEQ ID NO 222
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Val Tyr Gly Tyr Cys Gly Ser Gly Ser Trp Cys Gly Thr His Ile
1               5                   10                  15

Ile Asp Ala Trp
            20

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Ala Gly Gly Gly Cys Pro Thr Cys Thr Tyr Thr Asp Gly Ile Asp
1               5                   10                  15

Ala Trp

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 224

Asn Ala Gly Ala Gly Cys Asp Trp Gly Ala Gly Cys Ile Asp Ala Trp
1               5                   10                  15

<210> SEQ ID NO 225
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Ser Tyr Asp Cys Gly Thr Gly Cys Trp Gly Tyr Ile Gly Ser Ile
1               5                   10                  15

Asp Ala Trp

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Phe Gly Cys Ser Gly Ser Ser Cys Val Gly Tyr Asn Ile Asp Ala
1               5                   10                  15

Trp

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Val Ser Ser Asp Ile Asp Ala Trp
1               5

<210> SEQ ID NO 228
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Ser Tyr Gln Cys Ala Asp Asn Cys Trp Gly Tyr Pro Tyr Gly Ile
1               5                   10                  15

Asp Thr Trp

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Ser Ala Ile Asp Ala Trp
```

<210> SEQ ID NO 230
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Leu Glu Ile Val Met Thr Gln Ser Pro Ser Ser Val Thr Ala Ser Ala
1               5                   10                  15

Gly Glu Arg Val Thr Ile Asn Cys Lys Ser Ser Gln Ser Val Leu Ser
            20                  25                  30

Gly Ser Asn Gln Lys Thr Tyr Leu Asn Trp Tyr Gln Gln Arg Pro Gly
        35                  40                  45

Gln Ser Pro Arg Leu Leu Ile Tyr Tyr Ala Ser Thr Arg Glu Leu Gly
    50                  55                  60

Ile Pro Asp Arg Phe Ser Gly Ser Gly Ser Thr Thr Asp Phe Thr Leu
65                  70                  75                  80

Thr Ile Ser Ser Val Gln Pro Glu Asp Ala Ala Val Tyr Tyr Cys Gln
                85                  90                  95

Gln Ala Tyr Ser Ala Pro Tyr Asn Phe Gly Ser Gly Thr Arg Leu Glu
            100                 105                 110

Ile Lys

<210> SEQ ID NO 231
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Leu Asp Ile Gln Met Thr Gln Ser Pro Ser Ser Val Thr Ala Ser Val
1               5                   10                  15

Gly Glu Lys Val Thr Ile Asn Cys Lys Ser Ser Gln Ser Val Val Ser
            20                  25                  30

Ala Ser Asn Gln Lys Ser Tyr Leu Asn Trp Tyr Gln Gln Arg Pro Gly
        35                  40                  45

Gln Ser Pro Arg Leu Leu Ile Tyr Tyr Ala Ser Thr Gln Glu Leu Gly
    50                  55                  60

Ile Pro Asp Arg Phe Ser Gly Ser Gly Ser Thr Thr Asp Phe Thr Leu
65                  70                  75                  80

Thr Ile Ser Ser Val Gln Pro Glu Asp Ala Ala Val Tyr Tyr Cys Gln
                85                  90                  95

Gln Ala Tyr Ser Ala Pro Tyr Asn Phe Gly Ser Gly Thr Arg Leu Glu
            100                 105                 110

Ile Lys

<210> SEQ ID NO 232
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 232

Leu Glu Ile Val Leu Thr Gln Ser Pro Ser Ser Val Thr Ala Ser Val
1               5                   10                  15

Gly Glu Lys Val Thr Ile Asn Cys Lys Ser Gln Ser Val Val Ser
            20                  25                  30

Gly Ser Asn Gln Lys Ser Tyr Leu Asn Trp Tyr Gln Arg Pro Gly
        35                  40                  45

Gln Ser Pro Arg Leu Leu Ile Tyr Tyr Ala Ser Thr Gln Glu Leu Gly
    50                  55                  60

Ile Pro Asp Arg Phe Ser Gly Ser Gly Ser Thr Thr Asp Phe Thr Leu
65                  70                  75                  80

Thr Ile Ser Ser Val Gln Pro Glu Asp Ala Ala Val Tyr Tyr Cys Gln
                85                  90                  95

Gln Ala Tyr Ser Ala Pro Tyr Ser Phe Gly Ser Gly Thr Arg Leu Glu
            100                 105                 110

Ile Lys

<210> SEQ ID NO 233
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Leu Asp Leu Val Leu Thr Gln Ile Pro Gly Ser Leu Ser Val Val Pro
1               5                   10                  15

Gly Glu Ser Val Ser Ile Ser Cys Lys Ser Ser Gln Ser Leu Leu His
            20                  25                  30

Thr Asp Gly Lys Thr Tyr Ala Tyr Trp Leu Gln Gln Lys Pro Gly Gln
        35                  40                  45

Arg Pro Gln Leu Leu Ile Ser Gln Val Ser Ile Arg Ser Ser Gly Val
    50                  55                  60

Ser Asp Arg Phe Thr Gly Ser Gly Ser Gly Thr Asp Phe Thr Leu Lys
65                  70                  75                  80

Ile Ser Gly Val Lys Ala Glu Asp Ala Gly Val Tyr Tyr Cys Ala Gln
                85                  90                  95

Ala Thr His Tyr Pro Trp Thr Phe Gly Gln Gly Thr Lys Leu Glu Ile
            100                 105                 110

Lys

<210> SEQ ID NO 234
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Leu Ala Thr Met Leu Thr Gln Ser Pro Gly Ser Leu Ser Val Val Pro
1               5                   10                  15

Gly Glu Ser Ala Ser Ile Ser Cys Lys Ala Ser Gln Ser Leu Met His
            20                  25                  30

Thr Asp Gly Lys Thr Tyr Phe Tyr Trp Leu Val Gln Lys Pro Gly Gln
        35                  40                  45

Arg Pro Gln Leu Leu Ile Tyr Gln Val Ser Asn Arg Asp Ser Gly Val
    50                  55                  60

Pro Asp Thr Phe Thr Gly Ser Gly Ser Gly Thr Asp Phe Thr Leu Lys
65                  70                  75                  80

Ile Ser Gly Val Lys Ala Thr Asp Ala Gly Val Tyr Tyr Cys Ala Gln
                85                  90                  95

Gly Thr His Tyr Pro Ile Ser Phe Gly Ser Gly Thr Arg Leu Glu Ile
                100                 105                 110

Lys

<210> SEQ ID NO 235
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Leu Ala Thr Met Leu Thr Gln Ser Pro Gly Ser Leu Ser Val Val Pro
1               5                   10                  15

Gly Glu Ser Ala Ser Ile Ser Cys Lys Ala Ser Gln Ser Leu Ile His
                20                  25                  30

Thr Asp Gly Lys Thr Tyr Leu Tyr Trp Leu Arg Gln Lys Pro Gly Gln
            35                  40                  45

Arg Pro Gln Leu Leu Ile Tyr Gln Val Ser Asn His Glu Ser Gly Val
    50                  55                  60

Pro Asp Arg Phe Thr Gly Ser Gly Ser Gly Thr Asp Phe Thr Leu Lys
65                  70                  75                  80

Ile Ser Gly Val Lys Ala Glu Asp Ala Gly Val Tyr Tyr Cys Ala Gln
                85                  90                  95

Ala Thr Tyr Tyr Pro Tyr Ala Phe Gly Ser Gly Thr Arg Leu Glu Ile
                100                 105                 110

Lys

<210> SEQ ID NO 236
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Leu Asp Val Val Leu Thr Gln Thr Pro Gly Ser Leu Ser Val Val Pro
1               5                   10                  15

Gly Glu Ser Ala Ser Ile Ser Cys Lys Thr Ser Gln Ser Leu Val Arg
                20                  25                  30

Ser Asp Gly Asn Thr Phe Leu Tyr Trp Leu Leu Gln Lys Pro Gly Gln
            35                  40                  45

Ser Pro Gln Arg Leu Ile Tyr Gln Val Ser Asn Arg Gly Ser Gly Val
    50                  55                  60

Pro Asp Arg Phe Thr Gly Ser Gly Ser Gly Thr Asp Phe Thr Leu Lys
65                  70                  75                  80

Ile Asn Gly Val Lys Ala Glu Asp Ala Gly Val Tyr Tyr Cys Ala Gln
                85                  90                  95

Ala Thr Tyr Tyr Pro Leu Ser Phe Gly Ser Gly Thr Arg Leu Glu Ile
                100                 105                 110

Lys

<210> SEQ ID NO 237
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

```
Leu Ala Thr Met Leu Thr Gln Ser Pro Gly Ser Leu Ser Val Val Pro
1               5                   10                  15

Gly Glu Ser Ala Ser Ile Ser Cys Lys Ala Ser Glu Ser Leu Val Phe
            20                  25                  30

Ser Asp Gly Lys Thr Tyr Leu Tyr Trp Leu Leu Gln Lys Pro Gly Gln
        35                  40                  45

Ser Pro Gln Arg Leu Ile Tyr Gln Val Ser Asn Arg Gly Ser Gly Val
    50                  55                  60

Pro Asp Arg Phe Thr Gly Ser Gly Ser Gly Thr Asp Phe Thr Leu Lys
65                  70                  75                  80

Ile Ser Gly Val Lys Ala Glu Asp Ala Gly Val Tyr Tyr Cys Ala Gln
                85                  90                  95

Gly Thr Tyr Phe Pro Leu Thr Phe Gly Ser Gly Thr Arg Leu Glu Ile
            100                 105                 110

Lys
```

<210> SEQ ID NO 238
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Leu Ala Thr Met Leu Thr Gln Ser Pro Asp Ser Leu Ser Val Val Pro
1               5                   10                  15

Gly Glu Ser Ala Ser Ile Ser Cys Lys Ala Ser Gln Ser Leu Ile His
            20                  25                  30

Thr Asp Glu Lys Thr Tyr Leu Tyr Trp Leu Leu Gln Lys Pro Gly Gln
        35                  40                  45

Ser Pro Gln Arg Leu Ile Tyr Gln Val Ser Asn Arg Gly Ser Gly Val
    50                  55                  60

Pro Asp Lys Phe Thr Gly Ser Gly Ser Gly Thr Asp Phe Thr Leu Lys
65                  70                  75                  80

Ile Ser Gly Val Lys Ala Glu Asp Ala Gly Val Tyr Tyr Cys Ala Gln
                85                  90                  95

Ala Thr Tyr Tyr Pro Met Thr Phe Gly Gln Gly Thr Lys Leu Glu Ile
            100                 105                 110

Lys
```

<210> SEQ ID NO 239
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 239

Leu Ala Thr Met Leu Thr Gln Ser Pro Gly Ser Leu Ser Val Val Pro
1               5                   10                  15

Gly Gln Ser Ala Ser Ile Ser Cys Lys Ala Ser Gln Thr Leu Val His
            20                  25                  30

Ser Asp Gly Lys Thr Tyr Phe Thr Trp Leu Leu Gln Lys Pro Gly Gln
        35                  40                  45

Ser Pro Gln Arg Leu Ile Tyr Gln Val Ala Asn Arg Gly Ser Gly Val
    50                  55                  60

Ser Asp Arg Phe Thr Ala Ser Gly Ser Gly Thr Asp Phe Thr Leu Lys
65                  70                  75                  80

Ile Ser Gly Val Lys Ala Glu Asp Ala Gly Val Tyr Tyr Cys Ala Gln
                85                  90                  95

Ala Thr Tyr Tyr Pro Val Thr Phe Gly Gln Gly Thr Lys Val Glu Leu
            100                 105                 110

Lys

<210> SEQ ID NO 240
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Leu Ala Thr Met Leu Thr Gln Ser Pro Gly Ser Leu Ser Val Val Pro
1               5                   10                  15

Gly Glu Ser Ala Ser Val Ser Cys Lys Ala Thr Gln Ser Leu Val His
            20                  25                  30

Ser Asp Gly Lys Thr Tyr Leu Tyr Trp Leu Leu Gln Lys Pro Gly Gln
        35                  40                  45

Ser Pro Gln Arg Leu Ile Tyr Gln Val Ser Asn Arg Ala Ser Gly Val
    50                  55                  60

Pro Asp Arg Phe Thr Gly Ser Gly Ser Gly Thr Asp Phe Thr Leu Lys
65                  70                  75                  80

Ile Ser Gly Val Lys Ala Glu Asp Ala Gly Val Tyr Tyr Cys Ala Gln
                85                  90                  95

Ala Thr Tyr Tyr Pro Val Thr Phe Gly Gln Gly Thr Lys Val Glu Leu
            100                 105                 110

Lys

<210> SEQ ID NO 241
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Leu Asp Leu Val Leu Thr Gln Ile Pro Gly Ser Leu Ser Val Val Pro
1               5                   10                  15

Gly Glu Ser Ala Ser Ile Ser Cys Lys Ala Ser Gln Ser Leu Val His
            20                  25                  30

Ser Asp Gly Lys Thr Tyr Leu Tyr Trp Leu Leu Gln Lys Pro Gly Gln
        35                  40                  45
```

```
Ser Pro Gln Arg Leu Ile Tyr Gln Val Ser Asn Arg Gly Ser Gly Val
 50                  55                  60

Pro Asp Arg Phe Thr Gly Ser Gly Ser Gly Thr Asp Phe Thr Leu Lys
 65                  70                  75                  80

Ile Ser Gly Val Lys Ala Glu Asp Ala Gly Val Tyr Tyr Cys Ala Gln
                 85                  90                  95

Val Thr Tyr Tyr Pro Val Thr Phe Gly Gln Gly Thr Lys Val Glu Leu
                100                 105                 110

Lys

<210> SEQ ID NO 242
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Leu Asp Leu Val Leu Thr Gln Ile Pro Gly Ser Leu Ser Val Val Pro
 1               5                  10                  15

Gly Glu Ser Ala Ser Ile Ser Cys Lys Gly Ser Gln Ser Leu Val His
                 20                  25                  30

Ser Asp Gly Lys Thr Tyr Leu Tyr Trp Leu His Lys Pro Gly Gln
             35                  40                  45

Ser Pro Gln Arg Leu Ile Tyr Gln Val Ser Asn Arg Ala Ser Gly Val
 50                  55                  60

Pro Asp Arg Phe Thr Gly Ser Gly Ser Gly Thr Asp Phe Thr Leu Lys
 65                  70                  75                  80

Ile Ser Gly Val Lys Ala Glu Asp Ala Gly Val Tyr Tyr Cys Ala Gln
                 85                  90                  95

Gly Thr Tyr Tyr Pro Leu Thr Phe Gly Gln Gly Thr Lys Leu Glu Ile
                100                 105                 110

Lys

<210> SEQ ID NO 243
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

His Ser Ala Val Thr Gln Pro Pro Ser Val Ser Gly Thr Leu Gly Lys
 1               5                  10                  15

Thr Val Thr Ile Ser Cys Ala Gly Thr Ser Ser Asp Val Gly Tyr Gly
                 20                  25                  30

Asn Tyr Val Ser Trp Tyr Gln Gln Leu Pro Gly Thr Ala Pro Lys Leu
             35                  40                  45

Leu Ile Tyr Arg Asp Thr Thr Arg Ala Ser Gly Ile Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Gly Asp Glu Ala Asp Tyr Tyr Cys Ala Ser Tyr Arg Thr Gly
                 85                  90                  95

Gly Thr Thr Ile Phe Gly Gly Gly Thr His Leu Thr Val Leu Gly
```

<210> SEQ ID NO 244
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 244

His Ser Ala Val Thr Gln Pro Pro Ser Val Ser Gly Thr Leu Gly Lys
1               5                   10                  15

Thr Leu Thr Ile Ser Cys Ala Gly Thr Ser Ser Asp Ile Gly Gly Tyr
            20                  25                  30

Asn Ser Val Ser Trp Tyr Gln Gln Leu Pro Gly Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Arg
                85                  90                  95

Ser Asn Tyr Val Phe Gly Gly Gly Thr His Leu Thr Val Leu Gly
            100                 105                 110

<210> SEQ ID NO 245
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 245

His Ser Ala Val Thr Gln Pro Pro Ser Val Ser Gly Thr Leu Gly Lys
1               5                   10                  15

Thr Val Thr Ile Ser Cys Ala Gly Thr Ser Ser Asp Ile Gly Gly Tyr
            20                  25                  30

Asn Tyr Val Ser Trp Tyr Gln Gln Leu Pro Gly Thr Ala Pro Lys Leu
        35                  40                  45

Leu Ile Tyr Lys Val Ser Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Ser Gly
                85                  90                  95

Gly Asn Leu Val Phe Gly Gly Gly Thr Arg Leu Thr Val Leu Gly
            100                 105                 110

<210> SEQ ID NO 246
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 246

Gln Ser Ala Leu Thr Gln Pro Pro Ser Val Ser Gly Thr Leu Gly Lys
1               5                   10                  15

```
Thr Val Thr Ile Ser Cys Thr Gly Thr Ser Ser Asp Ile Gly Gly Tyr
            20                  25                  30

Asn Tyr Val Ser Trp Tyr Gln Gln Leu Pro Gly Thr Ala Pro Lys Leu
        35                  40                  45

Leu Ile Tyr Lys Val Ser Thr Arg Ala Ser Gly Ile Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Ser Ile
                85                  90                  95

Asn Asn Ala Val Phe Gly Gly Gly Thr His Leu Thr Val Leu Gly
                100                 105                 110
```

<210> SEQ ID NO 247
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 247

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Ser Ser Ser
            20                  25                  30

Asn Tyr Pro Asn Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Tyr
 50                  55                  60

Ser Gly Ser Ile Ser Gly Asn Lys Ala Ala Leu Thr Ile Thr Gly Ala
 65                  70                  75                  80

Asp Pro Glu Asp Glu Ala Asp Tyr Tyr Cys Ala Leu His Lys Gly Ser
                85                  90                  95

Tyr Thr Val Val Phe Gly Gly Gly Thr Lys Leu Thr Val Leu Gly
                100                 105                 110
```

<210> SEQ ID NO 248
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 248

```
Gln Ala Val Val Thr Gln Glu Pro Ser Leu Ser Val Ser Pro Gly Gly
1               5                   10                  15

Thr Val Thr Leu Thr Cys Gly Leu Arg Ser Gly Ser Val Thr Ser Ser
            20                  25                  30

Asn Tyr Pro Asp Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Leu Tyr Ile Ser Ser
                85                  90                  95
```

Gly Ser Tyr Asn Ala Val Phe Gly Gly Gly Thr His Leu Thr Val Leu
            100                 105                 110

Gly

<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Lys Ser Ser Gln Ser Val Leu Ser Gly Ser Asn Gln Lys Thr Tyr Leu
1               5                   10                  15

Asn

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Lys Ser Ser Gln Ser Val Val Ser Ala Ser Asn Gln Lys Ser Tyr Leu
1               5                   10                  15

Asn

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Lys Ser Ser Gln Ser Val Val Ser Gly Ser Asn Gln Lys Ser Tyr Leu
1               5                   10                  15

Asn

<210> SEQ ID NO 252
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Lys Ser Ser Gln Ser Leu Leu His Thr Asp Gly Lys Thr Tyr Ala Tyr
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

```
Lys Ala Ser Gln Ser Leu Met His Thr Asp Gly Lys Thr Tyr Phe Tyr
1               5                   10                  15
```

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

```
Lys Ala Ser Gln Ser Leu Ile His Thr Asp Gly Lys Thr Tyr Leu Tyr
1               5                   10                  15
```

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

```
Lys Thr Ser Gln Ser Leu Val Arg Ser Asp Gly Asn Thr Phe Leu Tyr
1               5                   10                  15
```

<210> SEQ ID NO 256
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

```
Lys Ala Ser Glu Ser Leu Val Phe Ser Asp Gly Lys Thr Tyr Leu Tyr
1               5                   10                  15
```

<210> SEQ ID NO 257
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

```
Lys Ala Ser Gln Ser Leu Ile His Thr Asp Glu Lys Thr Tyr Leu Tyr
1               5                   10                  15
```

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

```
Lys Ala Ser Gln Thr Leu Val His Ser Asp Gly Lys Thr Tyr Phe Thr
1               5                   10                  15
```

<210> SEQ ID NO 259
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 259

Lys Ala Thr Gln Ser Leu Val His Ser Asp Gly Lys Thr Tyr Leu Tyr
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Lys Ala Ser Gln Ser Leu Val His Ser Asp Gly Lys Thr Tyr Leu Tyr
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Lys Gly Ser Gln Ser Leu Val His Ser Asp Gly Lys Thr Tyr Leu Tyr
1               5                   10                  15

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Gly Thr Ser Ser Asp Val Gly Tyr Gly Asn Tyr Val Ser
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ala Gly Thr Ser Ser Asp Ile Gly Gly Tyr Asn Ser Val Ser
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Gly Thr Ser Ser Asp Ile Gly Gly Tyr Asn Tyr Val Ser
1               5                   10
```

-continued

```
<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Thr Gly Thr Ser Ser Asp Ile Gly Gly Tyr Asn Tyr Val Ser
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Leu Ser Ser Gly Ser Val Ser Ser Ser Asn Tyr Pro Asn
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Leu Arg Ser Gly Ser Val Thr Ser Ser Asn Tyr Pro Asp
1               5                   10

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Tyr Ala Ser Thr Arg Glu Leu
1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Tyr Ala Ser Thr Gln Glu Leu
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270
```

Gln Val Ser Ile Arg Ser Ser
1               5

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Gln Val Ser Asn Arg Asp Ser
1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gln Val Ser Asn His Glu Ser
1               5

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Val Ser Asn Arg Gly Ser
1               5

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Val Ala Asn Arg Gly Ser
1               5

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gln Val Ser Asn Arg Gly Ser
1               5

<210> SEQ ID NO 276
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 276

Gln Val Ser Asn Arg Ala Ser
1               5

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Asp Thr Thr Arg Ala Ser
1               5

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Glu Val Asn Lys Arg Ala Ser
1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Lys Val Ser Thr Arg Ala Ser
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Asn Thr Asn Ser Arg His Ser
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Gln Ala Tyr Ser Ala Pro Tyr Asn
1               5
```

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Gln Ala Tyr Ser Ala Pro Tyr Ser
1               5

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Gln Ala Thr His Tyr Pro Trp Thr
1               5

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ala Gln Gly Thr His Tyr Pro Ile Ser
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ala Gln Ala Thr Tyr Tyr Pro Tyr Ala
1               5

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ala Gln Ala Thr Tyr Tyr Pro Leu Ser
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 287

Ala Gln Gly Thr Tyr Phe Pro Leu Thr
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ala Gln Ala Thr Tyr Tyr Pro Met Thr
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Gln Ala Thr Tyr Tyr Pro Val Thr
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Gln Val Thr Tyr Tyr Pro Val Thr
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Gln Gly Thr Tyr Tyr Pro Leu Thr
1               5

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Ser Tyr Arg Thr Gly Gly Thr Thr Ile
1               5                   10

<210> SEQ ID NO 293
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 293

Ala Ser Tyr Arg Ser Arg Ser Asn Tyr Val
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Ser Tyr Arg Ser Gly Gly Asn Leu Val
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ala Ser Tyr Arg Ser Ile Asn Asn Ala Val
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ala Leu His Lys Gly Ser Tyr Thr Val Val
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ala Leu Tyr Ile Ser Ser Gly Ser Tyr Asn Ala Val
1               5                   10

<210> SEQ ID NO 298
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Val Gln Val Gln Glu Ser Gly Pro Gly Leu Val Lys Pro Ser Gln
1               5                   10                  15
```

-continued

Thr Leu Ser Leu Thr Cys Thr Val Ser Gly Ala Ser Ile Ala Thr Asn
            20                  25                  30

Tyr Tyr Tyr Trp Thr Trp Ile Arg Gln Pro Pro Gly Lys Gly Leu Glu
        35                  40                  45

Trp Met Gly Ala Ile Ala Tyr Ser Gly Ser Phe Tyr Tyr Ser Pro Ser
 50                  55                  60

Leu Lys Ser Arg Thr Ser Met Ser Trp Asp Thr Ser Lys Asn His Ile
65                  70                  75                  80

Thr Leu Arg Leu Ser Ser Val Ala Pro Glu Asp Thr Ala Val Tyr Tyr
                85                  90                  95

Cys Ala Arg Asn Arg Gly Ala Tyr Tyr Ser Thr Gly Tyr Pro Gly Gly
            100                 105                 110

Tyr Glu Tyr Trp Gly Gln Gly Thr Gln Val Thr Val Ser Ser
        115                 120                 125

<210> SEQ ID NO 299
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Gln Val Gln Leu Val Glu Ser Gly Pro Gly Leu Val Lys Pro Ser Gln
1               5                   10                  15

Thr Leu Ser Leu Thr Cys Ala Val Ser Gly Asp Ser Ile Thr Thr Thr
            20                  25                  30

Tyr Tyr Ala Trp Ser Trp Ile Arg Gln Ala Pro Gly Lys Gly Leu Glu
        35                  40                  45

Trp Met Gly Val Ile Pro Gly Ala Gly Asn Thr Tyr Tyr Ser Pro Ala
 50                  55                  60

Leu Lys Ser Arg Ala Thr Ile Ser Arg Asp Ser Ser Lys Asn Gln Phe
65                  70                  75                  80

Ser Leu His Leu Asn Ser Val Thr Pro Glu Asp Thr Ala Val Tyr Tyr
                85                  90                  95

Cys Ala Arg Ala Ser Thr Trp Leu Thr Tyr Gly Leu Ala Ser Gly Tyr
            100                 105                 110

Asp Tyr Trp Gly Gln Gly Thr Gln Val Thr Val Ser Ser
        115                 120                 125

<210> SEQ ID NO 300
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Thr Thr
            20                  25                  30

Tyr Ser Ala Trp Ser Trp Ile Arg Gln Pro Pro Gly Lys Ala Leu Glu
        35                  40                  45

Trp Met Gly Val Ile Ser Asn Tyr Gly Asp Thr Tyr Tyr Thr Pro Ser
 50                  55                  60

```
Leu Lys Ser Arg Thr Ser Ile Ser Arg Asp Thr Ser Lys Asn Gln Phe
 65                  70                  75                  80

Ser Leu Gln Leu Asn Ser Val Thr Pro Glu Asp Thr Ala Val Tyr Tyr
                 85                  90                  95

Cys Val Arg Val Leu Tyr Gly Ser Lys Trp Pro Ile Gly Pro Asn Phe
            100                 105                 110

Gly Ser Trp Gly Gln Gly Thr Gln Val Thr Val Ser Ser
        115                 120                 125

<210> SEQ ID NO 301
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gln Val Gln Val Gln Glu Ser Gly Pro Gly Leu Val Lys Pro Ser Gln
 1               5                  10                  15

Thr Leu Ser Leu Thr Cys Thr Ala Ser Gly Gly Ser Ile Thr Thr Ser
                 20                  25                  30

Tyr Ser Gly Trp Gly Trp Ile Arg Gln Pro Pro Gly Lys Gly Leu Asp
            35                  40                  45

Trp Met Gly Val Ile Gly Tyr Asp Gly Arg Thr Tyr Tyr Asn Pro Ser
 50                  55                  60

Leu Lys Ser Arg Thr Ser Ile Ser Arg Asp Thr Ser Lys Asn Gln Phe
 65                  70                  75                  80

Ser Leu Gln Leu Ser Ser Val Thr Pro Glu Asp Thr Ala Val Tyr Tyr
                 85                  90                  95

Cys Ala Arg Ala Arg Pro Asp Gly Ser Arg Trp Tyr Thr Val Gly Glu
            100                 105                 110

Tyr Asp Tyr Trp Gly Gln Gly Thr Gln Val Thr Val Ser Ser
        115                 120                 125

<210> SEQ ID NO 302
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Leu Gln Leu Val Glu Ser Gly Pro Gly Leu Val Lys Pro Ser Gln
 1               5                  10                  15

Thr Leu Ser Leu Thr Cys Ile Val Thr Gly Gly Ser Ile Thr Thr Ser
                 20                  25                  30

Gly Tyr Ala Trp Ser Trp Ile Arg Gln Pro Pro Gly Lys Gly Leu Glu
            35                  40                  45

Trp Met Gly Val Ile Gly Tyr Asp Gly Thr Asn Tyr Tyr Ser Pro Ser
 50                  55                  60

Leu Lys Ser Arg Thr Ser Ile Ser Arg Asp Thr Ser Lys Asn Gln Phe
 65                  70                  75                  80

Ser Leu Gln Leu Ser Ser Val Thr Pro Glu Asp Thr Ala Val Tyr Tyr
                 85                  90                  95

Cys Ala Arg Val Gly Trp Gly Ser Trp Gly Gln Gly Thr Gln Val Thr
            100                 105                 110
```

-continued

Val Ser Ser
        115

<210> SEQ ID NO 303
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Val Gln Leu Gln Glu Ser Gly Pro Gly Leu Val Lys Pro Ser Gln
1               5                   10                  15

Thr Leu Ser Leu Thr Cys Thr Val Phe Gly Gly Ser Ile Thr Thr Asn
            20                  25                  30

Tyr Tyr Ala Trp Asn Trp Ile Arg Gln Thr Pro Gly Lys Gly Leu Glu
        35                  40                  45

Trp Met Gly Val Ile Ala Tyr Asp Gly Ala Thr Tyr Phe Asn Pro Ser
    50                  55                  60

Leu Lys Ser Arg Thr Ser Ile Ser Arg Asp Thr Ser Lys Asn Gln Phe
65                  70                  75                  80

Ser Leu Gln Leu Arg Ser Val Thr Pro Glu Asp Thr Ala Val Tyr Tyr
                85                  90                  95

Cys Ala Leu Arg Thr Arg Tyr Thr Gly Ser Tyr Gln Ser Thr Pro Asp
            100                 105                 110

Phe Gly Ser Trp Gly Gln Gly Thr Gln Val Thr Val Ser Ser
        115                 120                 125

<210> SEQ ID NO 304
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Glu Val Gln Leu Val Gln Pro Gly Ala Glu Leu Arg Asn Pro Gly Ala
1               5                   10                  15

Ser Val Lys Val Ser Cys Lys Ala Ser Gly Tyr Thr Phe Thr Lys Phe
            20                  25                  30

Tyr Ile Glu Trp Val Arg Gln Ala Pro Gly Gln Gly Leu Glu Trp Met
        35                  40                  45

Gly Asn Ile Leu Pro Glu Asp Gly Gly Thr Tyr Tyr Ala Gln Lys Phe
    50                  55                  60

Gln Gly Arg Leu Thr Phe Thr Thr Asp Thr Thr Thr Ser Thr Ala Tyr
65                  70                  75                  80

Leu Glu Leu Thr Asp Leu Arg Ser Glu Asp Thr Ala Val Tyr Tyr Cys
                85                  90                  95

Ala Ala Thr Phe Gly Ser Trp Gly Gln Gly Thr Gln Val Ile Val Ser
            100                 105                 110

Ser

<210> SEQ ID NO 305
<211> LENGTH: 116
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 305

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Thr Trp Val Arg Gln Val Pro Gly Lys Gly Leu Glu Trp Val
        35                  40                  45

Ser Thr Ile Ser Trp Lys Asp Asp Thr Thr Tyr Ala Glu Ser Met
    50                  55                  60

Lys Gly Arg Phe Thr Ile Ser Arg Asp Asn Ala Lys Met Thr Leu Tyr
65                  70                  75                  80

Leu Gln Met Asp Ser Leu Lys Pro Glu Asp Thr Ala Val Tyr Tyr Cys
                85                  90                  95

Ala Gln Asp Pro Val Asn Phe Gly Ser Trp Gly Gln Gly Thr Gln Val
            100                 105                 110

Ile Val Ser Ser
        115

<210> SEQ ID NO 306
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 306

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Asn
            20                  25                  30

Gly Met Ser Trp Val Arg Gln Ala Pro Gly Lys Glu Val Glu Trp Val
        35                  40                  45

Ser Ser Ile Asn Ser Gly Gly Glu Ile Thr Asn Tyr Arg Asp Ser Val
    50                  55                  60

Lys Gly Arg Phe Thr Ile Ser Arg Asp Asn Val Lys Asn Thr Leu Tyr
65                  70                  75                  80

Leu Gln Met Asn Ser Leu Lys Pro Glu Asp Thr Ala Phe Tyr His Cys
                85                  90                  95

Val Thr Gly Ile Val Ala Tyr Asp Tyr Trp Gly Gln Gly Thr Gln Val
            100                 105                 110

Thr Val Ser Ser
        115

<210> SEQ ID NO 307
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 307

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Asn

```
                    20                  25                  30

Gly Met Ser Trp Val Arg Gln Ala Pro Gly Lys Glu Val Glu Trp Val
                35                  40                  45

Ser Ser Ile Asn Ser Gly Gly Glu Ile Thr Asn Tyr Arg Asp Ser Val
            50                  55                  60

Lys Gly Arg Phe Thr Ile Ser Arg Asp Asn Val Lys Asn Thr Leu Tyr
65                  70                  75                  80

Leu Gln Met Asn Ser Leu Lys Pro Glu Asp Thr Ala Phe Tyr His Cys
                85                  90                  95

Val Thr Gly Ile Val Ala Tyr Asp Tyr Trp Gly Gln Gly Thr Gln Val
            100                 105                 110

Thr Val Ser Ser
            115

<210> SEQ ID NO 308
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Gly Ala Tyr
                20                  25                  30

Thr Met Ala Trp Leu Arg Gln Ala Pro Gly Lys Gly Pro Glu Trp Val
                35                  40                  45

Ser Gly Val Asn Ser Gly Gly Asp Ile Thr Ser Tyr Ala Asp Ser Val
            50                  55                  60

Lys Gly Arg Phe Thr Ile Ser Arg Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala Asp Pro Gly Met Gly Gly Gln Gly Thr Gln Val Thr Val Ser
            100                 105                 110

Ser

<210> SEQ ID NO 309
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Tyr Trp Val Arg Gln Ala Pro Gly Lys Gly Leu Glu Trp Val
                35                  40                  45

Ser Thr Phe Gly Ser Gly Ser Asn Thr Trp Tyr Ala Asp Ser Val Lys
            50                  55                  60

Gly Arg Phe Thr Ile Ser Arg Asp Asn Ala Lys Asn Thr Leu Ser Leu
65                  70                  75                  80
```

Gln Met Thr Ser Leu Lys Ser Glu Asp Thr Ala Val Tyr Tyr Cys Ala
                85                  90                  95

Lys Asp Pro Thr Asn Gly Leu Gly Ser Phe Thr Phe Gly Ser Trp Gly
            100                 105                 110

Gln Gly Thr Gln Val Thr Val Ser Ser
        115                 120

<210> SEQ ID NO 310
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Gln Leu Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Thr Ile Asn Ser Gly Gly Val Thr Asn Tyr Ala Asp Ser Val Lys
    50                  55                  60

Gly Arg Phe Thr Phe Ser Arg Asp Asn Ala Lys Asn Thr Leu Thr Leu
65                  70                  75                  80

Gln Met Asn Ser Leu Lys Pro Glu Asp Thr Ala Val Tyr Tyr Cys Val
                85                  90                  95

Ser Ser Ala Tyr Ser Asp Trp Gly Gln Gly Thr Gln Val Leu Val Ser
            100                 105                 110

Ser

<210> SEQ ID NO 311
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gln Val Gln Val Gln Glu Ser Gly Gly Gly Leu Val Gln Pro Gly Gly
1               5                   10                  15

Ser Leu Arg Val Ser Cys Ala Ala Ser Gly Phe Thr Phe Gly Asn Tyr
            20                  25                  30

Ala Met Ser Trp Val Arg Gln Ala Pro Gly Lys Gly Pro Glu Trp Val
        35                  40                  45

Ser Gly Ile Asn Ser Gly Gly Ser Ser Ala Tyr Tyr Glu Asp Ser Val
    50                  55                  60

Lys Gly Arg Phe Thr Ile Ser Arg Asp Asn Ala Lys Asp Thr Leu Tyr
65                  70                  75                  80

Leu Gln Met Asn Ser Leu Lys Pro Glu Asp Thr Ala Val Tyr Tyr Cys
                85                  90                  95

Ala Ile Ser Trp Ala Thr Tyr Gln Tyr Trp Gly Gln Gly Thr Gln Val
            100                 105                 110

Thr Val Ser Ser
        115

<210> SEQ ID NO 312
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Glu Val Gln Leu Val Gln Pro Gly Gly Ser Leu Arg Leu Ser Cys Ala
1               5                   10                  15

Ala Ser Gly Phe Thr Phe Ser Ser Ser Met His Trp Val Arg Gln
            20                  25                  30

Ala Pro Gly Lys Gly Leu Glu Trp Val Ser Ser Ile Asn Ser Gly Gly
        35                  40                  45

Asp Thr Thr Asn Tyr Ala Asp Ser Val Lys Gly Arg Phe Thr Ile Ser
    50                  55                  60

Arg Asp Asn Ala Lys Asn Thr Leu Tyr Leu Gln Met Asn Ser Leu Lys
65                  70                  75                  80

Pro Glu Asp Thr Ala Val Tyr Tyr Cys Ser Ala Thr Ser Tyr Ile Tyr
                85                  90                  95

Trp Gly Gln Gly Thr Gln Val Thr Val Ser Ser
            100                 105

<210> SEQ ID NO 313
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ala Val Val Asn Ser Gly Gly Gly Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Thr Tyr Pro Ser Leu Gly Ser Trp Gly Gln Gly Thr Gln Val Thr Val
            100                 105                 110

Ser Ser

<210> SEQ ID NO 314
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Gln Val Gln Val Gln Glu Ser Gly Gly Gly Leu Val Gln Pro Gly Gly
1               5                   10                  15

```
Ser Leu Arg Val Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gln Ile Asn Thr Gly Gly Asp Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Asp Asp Thr Ala Leu Tyr Tyr Cys
                85                  90                  95

Ala Met Gly Asn Leu Gly Tyr Trp Gly Gln Gly Thr Gln Val Thr Val
            100                 105                 110

Ser Ser

<210> SEQ ID NO 315
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gln Val Gln Leu Gln Glu Ser Gly Gly Gly Leu Val Gln Pro Gly Gly
1               5                   10                  15

Ser Leu Arg Val Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Gln Ile Asn Thr Gly Gly Asp Arg Thr Tyr Tyr Thr Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Ser Leu Lys Pro Glu Asp Thr Ala Leu Tyr Phe Cys
                85                  90                  95

Val Thr Ser Ser Leu Ser Ser Trp Gly Gln Gly Thr Gln Val Thr Val
            100                 105                 110

Ser Ser

<210> SEQ ID NO 316
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Glu Val Gln Val Gln Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Tyr Trp Val Arg Gln Ala Pro Gly Lys Gly Pro Glu Trp Val
        35                  40                  45

Ser Thr Ile Asn Ser Gly Gly Asp Ser Thr Asn Tyr Ala Asp Ser Leu
    50                  55                  60

Lys Gly Arg Phe Thr Ile Ser Arg Asp Asn Ala Lys Asn Met Leu Tyr
```

```
                65                  70                  75                  80
Leu Gln Met Asn Ser Leu Lys Pro Glu Asp Thr Ala Val Tyr Phe Cys
                        85                  90                  95
Val Thr Pro Gly Phe Gly Ser Trp Gly Gln Gly Thr Gln Val Thr Val
                100                 105                 110
Ser Ser

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Thr Asn Tyr Tyr Tyr Trp Thr
1               5

<210> SEQ ID NO 318
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Thr Thr Tyr Tyr Ala Trp Ser
1               5

<210> SEQ ID NO 319
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Thr Thr Tyr Ser Ala Trp Ser
1               5

<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Thr Ser Tyr Ser Gly Trp Gly
1               5

<210> SEQ ID NO 321
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Thr Ser Gly Tyr Ala Trp Ser
1               5
```

```
<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Thr Asn Tyr Tyr Ala Trp Asn
1               5

<210> SEQ ID NO 323
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Lys Phe Tyr Ile Glu
1               5

<210> SEQ ID NO 324
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Asp Tyr Ala Met Thr
1               5

<210> SEQ ID NO 325
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ile Asn Gly Met Ser
1               5

<210> SEQ ID NO 326
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ala Tyr Thr Met Ala
1               5

<210> SEQ ID NO 327
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 327

Ser Tyr Trp Met Tyr
1               5

<210> SEQ ID NO 328
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ser Tyr Thr Met Ser
1               5

<210> SEQ ID NO 329
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Asn Tyr Ala Met Ser
1               5

<210> SEQ ID NO 330
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Ser Ser Met His
1               5

<210> SEQ ID NO 331
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asn Tyr Ala Met Thr
1               5

<210> SEQ ID NO 332
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ser Tyr Tyr Met Asn
1               5

<210> SEQ ID NO 333
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Asp Tyr Tyr Met Asn
1               5

<210> SEQ ID NO 334
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ser Tyr Ala Met Tyr
1               5

<210> SEQ ID NO 335
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ala Ile Ala Tyr Ser Gly Ser Phe Tyr Tyr Ser Pro Ser Leu Lys Ser
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Val Ile Pro Gly Ala Gly Asn Thr Tyr Tyr Ser Pro Ala Leu Lys Ser
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Val Ile Ser Asn Tyr Gly Asp Thr Tyr Tyr Thr Pro Ser Leu Lys Ser
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Val Ile Gly Tyr Asp Gly Arg Thr Tyr Tyr Asn Pro Ser Leu Lys Ser
```

```
<210> SEQ ID NO 339
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Val Ile Gly Tyr Asp Gly Thr Asn Tyr Tyr Ser Pro Ser Leu Lys Ser
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Val Ile Ala Tyr Asp Gly Ala Thr Tyr Phe Asn Pro Ser Leu Lys Ser
1               5                   10                  15

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asn Ile Leu Pro Glu Asp Gly Gly Thr Tyr Tyr Ala Gln Lys Phe Gln
1               5                   10                  15

Gly

<210> SEQ ID NO 342
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Thr Ile Ser Trp Lys Asp Asp Thr Thr Asp Tyr Ala Glu Ser Met Lys
1               5                   10                  15

Gly

<210> SEQ ID NO 343
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ser Ile Asn Ser Gly Gly Glu Ile Thr Asn Tyr Arg Asp Ser Val Lys
1               5                   10                  15

Gly
```

```
<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Val Asn Ser Gly Gly Asp Ile Thr Ser Tyr Ala Asp Ser Val Lys
1               5                   10                  15

Gly

<210> SEQ ID NO 345
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Thr Phe Gly Ser Gly Ser Asn Thr Trp Tyr Ala Asp Ser Val Lys Gly
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Thr Ile Asn Ser Gly Gly Val Thr Asn Tyr Ala Asp Ser Val Lys Gly
1               5                   10                  15

<210> SEQ ID NO 347
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gly Ile Asn Ser Gly Gly Ser Ser Ala Tyr Tyr Glu Asp Ser Val Lys
1               5                   10                  15

Gly

<210> SEQ ID NO 348
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ser Ile Asn Ser Gly Gly Asp Thr Thr Asn Tyr Ala Asp Ser Val Lys
1               5                   10                  15

Gly

<210> SEQ ID NO 349
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 349

Val Val Asn Ser Gly Gly Gly Ser Thr Thr Tyr Ala Asp Ser Val Lys
1               5                   10                  15

Gly

<210> SEQ ID NO 350
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gln Ile Asn Thr Gly Gly Asp Ser Thr Tyr Tyr Ala Asp Ser Val Lys
1               5                   10                  15

Gly

<210> SEQ ID NO 351
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Ile Asn Thr Gly Gly Asp Arg Thr Tyr Tyr Thr Asp Ser Val Lys
1               5                   10                  15

Gly

<210> SEQ ID NO 352
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Thr Ile Asn Ser Gly Gly Asp Ser Thr Asn Tyr Ala Asp Ser Leu Lys
1               5                   10                  15

Gly

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asn Arg Gly Ala Tyr Tyr Ser Thr Gly Tyr Pro Gly Gly Tyr Glu Tyr
1               5                   10                  15

<210> SEQ ID NO 354
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 354

Ala Ser Thr Trp Leu Thr Tyr Gly Leu Ala Ser Gly Tyr Asp Tyr
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Val Leu Tyr Gly Ser Lys Trp Pro Ile Gly Pro Asn Phe Gly Ser
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Arg Pro Asp Gly Ser Arg Trp Tyr Thr Val Gly Glu Tyr Asp Tyr
1               5                   10                  15

<210> SEQ ID NO 357
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Val Gly Trp Gly Ser
1               5

<210> SEQ ID NO 358
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Arg Thr Arg Tyr Thr Gly Ser Tyr Gln Ser Thr Pro Asp Phe Gly Ser
1               5                   10                  15

<210> SEQ ID NO 359
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Thr Phe Gly Ser
1
```

```
<210> SEQ ID NO 360
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asp Pro Val Asn Phe Gly Ser
1               5

<210> SEQ ID NO 361
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Gly Ile Val Ala Tyr Asp Tyr
1               5

<210> SEQ ID NO 362
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Asp Pro Gly Met
1

<210> SEQ ID NO 363
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Asp Pro Thr Asn Gly Leu Gly Ser Phe Thr Phe Gly Ser
1               5                   10

<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ser Ala Tyr Ser Asp
1               5

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 365

Ser Trp Ala Thr Tyr Gln Tyr
1               5

<210> SEQ ID NO 366
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Thr Ser Tyr Ile Tyr
1               5

<210> SEQ ID NO 367
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Pro Ser Leu Gly Ser
1               5

<210> SEQ ID NO 368
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Asn Leu Gly Tyr
1               5

<210> SEQ ID NO 369
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ser Ser Leu Ser Ser
1               5

<210> SEQ ID NO 370
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Pro Gly Phe Gly Ser
1               5

<210> SEQ ID NO 371
<211> LENGTH: 103
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 371

Ala Val Thr Gln Pro Ala Ser Val Ser Val Asn Pro Gly Glu Thr Val
1               5                   10                  15

Glu Ile Thr Cys Ser Gly Gly Tyr Tyr Gly Trp Tyr Gln Gln Lys
            20                  25                  30

Ser Pro Gly Ser Ala Pro Val Thr Val Ile Tyr Trp Asn Asp Lys Arg
        35                  40                  45

Pro Ser Asp Ile Pro Ser Arg Phe Ser Gly Ser Lys Ser Gly Ser Thr
    50                  55                  60

Ala Thr Leu Thr Ile Thr Gly Val Arg Ala Glu Asp Glu Ala Val Tyr
65                  70                  75                  80

Tyr Cys Gly Gly Tyr Asp Gly Ser Gly Thr Asp Ala Val Phe Gly Ala
                85                  90                  95

Gly Thr Thr Leu Thr Val Leu
            100

<210> SEQ ID NO 372
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Ala Val Thr Gln Pro Ala Ser Val Ser Val Asn Pro Gly Glu Thr Val
1               5                   10                  15

Glu Ile Thr Cys Ser Gly Gly Tyr Tyr Gly Trp Tyr Gln Gln Lys
            20                  25                  30

Ser Pro Gly Ser Ala Pro Val Thr Val Ile Tyr Trp Asn Asp Lys Arg
        35                  40                  45

Pro Ser Asp Ile Pro Ser Arg Phe Ser Gly Ser Lys Ser Gly Ser Thr
    50                  55                  60

Ala Thr Leu Thr Ile Thr Gly Val Arg Ala Glu Asp Glu Ala Val Tyr
65                  70                  75                  80

Tyr Cys Gly Asp Tyr Asp Gly Ser Gly Thr Asp Ala Val Phe Gly Ala
                85                  90                  95

Gly Thr Thr Leu Thr Val Leu
            100

<210> SEQ ID NO 373
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Val Leu Thr Gln Pro Ala Ser Val Ser Ala Asn Leu Gly Gly Thr Val
1               5                   10                  15

Glu Ile Thr Cys Ser Gly Gly Ser Asn Asn Tyr Gly Trp Tyr Gln Gln
            20                  25                  30

Lys Ser Pro Gly Ser Ala Pro Val Thr Val Ile Tyr Ser Asn Asn Gln
        35                  40                  45

```
Arg Pro Ser Asn Ile Pro Ser Arg Phe Ser Gly Ser Lys Ser Gly Ser
         50                  55                  60

Thr Gly Thr Leu Thr Ile Thr Gly Val Gln Ala Asp Asp Glu Ala Val
 65                  70                  75                  80

Tyr Phe Cys Gly Ser Tyr Asp Ser Thr Asp Arg Asp Met Phe Gly Ala
                 85                  90                  95

Gly Thr Thr Leu Thr Val Leu
                100
```

<210> SEQ ID NO 374
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

```
Val Leu Thr Gln Pro Ala Ser Val Ser Ala Asn Leu Gly Gly Thr Val
 1               5                  10                  15

Glu Ile Thr Cys Ser Gly Gly Ser Asn Asn Tyr Gly Trp Tyr Gln Gln
                 20                  25                  30

Lys Ser Pro Gly Ser Ala Pro Val Thr Val Ile Tyr Ser Asn Asn Gln
             35                  40                  45

Arg Pro Ser Asn Ile Pro Ser Arg Phe Ser Gly Ser Lys Ser Gly Ser
         50                  55                  60

Thr Gly Thr Leu Thr Ile Thr Gly Val Gln Val Glu Asp Glu Ala Val
 65                  70                  75                  80

Tyr Phe Cys Gly Ser Tyr Asp Ser Thr Asp Arg Asp Met Phe Gly Ala
                 85                  90                  95

Gly Thr Thr Leu Thr Val Leu
                100
```

<210> SEQ ID NO 375
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

```
Ala Leu Thr Gln Pro Ser Ser Val Ser Ala Asn Leu Gly Gly Thr Val
 1               5                  10                  15

Lys Ile Thr Cys Ser Gly Gly Tyr Ser Asp Ala Gly Ser Tyr Tyr Tyr
                 20                  25                  30

Gly Trp Tyr Gln Gln Lys Ser Pro Gly Ser Ala Pro Val Thr Val Ile
             35                  40                  45

Tyr Ser Asn Asp Lys Arg Pro Ser Asp Ile Pro Ser Arg Phe Ser Gly
         50                  55                  60

Ala Leu Ser Gly Ser Thr Ala Thr Leu Thr Ile Thr Gly Val Gln Ala
 65                  70                  75                  80

Asp Asp Glu Ala Val Tyr Phe Cys Gly Ser Arg Asp Ser Asn Thr Glu
                 85                  90                  95

Ala Ile Phe Gly Ala Gly Thr Thr Leu Thr Val Leu
                100                 105
```

<210> SEQ ID NO 376

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Ala Leu Thr Gln Pro Ala Ser Val Ser Ala Asn Leu Gly Gly Thr Val
1               5                   10                  15

Glu Ile Thr Cys Ser Gly Gly Tyr Ser Gly Tyr Asp Tyr Gly Tyr Gly
            20                  25                  30

Trp Tyr Gln Gln Lys Ser Pro Gly Ser Ala Pro Val Thr Val Ile Tyr
        35                  40                  45

Ser Asn Asp Lys Arg Pro Ser Asp Ile Pro Ser Arg Phe Ser Gly Ser
    50                  55                  60

Lys Ser Gly Ser Thr Gly Thr Leu Thr Ile Thr Gly Val Gln Ala Glu
65                  70                  75                  80

Asp Glu Ala Val Tyr Phe Cys Gly Ser Thr Asp Ser Ser Tyr Val Gly
                85                  90                  95

Ile Phe Gly Ala Gly Thr Thr Leu Thr Val Leu
            100                 105

<210> SEQ ID NO 377
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Ala Leu Thr Gln Pro Ala Ser Val Ser Ala Asn Leu Gly Gly Thr Val
1               5                   10                  15

Glu Ile Thr Cys Ser Gly Gly Tyr Ser Gly Tyr Asp Tyr Gly Tyr Gly
            20                  25                  30

Trp Tyr Gln Gln Lys Ser Pro Gly Ser Ala Pro Val Thr Val Ile Tyr
        35                  40                  45

Ser Asn Asp Lys Arg Pro Ser Asp Ile Pro Ser Arg Phe Ser Gly Ser
    50                  55                  60

Lys Ser Gly Ser Thr Gly Thr Leu Thr Ile Thr Gly Val Gln Ala Asp
65                  70                  75                  80

Asp Glu Ala Val Tyr Phe Cys Gly Ser Thr Asp Ser Ser Tyr Val Gly
                85                  90                  95

Ile Phe Gly Ala Gly Thr Thr Leu Thr Val Leu
            100                 105

<210> SEQ ID NO 378
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Ala Val Thr Gln Pro Ala Ser Val Ser Ala Asn Pro Gly Glu Thr Val
1               5                   10                  15

Lys Ile Thr Cys Ser Gly Gly Tyr Glu Tyr Gly Trp Phe Gln Gln
            20                  25                  30

```
Lys Ser Pro Gly Ser Ala Leu Val Thr Val Ile Tyr Asp Asn Thr Asn
         35                  40                  45

Arg Pro Ser Asp Ile Pro Ser Arg Phe Ser Gly Ser Ser Ser Gly Ser
 50                  55                  60

Ala Asn Thr Leu Thr Ile Thr Gly Val Gln Ala Glu Asp Glu Ala Val
 65                  70                  75                  80

Tyr Tyr Cys Gly Ser Ala Asp Ser Ser Gly Asn Gly Ile Phe Gly Ala
                 85                  90                  95

Gly Thr Thr Leu Thr Val Leu
            100

<210> SEQ ID NO 379
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Ala Leu Thr Gln Pro Ala Ser Val Ser Ala Asn Leu Gly Gly Thr Val
 1               5                  10                  15

Glu Ile Thr Cys Ser Gly Gly Ser Tyr Ser Tyr Gly Trp Phe Gln Gln
                 20                  25                  30

Lys Ala Pro Gly Ser Ala Pro Val Thr Val Ile Tyr Asp Asp Thr Asn
         35                  40                  45

Arg Pro Ser Gly Ile Pro Ser Arg Phe Ser Gly Ser Thr Ser Gly Ser
 50                  55                  60

Thr Ser Thr Leu Thr Ile Thr Ala Val Gln Ala Glu Asp Glu Ala Val
 65                  70                  75                  80

Tyr Tyr Cys Gly Ser Trp Asp Asn Ser Ile Tyr Ala Gly Ile Phe Gly
                 85                  90                  95

Ala Gly Thr Thr Leu Thr Val Leu
            100

<210> SEQ ID NO 380
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Ala Leu Thr Gln Pro Ala Ser Val Ser Ala Asn Leu Gly Gly Thr Val
 1               5                  10                  15

Glu Ile Thr Cys Ser Gly Gly Ser Tyr Ser Tyr Gly Trp Phe Gln Gln
                 20                  25                  30

Lys Ala Pro Gly Ser Ala Pro Val Thr Val Ile Tyr Asp Asp Thr Asn
         35                  40                  45

Arg Pro Ser Gly Ile Pro Ser Arg Phe Ser Gly Ser Thr Ser Gly Ser
 50                  55                  60

Thr Ser Thr Leu Thr Ile Thr Ala Val Gln Ala Glu Asp Glu Ala Val
 65                  70                  75                  80

Tyr Tyr Cys Gly Ser Trp Asp Asn Ser Ile Tyr Ala Gly Ile Phe Gly
                 85                  90                  95

Ala Gly Thr Thr Leu Thr Val Leu
            100
```

```
<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Gly Gly Gly Tyr Tyr Gly
1               5

<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ser Gly Gly Ser Asn Asn Tyr Gly
1               5

<210> SEQ ID NO 383
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ser Gly Gly Tyr Ser Asp Ala Gly Ser Tyr Tyr Tyr Gly
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ser Gly Gly Tyr Ser Gly Tyr Asp Tyr Gly Tyr Gly
1               5                   10

<210> SEQ ID NO 385
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ser Gly Gly Ser Tyr Glu Tyr Gly
1               5

<210> SEQ ID NO 386
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 386

Ser Gly Gly Ser Tyr Ser Tyr Gly
1               5

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Trp Asn Asp Lys Arg Pro Ser
1               5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ser Asn Asn Gln Arg Pro Ser
1               5

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ser Asn Asp Lys Arg Pro Ser
1               5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Asp Asn Thr Asn Arg Pro Ser
1               5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Asp Asp Thr Asn Arg Pro Ser
1               5

<210> SEQ ID NO 392
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 392

Gly Gly Tyr Asp Gly Ser Gly Thr Asp
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Asp Tyr Asp Gly Ser Gly Thr Asp
1               5

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gly Ser Tyr Asp Ser Thr Asp Arg
1               5

<210> SEQ ID NO 395
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gly Ser Arg Asp Ser Asn Thr Glu
1               5

<210> SEQ ID NO 396
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gly Ser Thr Asp Ser Ser Tyr Val
1               5

<210> SEQ ID NO 397
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Ser Ala Asp Ser Ser Gly Asn
1               5
```

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Ser Trp Asp Asn Ser Ile Tyr Ala
1               5

<210> SEQ ID NO 399
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Met Ala Ala Val Thr Leu Asp Glu Ser Gly Gly Gly Leu Gln Thr Pro
1               5                   10                  15

Gly Gly Gly Leu Ser Leu Val Cys Lys Ala Ser Gly Phe Thr Phe Ser
                20                  25                  30

Asp His Gly Met Phe Trp Val Arg Gln Ala Pro Gly Lys Gly Leu Glu
            35                  40                  45

Phe Val Thr Gly Ile Ser Lys Asp Gly Gly Ala Thr Trp Tyr Ala Thr
        50                  55                  60

Ala Val Asp Gly Arg Ala Thr Ile Ser Lys Asp Asn Gly Gln Ser Thr
65                  70                  75                  80

Leu Arg Leu Gln Leu Asn Asn Leu Arg Ala Glu Asp Thr Ala Thr Tyr
                85                  90                  95

Phe Cys Ala Lys Pro Ser Asn Val Gly Ala Cys Thr Phe Ser Tyr Pro
            100                 105                 110

Ser Cys Pro Tyr Thr Ala Gly Ser Ile Asp Ala Trp Gly His Gly Thr
        115                 120                 125

Glu Val Ile Val Ser Ser
    130

<210> SEQ ID NO 400
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Met Ala Ala Val Thr Leu Asp Glu Ser Gly Gly Gly Leu Gln Thr Pro
1               5                   10                  15

Gly Gly Gly Leu Gly Leu Val Cys Lys Ala Ser Gly Phe Thr Phe Ser
                20                  25                  30

Asp His Gly Met Phe Trp Val Arg Gln Ala Pro Gly Lys Gly Leu Glu
            35                  40                  45

Phe Val Thr Gly Ile Ser Lys Asp Gly Gly Ala Thr Trp Tyr Ala Thr
        50                  55                  60

Ala Val Asp Gly Arg Ala Thr Ile Ser Lys Asp Asn Gly Gln Ser Ala
65                  70                  75                  80

```
Leu Arg Leu Gln Leu Asn Asn Leu Arg Ala Glu Asp Thr Ala Thr Tyr
                85                  90                  95

Phe Cys Ala Lys Pro Ser Asn Val Gly Ala Cys Thr Phe Ser Tyr Pro
            100                 105                 110

Ser Cys Pro Tyr Thr Ala Gly Ser Ile Asp Ala Trp Gly His Gly Thr
        115                 120                 125

Glu Val Ile Val Ser Ser
        130

<210> SEQ ID NO 401
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Ser Asn Met Gly Trp Val Arg Gln Ala Pro Gly Lys Gly Leu Glu
        35                  40                  45

Trp Val Ala Glu Ile Thr Ser Thr Gly Arg Thr Thr Asp Tyr Gly Ser
50                  55                  60

Ala Val Lys Gly Arg Ala Thr Ile Ser Arg Asp Asn Gly Gln Ser Thr
65                  70                  75                  80

Leu Arg Leu Gln Leu Asn Asn Leu Arg Ala Glu Asp Thr Gly Thr Tyr
                85                  90                  95

Tyr Cys Ile Arg Tyr Ile Asp Asp Gly Ser Gly Cys Cys Gly Ser Ile
            100                 105                 110

Asp Val Trp Gly His Gly Thr Glu Val Ile Val Ser Ser
        115                 120                 125

<210> SEQ ID NO 402
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Thr Phe Ser
            20                  25                  30

Ser Tyr Asp Met Gly Trp Val Arg Gln Ala Pro Gly Lys Gly Leu Glu
        35                  40                  45

Tyr Val Ala Gly Ile Thr Ser Ala Gly Gly Gly Thr Glu Tyr Gly Ala
50                  55                  60

Ala Val Asp Gly Arg Ala Thr Ile Ser Lys Asp Asn Gly Gln Ser Thr
65                  70                  75                  80

Val Arg Leu Gln Leu Asn Asn Leu Gly Ala Glu Asp Thr Gly Thr Tyr
                85                  90                  95

Tyr Cys Ala Lys Tyr Val Gly Ser Gly Gly Cys Gly Arg Gly Ser Cys
            100                 105                 110
```

```
Gly Asp Ser Ile Asp Ala Trp Gly His Gly Thr Glu Val Ile Val Ser
        115                 120                 125

Ser
```

<210> SEQ ID NO 403
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

```
Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Asp Phe Ser
            20                  25                  30

Ser Tyr Gln Met Asn Trp Ile Arg Gln Ala Pro Gly Lys Gly Leu Glu
        35                  40                  45

Phe Val Ala Ala Ile Asn Arg Phe Gly Asn Ser Thr Gly Gln Gly Glu
    50                  55                  60

Ala Val Lys Gly Arg Val Thr Ile Ser Arg Asp Asp Gly Gln Ser Thr
65                  70                  75                  80

Val Arg Leu Gln Leu Ser Asn Leu Arg Ala Glu Asp Thr Ala Thr Tyr
                85                  90                  95

Tyr Cys Ala Lys Gly Ala Tyr Gly Tyr Cys Gly Ser Gly Gly Trp Cys
            100                 105                 110

Gly Val Gly Asn Ile Asp Ala Trp Gly His Gly Thr Glu Val Ile Val
        115                 120                 125

Ser Ser
130
```

<210> SEQ ID NO 404
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

```
Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Asp Phe Ser
            20                  25                  30

Ser Tyr Gln Met Asn Trp Ile Arg Gln Ala Pro Gly Lys Gly Leu Glu
        35                  40                  45

Phe Val Ala Ala Ile Asn Arg Phe Gly Asn Ser Thr Gly Gln Gly Glu
    50                  55                  60

Ala Val Lys Gly Arg Val Thr Ile Ser Arg Asp Asp Gly Gln Ser Thr
65                  70                  75                  80

Val Arg Leu Gln Leu Ser Asn Leu Arg Ala Glu Asp Thr Ala Thr Tyr
                85                  90                  95

Tyr Cys Ala Lys Gly Ala Tyr Gly Tyr Cys Gly Ser Gly Gly Trp Cys
            100                 105                 110

Gly Val Gly Asn Ile Asp Ala Trp Gly His Gly Thr Glu Val Ile Val
        115                 120                 125

Ser Ser
```

<210> SEQ ID NO 405
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 405

Met Ala Ala Val Thr Leu Asp Glu Ser Gly Gly Leu Gln Thr Pro
1               5                   10                  15

Gly Gly Ala Leu Ser Leu Val Cys Lys Ala Ser Gly Phe Thr Phe Ser
                20                  25                  30

Asp Tyr Ala Met Gly Trp Val Arg Gln Ala Pro Gly Lys Gly Leu Glu
            35                  40                  45

Tyr Val Ala Ser Ile Asn Arg Phe Gly Asn Ser Thr Gly Tyr Ala Ala
    50                  55                  60

Ala Val Lys Gly Arg Ala Thr Ile Ser Arg Asp Ser Gly Gln Ser Thr
65                  70                  75                  80

Val Arg Leu Gln Leu Asn Asn Leu Arg Ala Glu Asp Thr Gly Ile Tyr
                85                  90                  95

Tyr Cys Thr Lys Ser Ala Tyr Ser Gly Tyr Asn Ser Gly Ile Leu Asp
            100                 105                 110

Ala Trp Gly His Gly Thr Glu Val Ile Val Ser Ser
        115                 120

<210> SEQ ID NO 406
<211> LENGTH: 137
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 406

Met Ala Ala Val Thr Leu Asp Glu Ser Gly Gly Gly Leu Gln Thr Pro
1               5                   10                  15

Gly Gly Ala Leu Ser Leu Val Cys Lys Gly Ser Gly Phe Thr Phe Ser
                20                  25                  30

Ser Phe Asn Met Ile Trp Val Arg Gln Ala Pro Gly Lys Gly Leu Glu
            35                  40                  45

Tyr Val Ala Ser Ile Tyr Ser Gly Gly Gly Tyr Thr Asn Tyr Gly
    50                  55                  60

Ala Ala Val Lys Gly Arg Ala Thr Ile Ser Arg Asp Asn Gly Gln Ser
65                  70                  75                  80

Thr Val Arg Leu Gln Leu Asn Asn Leu Arg Ala Glu Asp Thr Ala Thr
                85                  90                  95

Tyr Tyr Cys Ala Lys Asp Ala Gly Ser Asp Cys Trp His Thr Asp Gly
            100                 105                 110

Trp Ser Thr Tyr Asn Cys Gly Asp Ser Gly Arg Ile Asp Ala Trp Gly
        115                 120                 125

His Gly Thr Glu Val Ile Val Ser Ser
        130                 135

<210> SEQ ID NO 407
<211> LENGTH: 127
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 407

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Asp Phe Ser
            20                  25                  30

Ser Tyr Ala Met Phe Trp Val Arg Gln Ala Pro Gly Lys Gly Leu Glu
        35                  40                  45

Tyr Val Ala Ser Ile Asp Asp Ala Gly Gly Thr Glu Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Asp Ala Arg Ser Arg Ser Arg Ser Trp Cys Ala Ala Gly
            100                 105                 110

Cys Ile Asp Thr Trp Gly His Gly Thr Glu Val Ile Val Ser Ser
            115                 120                 125

<210> SEQ ID NO 408
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Met Ala Ala Val Thr Leu Asp Glu Ser Gly Gly Gly Leu Gln Thr Pro
1               5                   10                  15

Gly Gly Ala Leu Ser Leu Val Cys Lys Ala Ser Gly Phe Asp Phe Ser
            20                  25                  30

Ser Tyr Ala Met Phe Trp Val Arg Gln Ala Pro Gly Lys Gly Leu Glu
        35                  40                  45

Tyr Val Ala Ser Ile Asp Asp Ala Gly Gly Thr Glu Tyr Gly Ala Ala
    50                  55                  60

Val Lys Gly Arg Ala Thr Ile Ser Arg Asp Asn Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Asp Ala Arg Ser Arg Ser Arg Ser Trp Cys Ala Ala Gly
            100                 105                 110

Cys Ile Asp Thr Trp Gly His Gly Thr Glu Val Ile Val Ser Ser
            115                 120                 125

<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Ser Asp His Gly Met
1               5
```

<210> SEQ ID NO 410
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ser Ser Ser Asn Met
1               5

<210> SEQ ID NO 411
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Ser Ser Tyr Asp Met
1               5

<210> SEQ ID NO 412
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ser Ser Tyr Gln Met
1               5

<210> SEQ ID NO 413
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Ser Asp Tyr Ala Met
1               5

<210> SEQ ID NO 414
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ser Ser Phe Asn Met
1               5

<210> SEQ ID NO 415
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 415

Ser Ser Tyr Ala Met
1               5

<210> SEQ ID NO 416
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Ile Ser Lys Asp Gly Gly Ala Thr Trp Tyr Ala Thr Ala Val Asp
1               5                   10                  15

<210> SEQ ID NO 417
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Glu Ile Thr Ser Thr Gly Arg Thr Thr Asp Tyr Gly Ser Ala Val Lys
1               5                   10                  15

<210> SEQ ID NO 418
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gly Ile Thr Ser Ala Gly Gly Gly Thr Glu Tyr Gly Ala Ala Val Asp
1               5                   10                  15

<210> SEQ ID NO 419
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Ala Ile Asn Arg Phe Gly Asn Ser Thr Gly Gln Gly Glu Ala Val Lys
1               5                   10                  15

<210> SEQ ID NO 420
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ser Ile Asn Arg Phe Gly Asn Ser Thr Gly Tyr Ala Ala Ala Val Lys
1               5                   10                  15

<210> SEQ ID NO 421
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Ser Ile Tyr Ser Gly Gly Gly Gly Tyr Thr Asn Tyr Gly Ala Ala Val
1               5                   10                  15

Lys

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Ser Ile Asp Asp Ala Gly Gly Thr Glu Tyr Gly Ala Ala Val Lys
1               5                   10                  15

<210> SEQ ID NO 423
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Pro Ser Asn Val Gly Ala Cys Thr Phe Ser Tyr Pro Ser Cys Pro Tyr
1               5                   10                  15

Thr Ala Gly Ser Ile Asp Ala Trp
            20

<210> SEQ ID NO 424
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Tyr Ile Asp Asp Gly Ser Gly Cys Cys Gly Ser Ile Asp Val Trp
1               5                   10                  15

<210> SEQ ID NO 425
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Tyr Val Gly Ser Gly Gly Cys Gly Arg Gly Ser Cys Gly Asp Ser Ile
1               5                   10                  15

Asp Ala Trp

<210> SEQ ID NO 426
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 426

Gly Ala Tyr Gly Tyr Cys Gly Ser Gly Gly Trp Cys Gly Val Gly Asn
1               5                   10                  15

Ile Asp Ala Trp
            20

<210> SEQ ID NO 427
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ser Ala Tyr Ser Gly Tyr Asn Ser Gly Ile Leu Asp Ala Trp
1               5                   10

<210> SEQ ID NO 428
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Asp Ala Gly Ser Asp Cys Trp His Thr Asp Gly Trp Ser Thr Tyr Asn
1               5                   10                  15

Cys Gly Asp Ser Gly Arg Ile Asp Ala Trp
            20                  25

<210> SEQ ID NO 429
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Asp Ala Arg Ser Arg Ser Arg Ser Trp Cys Ala Ala Gly Cys Ile Asp
1               5                   10                  15

Thr Trp

<210> SEQ ID NO 430
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: K, R, H, V, L, I, M, A, G, S, T or C
<220> FEATURE:
<221> NAME/KEY: MOD_RES
<222> LOCATION: (2)..(2)
<223> OTHER INFORMATION: S, T, C, G, V, L, I, M or A
<220> FEATURE:
<221> NAME/KEY: MOD_RES
<222> LOCATION: (3)..(3)
<223> OTHER INFORMATION: S, T, C, K, R or H
```

```
<220> FEATURE:
<221> NAME/KEY: MOD_RES
<222> LOCATION: (4)..(4)
<223> OTHER INFORMATION: Q, N, E, D, S, T or C
<220> FEATURE:
<221> NAME/KEY: MOD_RES
<222> LOCATION: (5)..(5)
<223> OTHER INFORMATION: S, T, C, G, V, L, I, M or A
<220> FEATURE:
<221> NAME/KEY: MOD_RES
<222> LOCATION: (6)..(6)
<223> OTHER INFORMATION: V, L, I, M, A, G, D, E, S, T or C
<220> FEATURE:
<221> NAME/KEY: MOD_RES
<222> LOCATION: (7)..(7)
<223> OTHER INFORMATION: A, G, V, L, I, or M
<220> FEATURE:
<221> NAME/KEY: MOD_RES
<222> LOCATION: (8)..(8)
<223> OTHER INFORMATION: S, T, C, H, K, R, F, W, Y, G, V, L, I, M or A
<220> FEATURE:
<221> NAME/KEY: MOD_RES
<222> LOCATION: (9)..(9)
<223> OTHER INFORMATION: G, A, V, L, I, M or absent
<220> FEATURE:
<221> NAME/KEY: MOD_RES
<222> LOCATION: (10)..(10)
<223> OTHER INFORMATION: S, T, C or absent
<220> FEATURE:
<221> NAME/KEY: MOD_RES
<222> LOCATION: (11)..(11)
<223> OTHER INFORMATION: N, Q, D, E or absent
<220> FEATURE:
<221> NAME/KEY: MOD_RES
<222> LOCATION: (12)..(12)
<223> OTHER INFORMATION: Q, N, G, V, L, I, M, A, E, D, Y, F, W, S, T or
    C
<220> FEATURE:
<221> NAME/KEY: MOD_RES
<222> LOCATION: (13)..(13)
<223> OTHER INFORMATION: K, R, H, N, Q, G, V, L, I, M, A, F, Y, W, S, T
    or C
<220> FEATURE:
<221> NAME/KEY: MOD_RES
<222> LOCATION: (14)..(14)
<223> OTHER INFORMATION: T, S, C, N or Q
<220> FEATURE:
<221> NAME/KEY: MOD_RES
<222> LOCATION: (15)..(15)
<223> OTHER INFORMATION: F, Y, W, S, T or C
<220> FEATURE:
<221> NAME/KEY: MOD_RES
<222> LOCATION: (16)..(16)
<223> OTHER INFORMATION: G, V, L, I, M, A, F, Y, W or P
<220> FEATURE:
<221> NAME/KEY: MOD_RES
<222> LOCATION: (17)..(17)
<223> OTHER INFORMATION: N, Q, Y, F, W, T, S, C, D or E

<400> SEQUENCE: 430

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 431
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: K, R or H
<220> FEATURE:
```

<221> NAME/KEY: MOD_RES
<222> LOCATION: (2)..(2)
<223> OTHER INFORMATION: S, T or C
<220> FEATURE:
<221> NAME/KEY: MOD_RES
<222> LOCATION: (3)..(3)
<223> OTHER INFORMATION: S, T or C
<220> FEATURE:
<221> NAME/KEY: MOD_RES
<222> LOCATION: (4)..(4)
<223> OTHER INFORMATION: Q or N
<220> FEATURE:
<221> NAME/KEY: MOD_RES
<222> LOCATION: (5)..(5)
<223> OTHER INFORMATION: S, T, or C
<220> FEATURE:
<221> NAME/KEY: MOD_RES
<222> LOCATION: (6)..(6)
<223> OTHER INFORMATION: V, L, I, M, A or G
<220> FEATURE:
<221> NAME/KEY: MOD_RES
<222> LOCATION: (7)..(7)
<223> OTHER INFORMATION: V, L, I, M, A or G
<220> FEATURE:
<221> NAME/KEY: MOD_RES
<222> LOCATION: (8)..(8)
<223> OTHER INFORMATION: S, T or C
<220> FEATURE:
<221> NAME/KEY: MOD_RES
<222> LOCATION: (9)..(9)
<223> OTHER INFORMATION: V, L, I, M, A or G
<220> FEATURE:
<221> NAME/KEY: MOD_RES
<222> LOCATION: (10)..(10)
<223> OTHER INFORMATION: S, T or C
<220> FEATURE:
<221> NAME/KEY: MOD_RES
<222> LOCATION: (11)..(11)
<223> OTHER INFORMATION: N or Q
<220> FEATURE:
<221> NAME/KEY: MOD_RES
<222> LOCATION: (12)..(12)
<223> OTHER INFORMATION: N or Q
<220> FEATURE:
<221> NAME/KEY: MOD_RES
<222> LOCATION: (13)..(13)
<223> OTHER INFORMATION: K, R or H
<220> FEATURE:
<221> NAME/KEY: MOD_RES
<222> LOCATION: (14)..(14)
<223> OTHER INFORMATION: S, T or C
<220> FEATURE:
<221> NAME/KEY: MOD_RES
<222> LOCATION: (15)..(15)
<223> OTHER INFORMATION: Y, F or W
<220> FEATURE:
<221> NAME/KEY: MOD_RES
<222> LOCATION: (16)..(16)
<223> OTHER INFORMATION: V, L, I, M, A or G
<220> FEATURE:
<221> NAME/KEY: MOD_RES
<222> LOCATION: (17)..(17)
<223> OTHER INFORMATION: N or Q

<400> SEQUENCE: 431

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 432
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Y, F, W, Q, N, R, K, H, E or D
<220> FEATURE:
<221> NAME/KEY: MOD_RES
<222> LOCATION: (2)..(2)
<223> OTHER INFORMATION: V, L, I, M, A, G, D, E, S, T or C
<220> FEATURE:
<221> NAME/KEY: MOD_RES
<222> LOCATION: (3)..(3)
<223> OTHER INFORMATION: S, T, C, V, L, I, M, A, G, N or Q
<220> FEATURE:
<221> NAME/KEY: MOD_RES
<222> LOCATION: (4)..(4)
<223> OTHER INFORMATION: S, T, C, N, Q, K, R, H, V, L, I, M, A or G
<220> FEATURE:
<221> NAME/KEY: MOD_RES
<222> LOCATION: (5)..(5)
<223> OTHER INFORMATION: R, K, H, Q or N
<220> FEATURE:
<221> NAME/KEY: MOD_RES
<222> LOCATION: (6)..(6)
<223> OTHER INFORMATION: E, D, S, T, C, G, V, L, I, M, A, K, R or H
<220> FEATURE:
<221> NAME/KEY: MOD_RES
<222> LOCATION: (7)..(7)
<223> OTHER INFORMATION: V, L, I, M, A, G, S, T or C

<400> SEQUENCE: 432

Xaa Xaa Xaa Xaa Xaa Xaa Xaa
1               5

<210> SEQ ID NO 433
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Y, F or W
<220> FEATURE:
<221> NAME/KEY: MOD_RES
<222> LOCATION: (2)..(2)
<223> OTHER INFORMATION: V, L, I, M, A or G
<220> FEATURE:
<221> NAME/KEY: MOD_RES
<222> LOCATION: (3)..(3)
<223> OTHER INFORMATION: S, T or C
<220> FEATURE:
<221> NAME/KEY: MOD_RES
<222> LOCATION: (4)..(4)
<223> OTHER INFORMATION: S, T or C
<220> FEATURE:
<221> NAME/KEY: MOD_RES
<222> LOCATION: (5)..(5)
<223> OTHER INFORMATION: Q or N
<220> FEATURE:
<221> NAME/KEY: MOD_RES
<222> LOCATION: (6)..(6)
<223> OTHER INFORMATION: E or D
<220> FEATURE:
<221> NAME/KEY: MOD_RES
<222> LOCATION: (7)..(7)
<223> OTHER INFORMATION: V, L, I, M, A or G

<400> SEQUENCE: 433

Xaa Xaa Xaa Xaa Xaa Xaa Xaa
1               5

<210> SEQ ID NO 434
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q, N, V, L, I, M, A or G
<220> FEATURE:
<221> NAME/KEY: MOD_RES
<222> LOCATION: (2)..(2)
<223> OTHER INFORMATION: Q, N, S, T, C, V, L, I, M, A or G
<220> FEATURE:
<221> NAME/KEY: MOD_RES
<222> LOCATION: (3)..(3)
<223> OTHER INFORMATION: V, L, I, M, A, G, F, Y, W or absent
<220> FEATURE:
<221> NAME/KEY: MOD_RES
<222> LOCATION: (4)..(4)
<223> OTHER INFORMATION: K, R, H, V, L, I, M, A, G or absent
<220> FEATURE:
<221> NAME/KEY: MOD_RES
<222> LOCATION: (5)..(5)
<223> OTHER INFORMATION: S, T, C, R, K, H or absent
<220> FEATURE:
<221> NAME/KEY: MOD_RES
<222> LOCATION: (6)..(6)
<223> OTHER INFORMATION: V, L, I, M, A, G, R, K, H, S, T, C or absent
<220> FEATURE:
<221> NAME/KEY: MOD_RES
<222> LOCATION: (7)..(7)
<223> OTHER INFORMATION: Y, F, W, S, T, C, G, V, L, I, M, A, N or Q
<220> FEATURE:
<221> NAME/KEY: MOD_RES
<222> LOCATION: (8)..(8)
<223> OTHER INFORMATION: S, T, C, R, K, H, Y, F, W or absent
<220> FEATURE:
<221> NAME/KEY: MOD_RES
<222> LOCATION: (9)..(9)
<223> OTHER INFORMATION: V, L, I, M, A, G, Y, F, W or absent
<220> FEATURE:
<221> NAME/KEY: MOD_RES
<222> LOCATION: (10)..(10)
<223> OTHER INFORMATION: P, S, T, C, N or Q
<220> FEATURE:
<221> NAME/KEY: MOD_RES
<222> LOCATION: (11)..(11)
<223> OTHER INFORMATION: F, Y, W, V, L, I, M, A, G, S, T or C
<220> FEATURE:
<221> NAME/KEY: MOD_RES
<222> LOCATION: (12)..(12)
<223> OTHER INFORMATION: N, Q, S, T, C, G, V, L, I, M, A or G

<400> SEQUENCE: 434

Xaa Xaa Xaa Xaa Xaa Xaa Xaa Xaa Xaa Xaa Xaa Xaa
1               5                   10

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Q or N
<220> FEATURE:
<221> NAME/KEY: MOD_RES
<222> LOCATION: (2)..(2)
<223> OTHER INFORMATION: Q or N
<220> FEATURE:
<221> NAME/KEY: MOD_RES
<222> LOCATION: (3)..(3)
<223> OTHER INFORMATION: V, L, I, M, A or G
```

```
<220> FEATURE:
<221> NAME/KEY: MOD_RES
<222> LOCATION: (4)..(4)
<223> OTHER INFORMATION: Y, F or W
<220> FEATURE:
<221> NAME/KEY: MOD_RES
<222> LOCATION: (5)..(5)
<223> OTHER INFORMATION: S, T or C
<220> FEATURE:
<221> NAME/KEY: MOD_RES
<222> LOCATION: (6)..(6)
<223> OTHER INFORMATION: V, L, I, M, A or G
<220> FEATURE:
<221> NAME/KEY: MOD_RES
<222> LOCATION: (8)..(8)
<223> OTHER INFORMATION: Y, F or W
<220> FEATURE:
<221> NAME/KEY: MOD_RES
<222> LOCATION: (9)..(9)
<223> OTHER INFORMATION: N or Q

<400> SEQUENCE: 435

Xaa Xaa Xaa Xaa Xaa Xaa Pro Xaa Xaa
 1               5

<210> SEQ ID NO 436
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T, C or absent
<220> FEATURE:
<221> NAME/KEY: MOD_RES
<222> LOCATION: (2)..(2)
<223> OTHER INFORMATION: S, T, C, N, Q or absent
<220> FEATURE:
<221> NAME/KEY: MOD_RES
<222> LOCATION: (3)..(3)
<223> OTHER INFORMATION: Y, F, W, G, V, L, I, M, A, K, R, H, D, E, S, T,
      C, N or Q
<220> FEATURE:
<221> NAME/KEY: MOD_RES
<222> LOCATION: (4)..(4)
<223> OTHER INFORMATION: Y, F, W, S, T, C, N or Q
<220> FEATURE:
<221> NAME/KEY: MOD_RES
<222> LOCATION: (5)..(5)
<223> OTHER INFORMATION: Y, F, W, V, L, I, M, A, G, S, T or C
<220> FEATURE:
<221> NAME/KEY: MOD_RES
<222> LOCATION: (6)..(6)
<223> OTHER INFORMATION: F, Y, W, V, L, I, M, A or G
<220> FEATURE:
<221> NAME/KEY: MOD_RES
<222> LOCATION: (7)..(7)
<223> OTHER INFORMATION: S, T, C, V, L, I, M, A, G, N, Q, D, E, F, Y, W,
      K, R, or H

<400> SEQUENCE: 436

Xaa Xaa Xaa Xaa Xaa Xaa Xaa
 1               5

<210> SEQ ID NO 437
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: V, L, I, M, A or G
<220> FEATURE:
<221> NAME/KEY: MOD_RES
<222> LOCATION: (2)..(2)
<223> OTHER INFORMATION: N or Q
<220> FEATURE:
<221> NAME/KEY: MOD_RES
<222> LOCATION: (3)..(3)
<223> OTHER INFORMATION: V, L, I, M, A or G
<220> FEATURE:
<221> NAME/KEY: MOD_RES
<222> LOCATION: (4)..(4)
<223> OTHER INFORMATION: V, L, I, M, A or G
<220> FEATURE:
<221> NAME/KEY: MOD_RES
<222> LOCATION: (5)..(5)
<223> OTHER INFORMATION: S, T or C

<400> SEQUENCE: 437

Xaa Xaa Xaa Xaa Xaa
1               5

<210> SEQ ID NO 438
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, L, I, M, A, G, N, Q, S, T or C
<220> FEATURE:
<221> NAME/KEY: MOD_RES
<222> LOCATION: (2)..(2)
<223> OTHER INFORMATION: V, L, I, M, A, G, F, W or Y
<220> FEATURE:
<221> NAME/KEY: MOD_RES
<222> LOCATION: (3)..(3)
<223> OTHER INFORMATION: V, L, I, M, A, G, P, S, T, C, N or Q
<220> FEATURE:
<221> NAME/KEY: MOD_RES
<222> LOCATION: (4)..(4)
<223> OTHER INFORMATION: F, Y, W, V, L, I, M, A, G, N, Q, P, S, T or C
<220> FEATURE:
<221> NAME/KEY: MOD_RES
<222> LOCATION: (5)..(5)
<223> OTHER INFORMATION: S, T, C, V, L, I, M, A, G, Y, F, W, D, E, K, R
      or H
<220> FEATURE:
<221> NAME/KEY: MOD_RES
<222> LOCATION: (6)..(6)
<223> OTHER INFORMATION: V, L, I, M, A, G, D, E, S, T or C
<220> FEATURE:
<221> NAME/KEY: MOD_RES
<222> LOCATION: (7)..(7)
<223> OTHER INFORMATION: V, L, I, M, A, G, D, E, S, T, C or absent
<220> FEATURE:
<221> NAME/KEY: MOD_RES
<222> LOCATION: (8)..(8)
<223> OTHER INFORMATION: S, T, C, N, Q, D, E, R, K, H, V, L, I, M, A, G,
      N, Q or absent
<220> FEATURE:
<221> NAME/KEY: MOD_RES
<222> LOCATION: (9)..(9)
<223> OTHER INFORMATION: F, Y, W, S, T, C, N, Q, V, L, I, M, A or G
<220> FEATURE:
<221> NAME/KEY: MOD_RES
<222> LOCATION: (10)..(10)
<223> OTHER INFORMATION: Y, F, W, D, E, N, Q, S, T or C
<220> FEATURE:
<221> NAME/KEY: MOD_RES
<222> LOCATION: (11)..(11)
<223> OTHER INFORMATION: Y, F or W
```

```
<220> FEATURE:
<221> NAME/KEY: MOD_RES
<222> LOCATION: (12)..(12)
<223> OTHER INFORMATION: S, T, C, N, Q, V, L, I, M, A, G, R, K, H, D or
      E
<220> FEATURE:
<221> NAME/KEY: MOD_RES
<222> LOCATION: (13)..(13)
<223> OTHER INFORMATION: P, N, Q, E or D
<220> FEATURE:
<221> NAME/KEY: MOD_RES
<222> LOCATION: (14)..(14)
<223> OTHER INFORMATION: S, T, C, V, L, I, M, A, G, K, R or H
<220> FEATURE:
<221> NAME/KEY: MOD_RES
<222> LOCATION: (15)..(15)
<223> OTHER INFORMATION: V, L, I, M, A, G, F, Y or W
<220> FEATURE:
<221> NAME/KEY: MOD_RES
<222> LOCATION: (16)..(16)
<223> OTHER INFORMATION: K, R, H, N or Q
<220> FEATURE:
<221> NAME/KEY: MOD_RES
<222> LOCATION: (17)..(17)
<223> OTHER INFORMATION: S, T, C, V, L, I, M, A or G

<400> SEQUENCE: 438

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 439
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: V, L, I, M, A or G
<220> FEATURE:
<221> NAME/KEY: MOD_RES
<222> LOCATION: (3)..(3)
<223> OTHER INFORMATION: N or Q
<220> FEATURE:
<221> NAME/KEY: MOD_RES
<222> LOCATION: (4)..(4)
<223> OTHER INFORMATION: S, T or C
<220> FEATURE:
<221> NAME/KEY: MOD_RES
<222> LOCATION: (5)..(5)
<223> OTHER INFORMATION: V, L, I, M, A or G
<220> FEATURE:
<221> NAME/KEY: MOD_RES
<222> LOCATION: (6)..(6)
<223> OTHER INFORMATION: V, L, I, M, A or G
<220> FEATURE:
<221> NAME/KEY: MOD_RES
<222> LOCATION: (7)..(7)
<223> OTHER INFORMATION: E or D
<220> FEATURE:
<221> NAME/KEY: MOD_RES
<222> LOCATION: (8)..(8)
<223> OTHER INFORMATION: V, L, I, M, A or G
<220> FEATURE:
<221> NAME/KEY: MOD_RES
<222> LOCATION: (9)..(9)
<223> OTHER INFORMATION: S, T or C
<220> FEATURE:
<221> NAME/KEY: MOD_RES
```

```
<222> LOCATION: (10)..(10)
<223> OTHER INFORMATION: N or Q
<220> FEATURE:
<221> NAME/KEY: MOD_RES
<222> LOCATION: (11)..(11)
<223> OTHER INFORMATION: Y, F or W
<220> FEATURE:
<221> NAME/KEY: MOD_RES
<222> LOCATION: (12)..(12)
<223> OTHER INFORMATION: R, K or H
<220> FEATURE:
<221> NAME/KEY: MOD_RES
<222> LOCATION: (13)..(13)
<223> OTHER INFORMATION: D or E
<220> FEATURE:
<221> NAME/KEY: MOD_RES
<222> LOCATION: (14)..(14)
<223> OTHER INFORMATION: S, T or C
<220> FEATURE:
<221> NAME/KEY: MOD_RES
<222> LOCATION: (15)..(15)
<223> OTHER INFORMATION: V, L, I, M, A or G
<220> FEATURE:
<221> NAME/KEY: MOD_RES
<222> LOCATION: (16)..(16)
<223> OTHER INFORMATION: K, R or H
<220> FEATURE:
<221> NAME/KEY: MOD_RES
<222> LOCATION: (17)..(17)
<223> OTHER INFORMATION: V, L, I, M, A or G

<400> SEQUENCE: 439

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 440
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N, Q, V, L, I, M, A, G, R, K, H, D, E, S, T, C
      or absent
<220> FEATURE:
<221> NAME/KEY: MOD_RES
<222> LOCATION: (2)..(2)
<223> OTHER INFORMATION: R, K, H, S, T, C, V, L, I, M, A, G, P, F, Y, W
      or absent
<220> FEATURE:
<221> NAME/KEY: MOD_RES
<222> LOCATION: (3)..(3)
<223> OTHER INFORMATION: V, L, I, M, A, G, S, T, C, P, R, K, H or absent
<220> FEATURE:
<221> NAME/KEY: MOD_RES
<222> LOCATION: (4)..(4)
<223> OTHER INFORMATION: V, L, I, M, A, G, F, Y, W, D, E, N, Q or absent
<220> FEATURE:
<221> NAME/KEY: MOD_RES
<222> LOCATION: (5)..(5)
<223> OTHER INFORMATION: F, Y, W, V, L, I, M, A, G, S, T, C or absent
<220> FEATURE:
<221> NAME/KEY: MOD_RES
<222> LOCATION: (6)..(6)
<223> OTHER INFORMATION: F, Y, W, S, T, C, V, L, I, M, A, G or absent
<220> FEATURE:
<221> NAME/KEY: MOD_RES
<222> LOCATION: (7)..(7)
<223> OTHER INFORMATION: S, T, C, K, R, H or absent
<220> FEATURE:
<221> NAME/KEY: MOD_RES
<222> LOCATION: (8)..(8)
```

```
<223> OTHER INFORMATION: S, T, C, F, Y, W or absent
<220> FEATURE:
<221> NAME/KEY: MOD_RES
<222> LOCATION: (9)..(9)
<223> OTHER INFORMATION: V, L, I, M, A, G, P, F, Y, W, Q, N or absent
<220> FEATURE:
<221> NAME/KEY: MOD_RES
<222> LOCATION: (10)..(10)
<223> OTHER INFORMATION: F, Y, W, V, L, I, M, A, G, S, T, C or absent
<220> FEATURE:
<221> NAME/KEY: MOD_RES
<222> LOCATION: (11)..(11)
<223> OTHER INFORMATION: P, V, L, I, M, A, G, S, T, C or absent
<220> FEATURE:
<221> NAME/KEY: MOD_RES
<222> LOCATION: (12)..(12)
<223> OTHER INFORMATION: V, L, I, M, A, G, S, T, C, P, F, Y, W or absent
<220> FEATURE:
<221> NAME/KEY: MOD_RES
<222> LOCATION: (13)..(13)
<223> OTHER INFORMATION: V, L, I, M, A, G, N, Q, E, D, S, T, C or absent
<220> FEATURE:
<221> NAME/KEY: MOD_RES
<222> LOCATION: (14)..(14)
<223> OTHER INFORMATION: Y, F, W, V, L, I, M, A, G or absent
<220> FEATURE:
<221> NAME/KEY: MOD_RES
<222> LOCATION: (15)..(15)
<223> OTHER INFORMATION: E, D, V, L, I, M, A, G, S, T, C, Q, N or absent
<220> FEATURE:
<221> NAME/KEY: MOD_RES
<222> LOCATION: (16)..(16)
<223> OTHER INFORMATION: F, Y, W, S, T, C, V, L, I, M, A, G, D or E

<400> SEQUENCE: 440

Xaa Xaa Xaa Xaa Xaa Xaa Xaa Xaa Xaa Xaa Xaa Xaa Xaa Xaa Xaa Xaa
1               5                   10                  15

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: V, L, I, M, A or G
<220> FEATURE:
<221> NAME/KEY: MOD_RES
<222> LOCATION: (2)..(2)
<223> OTHER INFORMATION: V, L, I, M, A or G
<220> FEATURE:
<221> NAME/KEY: MOD_RES
<222> LOCATION: (3)..(3)
<223> OTHER INFORMATION: V, L, I, M, A or G
<220> FEATURE:
<221> NAME/KEY: MOD_RES
<222> LOCATION: (4)..(4)
<223> OTHER INFORMATION: V, L, I, M, A or G
<220> FEATURE:
<221> NAME/KEY: MOD_RES
<222> LOCATION: (5)..(5)
<223> OTHER INFORMATION: Y, F or W
<220> FEATURE:
<221> NAME/KEY: MOD_RES
<222> LOCATION: (6)..(6)
<223> OTHER INFORMATION: D or E
<220> FEATURE:
<221> NAME/KEY: MOD_RES
<222> LOCATION: (7)..(7)
<223> OTHER INFORMATION: Y, F or W

<400> SEQUENCE: 441

Xaa Xaa Xaa Xaa Xaa Xaa Xaa
```

```
<210> SEQ ID NO 442
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N, Q, S, T or C
<220> FEATURE:
<221> NAME/KEY: MOD_RES
<222> LOCATION: (2)..(2)
<223> OTHER INFORMATION: D, E, S, T or C
<220> FEATURE:
<221> NAME/KEY: MOD_RES
<222> LOCATION: (3)..(3)
<223> OTHER INFORMATION: Y, F, W, H, K or R
<220> FEATURE:
<221> NAME/KEY: MOD_RES
<222> LOCATION: (4)..(4)
<223> OTHER INFORMATION: G, A, N, Q, V, L, M, I, S, T or C
<220> FEATURE:
<221> NAME/KEY: MOD_RES
<222> LOCATION: (5)..(5)
<223> OTHER INFORMATION: M, V, L, I, G or A

<400> SEQUENCE: 442

Xaa Xaa Xaa Xaa Xaa
1               5

<210> SEQ ID NO 443
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T, C, N or Q
<220> FEATURE:
<221> NAME/KEY: MOD_RES
<222> LOCATION: (2)..(2)
<223> OTHER INFORMATION: S, T, C, D or E
<220> FEATURE:
<221> NAME/KEY: MOD_RES
<222> LOCATION: (3)..(3)
<223> OTHER INFORMATION: Y, F, W, K, R or H
<220> FEATURE:
<221> NAME/KEY: MOD_RES
<222> LOCATION: (4)..(4)
<223> OTHER INFORMATION: G, A, V, L, I or M
<220> FEATURE:
<221> NAME/KEY: MOD_RES
<222> LOCATION: (5)..(5)
<223> OTHER INFORMATION: M, A, V, L, G or I

<400> SEQUENCE: 443

Xaa Xaa Xaa Xaa Xaa
1               5

<210> SEQ ID NO 444
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: D, E, S, T or C
<220> FEATURE:
<221> NAME/KEY: MOD_RES
<222> LOCATION: (3)..(3)
<223> OTHER INFORMATION: R, K, H, Y, F or W
<220> FEATURE:
<221> NAME/KEY: MOD_RES
<222> LOCATION: (4)..(4)
<223> OTHER INFORMATION: G, A, V, L, I, M, N or Q
<220> FEATURE:
<221> NAME/KEY: MOD_RES
<222> LOCATION: (5)..(5)
<223> OTHER INFORMATION: M, A, G, V, L, or I

<400> SEQUENCE: 444

Xaa Xaa Xaa Xaa Xaa
1               5

<210> SEQ ID NO 445
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: S, T or C
<220> FEATURE:
<221> NAME/KEY: MOD_RES
<222> LOCATION: (3)..(3)
<223> OTHER INFORMATION: H, R or K
<220> FEATURE:
<221> NAME/KEY: MOD_RES
<222> LOCATION: (4)..(4)
<223> OTHER INFORMATION: G, A, V, I, L or M
<220> FEATURE:
<221> NAME/KEY: MOD_RES
<222> LOCATION: (5)..(5)
<223> OTHER INFORMATION: M, A, G, I, L, or V

<400> SEQUENCE: 445

Xaa Xaa Xaa Xaa Xaa
1               5

<210> SEQ ID NO 446
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, A, V, L, I, M, E, D, K, R, H, S, T or C
<220> FEATURE:
<221> NAME/KEY: MOD_RES
<222> LOCATION: (2)..(2)
<223> OTHER INFORMATION: I, V, L, M or A
<220> FEATURE:
<221> NAME/KEY: MOD_RES
<222> LOCATION: (3)..(3)
<223> OTHER INFORMATION: Y, F, W, S, T, C, D, E, N or Q
```

```
<220> FEATURE:
<221> NAME/KEY: MOD_RES
<222> LOCATION: (4)..(4)
<223> OTHER INFORMATION: S, T, C or absent
<220> FEATURE:
<221> NAME/KEY: MOD_RES
<222> LOCATION: (5)..(5)
<223> OTHER INFORMATION: S, T, C, N, Q, R, K, H, A, G, V, L, I, M, D or
      E
<220> FEATURE:
<221> NAME/KEY: MOD_RES
<222> LOCATION: (6)..(6)
<223> OTHER INFORMATION: S, T, C, D, E, A, G, V, L, I, M, F, Y or W
<220> FEATURE:
<221> NAME/KEY: MOD_RES
<222> LOCATION: (7)..(7)
<223> OTHER INFORMATION: G, A, V, L, I, M, D or E
<220> FEATURE:
<221> NAME/KEY: MOD_RES
<222> LOCATION: (8)..(8)
<223> OTHER INFORMATION: R, K, H, N, Q, S, T, C, G, A, V, L, I or M
<220> FEATURE:
<221> NAME/KEY: MOD_RES
<222> LOCATION: (9)..(9)
<223> OTHER INFORMATION: Y, F, W, S, T, C, R, K, H, E, D, G, A, V, L, I,
      M or absent
<220> FEATURE:
<221> NAME/KEY: MOD_RES
<222> LOCATION: (10)..(10)
<223> OTHER INFORMATION: T, S, C, A, G, V, L, I or M
<220> FEATURE:
<221> NAME/KEY: MOD_RES
<222> LOCATION: (11)..(11)
<223> OTHER INFORMATION: Y, F, W, A, G, V, L, I, M, R, K, H, S, T, C, D,
      E, N or Q
<220> FEATURE:
<221> NAME/KEY: MOD_RES
<222> LOCATION: (12)..(12)
<223> OTHER INFORMATION: Y, F, W, H, K, R or P
<220> FEATURE:
<221> NAME/KEY: MOD_RES
<222> LOCATION: (13)..(13)
<223> OTHER INFORMATION: G, A, V, L, I, M, T, S or C
<220> FEATURE:
<221> NAME/KEY: MOD_RES
<222> LOCATION: (14)..(14)
<223> OTHER INFORMATION: A, G, V, L, I, M, S, T, C or P
<220> FEATURE:
<221> NAME/KEY: MOD_RES
<222> LOCATION: (15)..(15)
<223> OTHER INFORMATION: A, G, V, L, I or M
<220> FEATURE:
<221> NAME/KEY: MOD_RES
<222> LOCATION: (16)..(16)
<223> OTHER INFORMATION: V, L, I, M, A or G
<220> FEATURE:
<221> NAME/KEY: MOD_RES
<222> LOCATION: (17)..(17)
<223> OTHER INFORMATION: Q, N, K, R, H, D or E

<400> SEQUENCE: 446

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 447
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T, C, G, A, V, L, I, M or absent
```

```
<220> FEATURE:
<221> NAME/KEY: MOD_RES
<222> LOCATION: (2)..(2)
<223> OTHER INFORMATION: I, V, L, M, A or G
<220> FEATURE:
<221> NAME/KEY: MOD_RES
<222> LOCATION: (3)..(3)
<223> OTHER INFORMATION: I, V, L, M, A, G, S, T, C, Y, F or W
<220> FEATURE:
<221> NAME/KEY: MOD_RES
<222> LOCATION: (4)..(4)
<223> OTHER INFORMATION: N, Q, S, T, C or absent
<220> FEATURE:
<221> NAME/KEY: MOD_RES
<222> LOCATION: (5)..(5)
<223> OTHER INFORMATION: A, V, L, I, M, G, S, T, C, R, K or H
<220> FEATURE:
<221> NAME/KEY: MOD_RES
<222> LOCATION: (6)..(6)
<223> OTHER INFORMATION: D, E, G, A, V, L, I, M, F, Y, W, S, T or C
<220> FEATURE:
<221> NAME/KEY: MOD_RES
<222> LOCATION: (7)..(7)
<223> OTHER INFORMATION: D, E, G, A, V, L, I, A or M
<220> FEATURE:
<221> NAME/KEY: MOD_RES
<222> LOCATION: (8)..(8)
<223> OTHER INFORMATION: S, T, C, N, Q, R, K or H
<220> FEATURE:
<221> NAME/KEY: MOD_RES
<222> LOCATION: (9)..(9)
<223> OTHER INFORMATION: T, S, C, Y, F, W, R, K or H
<220> FEATURE:
<221> NAME/KEY: MOD_RES
<222> LOCATION: (10)..(10)
<223> OTHER INFORMATION: S, T, C, A, V, L, I, M or G
<220> FEATURE:
<221> NAME/KEY: MOD_RES
<222> LOCATION: (11)..(11)
<223> OTHER INFORMATION: Y, F, W, K, R, H, G, V, L, I, M or A
<220> FEATURE:
<221> NAME/KEY: MOD_RES
<222> LOCATION: (12)..(12)
<223> OTHER INFORMATION: Y, F, W, K, R or H
<220> FEATURE:
<221> NAME/KEY: MOD_RES
<222> LOCATION: (13)..(13)
<223> OTHER INFORMATION: A, G, V, L, I or M
<220> FEATURE:
<221> NAME/KEY: MOD_RES
<222> LOCATION: (14)..(14)
<223> OTHER INFORMATION: A, G, V, L, I or M
<220> FEATURE:
<221> NAME/KEY: MOD_RES
<222> LOCATION: (15)..(15)
<223> OTHER INFORMATION: V, L, I, M, A or G
<220> FEATURE:
<221> NAME/KEY: MOD_RES
<222> LOCATION: (16)..(16)
<223> OTHER INFORMATION: V, L, I, M, A or G
<220> FEATURE:
<221> NAME/KEY: MOD_RES
<222> LOCATION: (17)..(17)
<223> OTHER INFORMATION: K, R, H, Q or N

<400> SEQUENCE: 447

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 448
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: G, A, V, L, I or M
<220> FEATURE:
<221> NAME/KEY: MOD_RES
<222> LOCATION: (2)..(2)
<223> OTHER INFORMATION: I, V, L, A, G or M
<220> FEATURE:
<221> NAME/KEY: MOD_RES
<222> LOCATION: (3)..(3)
<223> OTHER INFORMATION: S, T, C, N or Q
<220> FEATURE:
<221> NAME/KEY: MOD_RES
<222> LOCATION: (4)..(4)
<223> OTHER INFORMATION: S, T, C, R, K or H
<220> FEATURE:
<221> NAME/KEY: MOD_RES
<222> LOCATION: (5)..(5)
<223> OTHER INFORMATION: S, T, C, F, Y, W, D or E
<220> FEATURE:
<221> NAME/KEY: MOD_RES
<222> LOCATION: (6)..(6)
<223> OTHER INFORMATION: G, A, V, L, I or M
<220> FEATURE:
<221> NAME/KEY: MOD_RES
<222> LOCATION: (7)..(7)
<223> OTHER INFORMATION: R, K, H, N, Q, S, T or C
<220> FEATURE:
<221> NAME/KEY: MOD_RES
<222> LOCATION: (8)..(8)
<223> OTHER INFORMATION: S, T, C, R, K or H
<220> FEATURE:
<221> NAME/KEY: MOD_RES
<222> LOCATION: (9)..(9)
<223> OTHER INFORMATION: S, T, C, A, G, V, L, I or M
<220> FEATURE:
<221> NAME/KEY: MOD_RES
<222> LOCATION: (10)..(10)
<223> OTHER INFORMATION: A, G, V, L, I, M, R, K or H
<220> FEATURE:
<221> NAME/KEY: MOD_RES
<222> LOCATION: (11)..(11)
<223> OTHER INFORMATION: Y, F, W, H, R or K
<220> FEATURE:
<221> NAME/KEY: MOD_RES
<222> LOCATION: (12)..(12)
<223> OTHER INFORMATION: G, A, V, I, L or M
<220> FEATURE:
<221> NAME/KEY: MOD_RES
<222> LOCATION: (13)..(13)
<223> OTHER INFORMATION: A, G, V, I, L or M
<220> FEATURE:
<221> NAME/KEY: MOD_RES
<222> LOCATION: (14)..(14)
<223> OTHER INFORMATION: A, G, V, I, L or M
<220> FEATURE:
<221> NAME/KEY: MOD_RES
<222> LOCATION: (15)..(15)
<223> OTHER INFORMATION: V, A, G, I, L or M
<220> FEATURE:
<221> NAME/KEY: MOD_RES
<222> LOCATION: (16)..(16)
<223> OTHER INFORMATION: K, R or H

<400> SEQUENCE: 448

Xaa Xaa Xaa Xaa Xaa Xaa Xaa Xaa Xaa Xaa Xaa Xaa Xaa Xaa Xaa Xaa
1               5                   10                  15

<210> SEQ ID NO 449
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: G, A, V, I, L or M
<220> FEATURE:
<221> NAME/KEY: MOD_RES
<222> LOCATION: (2)..(2)
<223> OTHER INFORMATION: I, V, L, M, G or A
<220> FEATURE:
<221> NAME/KEY: MOD_RES
<222> LOCATION: (3)..(3)
<223> OTHER INFORMATION: S, T or C
<220> FEATURE:
<221> NAME/KEY: MOD_RES
<222> LOCATION: (4)..(4)
<223> OTHER INFORMATION: R, K or H
<220> FEATURE:
<221> NAME/KEY: MOD_RES
<222> LOCATION: (5)..(5)
<223> OTHER INFORMATION: D or E
<220> FEATURE:
<221> NAME/KEY: MOD_RES
<222> LOCATION: (6)..(6)
<223> OTHER INFORMATION: G, A, V, I, L or M
<220> FEATURE:
<221> NAME/KEY: MOD_RES
<222> LOCATION: (7)..(7)
<223> OTHER INFORMATION: S, T or C
<220> FEATURE:
<221> NAME/KEY: MOD_RES
<222> LOCATION: (8)..(8)
<223> OTHER INFORMATION: R, K or H
<220> FEATURE:
<221> NAME/KEY: MOD_RES
<222> LOCATION: (9)..(9)
<223> OTHER INFORMATION: T, S or C
<220> FEATURE:
<221> NAME/KEY: MOD_RES
<222> LOCATION: (10)..(10)
<223> OTHER INFORMATION: R, K or H
<220> FEATURE:
<221> NAME/KEY: MOD_RES
<222> LOCATION: (11)..(11)
<223> OTHER INFORMATION: Y, F or W
<220> FEATURE:
<221> NAME/KEY: MOD_RES
<222> LOCATION: (12)..(12)
<223> OTHER INFORMATION: G, A, V, I, L or M
<220> FEATURE:
<221> NAME/KEY: MOD_RES
<222> LOCATION: (13)..(13)
<223> OTHER INFORMATION: A, G, V, I, L or M
<220> FEATURE:
<221> NAME/KEY: MOD_RES
<222> LOCATION: (14)..(14)
<223> OTHER INFORMATION: A, G, V, I, L or M
<220> FEATURE:
<221> NAME/KEY: MOD_RES
<222> LOCATION: (15)..(15)
<223> OTHER INFORMATION: V, G, A, I, L or M
<220> FEATURE:
<221> NAME/KEY: MOD_RES
<222> LOCATION: (16)..(16)
<223> OTHER INFORMATION: K, R or H

<400> SEQUENCE: 449

Xaa Xaa Xaa Xaa Xaa Xaa Xaa Xaa Xaa Xaa Xaa Xaa Xaa Xaa Xaa Xaa
1               5                   10                  15

<210> SEQ ID NO 450
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: N, Q, S, T, C, A, G, V, L, I, M, D or E
<220> FEATURE:
<221> NAME/KEY: MOD_RES
<222> LOCATION: (2)..(2)
<223> OTHER INFORMATION: A, G, V, L, I, M, S, T, C, Y, F, W, N or Q
<220> FEATURE:
<221> NAME/KEY: MOD_RES
<222> LOCATION: (3)..(3)
<223> OTHER INFORMATION: D, E, G, A, V, L, I, M, Y, F, W, S, T, C, H, R,
      K or absent
<220> FEATURE:
<221> NAME/KEY: MOD_RES
<222> LOCATION: (4)..(4)
<223> OTHER INFORMATION: S, T, C, E, D, N, Q, G, A, V, I, L, M, R, K, H
      or absent
<220> FEATURE:
<221> NAME/KEY: MOD_RES
<222> LOCATION: (5)..(5)
<223> OTHER INFORMATION: G, A, V, L, I, M, C, S, T or absent
<220> FEATURE:
<221> NAME/KEY: MOD_RES
<222> LOCATION: (6)..(6)
<223> OTHER INFORMATION: Y, F, W, C, S, T, R, K, H or absent
<220> FEATURE:
<221> NAME/KEY: MOD_RES
<222> LOCATION: (7)..(7)
<223> OTHER INFORMATION: Y, F, W, N, Q, C, S, T or absent
<220> FEATURE:
<221> NAME/KEY: MOD_RES
<222> LOCATION: (8)..(8)
<223> OTHER INFORMATION: W, F, Y or absent
<220> FEATURE:
<221> NAME/KEY: MOD_RES
<222> LOCATION: (9)..(9)
<223> OTHER INFORMATION: N, Q or absent
<220> FEATURE:
<221> NAME/KEY: MOD_RES
<222> LOCATION: (10)..(10)
<223> OTHER INFORMATION: T, S, C or absent
<220> FEATURE:
<221> NAME/KEY: MOD_RES
<222> LOCATION: (11)..(11)
<223> OTHER INFORMATION: C, S, T, Y, F, W, A, G, V, L, I, M or absent
<220> FEATURE:
<221> NAME/KEY: MOD_RES
<222> LOCATION: (12)..(12)
<223> OTHER INFORMATION: T, S, C, N, Q, G, A, V, L, I, M, D, E, Y, F, W
      or absent
<220> FEATURE:
<221> NAME/KEY: MOD_RES
<222> LOCATION: (13)..(13)
<223> OTHER INFORMATION: G, A, V, L, I, M, C, S, T, D, E, K, R, H or
      absent
<220> FEATURE:
<221> NAME/KEY: MOD_RES
<222> LOCATION: (14)..(14)
<223> OTHER INFORMATION: Y, F, W, A, G, V, L, I, M, S, T, C, P, D, E or
      absent
<220> FEATURE:
<221> NAME/KEY: MOD_RES
<222> LOCATION: (15)..(15)
<223> OTHER INFORMATION: N, Q, S, T, C, G, A, V, L, I, M, R, K, H or
      absent
<220> FEATURE:
<221> NAME/KEY: MOD_RES
<222> LOCATION: (16)..(16)
<223> OTHER INFORMATION: C, S, T, G, A, V, L, I, M or absent
<220> FEATURE:
<221> NAME/KEY: MOD_RES
<222> LOCATION: (17)..(17)
<223> OTHER INFORMATION: A, G, V, L, I M, W, F, Y, T, S, C, D, E or
      absent
<220> FEATURE:
<221> NAME/KEY: MOD_RES
<222> LOCATION: (18)..(18)
<223> OTHER INFORMATION: D, E, T, S, C, A, G, V, L, I, M, P, W, F, Y or
      absent
```

-continued

```
<220> FEATURE:
<221> NAME/KEY: MOD_RES
<222> LOCATION: (19)..(19)
<223> OTHER INFORMATION: Y, F, W, A, G, V, L, I, M, N, Q, S, T, C or
      absent
<220> FEATURE:
<221> NAME/KEY: MOD_RES
<222> LOCATION: (20)..(20)
<223> OTHER INFORMATION: G, A, V, L, I, M, T, S, C or absent
<220> FEATURE:
<221> NAME/KEY: MOD_RES
<222> LOCATION: (21)..(21)
<223> OTHER INFORMATION: A, G, V, L, I, M, P, Y, F, W, S, T, C or absent
<220> FEATURE:
<221> NAME/KEY: MOD_RES
<222> LOCATION: (22)..(22)
<223> OTHER INFORMATION: G, A, V, L, I, M, H, K, R, D, E, S, T, C, Y, F,
      W or absent
<220> FEATURE:
<221> NAME/KEY: MOD_RES
<222> LOCATION: (23)..(23)
<223> OTHER INFORMATION: Y, F, W, E, D, S, T, C, N, Q, L, A, G, V, I or
      M
<220> FEATURE:
<221> NAME/KEY: MOD_RES
<222> LOCATION: (24)..(24)
<223> OTHER INFORMATION: I, V, L, A, G or M
<220> FEATURE:
<221> NAME/KEY: MOD_RES
<222> LOCATION: (25)..(25)
<223> OTHER INFORMATION: D or E
<220> FEATURE:
<221> NAME/KEY: MOD_RES
<222> LOCATION: (26)..(26)
<223> OTHER INFORMATION: A, G, V, L, I, M, S, T or C
<220> FEATURE:
<221> NAME/KEY: MOD_RES
<222> LOCATION: (27)..(27)
<223> OTHER INFORMATION: W, F or Y

<400> SEQUENCE: 450

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 451
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T, C, V, L, I, M, A, G or absent
<220> FEATURE:
<221> NAME/KEY: MOD_RES
<222> LOCATION: (2)..(2)
<223> OTHER INFORMATION: S, T, C, V, L, I, M, A, G or absent
<220> FEATURE:
<221> NAME/KEY: MOD_RES
<222> LOCATION: (3)..(3)
<223> OTHER INFORMATION: Y, F, W or absent
<220> FEATURE:
<221> NAME/KEY: MOD_RES
<222> LOCATION: (4)..(4)
<223> OTHER INFORMATION: Q, N, D, E, V, L, I, M, A, G or absent
<220> FEATURE:
<221> NAME/KEY: MOD_RES
<222> LOCATION: (5)..(5)
<223> OTHER INFORMATION: C, S, T, N, Q, Y, F, W or absent
<220> FEATURE:
<221> NAME/KEY: MOD_RES
<222> LOCATION: (6)..(6)
```

```
<223> OTHER INFORMATION: A, G, V, L, I, M, S, T, C, D or E
<220> FEATURE:
<221> NAME/KEY: MOD_RES
<222> LOCATION: (7)..(7)
<223> OTHER INFORMATION: G, V, L, I, M, A, D, E, S, T, C or absent
<220> FEATURE:
<221> NAME/KEY: MOD_RES
<222> LOCATION: (8)..(8)
<223> OTHER INFORMATION: D, E, Y, F, W, G, V, L, I, M, A, S, T or C
<220> FEATURE:
<221> NAME/KEY: MOD_RES
<222> LOCATION: (9)..(9)
<223> OTHER INFORMATION: C, S, T, N, Q, G, V, L, I, M or A
<220> FEATURE:
<221> NAME/KEY: MOD_RES
<222> LOCATION: (10)..(10)
<223> OTHER INFORMATION: C, S, T, F, Y, W, G, V, L, I, M or A
<220> FEATURE:
<221> NAME/KEY: MOD_RES
<222> LOCATION: (11)..(11)
<223> OTHER INFORMATION: F, Y or W
<220> FEATURE:
<221> NAME/KEY: MOD_RES
<222> LOCATION: (12)..(12)
<223> OTHER INFORMATION: T, S, C or absent
<220> FEATURE:
<221> NAME/KEY: MOD_RES
<222> LOCATION: (13)..(13)
<223> OTHER INFORMATION: G, V, L, I, M, A, F, Y, W, S, T or C
<220> FEATURE:
<221> NAME/KEY: MOD_RES
<222> LOCATION: (14)..(14)
<223> OTHER INFORMATION: Y, F, W, G, V, L, I, M or A
<220> FEATURE:
<221> NAME/KEY: MOD_RES
<222> LOCATION: (15)..(15)
<223> OTHER INFORMATION: P, G, A, V, I, L or M
<220> FEATURE:
<221> NAME/KEY: MOD_RES
<222> LOCATION: (16)..(16)
<223> OTHER INFORMATION: F, Y, W, G, V, L, I, M or A
<220> FEATURE:
<221> NAME/KEY: MOD_RES
<222> LOCATION: (17)..(17)
<223> OTHER INFORMATION: G, A, V, I, L, M, S, T, C, D, E, F, Y or W
<220> FEATURE:
<221> NAME/KEY: MOD_RES
<222> LOCATION: (18)..(18)
<223> OTHER INFORMATION: V, L, I, M, A or G
<220> FEATURE:
<221> NAME/KEY: MOD_RES
<222> LOCATION: (19)..(19)
<223> OTHER INFORMATION: D or E
<220> FEATURE:
<221> NAME/KEY: MOD_RES
<222> LOCATION: (20)..(20)
<223> OTHER INFORMATION: S, T, C, V, L, I, M, A or G
<220> FEATURE:
<221> NAME/KEY: MOD_RES
<222> LOCATION: (21)..(21)
<223> OTHER INFORMATION: W, F or Y

<400> SEQUENCE: 451

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 452
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (1)..(1)
<223> OTHER INFORMATION: G, A, V, I, L, M, S, T, C or absent
<220> FEATURE:
<221> NAME/KEY: MOD_RES
<222> LOCATION: (2)..(2)
<223> OTHER INFORMATION: A, G, V, I, L, M or absent
<220> FEATURE:
<221> NAME/KEY: MOD_RES
<222> LOCATION: (3)..(3)
<223> OTHER INFORMATION: Y, F, W or absent
<220> FEATURE:
<221> NAME/KEY: MOD_RES
<222> LOCATION: (4)..(4)
<223> OTHER INFORMATION: D, E, G, A, V, I, L, M or absent
<220> FEATURE:
<221> NAME/KEY: MOD_RES
<222> LOCATION: (5)..(5)
<223> OTHER INFORMATION: S, T, C, Y, F, W or absent
<220> FEATURE:
<221> NAME/KEY: MOD_RES
<222> LOCATION: (6)..(6)
<223> OTHER INFORMATION: D, E, S, T or C
<220> FEATURE:
<221> NAME/KEY: MOD_RES
<222> LOCATION: (7)..(7)
<223> OTHER INFORMATION: T, S, C, G, A, V, I, L or M
<220> FEATURE:
<221> NAME/KEY: MOD_RES
<222> LOCATION: (8)..(8)
<223> OTHER INFORMATION: Y, F, W, S, T, C, G, A, V, I, L or M
<220> FEATURE:
<221> NAME/KEY: MOD_RES
<222> LOCATION: (9)..(9)
<223> OTHER INFORMATION: T, S, C, G, A, V, I, L or M
<220> FEATURE:
<221> NAME/KEY: MOD_RES
<222> LOCATION: (10)..(10)
<223> OTHER INFORMATION: S, T or C
<220> FEATURE:
<221> NAME/KEY: MOD_RES
<222> LOCATION: (11)..(11)
<223> OTHER INFORMATION: G, V, L, I, M, A, Y, F or W
<220> FEATURE:
<221> NAME/KEY: MOD_RES
<222> LOCATION: (12)..(12)
<223> OTHER INFORMATION: S, T, C, Y, F or W
<220> FEATURE:
<221> NAME/KEY: MOD_RES
<222> LOCATION: (13)..(13)
<223> OTHER INFORMATION: F, Y, W, G, A, V, I, L, M or absent
<220> FEATURE:
<221> NAME/KEY: MOD_RES
<222> LOCATION: (14)..(14)
<223> OTHER INFORMATION: G, A, V, I, L or M
<220> FEATURE:
<221> NAME/KEY: MOD_RES
<222> LOCATION: (15)..(15)
<223> OTHER INFORMATION: G, A, V, I, L or M
<220> FEATURE:
<221> NAME/KEY: MOD_RES
<222> LOCATION: (16)..(16)
<223> OTHER INFORMATION: G, A, V, L, I or M
<220> FEATURE:
<221> NAME/KEY: MOD_RES
<222> LOCATION: (17)..(17)
<223> OTHER INFORMATION: E, D, S, T, C, G, A, V, I, L or M
<220> FEATURE:
<221> NAME/KEY: MOD_RES
<222> LOCATION: (18)..(18)
<223> OTHER INFORMATION: V, L, I, M, A or G
<220> FEATURE:
<221> NAME/KEY: MOD_RES
<222> LOCATION: (19)..(19)
<223> OTHER INFORMATION: D or E
<220> FEATURE:
<221> NAME/KEY: MOD_RES
<222> LOCATION: (20)..(20)
<223> OTHER INFORMATION: V, L, I, M, A or G
```

```
<220> FEATURE:
<221> NAME/KEY: MOD_RES
<222> LOCATION: (21)..(21)
<223> OTHER INFORMATION: W, F or Y

<400> SEQUENCE: 452

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 453
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: S, T or C
<220> FEATURE:
<221> NAME/KEY: MOD_RES
<222> LOCATION: (2)..(2)
<223> OTHER INFORMATION: A, G, V, I, L or M
<220> FEATURE:
<221> NAME/KEY: MOD_RES
<222> LOCATION: (3)..(3)
<223> OTHER INFORMATION: Y, F or W
<220> FEATURE:
<221> NAME/KEY: MOD_RES
<222> LOCATION: (4)..(4)
<223> OTHER INFORMATION: E or D
<220> FEATURE:
<221> NAME/KEY: MOD_RES
<222> LOCATION: (5)..(5)
<223> OTHER INFORMATION: C, S or T
<220> FEATURE:
<221> NAME/KEY: MOD_RES
<222> LOCATION: (6)..(6)
<223> OTHER INFORMATION: D or E
<220> FEATURE:
<221> NAME/KEY: MOD_RES
<222> LOCATION: (7)..(7)
<223> OTHER INFORMATION: G, A, V, I, L or M
<220> FEATURE:
<221> NAME/KEY: MOD_RES
<222> LOCATION: (8)..(8)
<223> OTHER INFORMATION: Y, F or W
<220> FEATURE:
<221> NAME/KEY: MOD_RES
<222> LOCATION: (9)..(9)
<223> OTHER INFORMATION: S, T or C
<220> FEATURE:
<221> NAME/KEY: MOD_RES
<222> LOCATION: (10)..(10)
<223> OTHER INFORMATION: S, T or C
<220> FEATURE:
<221> NAME/KEY: MOD_RES
<222> LOCATION: (11)..(11)
<223> OTHER INFORMATION: W, F or Y
<220> FEATURE:
<221> NAME/KEY: MOD_RES
<222> LOCATION: (12)..(12)
<223> OTHER INFORMATION: T, S or C
<220> FEATURE:
<221> NAME/KEY: MOD_RES
<222> LOCATION: (13)..(13)
<223> OTHER INFORMATION: E or D
<220> FEATURE:
<221> NAME/KEY: MOD_RES
<222> LOCATION: (14)..(14)
<223> OTHER INFORMATION: I, A, G, V, L or M
<220> FEATURE:
<221> NAME/KEY: MOD_RES
```

```
<222> LOCATION: (15)..(15)
<223> OTHER INFORMATION: A, G, V, I, L or M
<220> FEATURE:
<221> NAME/KEY: MOD_RES
<222> LOCATION: (16)..(16)
<223> OTHER INFORMATION: G, A, V, I, L or M
<220> FEATURE:
<221> NAME/KEY: MOD_RES
<222> LOCATION: (17)..(17)
<223> OTHER INFORMATION: S, T or C
<220> FEATURE:
<221> NAME/KEY: MOD_RES
<222> LOCATION: (18)..(18)
<223> OTHER INFORMATION: I, G, A, V, L or M
<220> FEATURE:
<221> NAME/KEY: MOD_RES
<222> LOCATION: (19)..(19)
<223> OTHER INFORMATION: D or E
<220> FEATURE:
<221> NAME/KEY: MOD_RES
<222> LOCATION: (20)..(20)
<223> OTHER INFORMATION: A, G, V, I, L or M
<220> FEATURE:
<221> NAME/KEY: MOD_RES
<222> LOCATION: (21)..(21)
<223> OTHER INFORMATION: W, F or Y

<400> SEQUENCE: 453

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 454
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 454

His His His His His His His His His His
1               5                   10

<210> SEQ ID NO 455
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Asp Tyr Lys Asp Asp Asp Asp Lys
1               5
```